(12) United States Patent
Anderson

(10) Patent No.: US 12,185,944 B2
(45) Date of Patent: Jan. 7, 2025

(54) APPARATUS AND METHOD FOR ADHESION

(71) Applicant: MicroKoll Inc., Lompoc, CA (US)

(72) Inventor: Steven Craig Anderson, Lompoc, CA (US)

(73) Assignee: M1CROKOLL, INC., San Diego, CA (US)

(*) Notice: Subject to any disclaimer, the term of this patent is extended or adjusted under 35 U.S.C. 154(b) by 903 days.

(21) Appl. No.: 17/153,397

(22) Filed: Jan. 20, 2021

(65) Prior Publication Data
US 2021/0145435 A1 May 20, 2021

Related U.S. Application Data

(63) Continuation of application No. 15/762,278, filed as application No. PCT/US2016/053553 on Sep. 23, 2016, now Pat. No. 10,945,724.
(Continued)

(51) Int. Cl.
*A61B 17/064* (2006.01)
*A61B 17/00* (2006.01)
(Continued)

(52) U.S. Cl.
CPC .......... *A61B 17/064* (2013.01); *A61B 17/068* (2013.01); *A61B 17/072* (2013.01);
(Continued)

(58) Field of Classification Search
CPC ... A61B 17/064; A61B 17/068; A61B 17/072; A61B 17/10; A61B 17/11;
(Continued)

(56) References Cited

U.S. PATENT DOCUMENTS 5,624,380 A * 4/1997 Takayama ............ A61B 1/0058
600/141
10,945,724 B2 * 3/2021 Anderson ................. A61F 2/82
(Continued)

*Primary Examiner* — Tan-Uyen T Ho
*Assistant Examiner* — David P Stein
(74) *Attorney, Agent, or Firm* — Felix L. Fischer

(57) ABSTRACT

An adhesion device incorporates element block assemblies partially disposed within an element support body having an engagement surface. Each element block assembly may include an element activation sheet, an element deployment sheet, a plurality of engagement elements, and an element transition mechanism operatively coupled to the engagement elements. The element transition mechanism is reversible to transition from a neutral configuration wherein the element activation sheet is substantially adjacent to the element deployment sheet, and an expanded configuration wherein the element activation sheet and the element deployment sheet are separated by a transition gap. The element support body, while each element transition mechanism is disposed in the neutral configuration, constrains each engagement element in a deployment state with a substantially straightened configuration perpendicular to the engagement surface and suitable for insertion into (or removal from) a target material. The element support body, while each element transition mechanism is disposed in the expanded configuration, constrains each engagement element in an engagement state eccentrically tensioned as the result of the transition gap into a reactive flexure to capture surrounding target material.

13 Claims, 83 Drawing Sheets

Related U.S. Application Data

(60) Provisional application No. 62/232,930, filed on Sep. 25, 2015.

(51) Int. Cl.

| | | |
|---|---|---|
| *A61B 17/068* | (2006.01) | |
| *A61B 17/072* | (2006.01) | |
| *A61B 17/08* | (2006.01) | |
| *A61B 17/10* | (2006.01) | |
| *A61B 17/11* | (2006.01) | |
| *A61B 17/12* | (2006.01) | |
| *A61F 2/24* | (2006.01) | |
| *A61F 2/82* | (2013.01) | |
| *A61F 13/00* | (2024.01) | |
| *A61B 90/00* | (2016.01) | |
| *A61M 25/10* | (2013.01) | |

(52) U.S. Cl.
CPC .............. *A61B 17/10* (2013.01); *A61B 17/11* (2013.01); *A61B 17/12113* (2013.01); *A61B 17/12136* (2013.01); *A61F 2/24* (2013.01); *A61F 2/82* (2013.01); *A61F 13/00* (2013.01); *A61B 2017/00004* (2013.01); *A61B 2017/00022* (2013.01); *A61B 2017/00115* (2013.01); *A61B 2017/00199* (2013.01); *A61B 2017/00221* (2013.01); *A61B 2017/00327* (2013.01); *A61B 2017/00557* (2013.01); *A61B 2017/00862* (2013.01); *A61B 2017/00867* (2013.01); *A61B 2017/0641* (2013.01); *A61B 17/08* (2013.01); *A61B 2017/1107* (2013.01); *A61B 2017/1132* (2013.01); *A61B 2090/064* (2016.02); *A61B 90/37* (2016.02); *A61F 2013/00723* (2013.01); *A61F 2210/0004* (2013.01); *A61F 2220/0016* (2013.01); *A61M 25/1002* (2013.01)

(58) Field of Classification Search
CPC ........ A61B 17/12113; A61B 17/12136; A61B 17/08; A61B 90/37; A61B 2017/00004; A61B 2017/00022; A61B 2017/00115; A61B 2017/00199; A61B 2017/00221; A61B 2017/00327; A61B 2017/00557; A61B 2017/00862; A61B 2017/00867; A61B 2017/0641; A61B 2017/1107; A61B 2017/1132; A61B 2090/064; A61F 2/24; A61F 2/82; A61F 13/00; A61F 2013/00723; A61F 2210/0004; A61F 2220/0016; A61M 25/1002

See application file for complete search history.

(56) References Cited

U.S. PATENT DOCUMENTS

| | | | | |
|---|---|---|---|---|
| 2012/0324975 | A1* | 12/2012 | Anderson | A61B 17/064 72/324 |
| 2015/0051530 | A1* | 2/2015 | Noda | A61B 17/085 602/41 |
| 2016/0374685 | A1* | 12/2016 | Abbott | A61B 17/07207 606/157 |

* cited by examiner

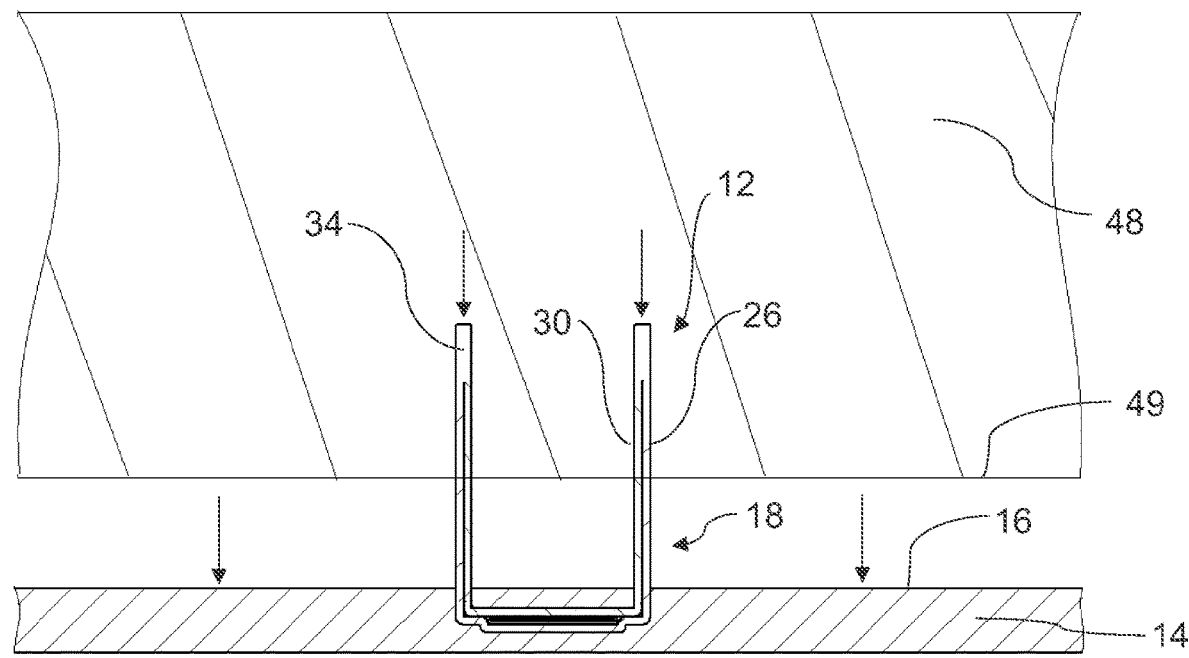
FIG. 31
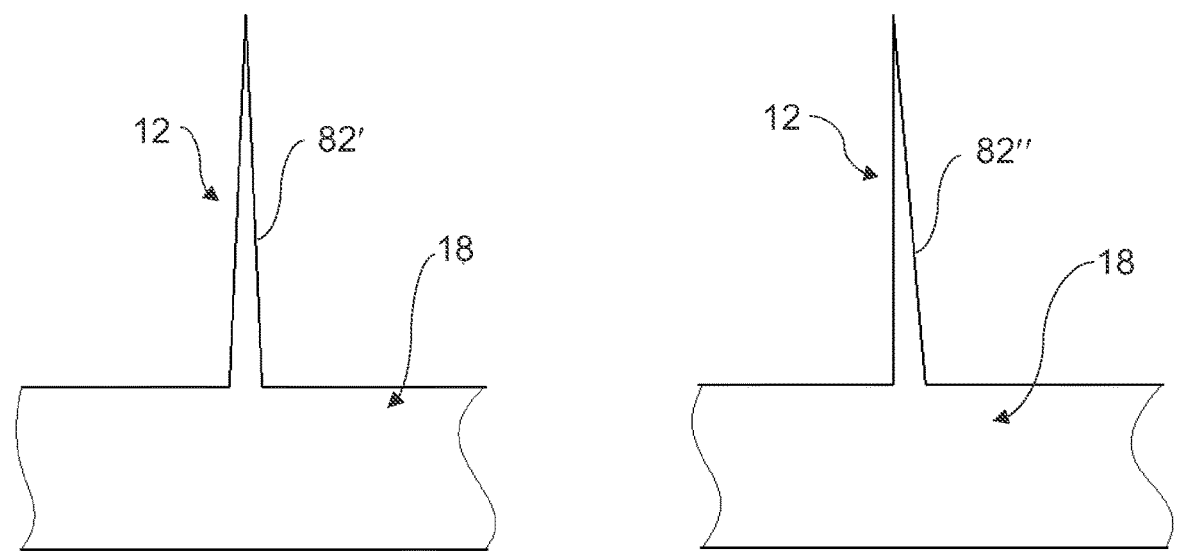
FIG. 32
FIG. 33

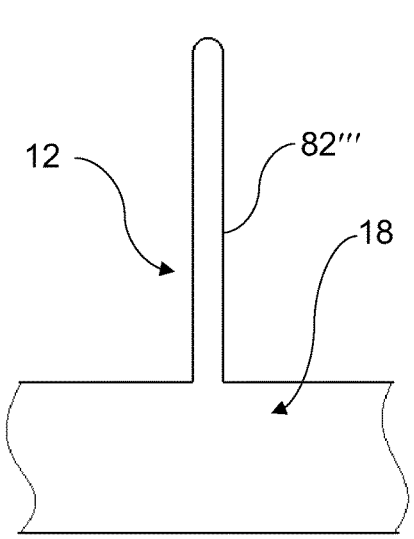
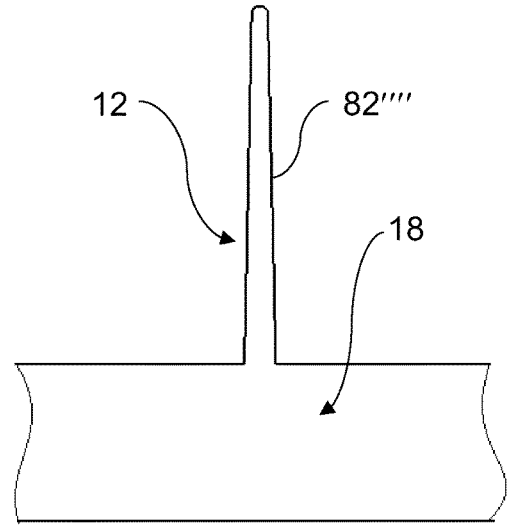
FIG. 34  FIG. 35
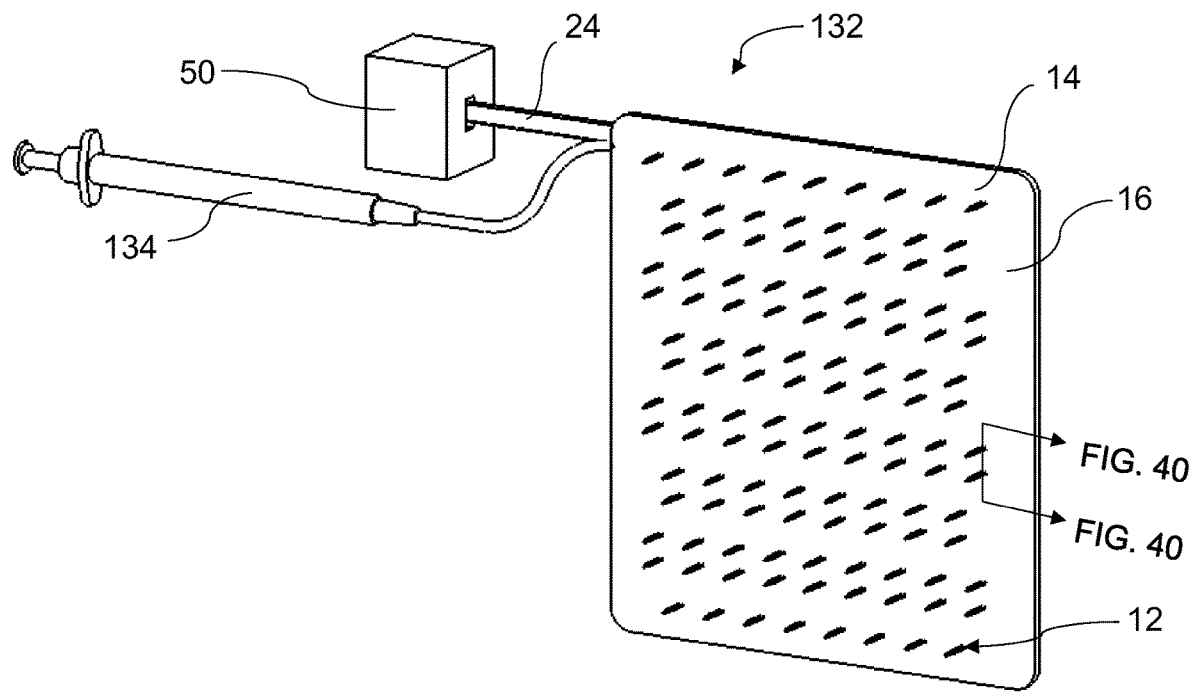
FIG. 36

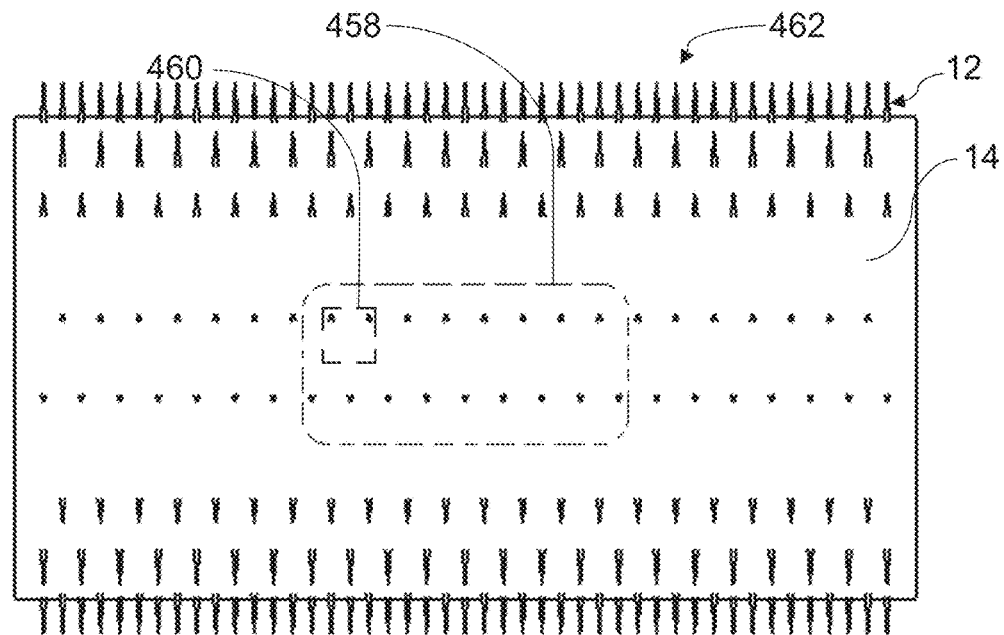
FIG. 168
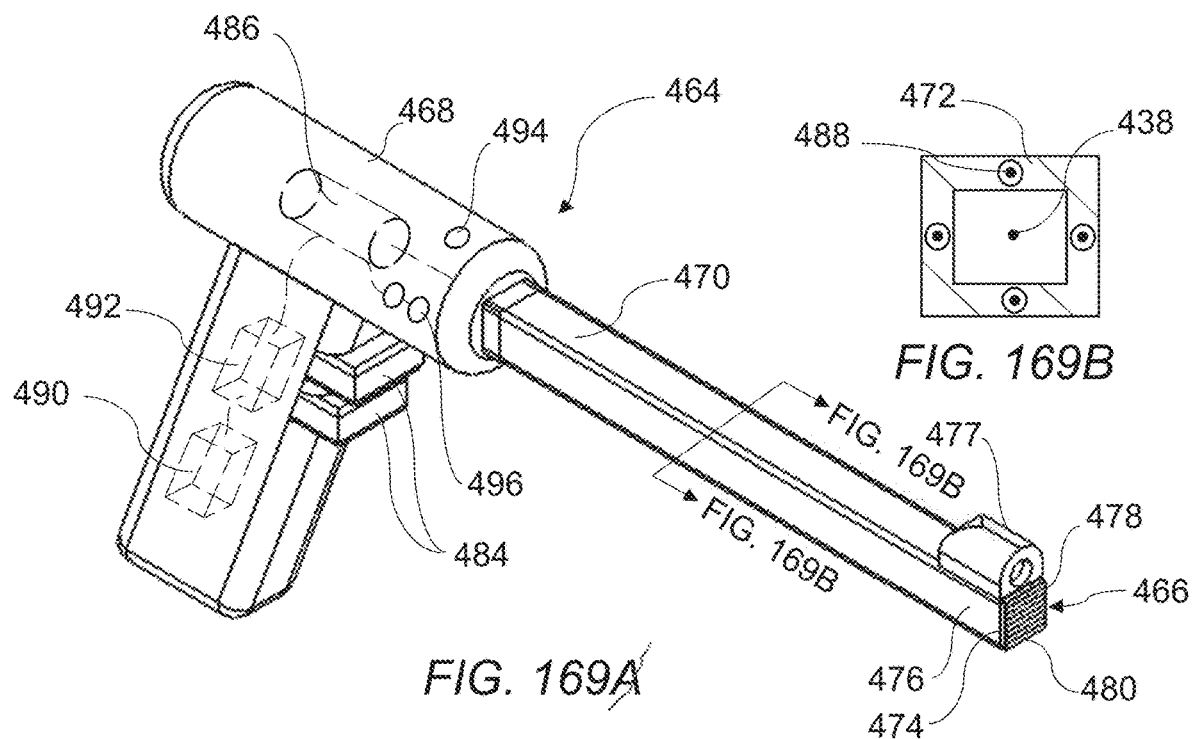
FIG. 169A
FIG. 169B

APPARATUS AND METHOD FOR ADHESION

REFERENCES TO RELATED APPLICATIONS

This application is a continuation of U.S. patent application Ser. No. 15/762,278 filed on Mar. 22, 2018 as a 371(c) national stage of Patent Cooperation Treaty application serial no. PCT/US2016/053553 having an international filing date of Sep. 23, 2016 and relied on the priority of U.S. provisional application Ser. No. 62/232,930 filed on Sep. 25, 2015, the disclosures of which are incorporated herein by reference.

BACKGROUND

Some previous embodiments of adhesion devices may utilize shape memory engagements elements which are fabricated from shape memory materials. For example shape memory engagement elements of an adhesion device may be inserted into a target material (for example tissue), a shape memory transition of the material may then transform the engagement elements from a deployment state to an engagement state thereby mechanically capturing target material adjacent to each engagement element and adhering the adhesion device embodiment to the surface of the target material. The shape memory materials for such shape memory engagement element embodiments may include shape memory polymers and/or shape memory alloys. Activation methods which cause the shape memory transition of the shape memory engagement element embodiments may include thermal activation, activation by the application of UV light, activation by a change in Ph of the surrounding material, or the like.

Some previous embodiments of adhesion devices which utilize shape memory engagement elements may be limited in that the shape memory engagement elements may be configured for a one time only transition from the deployment state to the engagement state. That is to say that after deployment into the target material, a shape memory transition may transform each engagement element to an engagement state and a subsequent shape memory transition may allow for their removal from the target material. However for most previous engagement element embodiments a subsequent suitably configured shape memory transition will not transform the engagement elements from the deployment state to the engagement state a second time in order to allow for a second application of the adhesion device.

The ability of each shape memory engagement element to mechanically capture the adjacent target material is dependent upon the physical size of the engagement element. Each shape memory engagement element may be configured to change shape when transitioned to the engagement state. The ability of each shape memory engagement element to maintain the deformed configuration (and continue to mechanically capture adjacent target material) is dependent upon the physical dimensions of each shape memory engagement element which can be quite small for some previous embodiments.

Additionally, some previous embodiments of shape memory engagement elements may be prematurely transitioned from the deployment state to the engagement state. For example, shape memory engagement elements which experience shape memory transition above a given threshold temperature may be prematurely activated in an all fluid environment which is above that threshold temperature. What are needed are adhesion devices and methods which utilize mechanical flexure of engagement elements which are fabricated from non-shape memory materials in order to reversibly transition the engagement elements from the deployment state to the engagement state, with the adhesion devices and methods being configured to allow for the multiple reversible transitions of each engagement element from the deployment state to the engagement state.

SUMMARY

Some embodiments of an adhesion device may include a plurality of element block assemblies. Each element block assembly in turn may include an element activation sheet which is formed from a resilient material and which has an activation sheet upper surface. Each element block assembly may also include an element deployment sheet which is formed from a resilient material and which has a deployment sheet lower surface. Each element block assembly may also include a plurality of engagement elements with each engagement element having an elongated element activation section which monolithically extends from the element activation sheet. Each engagement element may also include an elongated element deployment section which monolithically extends from the element deployment sheet. For each engagement element, the element activation section may be fused to the element deployment section within an element tip segment. Each element block assembly may also include an element transition mechanism which may be disposed between the element activation sheet and the element deployment sheet. The element transition mechanism may be operatively coupled to each engagement element. The element transition mechanism may be configured to reversibly transition between a neutral configuration wherein the activation sheet upper surface is substantially adjacent to the deployment sheet lower surface, and an expanded configuration wherein the activation sheet upper surface and the deployment sheet lower surface are separated by a transition gap.

The adhesion device may also include an element support body which may have an engagement surface. The element support body may encompass each element activation sheet and each element deployment sheet. The element support body may be configured while the element transition mechanism is disposed in the neutral configuration to constrain each engagement element in a deployment state which is suitable for insertion into (or the removal from) a target material wherein each engagement element is disposed in a substantially straightened configuration which is substantially perpendicular to the engagement surface. The element support body may also be configured while the element transition mechanism is disposed in the expanded configuration to constrain each engagement element in an engagement state wherein each engagement element is eccentrically tensioned as the result of the transition gap into a reactive flexure which is configured to mechanically capture surrounding target material. The adhesion device may also include a control system which is operatively coupled to each element transition mechanism. The control system may be configured to allow a user of the adhesion device to reversibly transition selected transition mechanisms from the neutral configuration to the expanded configuration thereby transitioning respective engagement elements from the deployment state to the engagement state.

BRIEF DESCRIPTION OF THE DRAWINGS

FIGS. 29-31 depict a removal sequence of the adhesion device of FIG. 1 from the target material.

FIGS. 32-35 depict embodiments of engagement elements which are configured with different engagement element profiles.

FIG. 36 is an isometric view of an adhesion device embodiment which is configured to deliver fluid through its respective engagement elements which are disposed a deployment state.

FIG. 64 is an isometric view of a shape memory insert element transition mechanism, the shape memory insert depicted in a neutral configuration and an expanded configuration.

FIGS. 78-80 are sectional views of the element block assembly of FIG. 72, in each case the patterned insert assembly being disposed in the expanded configuration and the engagement elements being disposed in the engagement state.

FIG. 156 depicts an embodiment of an element block array and a control system which is operatively coupled to the element block array.

Figure 156:
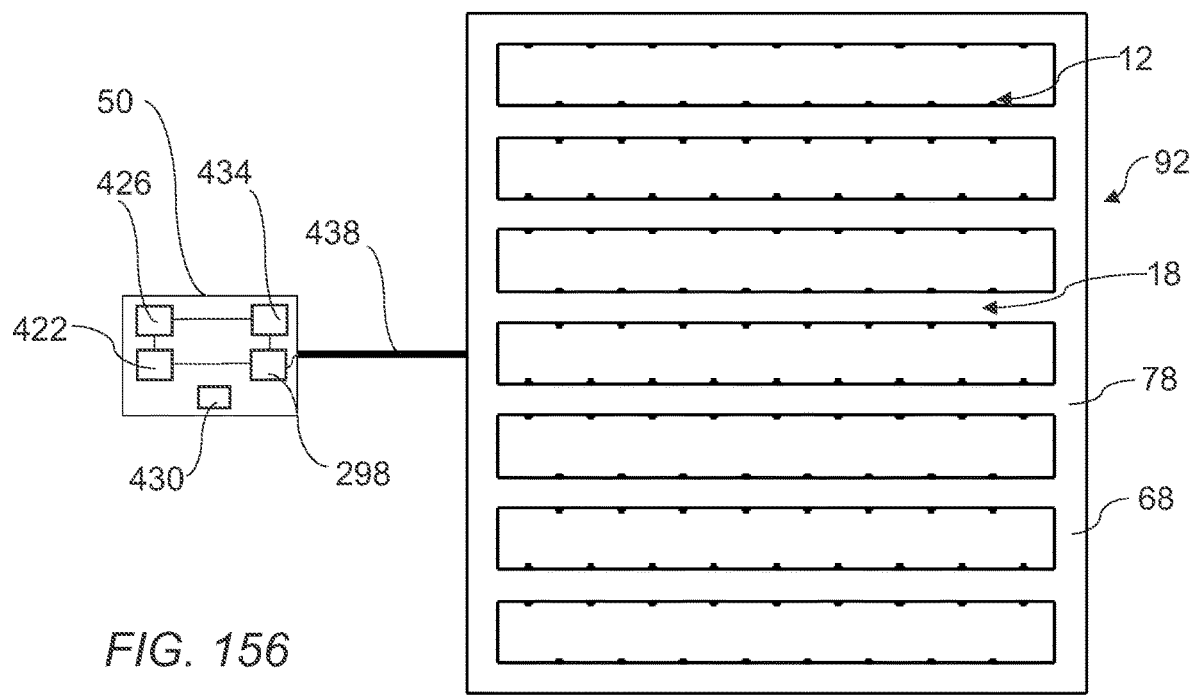
Figure 157:
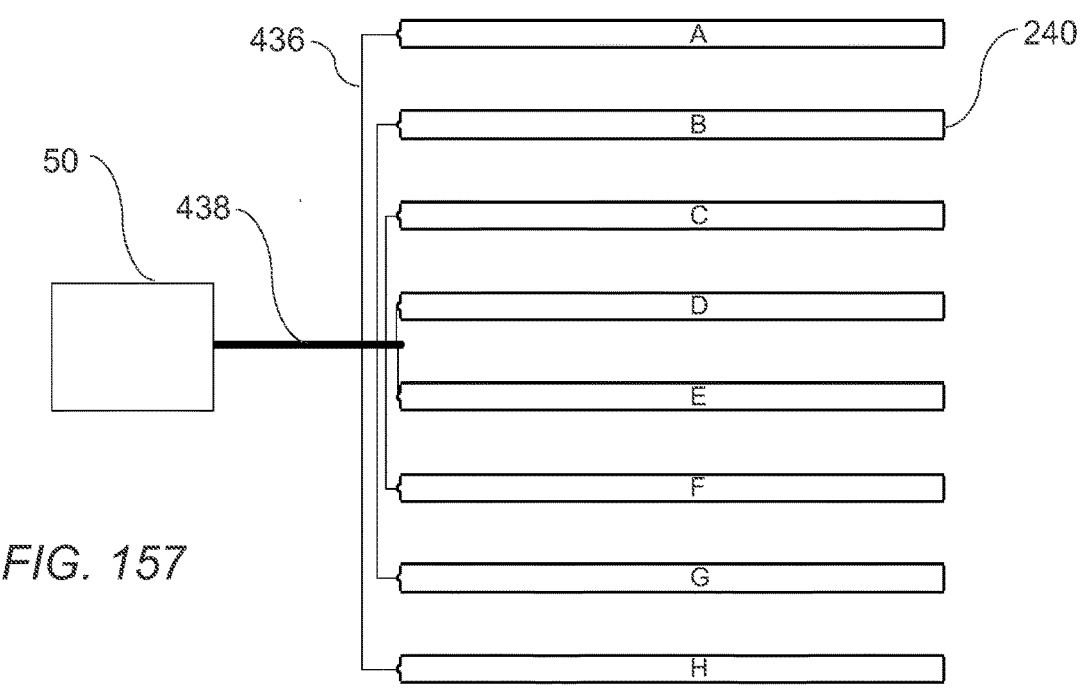
Figure 158:
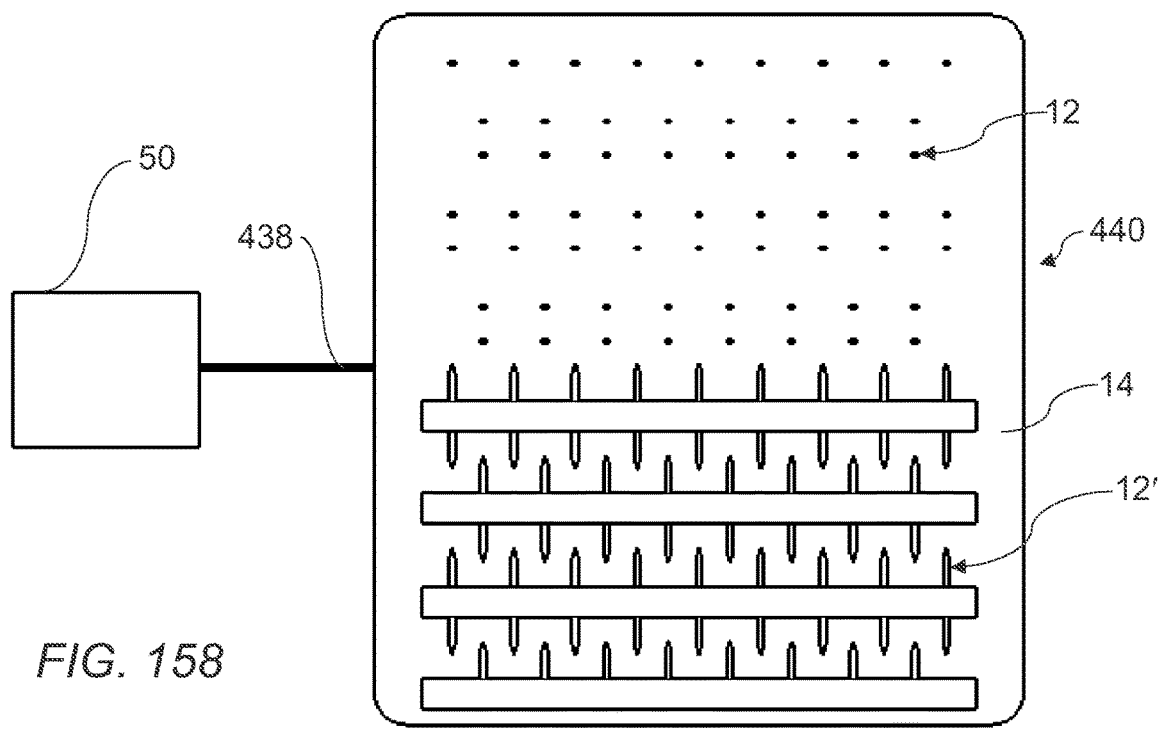
Figure 159:
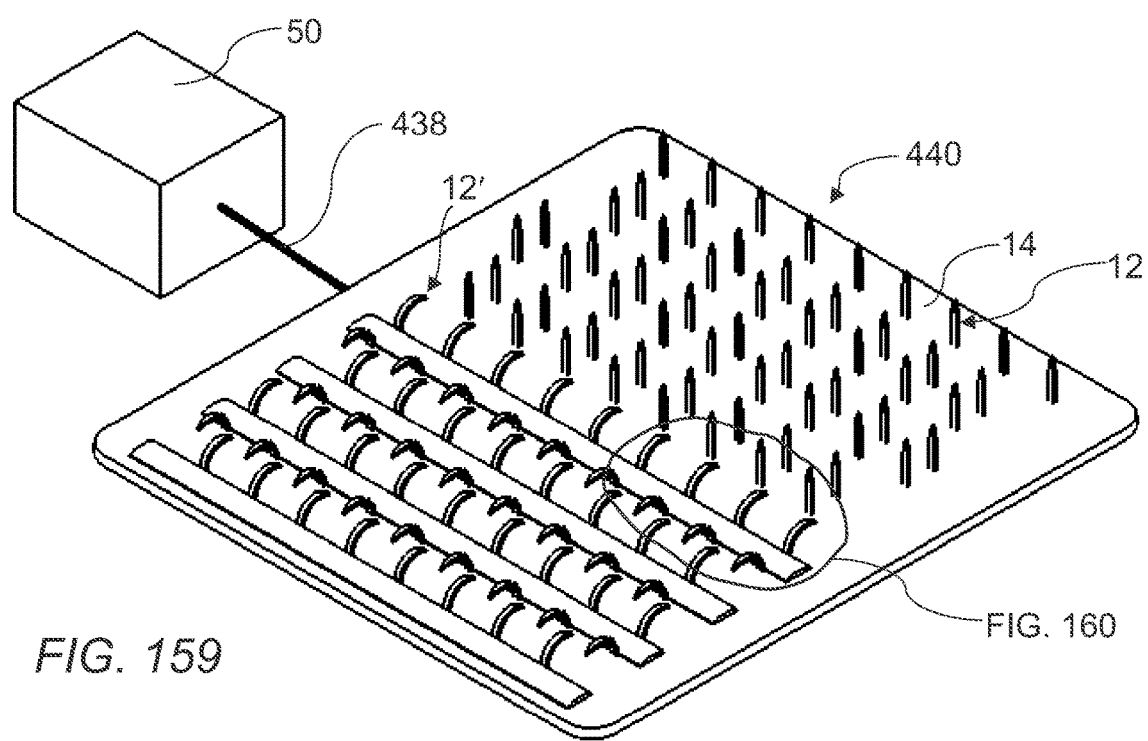
Figure 160:
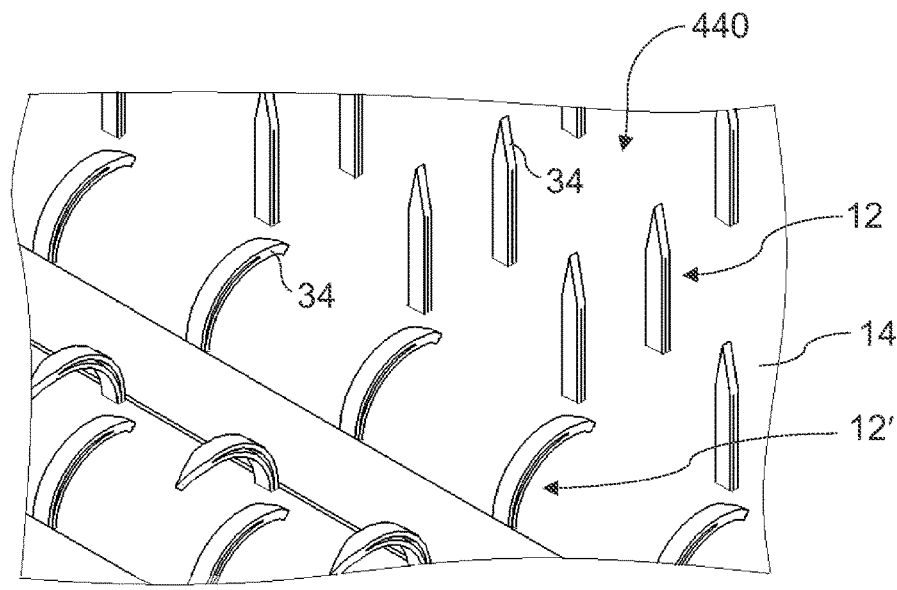

FIG. 157 is a schematic of the element block array of FIG. 156, depicting multiple element transition mechanisms which are individually coupled to the control system FIGS. 158-160 depict an embodiment of an adhesion device which incorporates the element block array of FIG. 156, the adhesion device having a plurality of engagement elements which are disposed in the engagement state and a plurality of engagement elements which are disposed in the deployment state.

Figure 161:
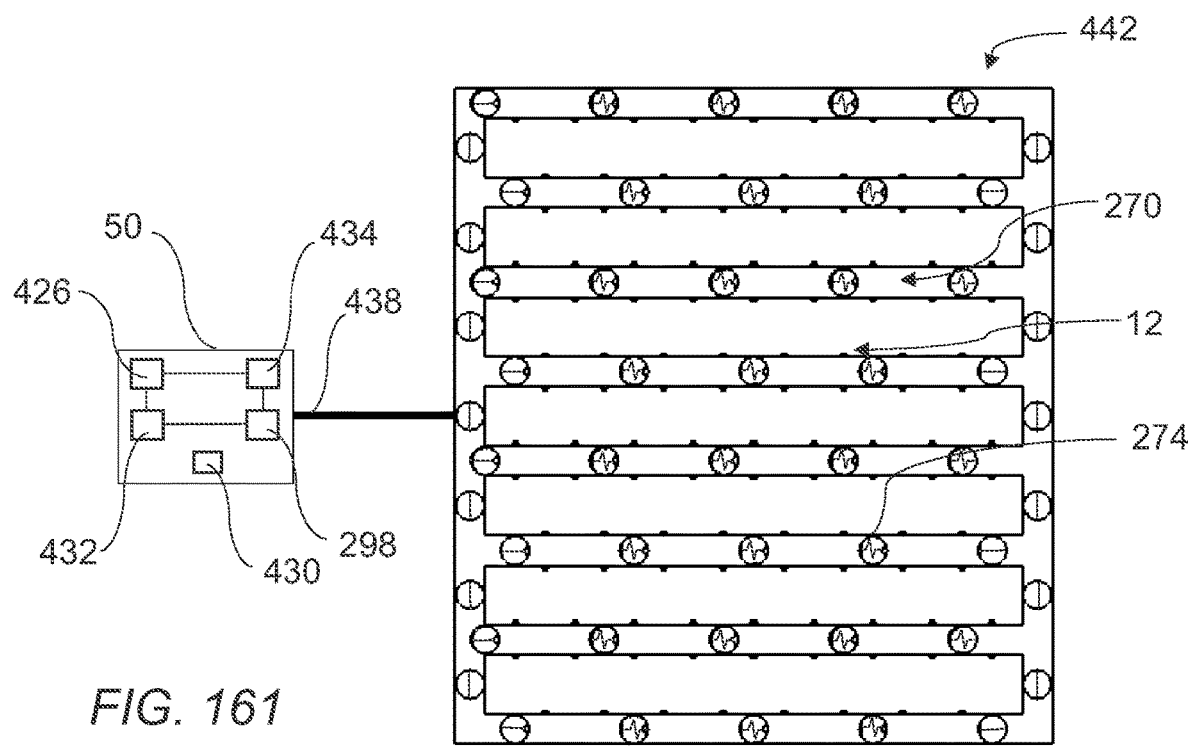

FIG. 161 depicts an embodiment of an element block array having multiple element block assemblies which are operatively coupled to a control system.

Figure 162:
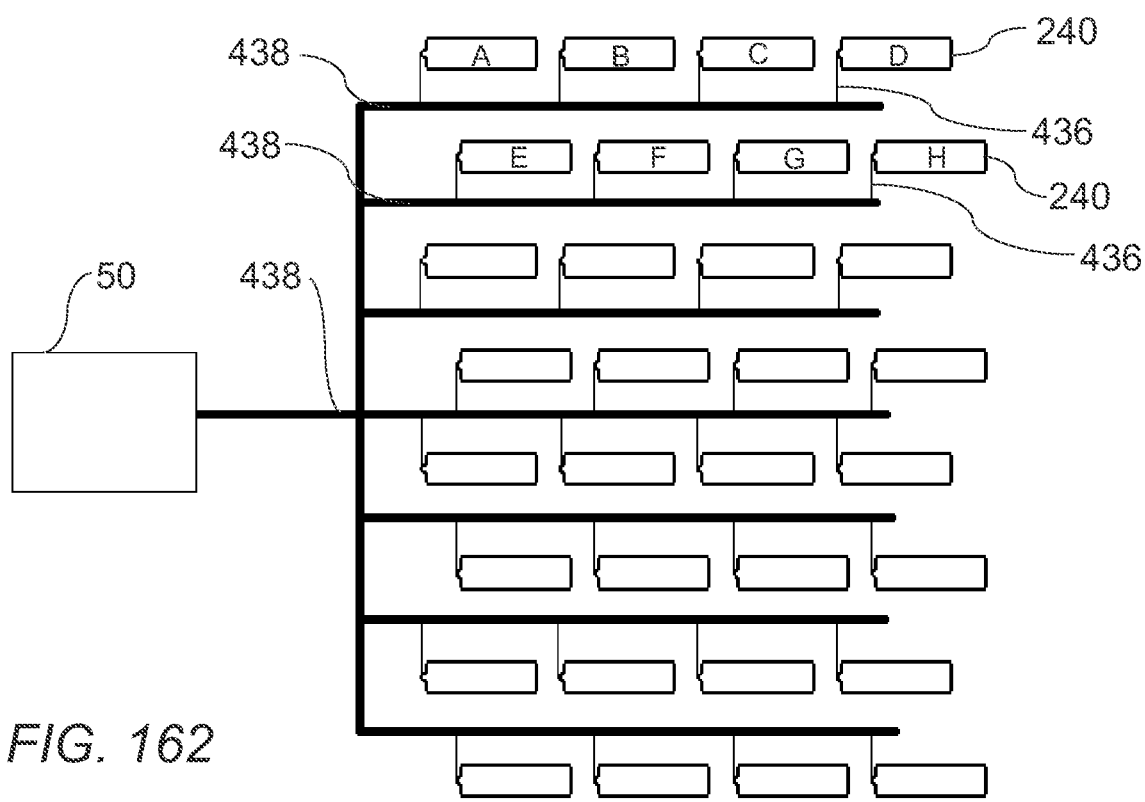

FIG. 162 is a schematic representation of FIG. 161, which depicts multiple element transition mechanisms which are serially connected to the control system.

Figure 163:
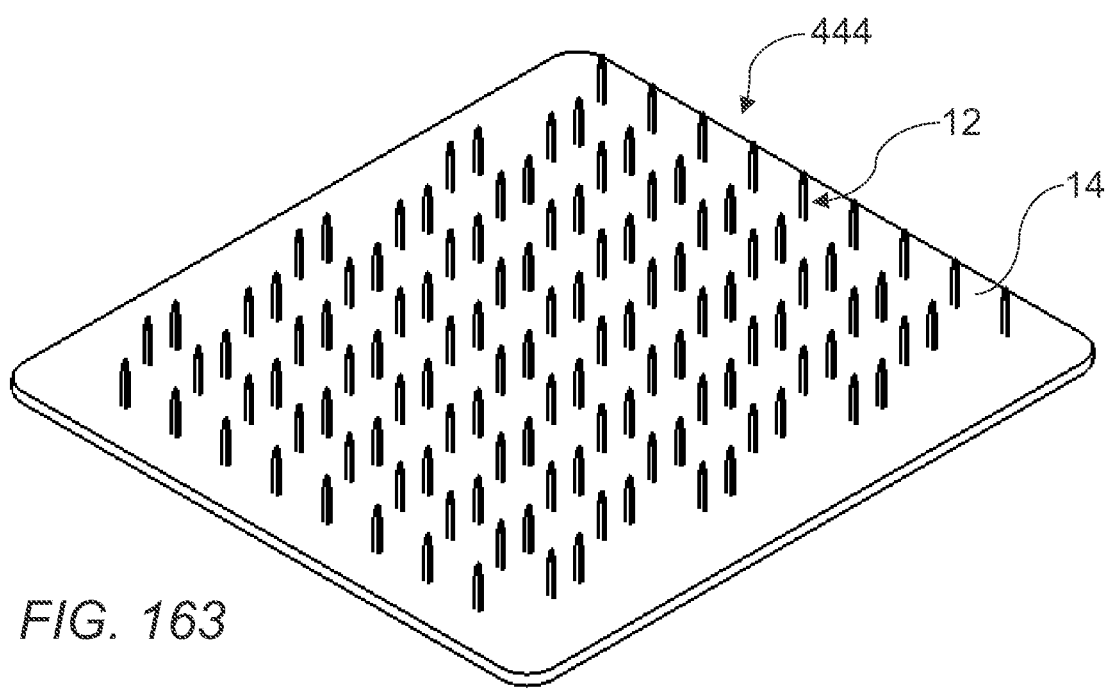
Figure 164:
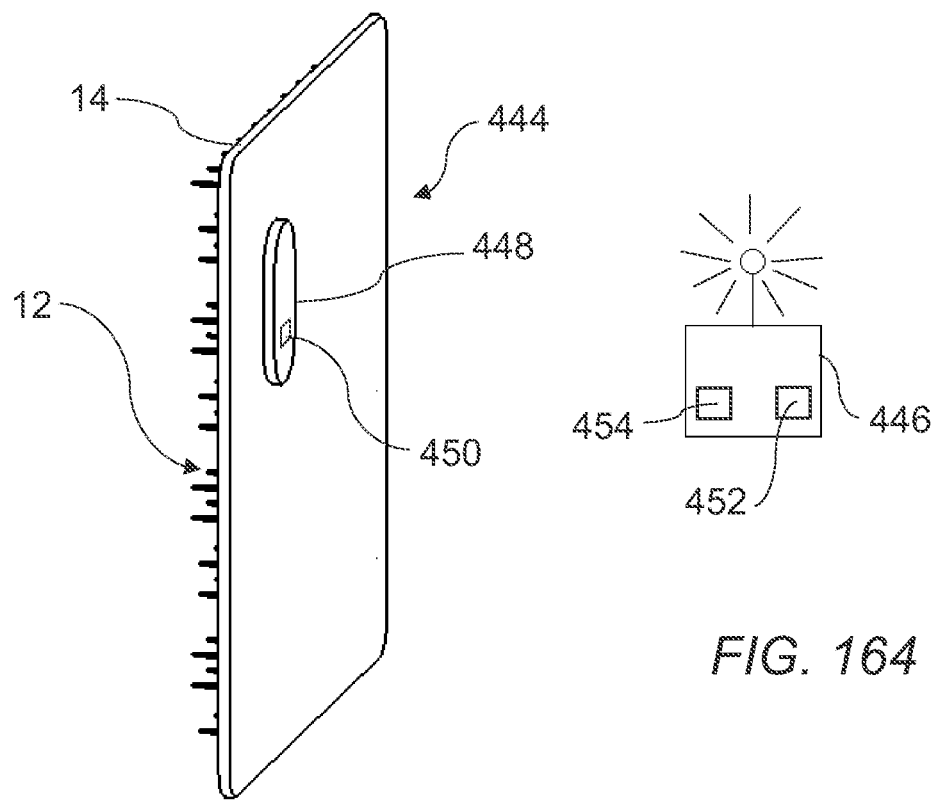

FIGS. 163 and 164 depict an embodiment of an adhesion device which incorporates an internal control system that is remotely activated by an external control system.

Figure 165:
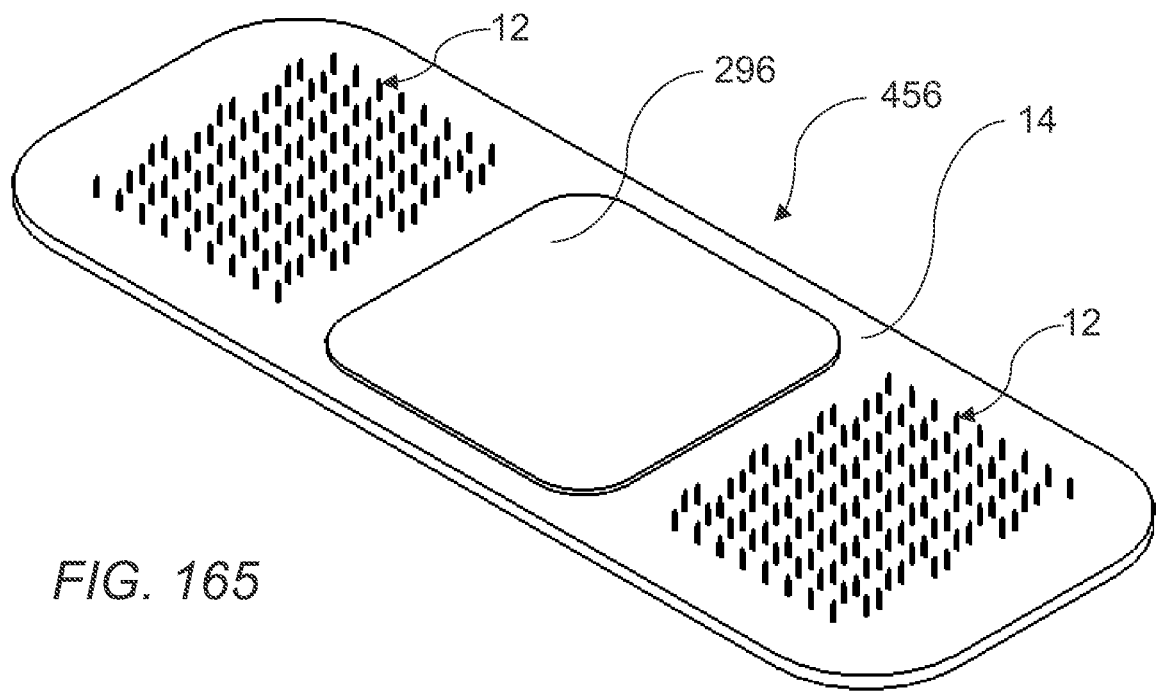
Figure 166:
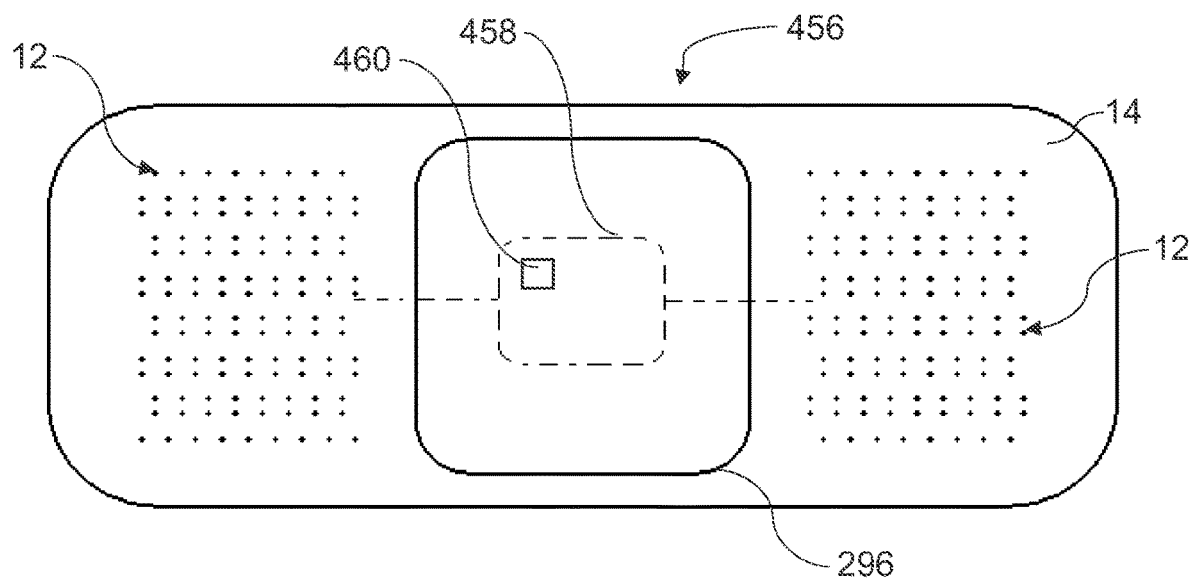

FIGS. 165 and 166 depict an embodiment of an adhesion device which is configured as a bandage, the adhesion device incorporating an integrated control system.

Figure 167:
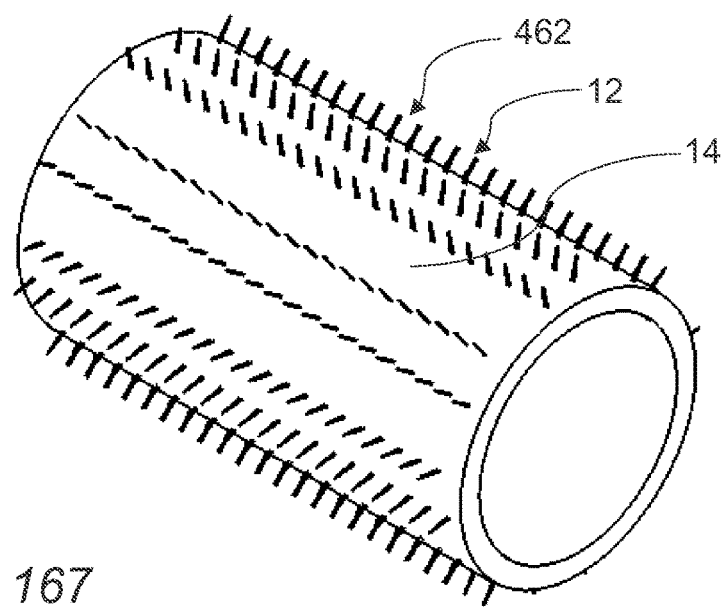

FIGS. 167 and 168 depict an embodiment of an adhesion device which is configured as a cylindrical tube, the adhesion device incorporating an integrated control system.

FIGS. 169-173 depict an embodiment of an adhesion device deployment apparatus with an adhesion device operatively coupled to a distal portion of the adhesion device deployment apparatus.

DETAILED DESCRIPTION

Some embodiments of adhesion devices may allow for user controlled adhesion of the device to the surface of a target material, and for user controlled release of the device from the surface of target material. The adhesion device may utilize a micro-mechanical adhesion system which includes a plurality of engagements elements which extend from a suitably configured element support body. A user of the adhesion device may utilize a control system in order to reversibly transition each engagement element from a deployment state wherein each element is configured to penetrate the target material, to an engagement state wherein each engagement element is configured to mechanically capture surrounding target material thereby securing the adhesion device to the surface of the target material. The user may then use the control system to reversibly transition the engagement elements to the deployment state (which is equivalent to a removal state) in order to disengage the engagement elements from the target material and remove the adhesion device from the surface of the target material. The various elements of the adhesion device may be configured such that the deployment and removal of the adhesion device may be repeated multiple times. For some embodiments of adhesion devices, the control system may be releasably secured to the adhesion device, for other embodiments the control system may be integrated into the adhesion device, and for other embodiments the control system may be incorporated into an engagement element deployment apparatus.

Some embodiments of adhesion devices may include at least one element block assembly which can be considered the fundamental building block of the adhesion device. Each element block assembly may include a plurality of engagement elements which may be operatively coupled to an element transition mechanism of the element block assembly. The element transition mechanism may in turn be operatively coupled to the control system which may be configured to reversibly transition the activation mechanism from a neutral configuration to an expanded configuration. The reversible transition from the neutral configuration to the expanded configuration may occur with an expansion of the element transition mechanism. The expansion of the element transition mechanism may occur as the result of any number of activation methods which may be applied to the element transition mechanism, including but not limited to fluid pressure, electric repulsion, mechanical augmentation, shape memory material transition, or the like.

The expansion of the element transition mechanism in turn results in eccentric tensioning of each engagement element which is operatively coupled to the element transition mechanism, thereby resulting in the mechanical flexure of and transformation to an engagement state of each respective engagement element. The materials used to form each engagement element may be configured such that each engagement element can be transitioned from the deployment state to the engagement state and back multiple times. This can be accomplished by choosing each engagement element material such that the stresses imposed on each engagement element material during the maximum flexure of the engagement element are well within the elastic limit of that material. Thus no engagement element material will experience plastic deformation during the mechanical flexure of the engagement element. The absence of plastic deformation within each engagement element material during the mechanical flexure of each engagement element allows for the elastic recovery of each engagement element from the engagement state to the deployment state.

Adhesion devices utilizing mechanical flexure of engagement elements in order to reversibly transition the engagement elements from the deployment state to the engagement state may utilized in a wide variety of fields. For some embodiments of adhesion devices utilizing mechanical flexure of engagement elements, the adhesion device may incorporate a large number of very small engagement elements with each engagement element providing a relatively small adhesion force when disposed in the engagement state. Each small adhesion force combined with the multitude of other small adhesion forces from other engagement elements similarly disposed in the engagement state creates a strong overall bond of the adhesion device to the surface of the target material.

In the medical industry adhesion devices utilizing mechanical flexure of engagement elements may be used for tissue modification, tissue joining, device attachment, graft attachment or the like for applications in any of the following: general surgery, robotic surgery, aneurism treatment, battlefield dressings, plastic surgery, gynecological surgery, cardiac surgery, dental surgery, implant attachment, or prosthetic attachment. Adhesion devices which utilize mechanical flexure of engagement elements may also be have similar applications in the veterinary fields, and may be used for animal tagging or the like. Adhesion devices utilizing mechanical flexure of engagement elements may also be utilized in a wide variety of industrial applications which require the temporary or permanent joining of components to each other, or the temporary joining of components to fixtures for manufacturing.

Adhesion devices utilizing mechanical flexure of engagement elements in order to reversibly transition the engagement elements from the deployment state to the engagement state have several advantages over some previous embodiments of adhesion devices which are configured with shape memory engagement elements. Some previous embodiments of adhesion devices which are configured with shape memory engagement elements rely on shape memory transitions in order to transition the engagement elements from the deployment state to the engagement state. The shape memory engagement elements typically can transition from the deployment state to the engagement state one time. Upon deployment into a target material, the shape memory engagement elements can be transformed from the deployment state to the engagement state with the application of an external stimulus which activates the shape memory material.

The external stimulus may include temperature change of the shape memory elements, a change in the Ph level of the material which surrounds the shape memory engagement elements, the application of UV light to the shape memory engagement elements, or the like. The application of the appropriate external stimulus may transition the shape memory engagement elements from the deployment state to the engagement state, and a subsequent external stimulus can allow the shape memory engagement elements to be removed. However for most previous engagement element embodiments a subsequent suitably configured shape memory transition will not transform the engagement elements from the deployment state to the engagement state a second time in order to allow for a second application of the adhesion device into the target material. In contrast adhesion devices utilizing mechanical flexure of engagement elements can be repeatably transitioned from the deployment state to the engagement state thereby allowing for removal of the adhesion device and redeployment of the adhesion device multiple times.

Previous embodiments of adhesion devices configured with shape memory engagement elements may also rely on the physical dimensions of each shape memory engagement element for the adhesion strength of the adhesion device. That is to say that when the shape memory engagement elements are deployed into a target material and transitioned from the deployment state to the engagement state, the adhesion strength of the adhesion device is dependent upon the ability of each shape memory engagement element to maintain its engagement state, the engagement state being configured to mechanically capture adjacent target material. The ability of each shape memory engagement element to maintain its engagement state is directly proportional to its size (more specifically proportional to the moment of inertia in the direction of shape change which occurs upon transition to the engagement state). Since the shape memory engagement elements are configured to be small in most cases, the ability each shape memory engagement element to maintain its engagement state may be limited when compared to adhesion devices which utilize mechanical flexure of engagement elements.

Adhesion devices utilizing mechanical flexure of engagement elements may rely on the expansion of each respective element transition mechanism to transition each engagement element from the deployment state to the engagement state. The element transition mechanism may be disposed in the element support body and can therefore be configured such that it is substantially larger than the respective engagement elements which are operatively coupled to it. A larger element transition mechanism allows for greater tension to be applied to respective engagement elements thereby resulting in a larger adhesion strength for each respective engagement element. In this case the adhesion strength of each engagement element is not proportional to the size of each engagement element (as it is for shape memory engagement elements), but proportional to the size of the respective element transition mechanism. For example if the element transition mechanism relies on the application of a voltage (capacitance) in order to expand the element transition mechanism, a larger element transition mechanism would result in a larger capacitance force which would translate to larger tension applied to each respective engagement element by the element transition mechanism.

As has been discussed, some embodiments of the element transition mechanism may be reversibly transitioned from the neutral configuration to the expanded configuration by the application of voltages or pressures to the element transition mechanism. In these cases the tension applied to each engagement element by a respective element transition mechanism is proportional to the magnitude of the applied voltage or the applied fluid pressure. This allows for a user of the adhesion device to adjust the adhesion strength of some engagement elements by adjusting the activation method which is applied to the respective element transition mechanisms. For example, an element transition mechanism may expand from the neutral configuration to an expanded configuration when repulsive voltages are applied to it. This would allow a user of the adhesion device to adjust the adhesion strength of respective engagement elements by adjusting the voltage applied to the respective element transition mechanism, with smaller applied repulsive voltages corresponding to a smaller tension applied to each respective engagement element and larger applied voltages corresponding to a larger tension applied to each respective engagement element. In this manner the adhesion strength of the adhesion device may be adjusted by the user.

For some element transition mechanisms, a force feedback system could be used in order to determine if some or all of the engagement elements have transitioned from the deployment state to the engagement state within the target material. As an example, an adhesion device which incorporates element transition mechanisms which are activated by the application of fluid pressure could have a control system which incorporates a force feedback system. The force feedback system could be configured to monitor the fluid pressure which is applied to each element transition mechanism as a function of time. Engagement elements which are deployed into target material would encounter resistance from the target material upon transition from the deployment state to the engagement state, and would thus require higher fluid pressure in order to complete the transition. Thus by analyzing fluid pressure during application of the adhesion device, the control system could be used to indicate the successful (or unsuccessful) transition of the engagement elements from the deployment state to the engagement state within the target material.

Adhesion devices utilizing mechanical flexure of engagement elements may allow for the reversible transition of the engagement elements from the deployment state to the engagement state instantly by a user of the adhesion device. This may not be the case for some previous embodiments of adhesion devices which utilize shape memory engagement elements. Shape memory engagement elements can potentially be prematurely activated before they have been deployed into the target material. As an example, consider an adhesion device configured with shape memory engagement elements which are activated by a temperature transition of the surrounding material. If the adhesion device is to be deployed in an all fluid environment such as an artery filled with blood, the shape memory engagement elements may be transitioned from the deployment state to the engagement state by the temperature of the blood before the shape memory engagement elements have been deployed into the artery. This is not the case for an adhesion device utilizing mechanical flexure of the engagement elements, wherein the user may utilize the control system in order to actively control when to transition the engagement elements from the deployment state to the engagement state.

Additionally, adhesion devices which utilize mechanical flexure of engagement elements may allow for the selective activation of the engagement elements by the control system. Multiple element transition mechanism may be operatively coupled to the control system individually thereby allowing a user to selectively activate desired element transition mechanisms. This configuration allows for multiple engagement elements to be disposed in the engagement state while other engagement elements are disposed in the deployment state. This differs from shape memory engagement elements which may be simultaneously transitioned from the deployment state to the transition state by the application of an appropriate external stimulus. As an example the application of heat to an adhesion device with thermally activated shape memory engagement elements may transition all of the shape memory engagement elements from the deployment state to the engagement state, there may be no selectivity by a user of the device with regard to which shape memory engagement elements are transitioned.

An embodiment of an adhesion device 10 which is configured as a rectangular pad and which utilizes mechanical flexure of a plurality engagement elements 12 is shown in FIGS. 1-5. The adhesion device 10 may include an element support body 14 which may be formed from a resilient flexible material and which incorporates an engagement surface 16. The adhesion device 10 may include a plurality of element block assemblies 18 (see FIG. 19), with each element block assembly 18 having an element activation sheet 20, an element deployment sheet 22, a plurality of engagement elements 12, and an element transition mechanism 24. Each element activation sheet 20 may include an elongated element activation section 26 which monolithically extends from the element activation sheet 20, and each element activation sheet may 20 have an activation sheet upper surface 28. Each element deployment sheet 22 may include an elongated element deployment section 30 which extends monolithically from the element deployment sheet 22, and each element deployment sheet 22 may have a deployment sheet lower surface 32. The element activation section 26 may be fused to the element deployment section 30 within an element tip segment 34 of each engagement element 12.

Figure 4:
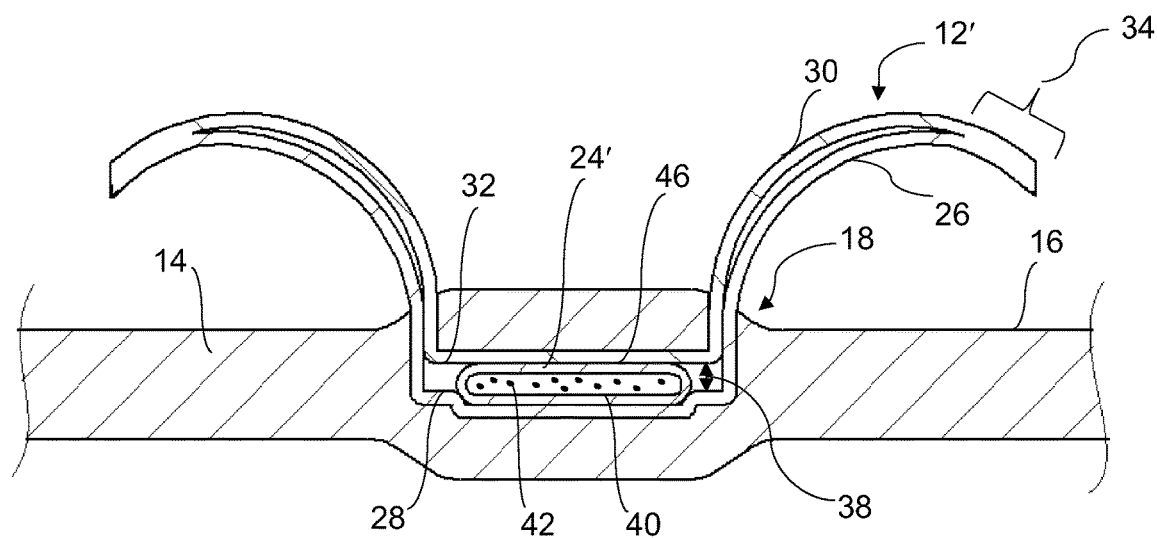
FIG. 4 is a sectional view of the adhesion device of FIG. 3 depicting the element block assembly and the respective engagement elements in the engagement state.
Figure 5:
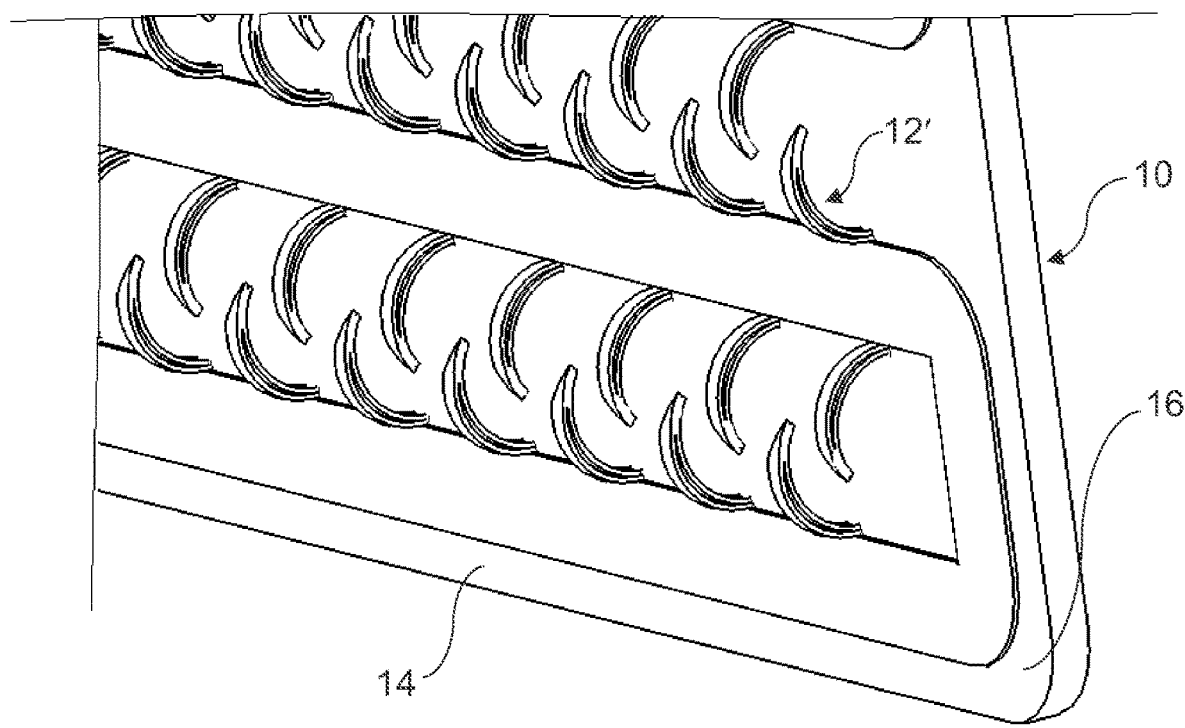
FIG. 5 is an enlarged view of FIG. 3 depicting the engagement elements in the engagement state.

Each element transition mechanism 24 may be disposed between a respective element activation sheet 20 and a respective element deployment sheet 22. For some adhesion device embodiments, each element transition mechanism 24 may be disposed within a transition mechanism filister 36 which may be disposed within a respective element activation sheet 20 or a respective element deployment sheet 22. Each element transition mechanism 24 may be operatively coupled to respective engagement elements 12. Each element transition mechanism 24 may be configured to reversibly transition between a neutral configuration 24 and an expanded configuration 24', with a transition gap 38 existing between the activation sheet upper surface 28 and the deployment sheet lower surface 32 when the element transition mechanism is disposed in the expanded configuration 24' (as shown in FIG. 4). For the adhesion device embodiment 10 shown, the element transition mechanism 24 is configured as a single expandable balloon apparatus, however the element transition mechanism 24 could be configured as any of the element transition mechanisms which are discussed herein.

Figure 2:
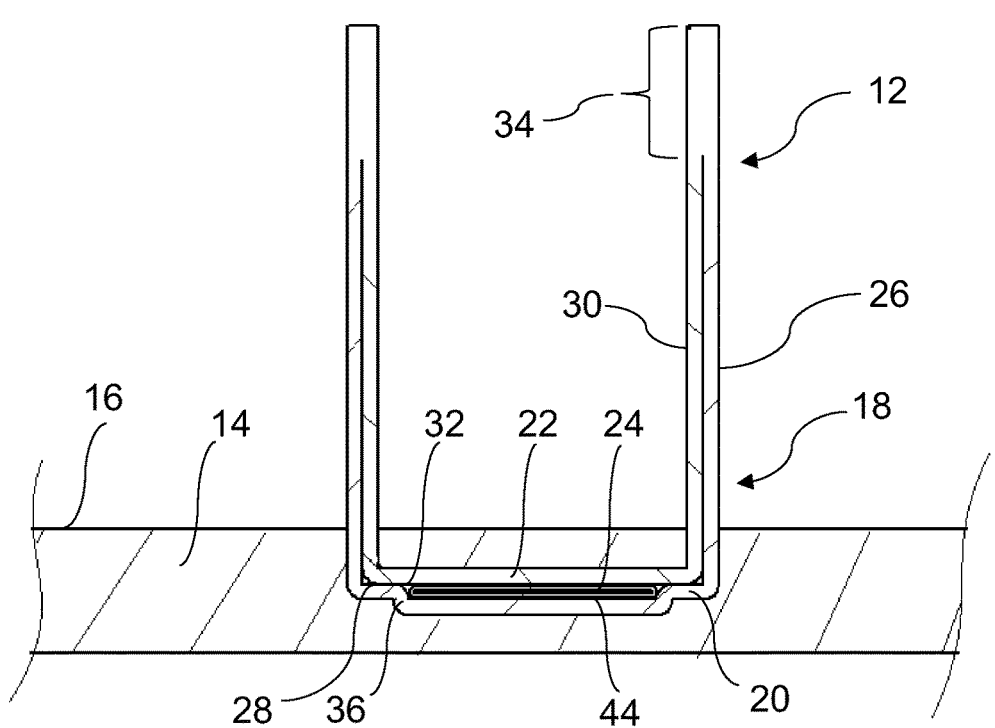
FIG. 2 is a sectional view of the adhesion device of FIG. 1 depicting an element block assembly and respective engagement elements which are disposed in the deployment state.
Figure 3:
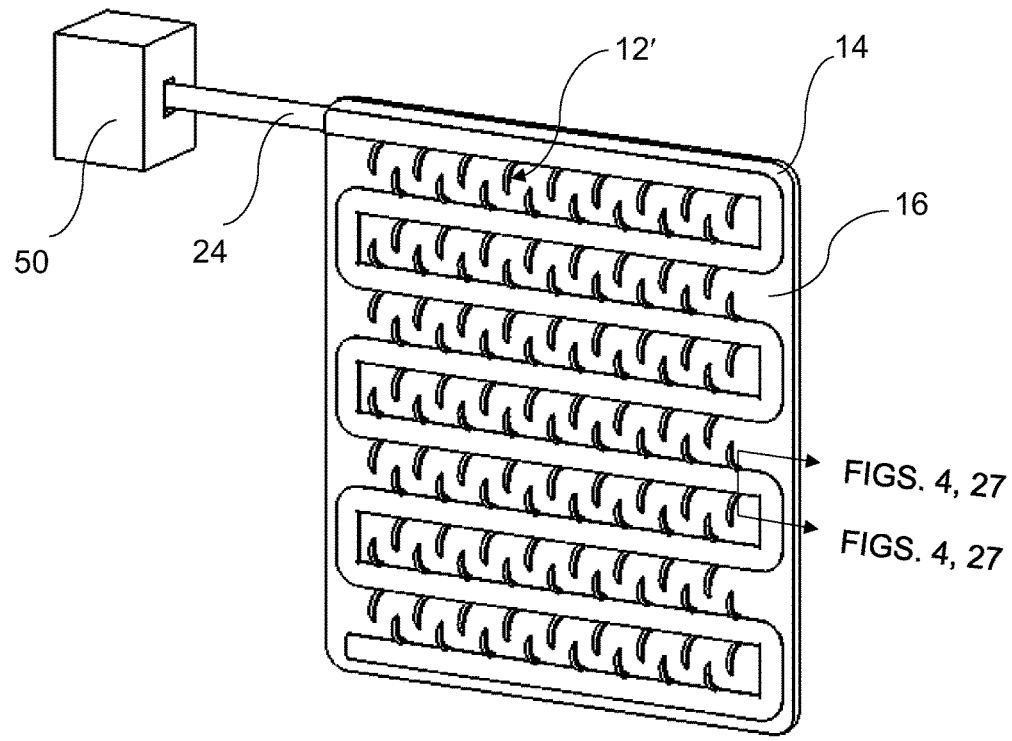
FIG. 3 is an isometric view of the adhesion device of FIG. 1 depicting the engagement elements in an engagement state.

The element transition mechanism 24 (which is configured as a balloon apparatus) may be configured with a balloon inner lumen 40 which is capable of containing a pressurized activation fluid 42 such as air, saline, or the like. The element transition mechanism 24 may be configured to reversibly transition between a neutral configuration 24 wherein low pressure activation fluid 42 within the balloon inner lumen 40 results in a neutral balloon profile 44 (as shown in FIG. 2), and an expanded configuration 24' wherein high pressure activation fluid 42 within the balloon inner lumen 40 results in an expanded balloon profile 46 (as shown in FIG. 4). The difference in height between the neutral balloon profile 44 and the expanded balloon profile 46 being substantially equal to the transition gap 38. The balloon apparatus may be fabricated from any suitable expandable elastic material such as urethane, silicone, or the like.

When the element transition mechanism is disposed in the neutral configuration 24, the activation sheet upper surface 28 may be substantially adjacent to the deployment sheet lower surface 32. When the element transition mechanism is disposed in the expanded configuration 24', the activation sheet upper surface 28 and the deployment sheet lower surface 32 may be separated by the transition gap 38. The adhesion device 10 may include multiple element transition mechanisms 24 which are operatively coupled to multiple respective engagement elements 12, however the adhesion device 10 which is depicted in FIGS. 1-5 incorporates a single element transition mechanism 24 which is coupled to each engagement element 12 of each respective element block assembly 18.

When the element transition mechanism is disposed in the neutral configuration 24, the element support body 14 is configured to constrain each engagement element in a deployment state 12 which is suitable for insertion into (or the removal from) a target material 48 (see FIG. 23) wherein each engagement element 12 is disposed in a substantially straightened configuration which is substantially perpendicular to the engagement surface 16. When the element transition mechanism is disposed in the expanded configuration 24', the element support body 14 is configured to constrain each engagement element in an engagement state 12' wherein each engagement element 12' is eccentrically tensioned as the result of the transition gap 38 into a reactive flexure (curvature) which is configured to mechanically capture surrounding target material 48.

Figure 1:
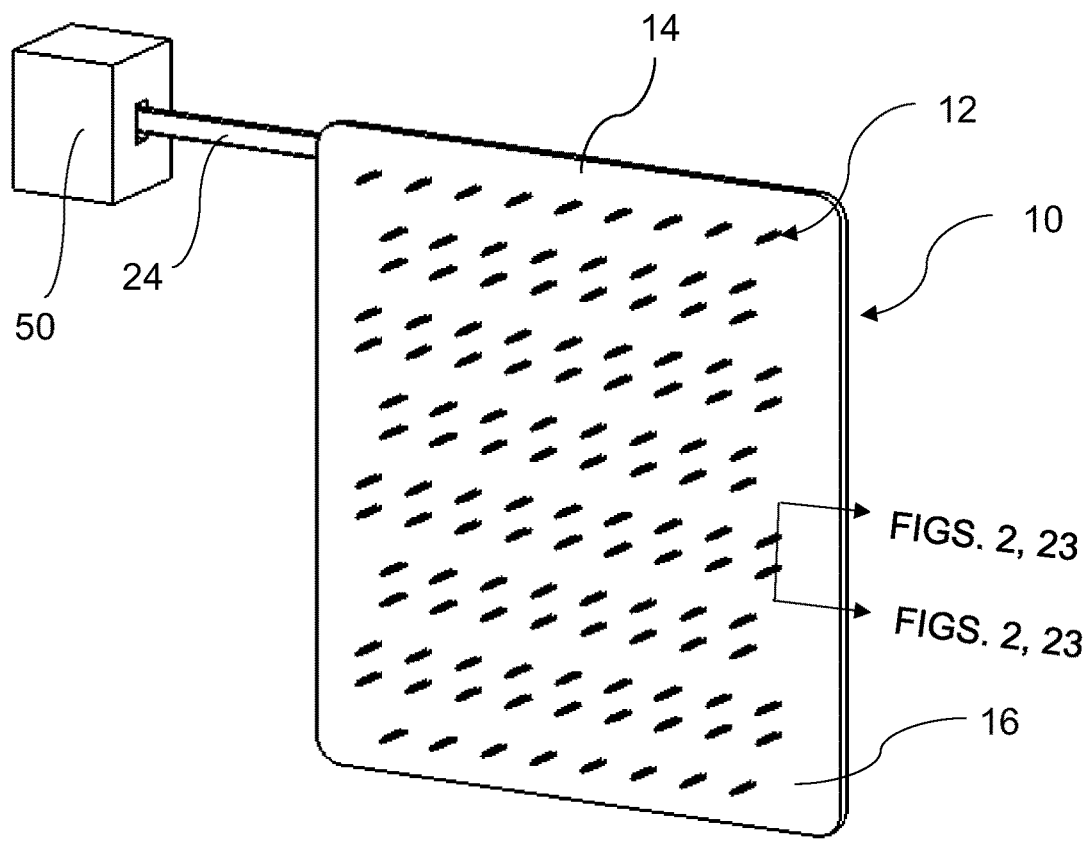
FIG. 1 is an isometric view of an adhesion device which includes a control system and a plurality of engagement elements which are disposed in a deployment state.

A control system 50 may be operatively coupled to each element transition mechanism 24. The control system 50 may be configured to allow a user of the adhesion device 10 to reversibly transition each element transition mechanism between the neutral configuration 24 and the expanded configuration 24' thereby transitioning respective engagement elements from the deployment state 12 to the engagement state 12'. The adhesion device 10 which is depicted in FIG. 1 is configured as a pad, however a similarly configured device could be configured as a bandage as will be discussed below. The adhesion device 10 which is depicted in FIG. 1 is configured as a rectangular pad, however it could be configured as a pad with any suitable shape such as a circular pad, a square pad, an elliptical pad, or the like.

The adhesion device 10 may be fabricated by selectively fusing and then selectively cutting multiple adjacent layers of materials, and then constraining selected portions of the resulting assembly with an overmolding process (or any other suitable molding process). A discussion of the manufacturing method is useful with regard to illustrating the operative couplings between and constraints applied to the various elements of the adhesion device 10. FIGS. 6-22 depict a method for manufacturing an adhesion device 10. The manufacturing methods (or suitable variations on the manufacturing methods), materials, fixturing, dimensions, and configurations discussed with regard to FIGS. 6-22 may be used to fabricate all of the embodiments of adhesion devices which are discussed herein.

Figure 6:
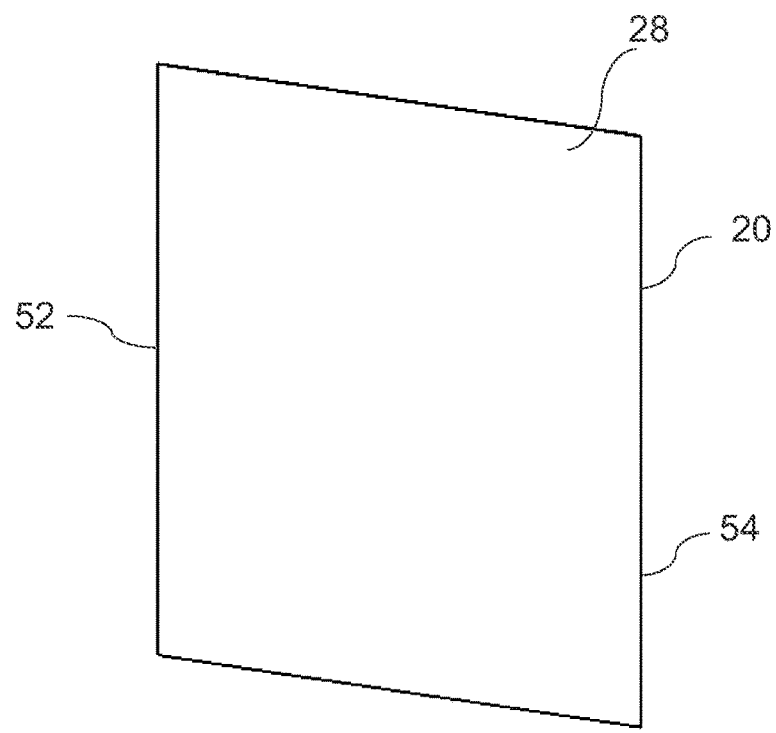
FIG. 6 is an isometric view of an embodiment of an element activation sheet.
Figure 7:
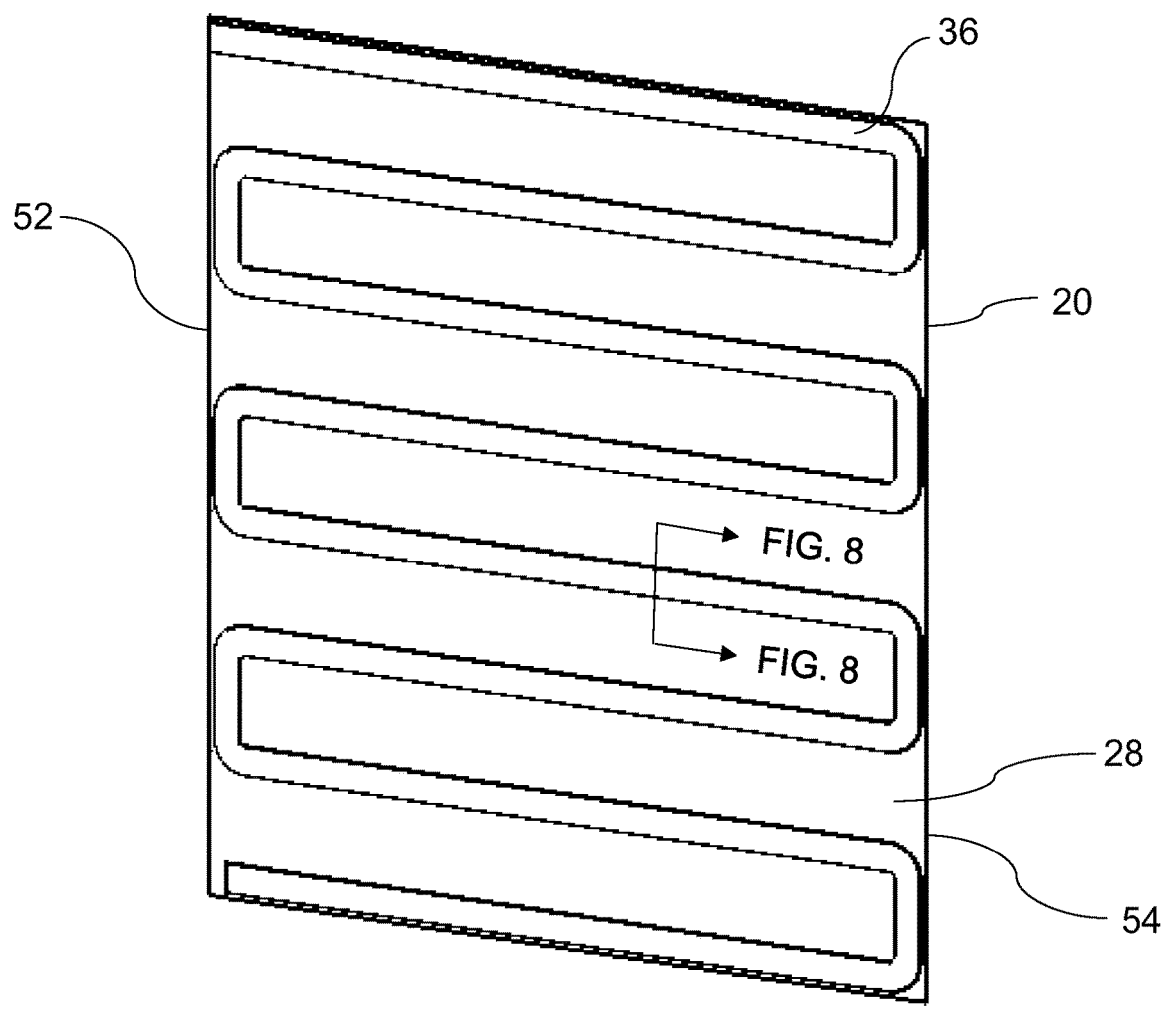
FIG. 7 depicts the element activation sheet of FIG. 6 with the addition of a transition mechanism fillister.
Figure 8:
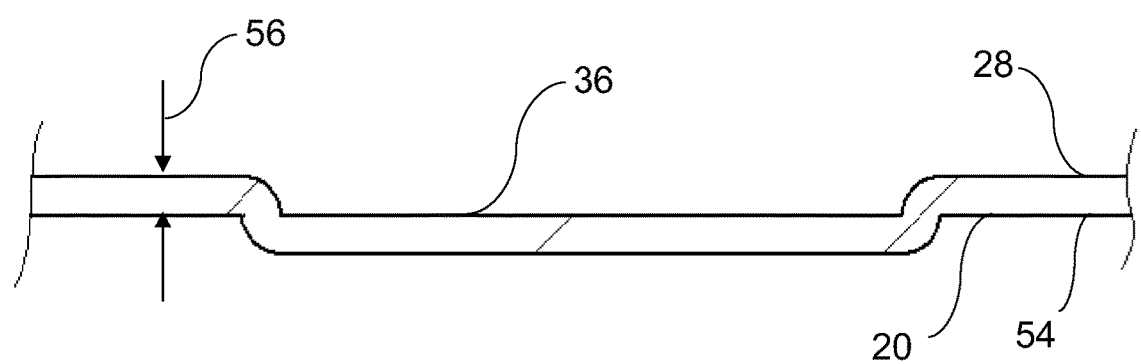
FIG. 8 is a sectional view of the element activation sheet of FIG. 7 depicting the transition mechanism fillister.

FIG. 6 depicts an element activation sheet 20, the element activation sheet 20 may be fabricated from any suitable resilient material such as a metal, a polymer or a composite. For some embodiments of the element activation sheet 20, the material may be configured to be highly flexible and resilient. Some embodiments of the element activation sheet 20 may be configured with a substantially rectangular activation sheet profile 52. The element activation sheet 20 may also include the activation sheet upper surface 28 and an activation sheet lower surface 54. FIGS. 7 and 8 depicts the formation of a transition mechanism filister 36 in the element activation sheet 20. For some adhesion device embodiments the transition mechanism filister 36 may be configured as a continuous groove which is formed into the activation sheet upper surface 28, with the purpose of the transition mechanism filister 36 being to maintain the position of a respective element transition mechanism 24 with respect to the activation sheet profile 52. For some embodiments, the thickness 56 of each element activation sheet 20 (and all respective element activation sections 26) may be from about 0.25 μm to about 0.25 mm, more specifically from about 0.0025 mm to about 0.025 mm.

Figure 9:
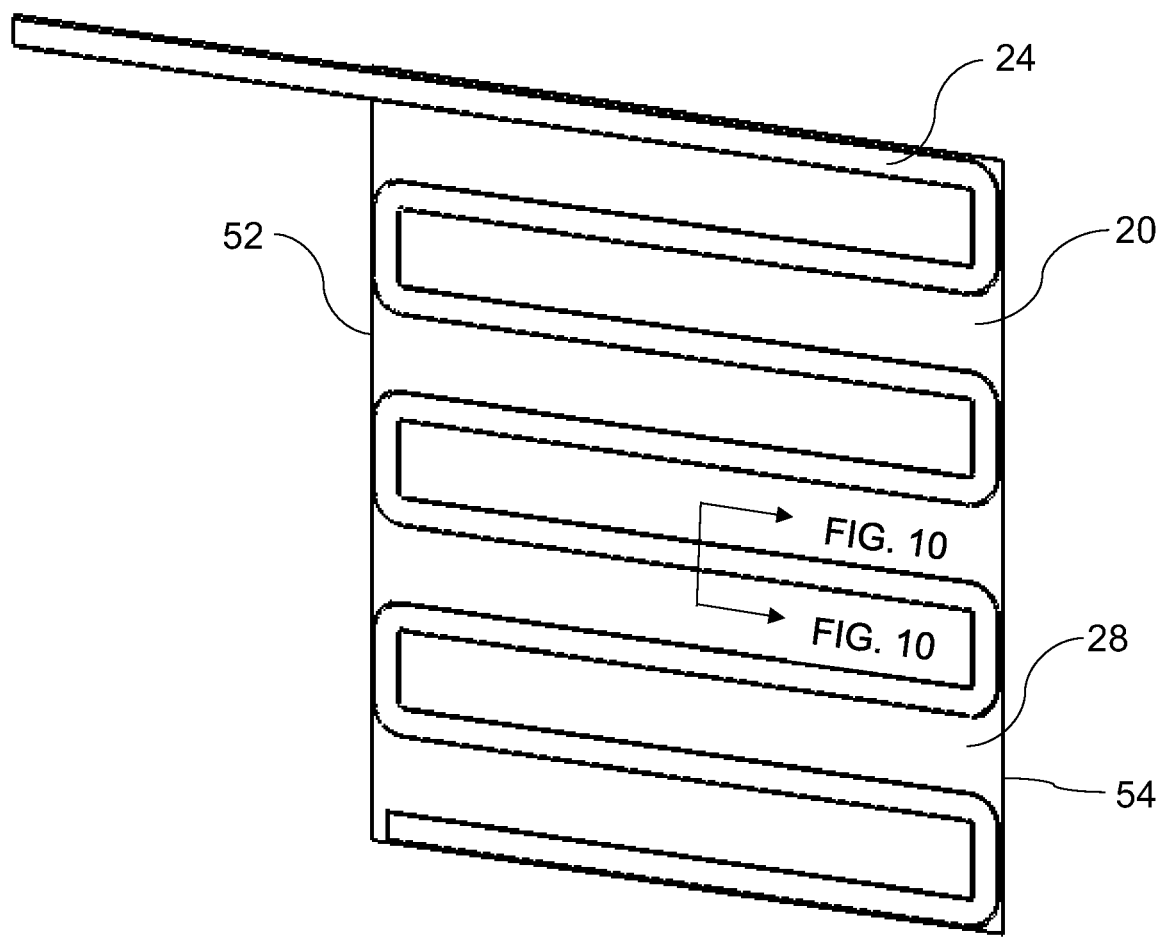
FIG. 9 depicts the element activation sheet of FIG. 7 with an element transition mechanism inserted into the transition mechanism fillister.
Figure 10:
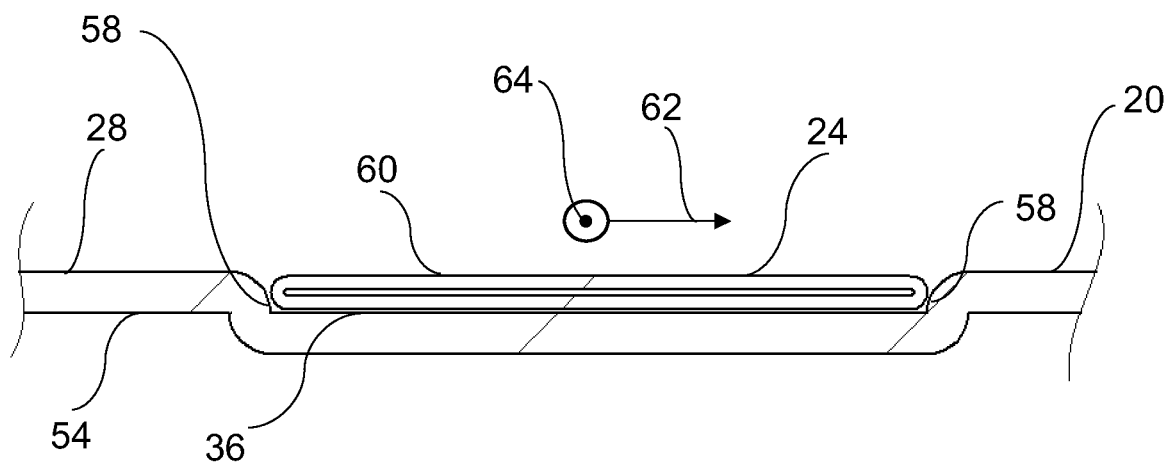
FIG. 10 is a sectional view of the embodiment of FIG. 9 depicting element transition mechanism which is disposed within the transition mechanism fillister.

FIGS. 9 and 10 depict the element transition mechanism 24 inserted into the transition mechanism filister 36 which is formed into the activation sheet upper surface 28. The transition mechanism filister 36 provides a space (between the element activation sheet and the element deployment sheet) for the element transition mechanism 24, and also acts to mechanically restrict the motion of the element transition mechanism 24 with respect to the activation sheet profile 52. The transition mechanism filister 36 may be configured such that lateral walls 58 of the transition mechanism filister 36 may be substantially adjacent an outer surface 60 of the element transition mechanism 24 thereby restricting motion of the element transition mechanism 24 along a first axis 62 (FIG. 10) and a second axis 64 (FIG. 10 into and out of the page). For other adhesion device embodiments which incorporate multiple element transition mechanisms 24, the transition mechanism filister 36 may be configured as multiple individual grooves which are formed into the activation sheet upper surface 28 with each transition mechanism filister 36 being configured to maintain the position of respective element transition mechanisms 24. For some embodiments, the element transition mechanism 24 may be bonded to the transition mechanism filister 36 with a suitable adhesive as shown in FIG. 10. For other embodiments of the adhesion device (not shown) the element activation sheet 20 may not incorporate a transition mechanism filister, the element transition mechanism 24 may be bonded directly to the activation sheet upper surface 28.

Figure 11:
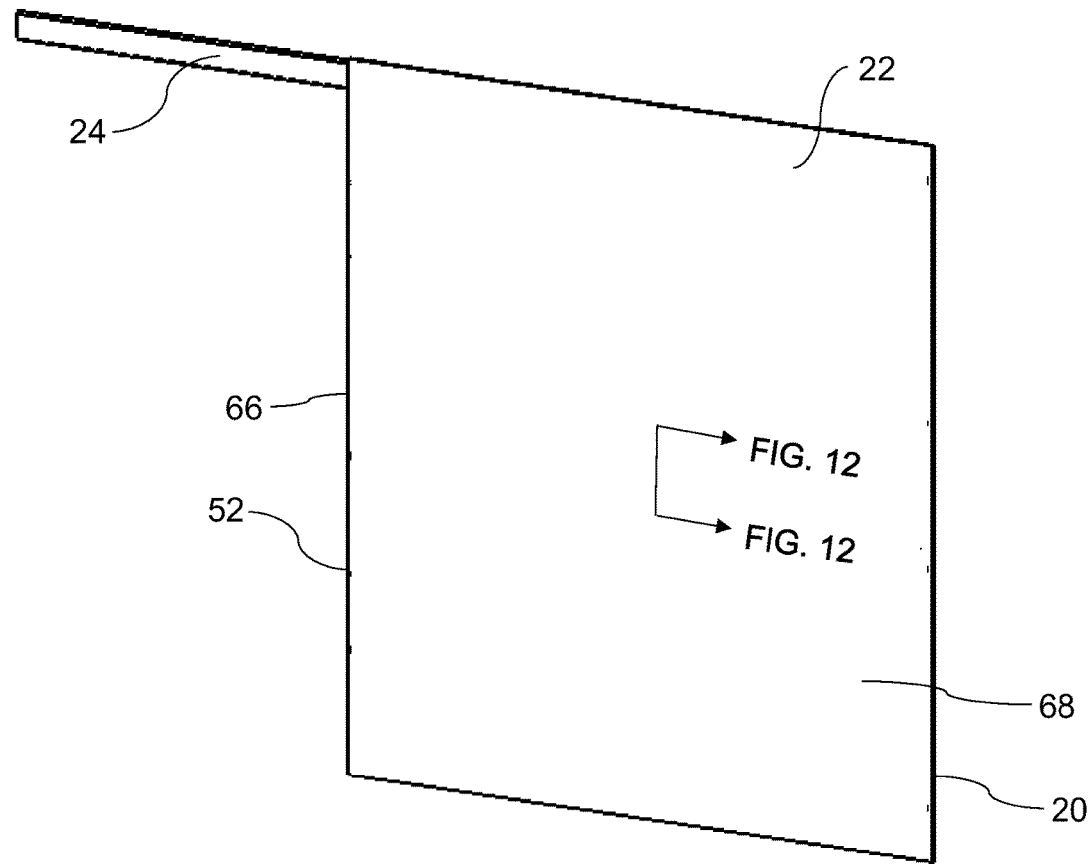
FIG. 11 depicts the embodiment of FIG. 9 with the addition of an element deployment sheet.
Figure 12:
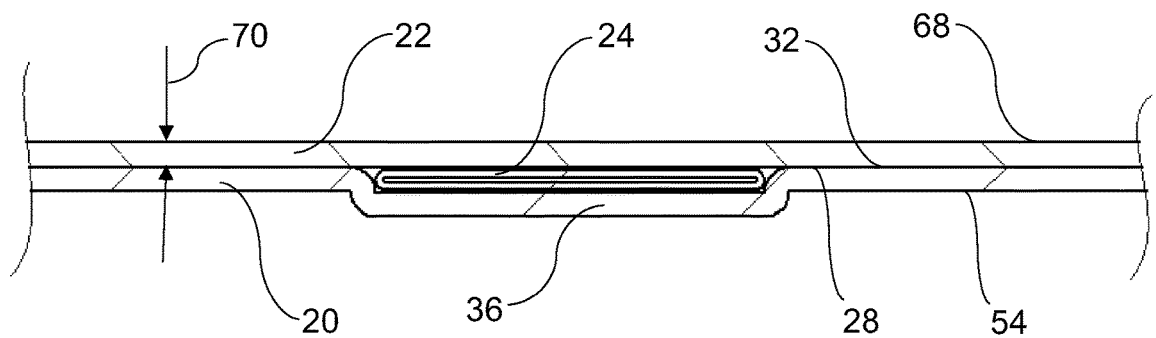
FIG. 12 is a sectional view of the embodiment of FIG. 11 depicting the element activation sheet, the transition mechanism fillister disposed within the activation sheet, the element transition mechanism disposed within the transition mechanism fillister, and the element deployment sheet.

An element deployment sheet 22 may be temporarily secured to the element activation sheet 20 such that the activation sheet upper surface 28 is substantially adjacent to the deployment sheet lower surface 32 as shown in FIGS. 11 and 12. Some embodiments of the element deployment sheet 22 may be configured with a substantially rectangular deployment sheet profile 66. In some cases the activation sheet profile 52 and the deployment sheet profile 66 may be substantially aligned as shown in FIG. 11. The element deployment sheet 22 may include the deployment sheet lower surface 32 and a deployment sheet upper surface 68.

The element deployment sheet 22 may be fabricated from any suitable resilient material. For some embodiments the material which forms each element deployment sheet 22 and each respective element deployment section 30 may be an elastic resilient material such as any suitable metal, polymer or composite. The thickness 70 of each element deployment sheet 22 (and all respective element deployment sections 30) may be from about 0.25 μm to about 0.25 mm, more specifically from about 0.0025 mm to about 0.025 mm. For some embodiments of the adhesion device, the thickness 56 of the element activation sheet 20 may be substantially equal to the thickness 70 of the element deployment sheet 22. For some other adhesion device embodiments, the thickness 56 of the element activation sheet 20 may be substantially different than the thickness 70 of the element deployment sheet 22. For example, the thickness 70 of the element deployment sheet 22 may be twice the thickness 56 of the element activation sheet 20.

For some adhesion device embodiments (not shown) each element deployment sheet 22 may include at least one transition mechanism filister 36 which is disposed on the deployment sheet lower surface 32. Such embodiments may have corresponding transition mechanism filisters 36 which are disposed on the activation sheet upper surface 28 of the element activation sheet 20. In some cases, the transition mechanism filisters 36 disposed on the element deployment sheet 22 may be substantially aligned with the transition mechanism filisters 36 on the element activation sheet 20. Thus transition mechanism filisters 36 may be suitably disposed only on the element activation sheet 20, only on the element deployment sheet 22, or both on the element activation sheet 20 and the element deployment sheet 22. The transition mechanism filisters 36 may be formed by a variety of methods, depending on the material of the respective sheet. For example metallic sheets may have transition mechanism filisters 36 which are formed by stamping. Polymer sheets may have transition mechanism filisters 36 which are molded into the sheets or which are thermally formed into the sheets.

Figure 13:
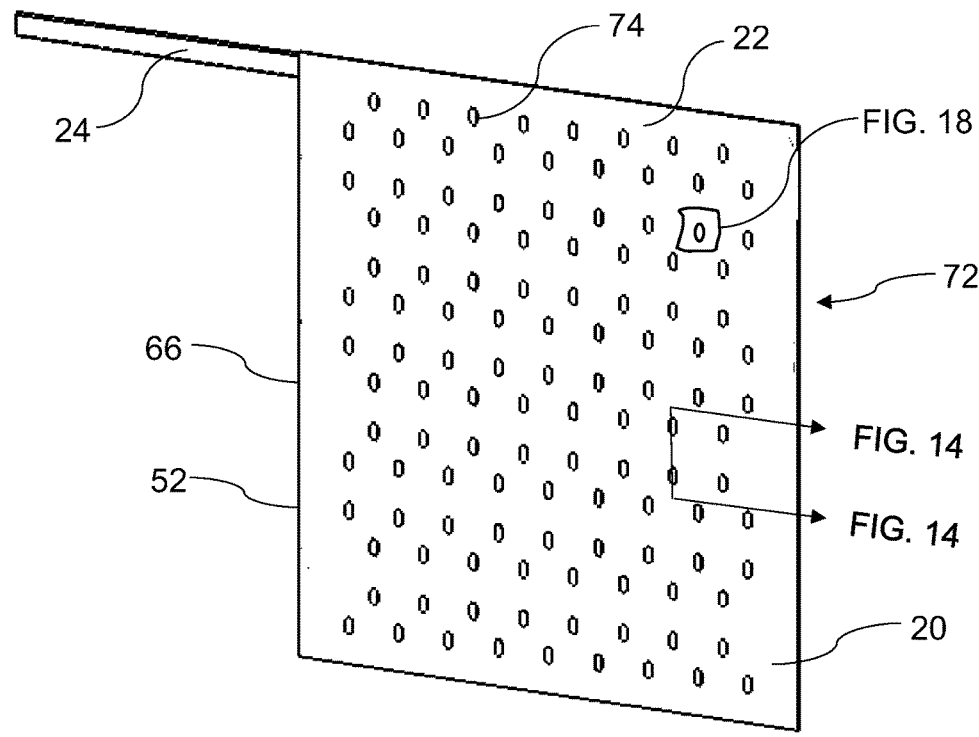
FIG. 13 is an isometric view of an embodiment of a fused sheet assembly which incorporates a plurality of fused sections, the fused sheet assembly being the embodiment of FIG. 11 with the addition of multiple fused sections.
Figure 14:
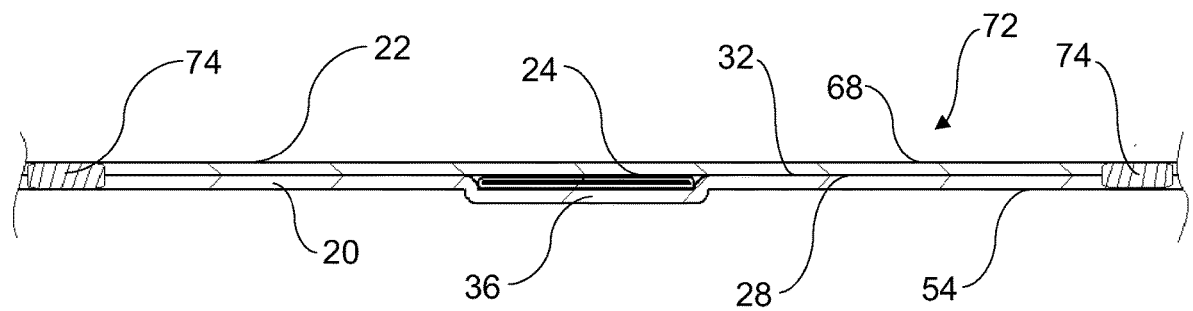
FIG. 14 is a section view of the fused sheet assembly of FIG. 13 depicting the element activation sheet, the transition mechanism fillister disposed within the activation sheet, the element transition mechanism disposed within the transition mechanism fillister, the element deployment sheet, and multiple fused sections.

The element activation sheet 20 may be selectively fused to the element deployment sheet 22. That is to say that portions of the element activation sheet 20 may be fused to respective portions of the element deployment sheet 22, with sections of the element activation sheet 20 remaining adjacent to and unconnected to respective portions of the element activation sheet 22. FIG. 13 depicts a fused sheet assembly 72, which includes a pattern of fused sections 74 which are disposed between the element activation sheet 20 and the element deployment sheet 22. Each fused section 74 may transversely span from the deployment sheet upper surface 68 to the activation sheet lower surface 54 as shown in FIG. 14.

Each fused section 74 may be disposed between adjacent transition mechanism filisters 36 and/or adjacent element transition mechanisms 24, with the location of each fused section 74 corresponding to the location of an element tip segment 34 of a respective engagement element 12. The pattern of fused sections 74 between the element activation sheet 20 and the element deployment sheet 22 may be created through a laser welding process, a resistance welding process, a plasma welding process, an ultrasonic welding process, or the like. For some embodiments of the adhesion device 10, the element activation sheet 20 may be selectively bonded to the element deployment sheet 22 using a suitable adhesive. In this case a plurality of adhesive sections similar to the fused section 74 pattern depicted if FIG. 13 could be applied to the element activation sheet 20. Then the element deployment sheet 22 could be secured to the element activation sheet 20 by the plurality of adhesive sections.

For some embodiments of the adhesion device 10, the element deployment sheet 22 material may be vapor deposited onto the element activation sheet 20 after a suitable sacrificial layer of material has been deposited onto the element activation sheet 20. This process would consist of vapor depositing a suitably configured sacrificial layer of material onto the element activation sheet 20. Sacrificial material would be deposited over the entire activation sheet upper surface 28 except for the location of each element tip segment 34 (which corresponds to the location of the fused sections 74 in FIG. 13) which would not be deposited with sacrificial material. The element deployment sheet 22 material could then be vapor deposited onto the element activation sheet 20 over the layer of sacrificial material. The element deployment sheet 20 material would be deposited directly onto the element activation sheet 20 at each element tip segment 34 (again, the location of which corresponds to the location of the fused sections 74 in FIG. 13). The sacrificial layer could then be chemically removed, leaving a configuration which is substantially similar to the fused sheet assembly 72 which is depicted in FIGS. 13 and 14.

Figure 15:
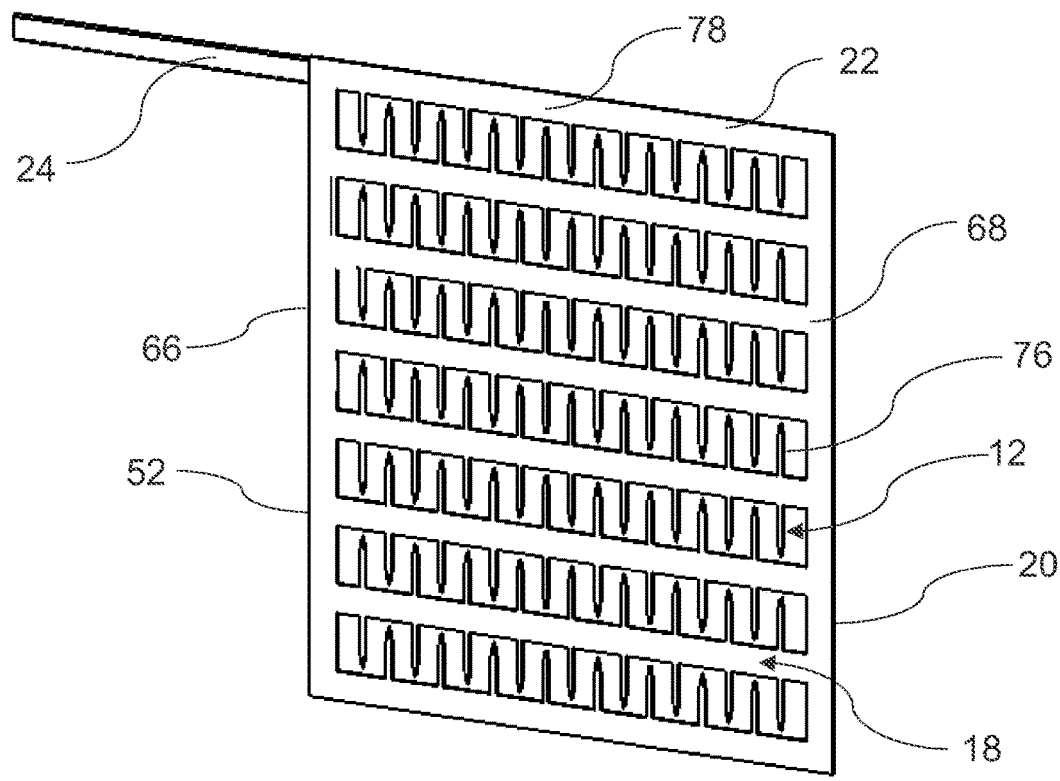
FIG. 15 is an isometric view of the fused sheet assembly of FIG. 13 after the application of an element block cut pattern.
Figure 16:
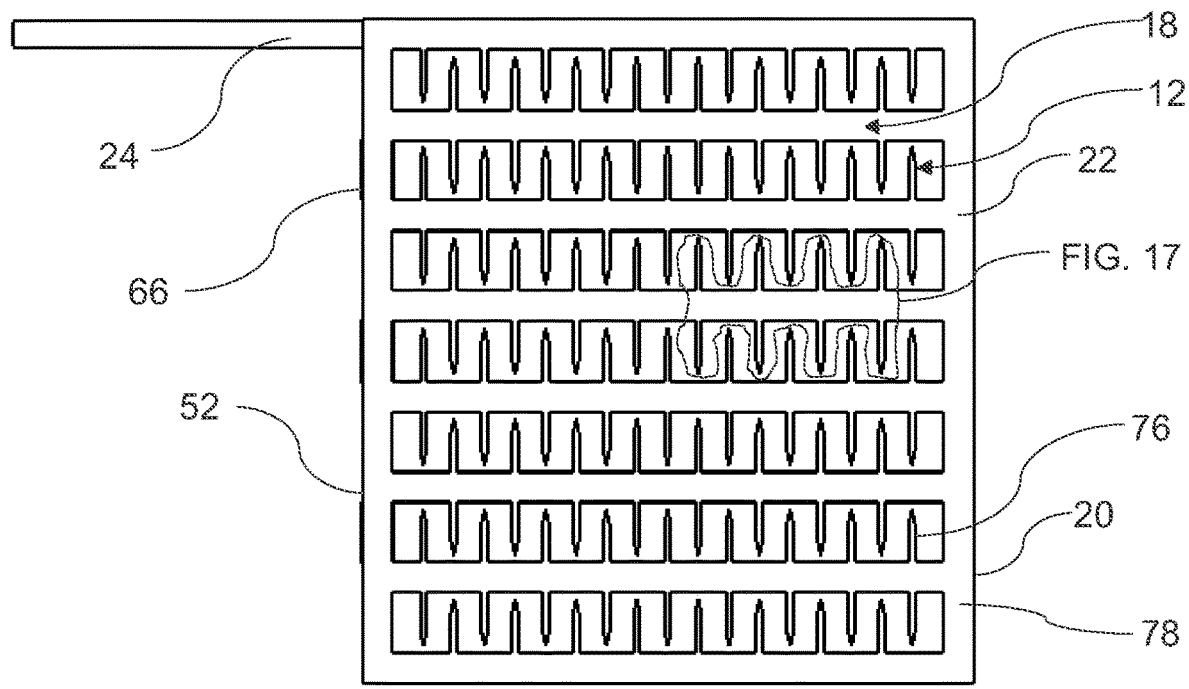
FIG. 16 is an elevation view of the embodiment of FIG. 15 which depicts the element block cut pattern within the fused sheet assembly.

After the element activation sheet 20 has been selectively fused to the element deployment sheet 22, an element block cut pattern 76 may be selectively cut into the resulting fused sheet assembly 72. The element block cut pattern 76 which is cut into the fused sheet assembly 72 may be configured to create a plurality of element block assemblies 18, with each element block assembly 18 including an element activation sheet 20, an element deployment sheet 22, a plurality of engagement elements 12, and an element transition mechanism 24. The element block cut pattern 76 may be cut into the fused sheet assembly 72 via a suitable laser cutting process, plasma etching process, waterjet cutting process, mechanical stamping process, or the like. Creating the element block cut pattern 76 may leave individual element block assemblies 18, element block assemblies 18 which are temporarily connected by tabs (as will be discussed), or element block assemblies 18 which are connected by an element sheet frame 78 as shown in FIGS. 15 and 16. As shown in FIGS. 15 and 16, the element sheet frame 78 connects multiple element block assemblies 18 which are positioned within the element sheet frame 78, and substantially fixes the position of adjacent element block assemblies 18 with respect to adjacent element block assemblies 18. Having the position of each element block assembly 18 substantially fixed with respect to adjacent element block assemblies 18 may be beneficial during the manufacturing process, because it allows for the simultaneous processing of multiple element block assemblies 18 by suitable fixturing.

Figure 18:
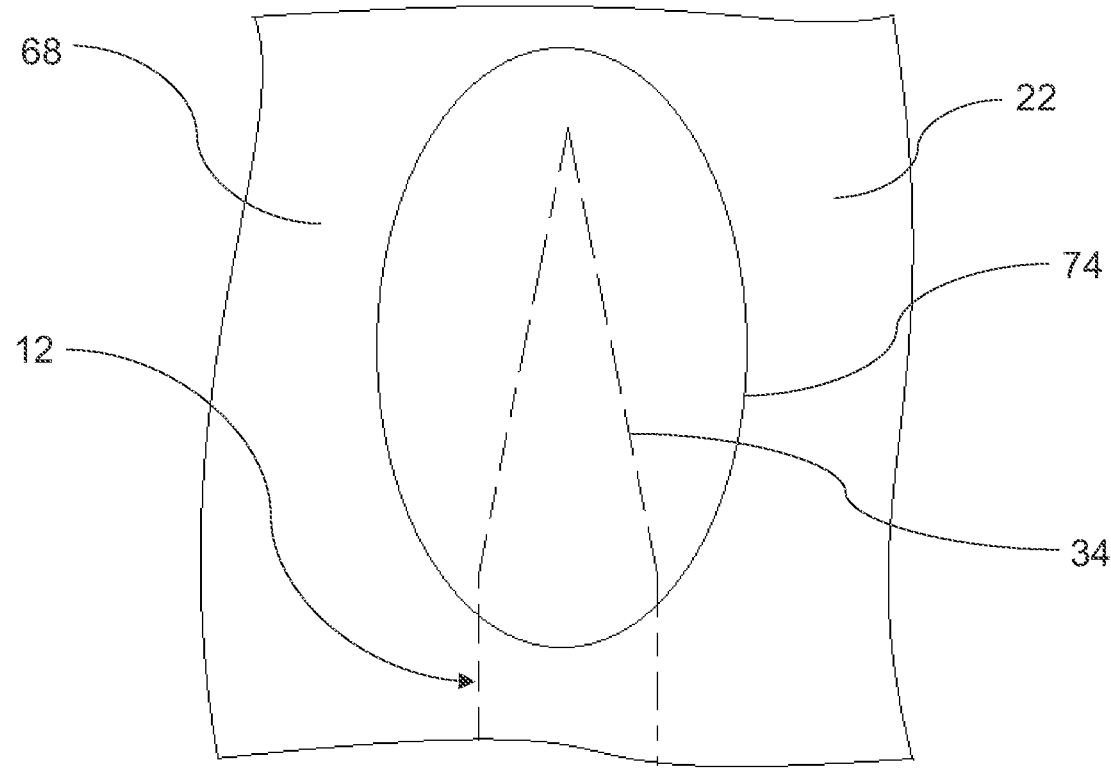
FIG. 18 is an enlarged view of FIG. 13, depicting a fused section and an outline of a respective element tip segment.

The element block cut pattern 76 creates a plurality of engagement elements which are operatively coupled to respective element transition mechanisms 24. The element block cut pattern 76 may be configured such that each fused section 74 of the fused sheet assembly 72 is aligned with a corresponding element tip segment 34 of a respective engagement element 12 which is cut during the formation of the element block cut pattern 76. FIG. 18 illustrates a fused section 74 of the fused sheet assembly 72, and a respective element tip segment 34 which is outlined as a dashed line. The fused section 74 may extend past the element tip segment 34 thus allowing for nominal position error in the creation of the element block cut pattern 76. Portions of the fused section 74 which are adjacent to the element tip segment 34 may be cut away during the formation of the element block cut pattern 76. The creation of the element block cut pattern 76 thus creates a plurality of engagement elements 12 wherein each element activation section 26 is fused to a respective element deployment section 30 within a respective element tip segment 34.

Figure 17:
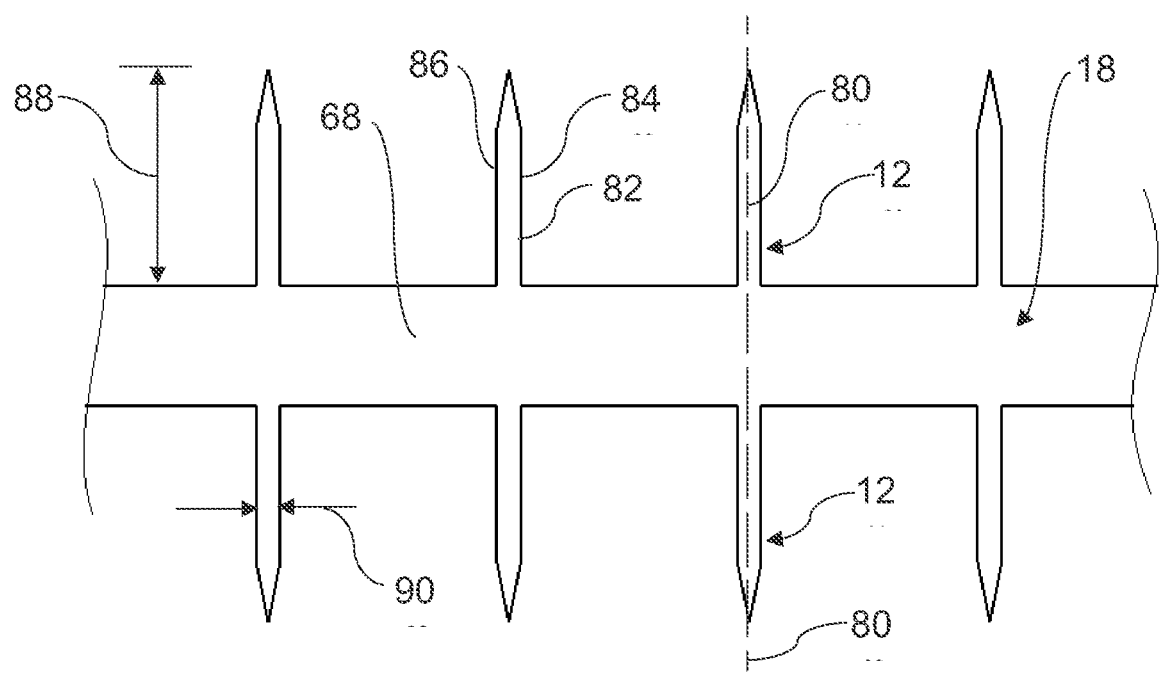
FIG. 17 is an enlarged view of FIG. 16.
Figure 142:
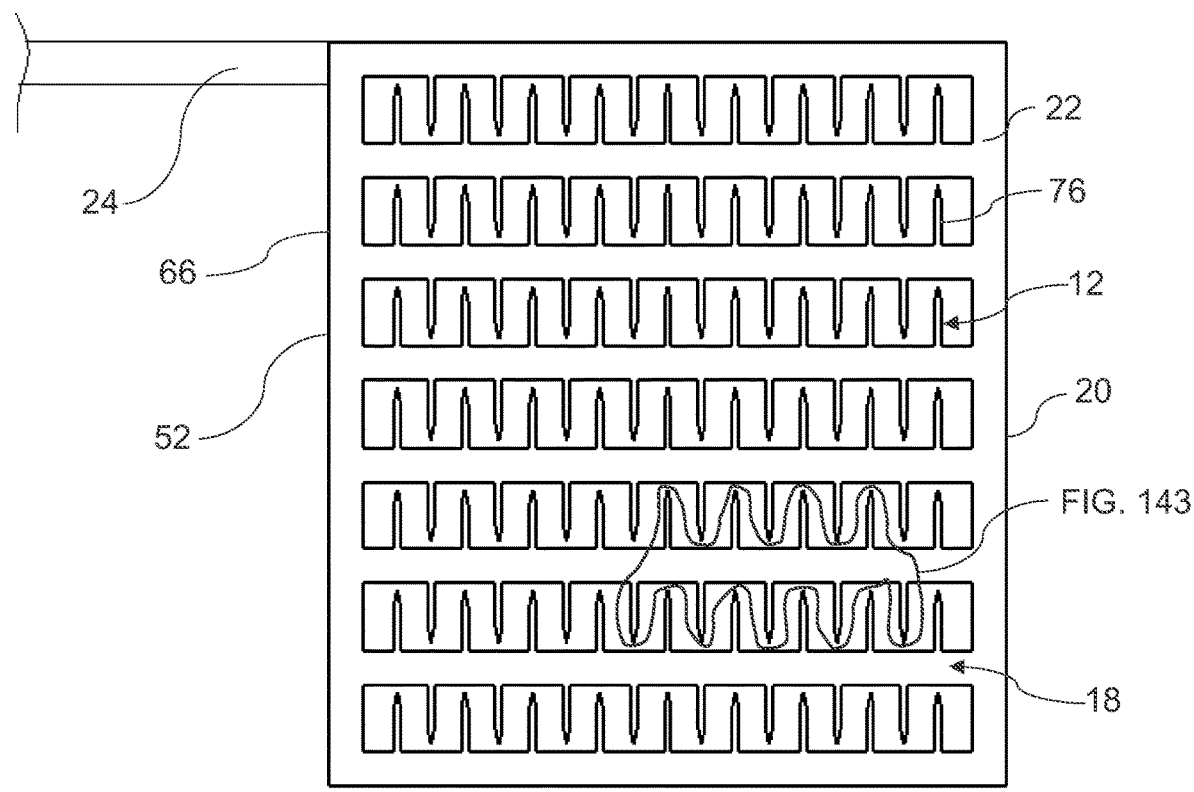
FIG. 142 depicts an element block array wherein engagement elements which are disposed on opposite surfaces of an element block assembly are skewed.
Figure 143:
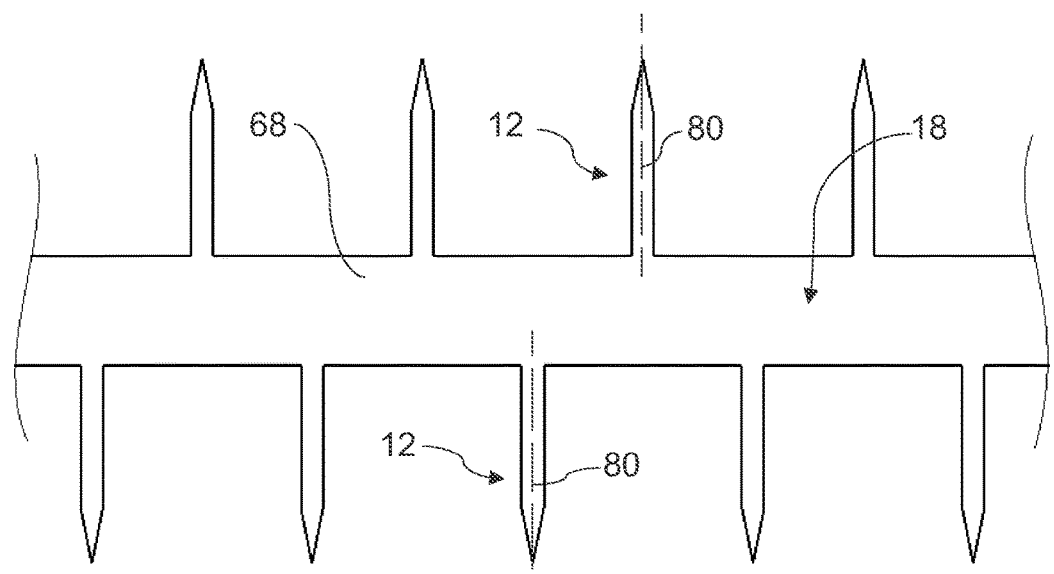
FIG. 143 is an enlarged view of FIG. 142.

The element block cut pattern 76 may be configured such that it creates a variety of patterns of element block assemblies 18 and respective engagement elements 12. For example, each element block assembly 18 may be configured such that engagement elements 12 which are disposed on opposing sides of the element block assembly 18 are substantially aligned. FIG. 17 depicts such an embodiment wherein a central element axis 80 of each engagement element 12 is substantially aligned with a respective central element axis 80 of a respective opposing engagement element 12 which is disposed on the same element block assembly 18. Alternatively, each element block assembly 18 may be configured such that engagement elements 12 which are disposed on opposing sides of the element block assembly 18 are substantially skewed. FIGS. 142 and 143 depict such an embodiment wherein a central element axis 80 of each engagement element 12 is substantially skewed from a respective central element axis 80 of a respective opposing engagement element 12 which is disposed on the same element block assembly 18.

The element block cut pattern 76 may also be configured such that it creates a variety of engagement element profiles 82. A given engagement element 12 which is formed from the element block cut pattern 76 may include an element activation section profile 84 and an element deployment section profile 86. For some embodiments, each element activation section profile 84 may be substantially aligned with the respective element deployment section profile 86. A given engagement element profile 82 is thus formed from the combined element activation section profile 84 and element deployment section profile 86 of the engagement element 12. The engagement elements 12 which are depicted in FIGS. 32 and 33 incorporate engagement element profiles 82' and 82'' which are configured as tapered sharp tips which may be suitable for penetrating target material 48 such as tissue, polymers, or the like. The engagement elements 12 which are depicted in FIGS. 34 and 35 incorporate engagement element profiles 84''' and 82'''' which are configured as blunt tips which may be suitable for penetrating target materials 48 such as loops or hooks.

For a given adhesion device embodiment 10, the length 88 (see FIG. 17) of each engagement element 12 may be configured (via the element block cut pattern 76) to suitably match the application for which the adhesion device 10 is intended. For some industrial applications it may be desirable to utilize adhesion devices 10 which are configured with relatively long engagement elements 12. While for most medical applications, it may be desirable to utilize adhesion devices 10 which are configured with relatively short engagement elements 12. For example, an adhesion device 10 which is used in the medical industry may be configured with engagement elements 12 which are shorter than the typical depth of nerves below the surface of the skin. In this manner the engagement elements 12 when deployed would penetrate the skin but not reach layer of nerves, and therefore the adhesion device 10 would not cause the patient any discomfort when deployed.

For some embodiments of adhesion devices 10, the length 88 of each engagement element 12 may be substantially equal to the length of each other engagement element 12. For other adhesion device embodiments, the length 88 of each engagement element 12 may vary. For such embodiments, the length 88 of each engagement element 12 may vary from an average engagement element length. For some embodiments of adhesion devices 10, the length 88 of each engagement element 12 may be from about 10 μm to about 10 mm, more specifically from about 0.1 mm to about 1 mm. Additionally, the width 90 see FIG. 17) of each engagement element 12 may be from about 1 μm to about 1 mm, more specifically from about 0.01 mm to about 0.1 mm.

After the element block cut pattern 76 has been cut, each engagement element 12 may be formed such that it is substantially perpendicular to the deployment sheet upper surface 68 of a respective element block assembly 18 thereby creating an element block array 92. The element block array 92 is formed from multiple element block assemblies 18 which are formed into a pattern and which have their respective engagement elements 12 formed perpendicular to respective deployment sheet upper surfaces 68. The engagement elements 12 may be formed such that they substantially perpendicular to the respective deployment sheet upper surface 68 with a suitably configured fixture. For some embodiments the engagement elements 12 may be thermally formed such that they are substantially perpendicular to the deployment sheet upper surface 68.

Figure 21:
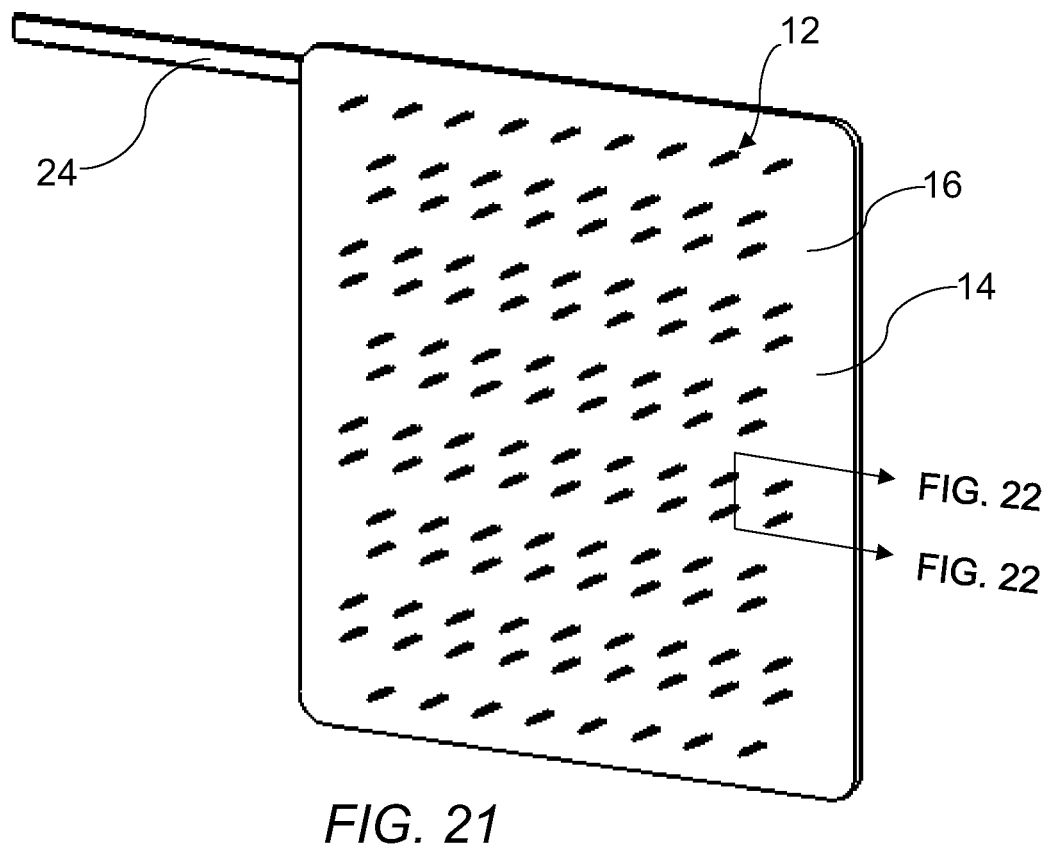
FIG. 21 is an isometric view of the element block array of FIG. 19 with the addition of an element support body.
Figure 22:
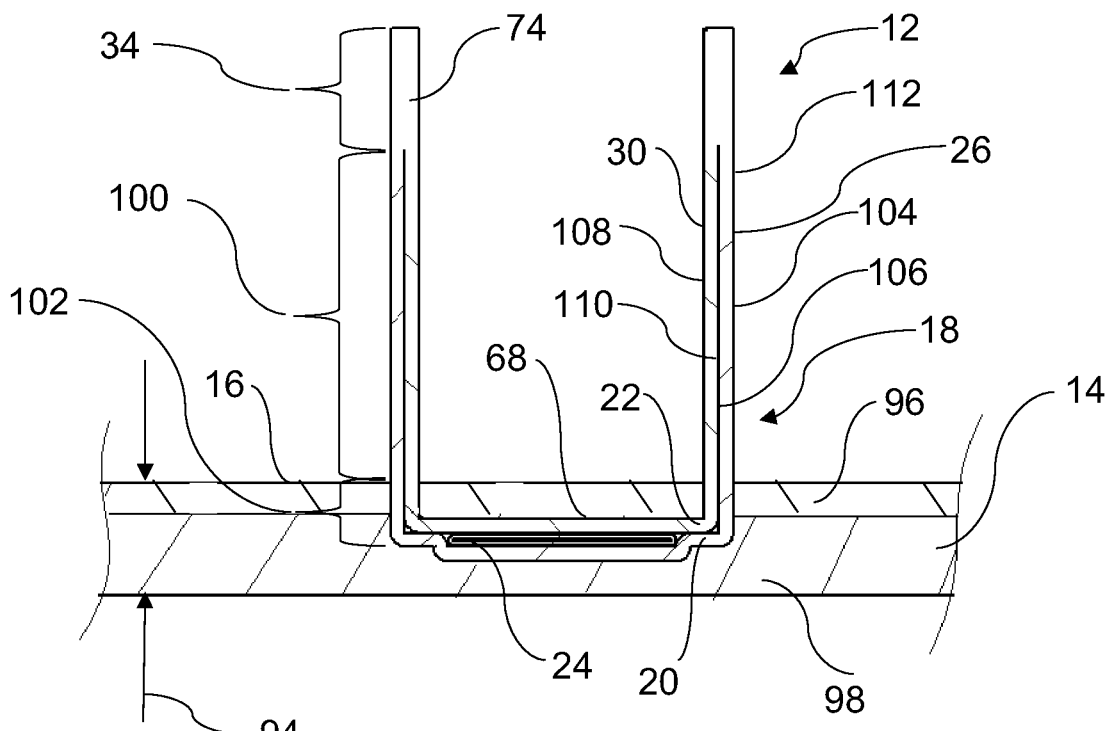
FIG. 22 is a sectional view of the embodiment of FIG. 21, the element activation sheet, the transition mechanism fillister disposed within the activation sheet, the element transition mechanism disposed within the transition mechanism fillister, the element deployment sheet, and multiple respective engagement elements disposed in the deployment state.

After the engagement elements 12 have been formed/constrained such that they are substantially perpendicular to a respective deployment sheet upper surface 68, the element support body 14 may be molded onto the adhesion device 10 as shown in FIGS. 21 and 22. The element support body 14 may be molded onto the adhesion device 10 utilizing any suitable molding techniques. The element support body 14 may be fabricated from any suitable resilient flexible material such as an elastomeric polymer. For example, the element support body 14 may be fabricated from silicone, urethane, or the like. For some embodiments of the adhesion device 10 which are configured for the grafting of tissue, the element support body 14 may be formed from cultured tissue. The thickness 94 of the element support body 14 may be from about 10 μm to about 10 mm. For some embodiments of the adhesion device 10, multiple materials may be used to create the element support body 14. FIG. 22 depicts an element support body 14 which consists of two layers of material. For example, a first support layer 96 may be fabricated using a high durometer/stiff material such that is provides support for the respective engagement elements 12. A second support layer 98 may be fabricated using a lower durometer/softer/elastic material which allows for the expansion and contraction of the element transition mechanism 24. For some medical embodiments of the adhesion device 10, all of the materials which are used to fabricate the adhesion device 10 may be configured as bio-absorbable materials. This allows for the absorption after a suitable time has elapsed of the adhesion device 10 by the body of the patient after the adhesion device 10 has been deployed into or onto the patient.

With the addition of the element support body 14, each engagement element 12 of the resulting adhesion device 10 may be separated into three different segments as shown in FIG. 22. Within each element tip segment 34, the element activation section 26 is operatively fused to the element deployment section 30. This prevents any translational motion of the element activation section 26 with respect to the element deployment section 30 within the element tip segment 34. Each engagement element 12 may also include an element body segment 100. Each element body segment 100 may be disposed between the element tip segment 34 and the engagement surface 16 of the element support body 14. Within each element body segment 100, the element activation section 26 and the element deployment section 30 are unconnected. This allows for the translational motion of the element activation section 26 with respect to the element deployment section 30 within the element body segment 100.

Each engagement element 12 may also include an element base segment 102 which is disposed within the element support body 14 and extends between the respective element activation sheet 20 and respective element deployment sheet 22 and the engagement surface 16 of the element support body 14. Within each element base segment 102, the element activation section 26 and the element deployment section 30 are unconnected. This allows for the translational motion of the element activation section 26 with respect to the element deployment section 30 within the element base segment 102.

Within each of the three segments of a given engagement element, the element activation section profile 84 may be substantially aligned with the element deployment section profile 86 (see FIG. 17). Each segment of each engagement element may include a portion which is formed from the same material which forms the element activation sheet 20, and a portion which is formed from the same material which forms the element deployment sheet 22. That is to say that both materials span the length of each engagement element 12, from the element tip segment 34 to the element base segment. For some embodiments, the fused section 74 of a given engagement element 12 may extend the length of the element tip segment 34. In some cases the fused section 74 for a given engagement element 12 may be from about 1/10 to about ½ the length of the engagement element.

The addition of the element support body 14 acts to physically constrain each engagement element 12 such that it is disposed in a substantially straightened configuration which is substantially perpendicular to the engagement surface 16 of the element support body 14 (while each engagement element is disposed in the deployment state 12 and each respective element transition mechanism is disposed in the neutral configuration 24). In order to elaborate, each engagement element 12 may include an exterior activation surface 104 and a corresponding interior activation surface 106 both of which are disposed on the respective element activation section 26.

Similarly, each engagement element 12 may include an exterior deployment surface 108 and a corresponding interior deployment surface 110 both of which are disposed on the respective element deployment section 30. When a given engagement element is disposed in the deployment state 12, the respective exterior activation surface 104, the respective interior activation surface 106, the respective exterior deployment surface 108, and the respective interior deployment surface 110 are all disposed in a substantially straightened configuration which is substantially perpendicular to the engagement surface 16 of the element support body 14.

For some embodiments of the adhesion device, a coating 112 may be applied to at least one surface of each engagement element 12 by any suitable coating application processing method. The applied coating 112 may have any suitable industrial purpose such as a coating to increase the lubricity of the engagement elements 12, an adhesive coating or the like. For medical applications the coating 112 which is applied may be a lubricious coating, an antimicrobial coating, a drug eluding coating, or the like.

Figure 19:
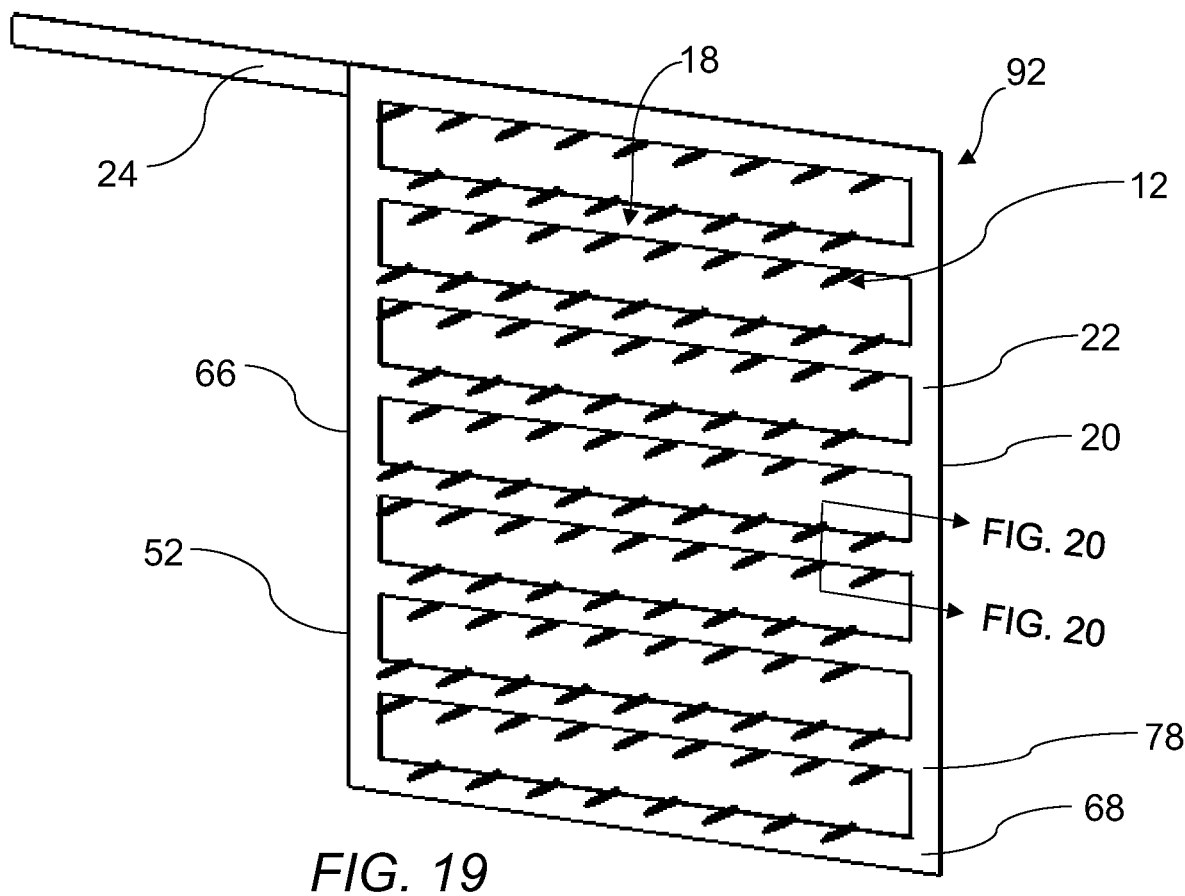
FIG. 19 is an isometric view of an element block array, the element block array including multiple element block assemblies which are connected by an element sheet frame.
Figure 20:
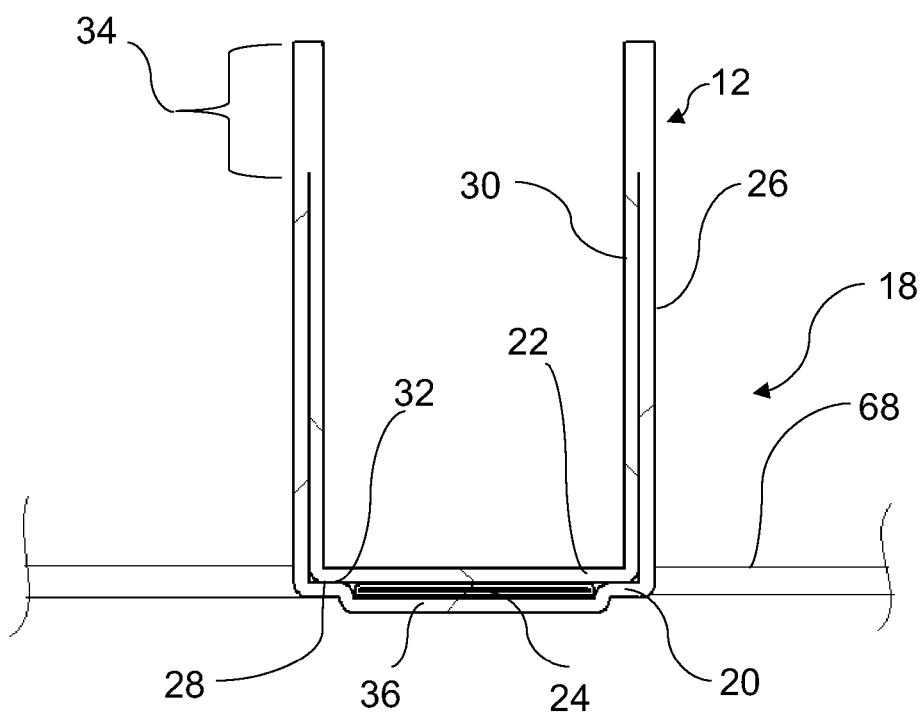
FIG. 20 is a sectional view of FIG. 19 depicting an element block assembly and respective engagement elements disposed in the deployment state.

To summarize the adhesion device 10 manufacturing method which has been discussed with regard to FIGS. 6-22, the manufacturing method begins with forming at least one transition mechanism filister 36 pattern in an element activation sheet 20 (FIGS. 6-8). The next step consists of inserting at least one suitably configured element transition mechanism 24 into a respective element transition filister 36 (FIGS. 9-10). The next step consists of fusing sections of an element deployment sheet 22 to the element activation sheet 20 thereby creating a fused sheet assembly 72 (FIGS. 11-14). The next step consists of cutting a plurality of element block assemblies 18 from the fused sheet assembly 72, with each element block assembly 18 including an element activation sheet 20, an element deployment sheet 22, a plurality of engagement elements 12, and an element transition mechanism 24 (FIGS. 15-18). The next step consists of constraining each engagement element 12 such that it is substantially perpendicular to a deployment sheet upper surface 68 of each respective element block assembly 18 (FIGS. 19-20). The final step consists of molding an element support body 14 such that it encompasses each element activation sheet 20 and each element deployment sheet 22 of each respective element block assembly 18 (FIGS. 21-22). Some embodiments of the adhesion device 10 may be manufactured using methods and fixtures for similarly configured embodiments which have been disclosed in U.S. application Ser. No. 14/240,668.

Figure 23:
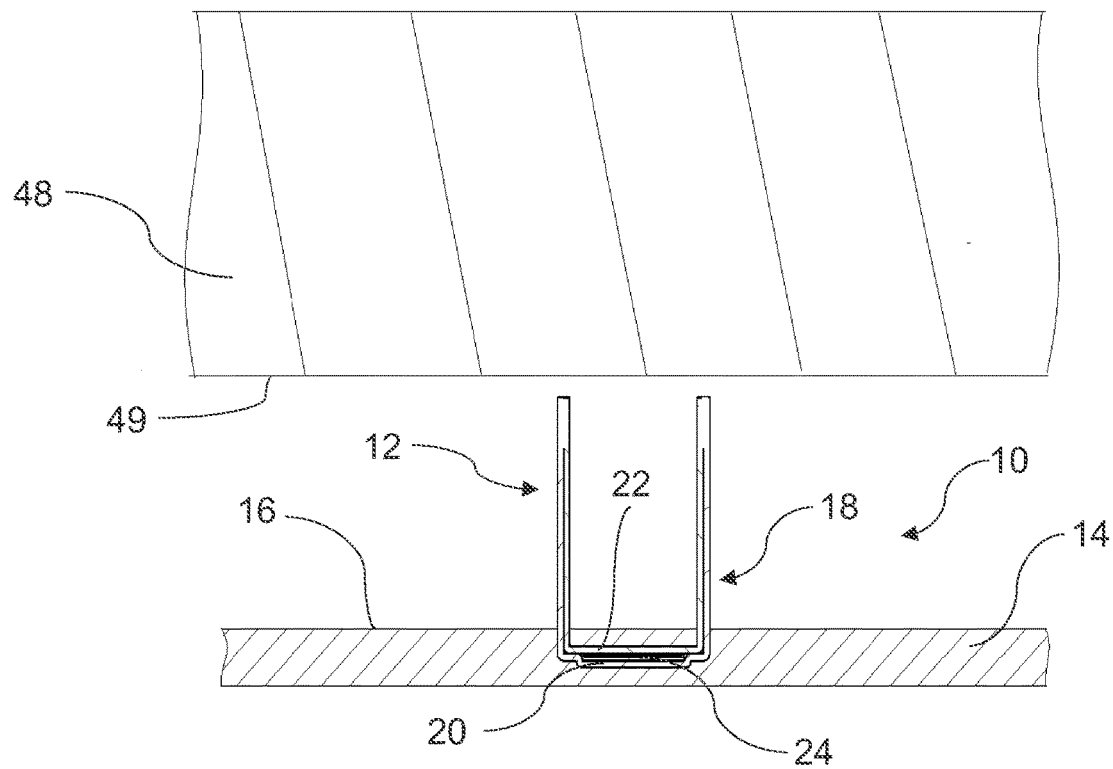
FIGS. 23-28 depict a deployment sequence of the adhesion device of FIG. 1 into a target material.

FIGS. 23-31 depict a method for the deployment and removal of an adhesion device 10 into a target material 48. The figures depict section views of an element block assembly 18 of an adhesion device 10 (most section views being equivalent to FIGS. 2 and 4). The deployment and removal sequence may be used in order to further illustrate the operative couplings between and constraints applied to the various elements of the adhesion device 10. The method for deployment and removal of the adhesion device 10, the dimensions, configurations, constraints, and materials may apply to all of the adhesion device embodiments discussed herein. FIG. 23 depicts an element block assembly 18 of an adhesion device 10 in proximity to a target material 48. The target material 48 could be any suitable target material 48 including but not limited to tissue, a polymer surface, mesh, fabric, a suitably configured pattern of loops, a suitably configured pattern of hooks, a suitably configured pattern of hooks, or a similarly configured adhesion device.

Figure 24:
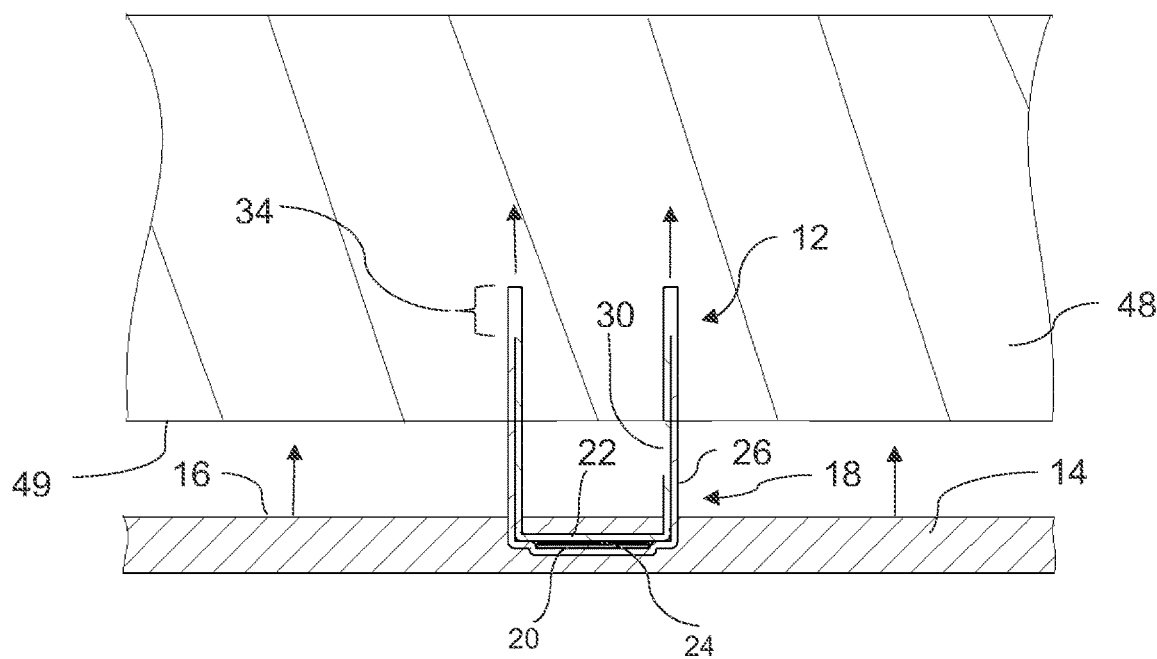

The adhesion device 10 of FIG. 23 (depicted in section view) may include a plurality of element block assemblies 18 which are partially disposed in an element support body 14 as has been previously discussed. FIG. 24 depicts the deployment a plurality of engagement elements 12 into the target material, 48 with each engagement element 12 being operatively coupled to a respective element transition mechanism 24 of a respective element block assembly 18. As has been discussed previously, each engagement element 12 may include an elongated element activation section 26 (which monolithically extends from an element activation sheet 20) and an elongated element deployment section 30 (which monolithically extends from an element deployment sheet 22) with each element activation section 26 being fused to each element deployment section 30 within an element tip segment 34.

During the insertion into the target material 48 (see FIG. 24), each engagement element of the adhesion device 10 may be disposed in the deployment state 12 wherein each engagement element 12 is substantially perpendicular to the engagement surface 16 of the element support body 14. Each element transition mechanism may be disposed during the deployment of the respective engagement elements 12 into the target material 48 in a neutral configuration 24. When disposed in the neutral configuration 24 each activation sheet upper surface 28 may be substantially adjacent to each respective deployment sheet lower surface 32 (see FIG. 26), with the element support body 14 constraining each respective engagement element in the deployment state 12.

For some adhesion device embodiments each exterior activation surface 104, each interior activation surface 106, each exterior deployment surface 108, and each interior deployment surface 110 of a respective engagement element which is disposed in the deployment state 12 may be substantially perpendicular to the respective deployment sheet upper surface 68 (see FIG. 22). Additionally, each exterior activation surface 104, each interior activation surface 106, each exterior deployment surface 108, and each interior deployment surface 110 of a respective engagement element which is disposed in the deployment state 12 may be substantially parallel to corresponding surfaces of the engagement elements 12 which are disposed on the same element block assembly 18 (see FIG. 22).

Each engagement element 12 is configured with an element activation section 26 and an element deployment section 30. The element activation section 26 may be fused to the element deployment section 30 within the element tip segment 34. For some adhesion device embodiments, the element tip segment 34 may be further sharpened in order to facilitate penetration into the target material 48. For example, adhesion device embodiments having metallic engagement elements 12 may be electro-polished to increase their sharpness thereby improving the ability of the engagement elements 12 to penetrate the target material 48.

The element activation section 26 may be unconnected to the element deployment section 30 within the element body segment 100. Embodiments of adhesion devices which are thus configured with multiple sections within each element body segment may have an advantage over previous embodiments of adhesion devices which incorporate elements fabricated from a single material. Elements which are fabricated using multiple sections within the element body segment 100 can be configured with any suitable combination of materials. For example the element deployment section 30 (and respective element deployment sheet 22) can be formed from a stiff elastic material in order to improve penetration into target material 48, while the element activation section 26 (and respective element activation sheet 20) may be fabricated from a flexible elastic material in order to allow for multiple reversible transitions from the deployment state 12 to the engagement state 12'. Additionally, having two sections disposed within the element body segment 100 may improve the overall stiffness of an engagement element 12 (when compared to single material engagement element embodiments) thereby improving the ability of the engagement element 12 to penetrate target material 48.

Figure 26:
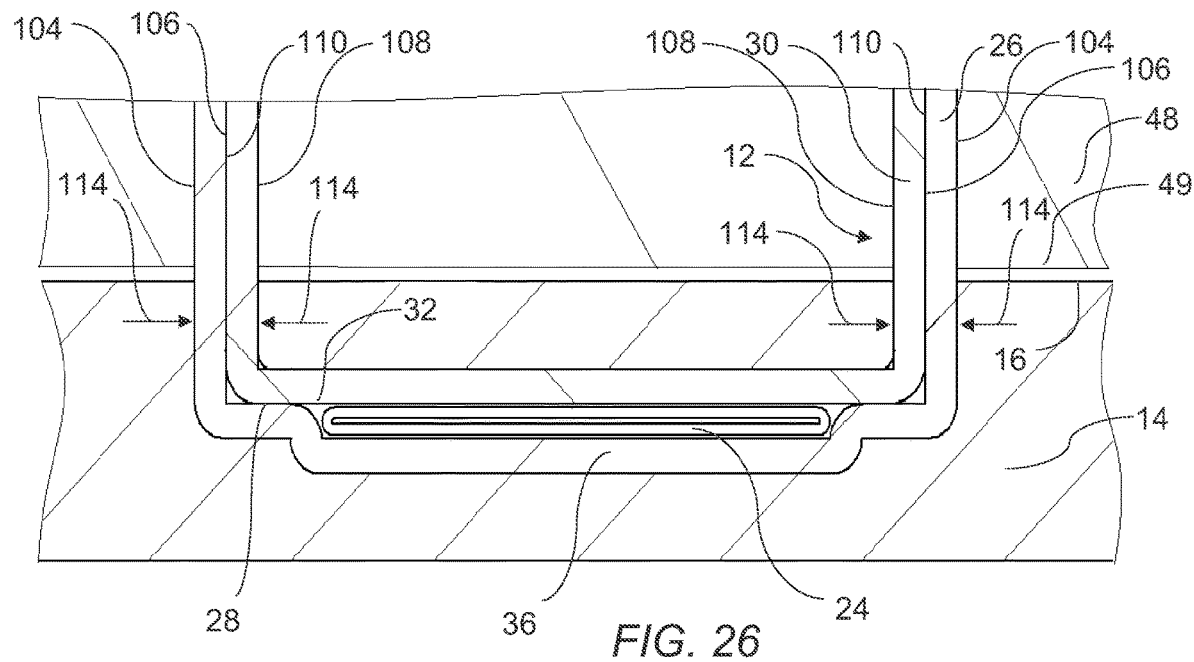

When a given element transition mechanism is disposed in the neutral configuration 24, the element support body 14 may apply specific constraints to each engagement element 12 which is operatively coupled to the element transition mechanism 24. As shown in FIG. 26, the elastic element support body 14 may apply a plurality of element support forces 114 to each engagement element 12. Multiple element support forces 114 may be directed such that they are normal to a respective exterior activation surface 104 and a respective exterior deployment surface 108 of each element base segment 102 which is disposed within the element support body 14. The element support forces 114 may act to constrain each engagement element 12 such that each engagement element 12 is disposed in a substantially straightened configuration which is substantially perpendicular to the engagement surface 16 as has been previously discussed.

Additionally, the element support forces 114 may constrain each element activation section 20 to be substantially adjacent to a respective element deployment section 22 within the element body segment 100 of a respective engagement element 12. When a given engagement element is in the deployment state 12, the length 116 of the element activation section 26 which is disposed within the element body segment 100 is substantially equal to the length 118 of the element deployment section 30 which is disposed within the element body segment 100 (see FIG. 25).

Figure 25:
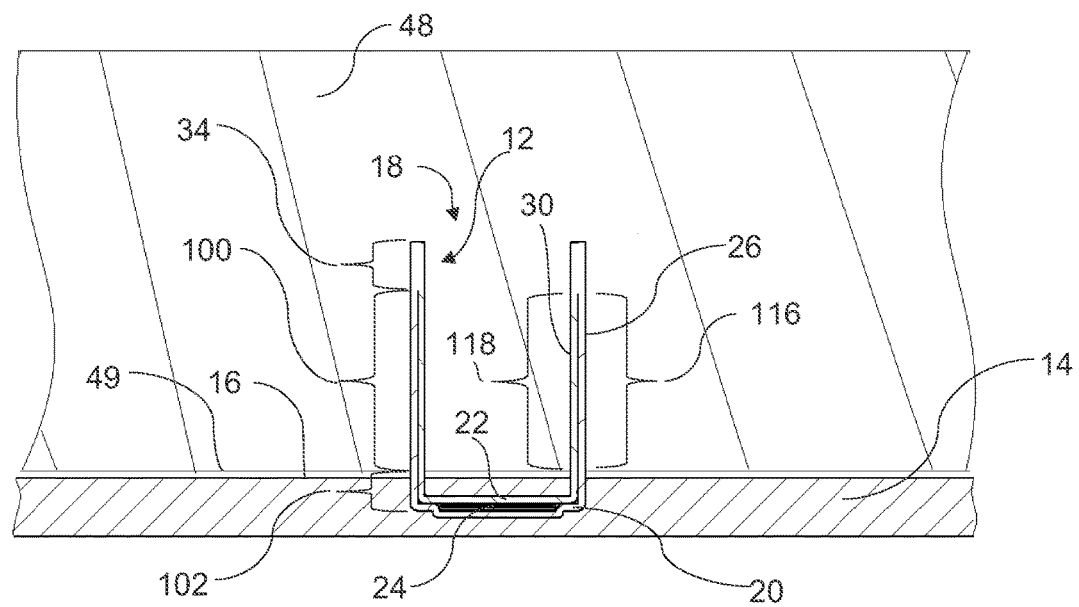
Figure 27:
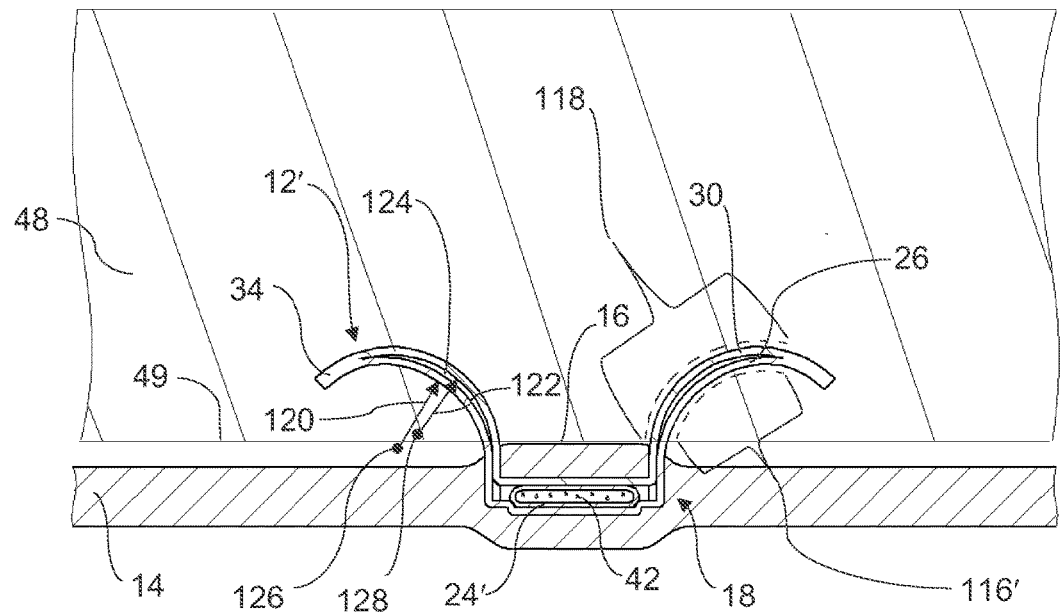
Figure 28:
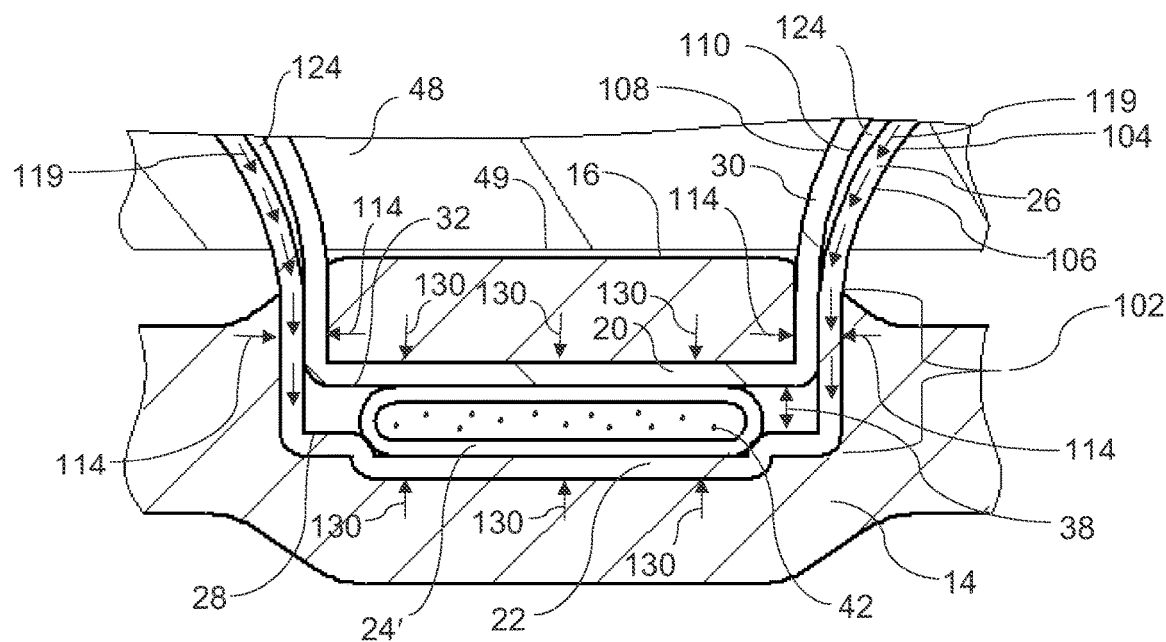
Figure 29:
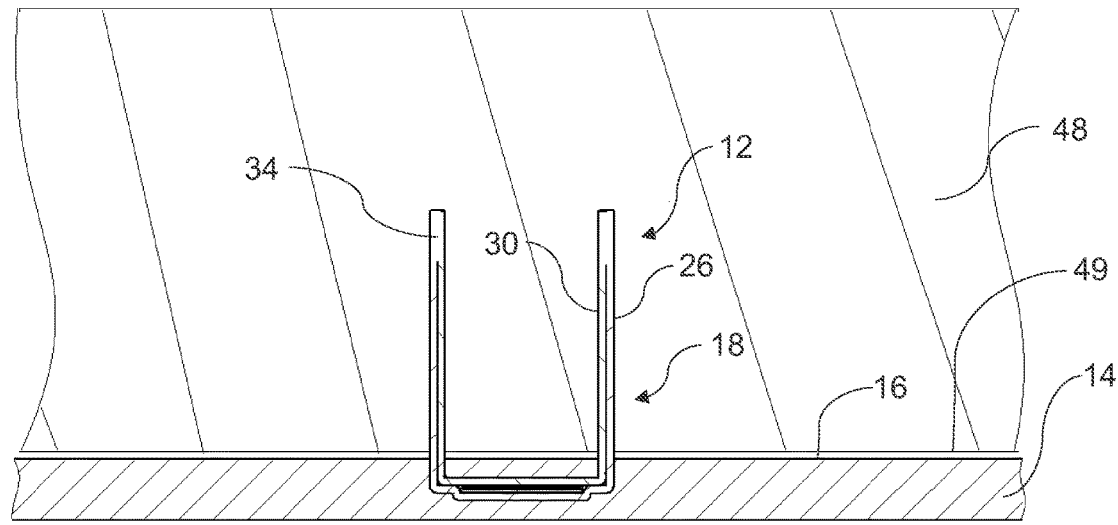

Once the engagement elements 12 have been deployed/inserted into the target material 48 as shown in FIG. 25, some or all of the engagement elements which have been deployed into the target material 48 may be transitioned to the engagement state 12'. Transitioning selected engagement elements to the engagement state 12' is accomplished by transitioning respective element transition mechanisms from the neutral configuration 24 to the expanded configuration 24' as shown in FIGS. 27 and 28. When an element transition mechanism is transitioned to the expanded configuration 24', the activation sheet upper surface 28 and the deployment sheet lower surface 32 may be separated by a transition gap 38 as shown in FIG. 28.

When the element transition mechanism is transitioned to the expanded configuration 24', the element activation sheet 20 and the element deployment sheet 22 may assume any suitable expanded profile which conforms to the expanded element transition mechanism 24' and which maintains the transition gap 38. For example, if the element transition mechanism 24' assumes a circular profile when expanded, the element activation sheet 20 and the element deployment sheet 22 could also assume a circular profile as long as the transition gap 38 is maintained. For most of the embodiments discussed and depicted herein, when the element transition mechanism is transitioned to the expanded configuration 24' a substantially flat element activation sheet 20 is depicted as being separated from a substantially flat element deployment sheet 22 by the transition gap 38.

The element support body 14 is configured for each element transition mechanism which is disposed in the expanded configuration 24' to constrain each respective engagement element in an engagement state 12' wherein each respective engagement element 12' is eccentrically tensioned as the result of the transition gap 38 into a reactive flexure (curvature) which is configured to mechanically capture surrounding target material 48 thereby securing the adhesion device 10 to a surface 49 of the target material 48. Thus the adhesion device 10 is secured to the surface 49 of the target material 48, in some cases portions of the engagement surface 16 of the adhesion device 10 may be substantially adjacent to the surface 49 of the target material 48.

When a given element transition mechanism is disposed in the expanded configuration 24', the element support forces 114 provided to each respective engagement element 12' by the element support body 14 produce specific constraints upon the respective engagement element 12'. In this manner the element support body 14 engages the plurality of element block assemblies 18, and the element support body 14 is in operative communication with each engagement element 12 of an associated element block assembly 18. each element block As has been previously discussed, the element activation section 20 is operatively fused to the element deployment section 22 within the element tip segment 34 of a given engagement element 12'. The fused element tip segment 34 prevents translational motion of the element activation section 26 with respect to the element deployment section 30 within the element tip segment 34. Within the element body segment 100 however, the element activation section 26 is unconnected to the element deployment section 30. This allows for translational motion of the element activation section 26 with respect to the element deployment section 30 within the element body section 100.

Translational motion of the element activation section 26 with respect to the element deployment section 30 (upon creation of the transition gap 38) may result in a portion of the element activation section 26 which was previously disposed in the element body segment 100 moving into the element support body 14 thereby effectively shortening the length 116' of the element activation section 26 which is disposed within the element body segment 100. Thus when a given engagement element is in the engagement state 12', the length 116' of the element activation section 26 which is disposed within the element body segment 100 may be substantially shorter than the length 118 of the element deployment section 30 which is disposed within the element body segment 100. (see FIG. 27) The length 118 of the element deployment section 30 which is disposed within the element body segment 100 may remain substantially unchanged during the translational motion of the element activation section 26 with respect to the element deployment section 30.

As shown in FIGS. 27 and 28, the translational motion (as indicated by the arrows 119 in FIG. 28) of the element activation section 26 with respect to the element deployment section 30 (combined with the constraint of the fused element tip segment 34 and constraints applied to the engagement element 12' by the element support body 14) results in the exterior activation surface 104 and the corresponding interior activation surface 106 of the respective element activation section 26 each assuming a reactive flexure, with the reactive flexure having a first flexure radius 120 which may be measured from the interior activation surface 106. Similarly, the exterior deployment surface 108 and the corresponding interior deployment surface 110 of the respective element deployment section 30 may each assume a reactive flexure, with the reactive flexure having a second flexure radius 122 which may be measured from the exterior deployment surface 108. For some engagement element embodiments, the first flexure radius 120 will be less than the second flexure radius 122, thereby resulting in the creation of an element engagement gap 124 between the interior activation surface 106 and the interior deployment surface 110. For some engagement element embodiments, the element tip segments 34 are directed away from the respective element transition mechanism 24' when the respective engagement elements are disposed in the engagement state 12'. That is to say that the first flexure radius 120 may have a first centroid 126 which is disposed adjacent to but separated from the element block assembly 18, and the second flexure radius 122 may have a second centroid 128 which is disposed adjacent to but separated from the element block assembly 18 as shown in FIG. 27. In general, the first centroid 126 and the second centroid 128 of each engagement element 12' will be disposed in different locations. For illustrative purposed, FIGS. 27 and 28 depict a gap between the surface of the target material 49 and the engagement surface 16. For some embodiments of adhesion devices discussed herein, the surface of the target material 49 and the engagement surface 16 would be in direct contact. Additionally for some embodiments of adhesion devices discussed herein a mechanical seal may be created between the surface of the target material 49 and the engagement surface 16. The seal may prevent fluids from entering the area between the surface of the target material 49 and the engagement surface 16.

As has been discussed the element activation section 26 is unconnected to the element deployment section 30 within the element body segment 100 of a given engagement element 12. This allows for the translational motion of the element activation section 26 with respect to the element deployment section 30 within the element body segment 100. When an element transition mechanism is transitioned from the neutral configuration 24 to the expanded configuration 24', a respective engagement element which is operatively coupled to the element transition mechanism is in turn transitioned from the deployment state 12 to the engagement state 12'.

The creation of the transition gap 38 causes the translational motion of the element activation section 26 with respect to the element deployment section 30 within the element body segment 100 and element base segment 102 of each respective engagement element 12. Translational motion of the element activation section 26 with respect to the element deployment section 30 is not possible within the element tip segment 34, and the element activation section 26 is constrained to be adjacent to the element deployment section 30 (specifically the interior activation surface 106 is constrained to be adjacent to the interior deployment surface 110) within the element base segment 102.

The translational motion of the element activation section 26 with respect to the element deployment section 30 therefore results in a shortening of the length 116' of the element activation section 26 which is disposed in the element body segment 100, while the length 118 of the element deployment section 30 which is disposed in the element body segment 100 remains substantially unchanged. This results in an eccentric tensioning of the engagement element 12' by the element activation section 26 as the result of the transition gap 40 which results in the reactive flexure of the engagement element 12'. It can thus be said that the engagement element 12 is operatively coupled to the element transition mechanism 24, specifically the element tip segment 34 is operatively coupled to the element activation sheet 20 by the element activation section 26 which monolithically extends from the element activation sheet 20.

When the element transition mechanism is disposed in the expanded configuration 24', the element support body 14 may provide restorative forces 130 to the element transition mechanism 24'. FIG. 28 depicts the element transition mechanism in the expanded configuration 24', and the respective engagement elements in the engagement state 12'. The expansion of the elastic element support body 14 material which surrounds the element transition mechanism 24' results in internal strains within the material. The internal strains within the material of the element support body 14 result in restorative forces 130 being applied to the element transition mechanism 24' by the element support body 14.

The restorative forces 130 may be normal forces which are applied to the deployment sheet upper surface 68 of the element deployment sheet 22 and the activation sheet lower surface 54 of the element activation sheet 26. The restorative forces 130 may act to facilitate the transition of the element transition mechanism from the expanded configuration 24' to the neutral configuration 24. That is to say that the restorative forces 130 are directed such that they facilitate the elimination of the transition gap 38 when the element transition mechanism is transitioned from the expanded configuration 24' to the neutral configuration 24. Additionally while the element transition mechanism is disposed in the expanded configuration, the element support forces may constrain respective element activation sections and element deployment sections which are disposed within the element base segment 102 to be substantially adjacent. That is to say that within a given element base segment 102, each interior activation surface 106 may be constrained to be substantially adjacent to the respective interior deployment surface 110 by the element support forces 114 (see FIG. 28).

For some embodiments of the adhesion device, transitioning selected element transition mechanisms from the neutral configuration 24 to the expanded configuration 24' (or from the expanded configuration 24' to the neutral configuration 24) may be accomplished using the control system 50. For the adhesion device embodiment 10 shown in FIGS. 23-31, each element transition mechanism 24 is configured as an expandable balloon apparatus. The control system 50 may in turn be configured as a user controlled pump which can inflate/deflate the element transition mechanism 24 which is configured as a balloon apparatus. When a user of the adhesion device 10 inflates selected element transition mechanisms 24 which are configured as balloon apparatuses using the control system 50, the selected element transition mechanisms may in turn be transitioned from the neutral configuration 24 to the expanded configuration 24'. When a user of the adhesion device 10 deflates the selected balloon apparatuses using the control system 50, the selected element transition mechanisms may in turn be transitioned from the expanded configuration 24' to the neutral configuration 24.

After being secured to the surface 49 of the target material 48 as shown in FIGS. 27 and 28, the adhesion device 10 may be removed from the surface 49 of the target material 48. A user of the adhesion device 10 may remove the adhesion device 10 by using the control system 50 to transition selected element transition mechanisms from the expanded configuration 24' to the neutral configuration 24. Transitioning each element transition mechanism which is disposed in the expanded configuration 24' to the neutral configuration 24 in turn transitions each respective engagement element from the engagement state 12' to the deployment state 12, and releases adjacent target material 48 from each respective engagement element 12 (see FIGS. 29 and 30).

Figure 30:
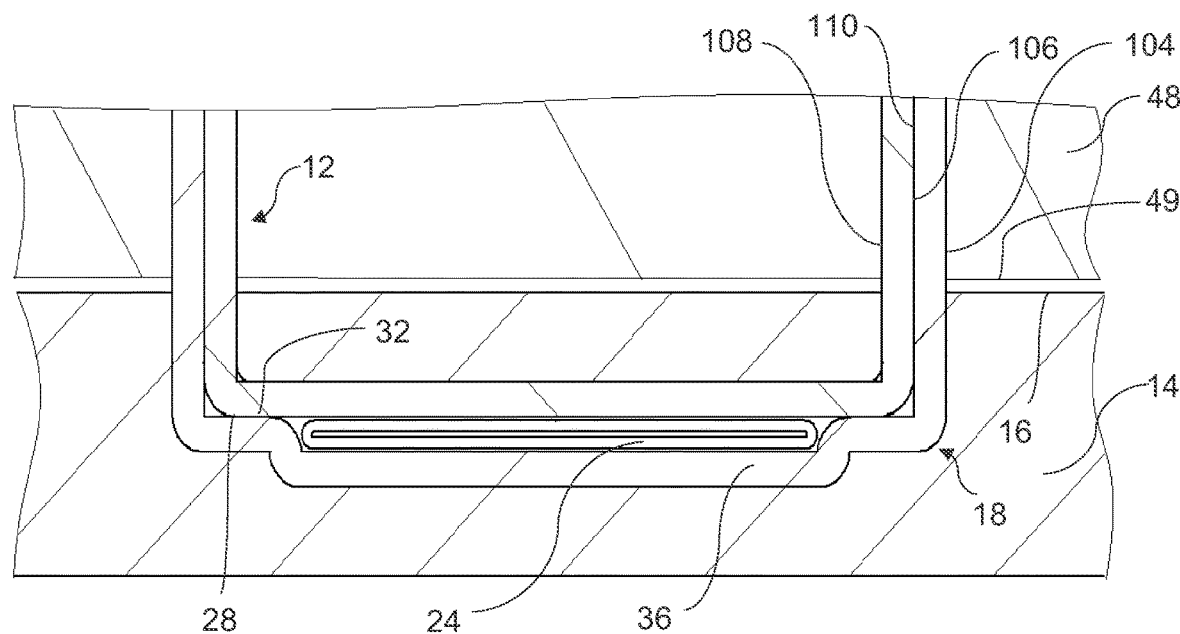

Transitioning selected element transition mechanisms from the expanded configuration 24' to the neutral configuration 24 results in the elimination of the transition gap 38 in those element transition mechanisms 24, thereby leaving each respective activation sheet upper surface 28 substantially adjacent to each respective deployment sheet lower surface 32 as shown in FIG. 30. This in turn results in the translational motion of each respective element activation section 26 with respect to each respective element deployment section 30, the translational motion resulting in the length 116 of each element activation section 26 which is disposed within each respective element body segment 100 being substantially equal to the length 118 of each element deployment section 30 which is disposed within each respective element body segment 100 and the respective engagement elements returning to the deployment state 12. The adhesion device 10 can then be removed from the surface 49 of the target material 48 (as shown in FIG. 31), thereby removing each engagement element 12 from the target material 48.

All of the adhesion devices which are discussed herein may be configured such that the engagement elements may be transitioned from the deployment state 12 to the engagement state 12' multiple time without any decrease in the performance of the adhesion device. That is to say that for all of the adhesion devices which are discussed herein, the dimensions of each respective engagement element 12 and the materials of each respective engagement element 12 may be configured such that the stresses imposed on each engagement element material upon transition from the deployment state 12 to the engagement state 12' are less than the elastic limit of that material. That is to say for a given engagement element 12 and its (respective element transition mechanism 24) all of the dimensions and materials of the engagement element 12 may be configured such that no plastic deformation occurs within the materials of the engagement element 12 during multiple transitions of the engagement element from the deployment state 12 to the engagement state 12' (and vice versa).

Some embodiments of adhesion devices may be configured for the delivery of fluids through the engagement elements after the engagement elements have been deployed into the target material. This may be useful in medical applications for the delivery of medications, dyes, or the like into tissue into which the engagement elements have been deployed. Similarly for industrial applications, adhesives, lubricants, solvents, dyes, paints, or any other suitable fluid could be delivered through the engagement elements once they have been deployed into a given target material. All of the configurations of adhesion devices which are discussed herein may be configured for the delivery of fluids through the engagement elements.

Figure 37:
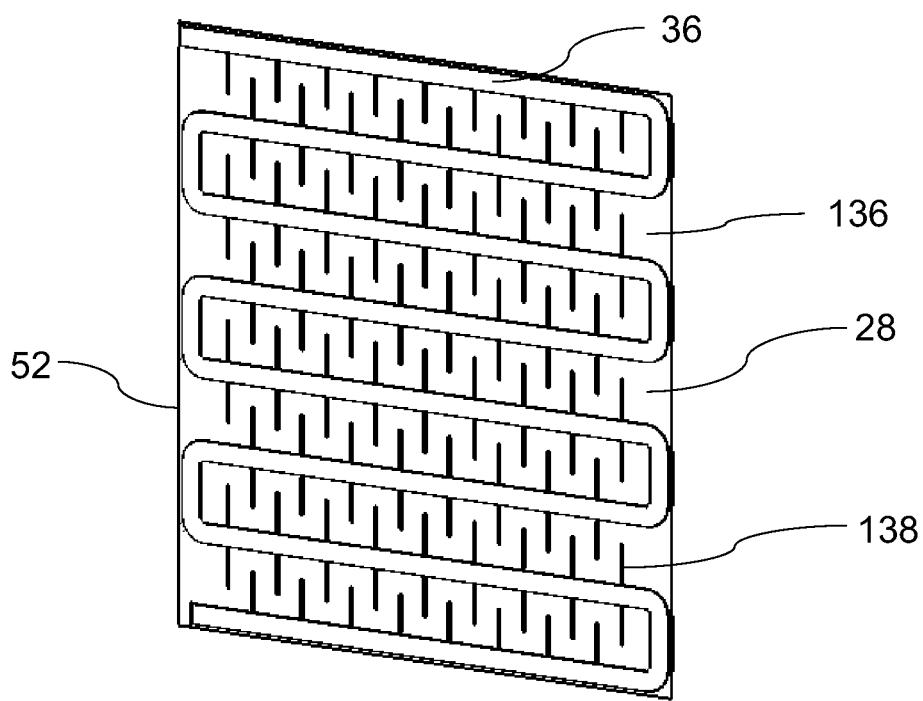
FIGS. 37 and 38 are isometric views of an element activation sheet having a transition mechanism fillister and multiple fluid delivery channels.
Figure 38:
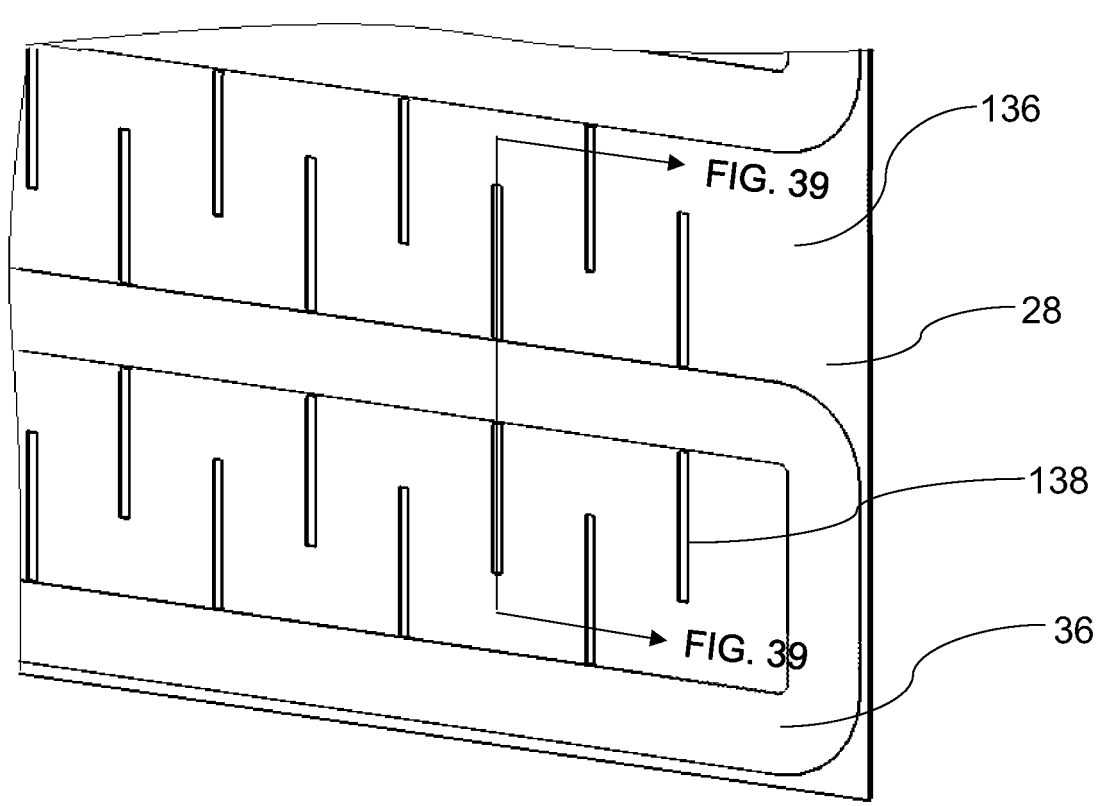

FIGS. 36-44 depict an adhesion device 132 with fluid delivery capability. The adhesion device 132 is configured to deliver fluid through some or all of its respective engagement elements 12 once the engagement elements 12 are deployed into the target material 48. The adhesion device 132 may be manufactured as discussed with regard to FIGS. 6-22, with the exceptions which are discussed below. FIG. 36 depicts an adhesion device 132 including a control system 50 and a fluid delivery device 134. For the adhesion device embodiment 132 shown, the fluid delivery device 134 is external to the control system 50, however for some other adhesion device embodiments the fluid delivery device 50 could be integrated into the control system 50. FIGS. 37 and 38 depict an embodiment of an element activation sheet 136. The element activation sheet 136 includes a transition mechanism filister 36 as has been previously discussed with regard to the embodiment depicted in FIG. 7.

Figure 39:
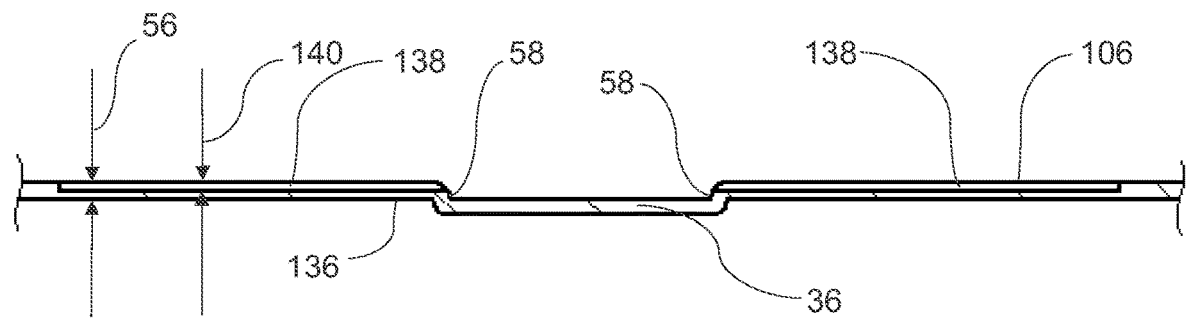
FIG. 39 is a sectional view of FIG. 38.

The element activation sheet embodiment 136 also includes a plurality of fluid delivery channels 138. For some embodiments of the adhesion device 132, similar fluid delivery channels 138 may be disposed on a respective element deployment sheet 22 (this is not shown). In some cases, the fluid delivery channels 138 may be configured as micro-fluidic channels. The fluid delivery channels 138 may be disposed on the activation sheet upper surface 28 such that they are in fluid communication with the transition mechanism fillister 36. The fluid delivery channels 138 may be disposed on the activation sheet upper surface 28 such that their location substantially aligns with to the location of engagement elements 12 which may be cut during the formation of the element block cut pattern 76 (see FIGS. 15 and 16). FIG. 39 is a sectional view of the element activation sheet 136 of FIGS. 37 and 38, which depicts the transition mechanism filister 36 and multiple fluid delivery channels 138.

The fluid delivery channels 138 may be configured as elongated slots which extend from a respective transition mechanism fillister 36. For some embodiments of the fluid delivery channels 138, the fluid delivery channels 138 may extend from the transition mechanism filister 36 such that each fluid delivery channel 138 is substantially perpendicular to a lateral wall 58 of the respective transition mechanism filister 36 as shown in FIGS. 38 and 39. Each fluid delivery channel 138 may be configured to reach a depth 140 within the thickness 142 of the element activation sheet 136. For some embodiments of the fluid delivery channels 138, the depth 140 of each fluid delivery channel 138 may be from about ¼ to about ½ the thickness 56 of the element activation sheet 136 (see FIG. 39).

Figure 40:
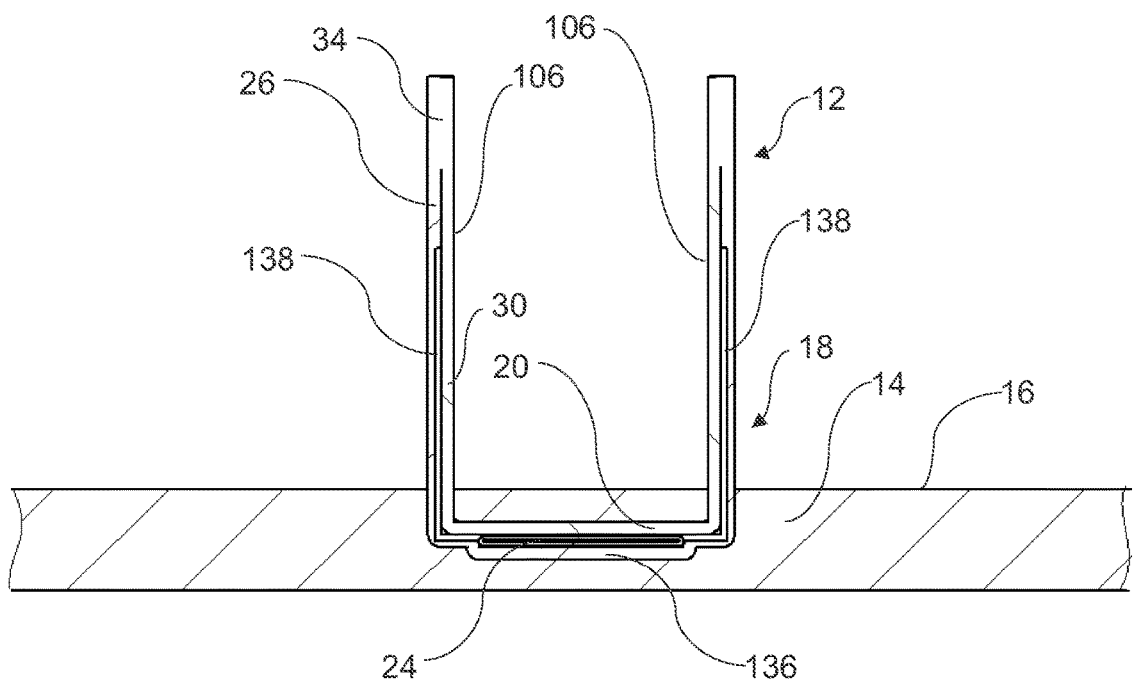
FIG. 40 is a sectional view of FIG. 36.
Figure 41:
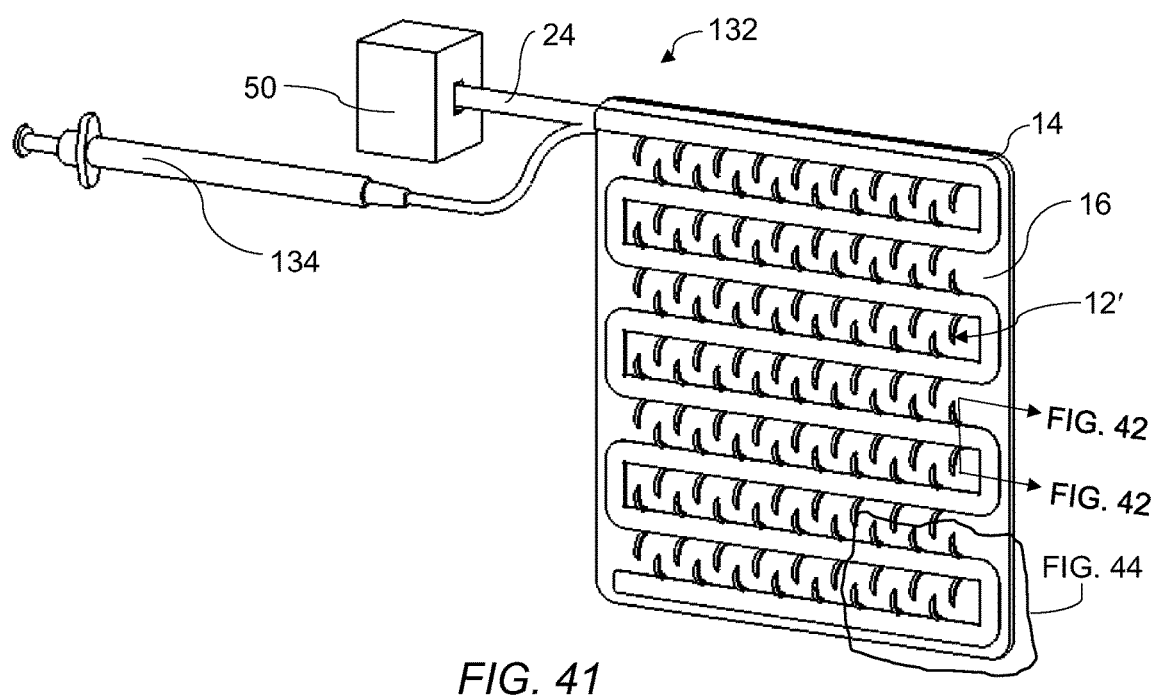
FIG. 41 depicts the adhesion device embodiment of FIG. 36 with the engagement elements in the engagement state.
Figure 42:
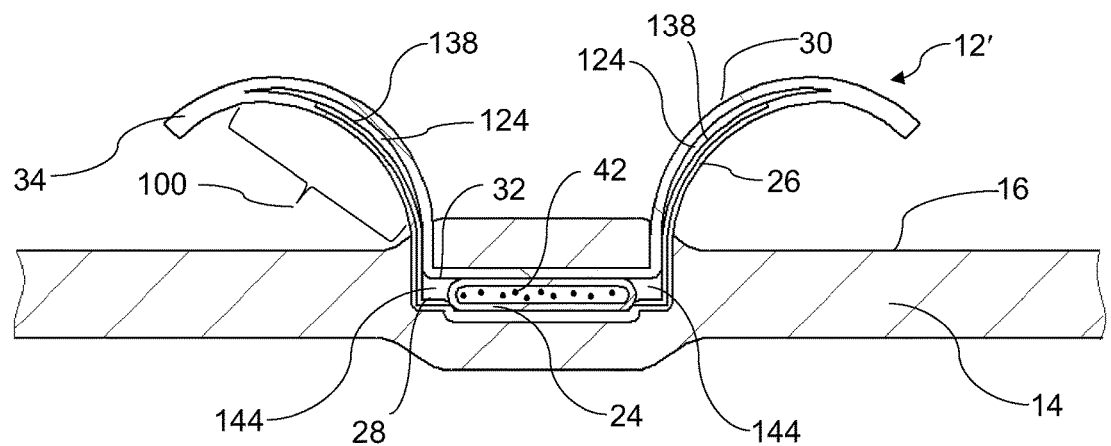
FIG. 42 is a sectional view of FIG. 41.

FIG. 40 is a section view of the adhesion device 132 which is depicted in FIG. 36 showing engagement elements in the deployment state 12 and a respective element transition mechanism 24 operatively coupled to the engagement elements 12. As depicted in FIG. 40, each engagement element 12 includes a fluid delivery channel 138 which is disposed on the interior activation surface 106 of the engagement element 12. FIG. 41 depicts the transition of the engagement elements from the deployment state 12 to the engagement state 12' by the control system 50. FIG. 42 is a sectional view of the adhesion device 132 showing engagement elements in the engagement state 12' and the respective element transition mechanism in the expanded configuration 24'.

Figure 43:
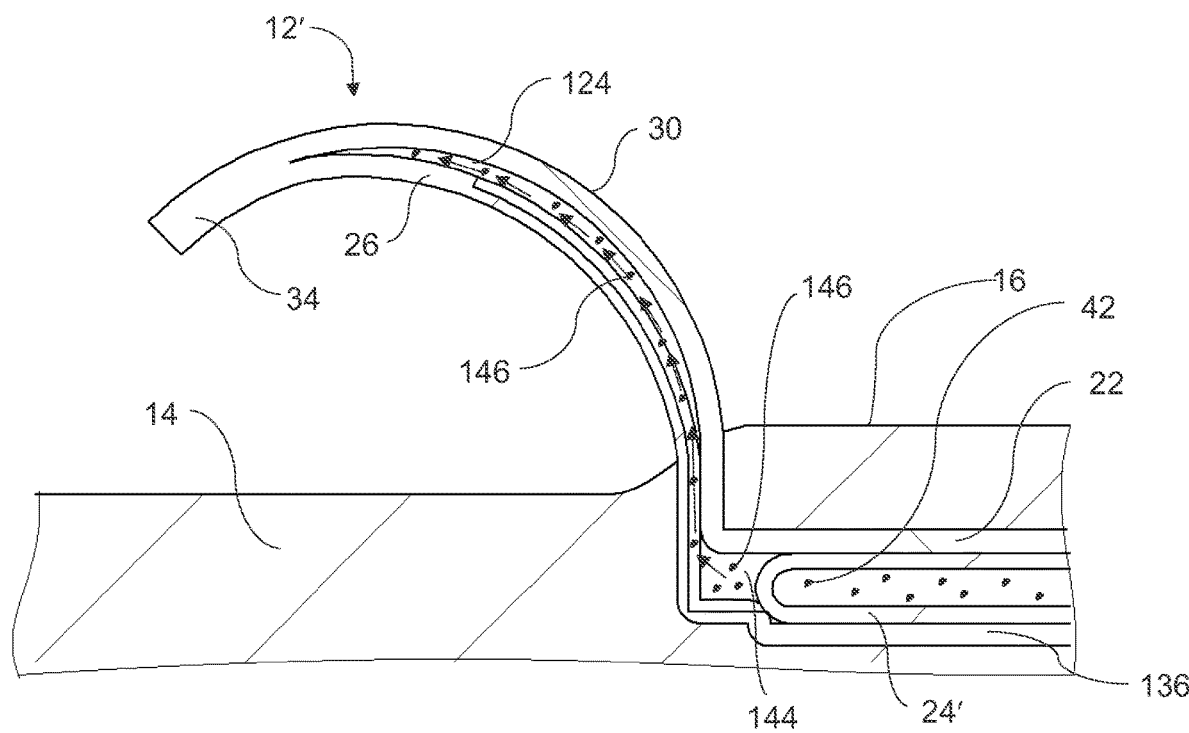
FIG. 43 is an enlarged view of FIG. 42.
Figure 44:
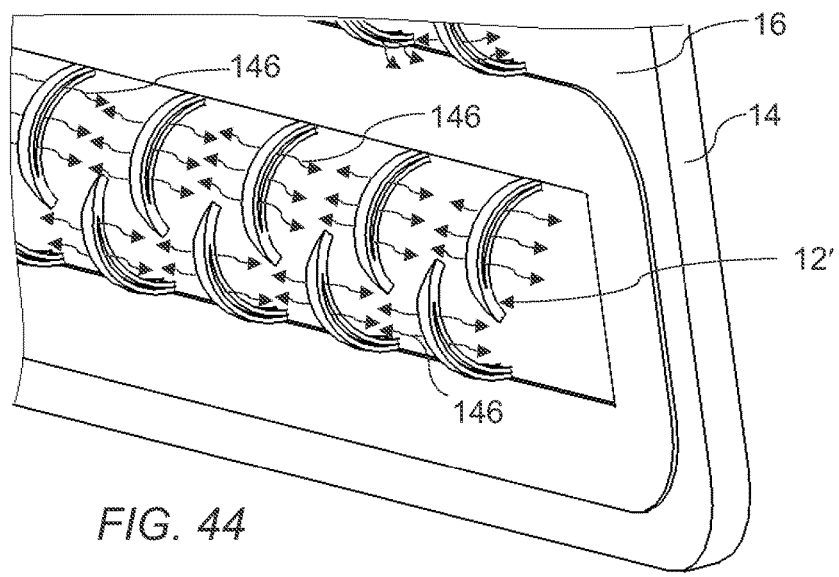
FIG. 44 is an enlarged view of FIG. 41.

FIG. 43 is a close-up view of FIG. 42 showing engagement elements in the engagement state 12' and the respective element transition mechanism disposed in the expanded configuration 24'. As shown in FIG. 43, expansion of the element transition mechanism to the expanded configuration 24' opens a transition channel 144 which is disposed between the deployment sheet lower surface 32 and the activation sheet upper surface 28. The transition channel 144 may be configured to be in fluid communication with the fluid delivery device 134. The transition channel 144 is in turn in fluid communication with respective fluid delivery channels 138 of respective engagement elements 12'. As has been discussed the transition of the engagement elements to the engagement state 12' results in the creation of the element engagement gap 124 within each element body segment 100 between each element activation section 26 and each element deployment section 30 as shown in FIG. 43. The element engagement gap 124 exposes the respective fluid delivery channel 138 to the surrounding target material 48 (not shown). Thus a fluid 146 could be delivered to the target material 48 as follows. A user could activate the fluid delivery device 134, which transports the fluid 146 into the transition channel 144. The fluid 146 could then enter each fluid delivery channel 138 of each respective engagement element 12'. The fluid 146 could then exit from each fluid delivery channel 138 through a respective element engagement gap 124 and into the target material 48 as shown in FIGS. 43 and 44.

Figure 45:
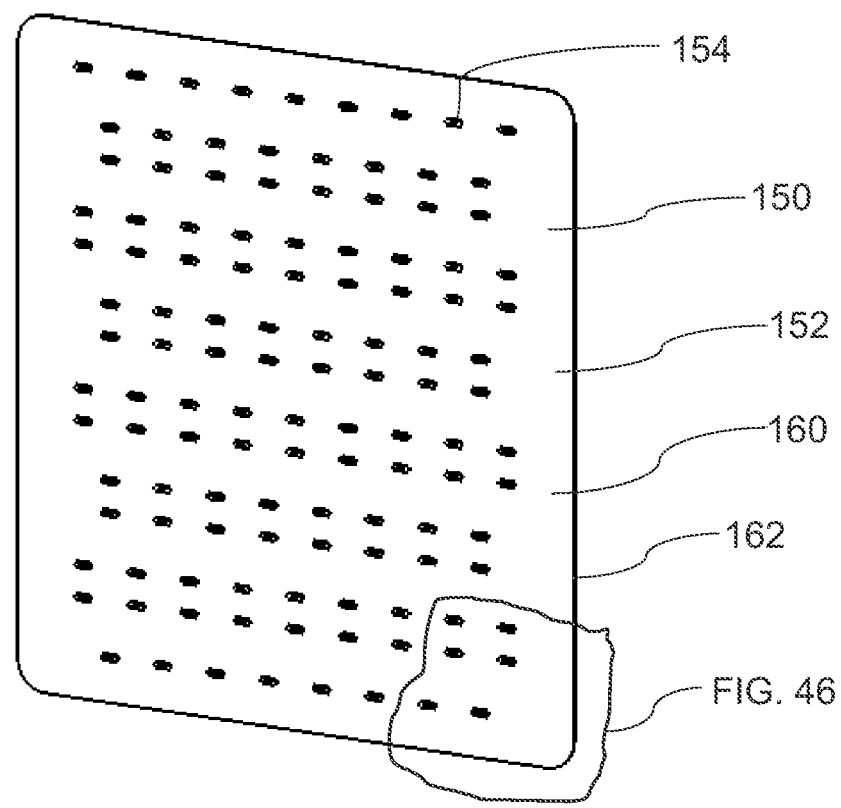
FIGS. 45 and 46 depict an embodiment of an element guide sheet.
Figure 46:
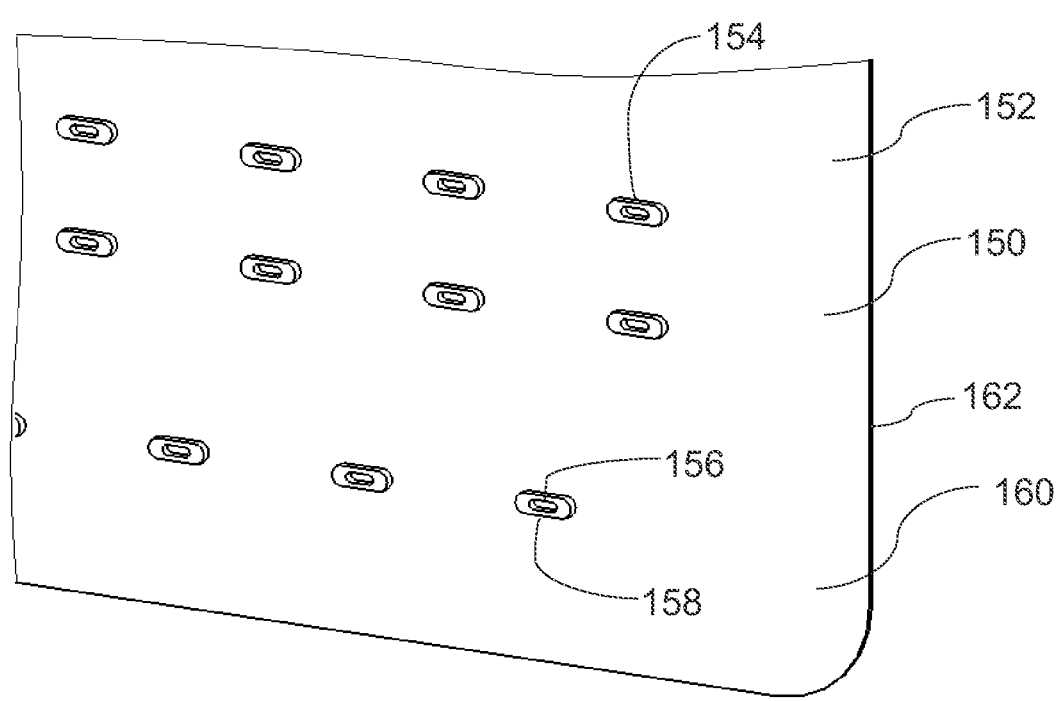
Figure 48:
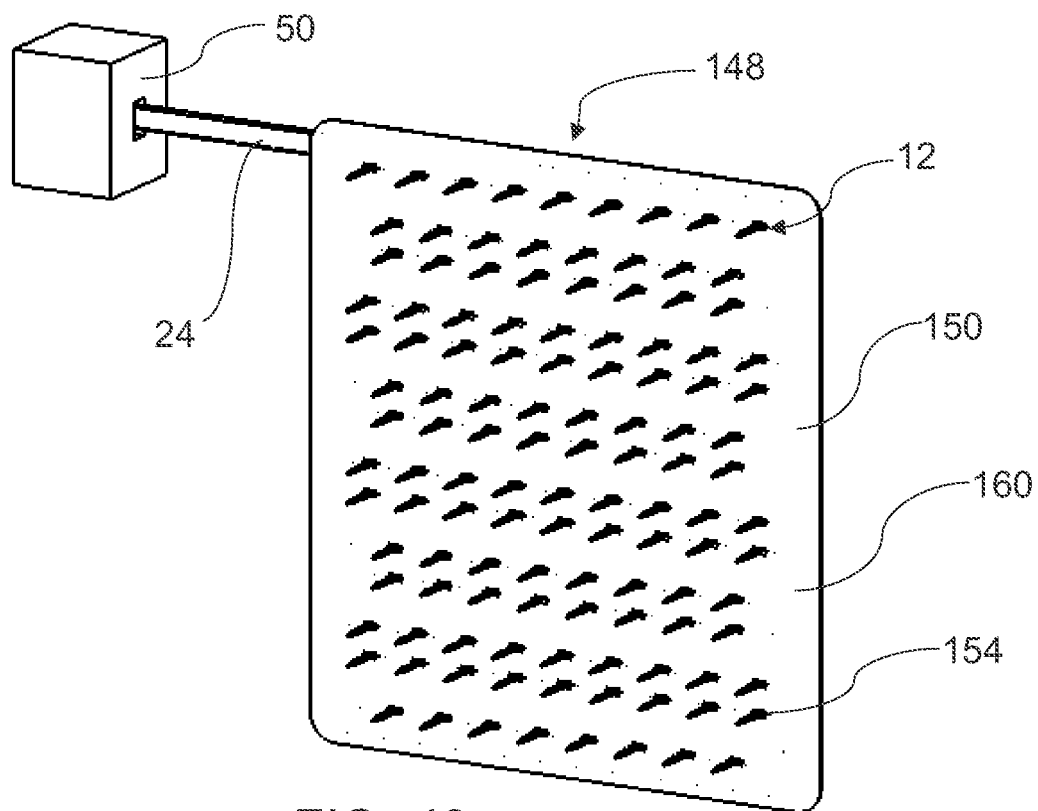
FIGS. 48 and 49 depicts the element guide sheet of FIG. 45 operatively coupled to the element block array of FIG. 47.
Figure 50:
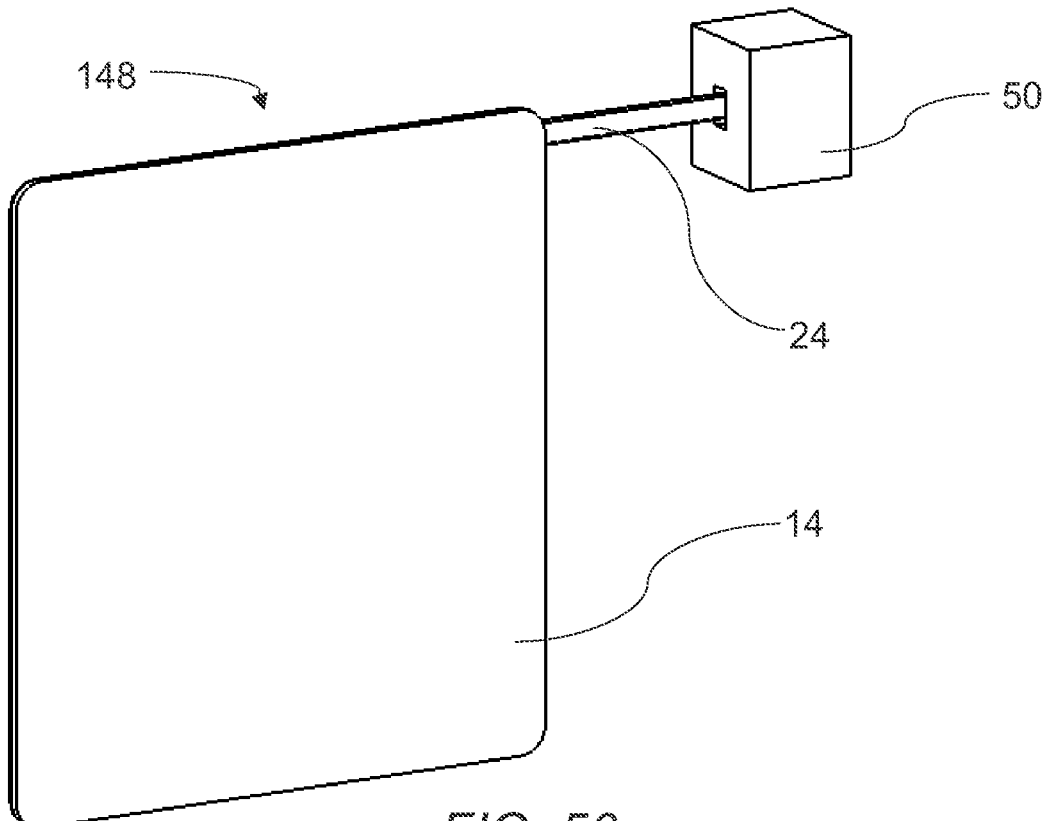
FIG. 50 depicts the element block array embodiment and element guide sheet embodiment of FIGS. 48 and 49 with the addition of an element support body.

FIGS. 48 and 50 depict an adhesion device embodiment 148 which incorporates an element guide sheet 150 (which is shown in FIGS. 45 and 46). The element guide sheet 150 may function as an alternative to, or an addition to the element support body 14. The adhesion device 148 may be configured as has been previously discussed with respect to the adhesion device embodiment 10, with the exception of the addition of the element guide sheet 150. That is to say that the component configurations, dimensions, and materials of the adhesion device 148 may be substantially equivalent to the adhesion device embodiment 10, except that adhesion device 148 includes the element guide sheet 150.

Figure 47:
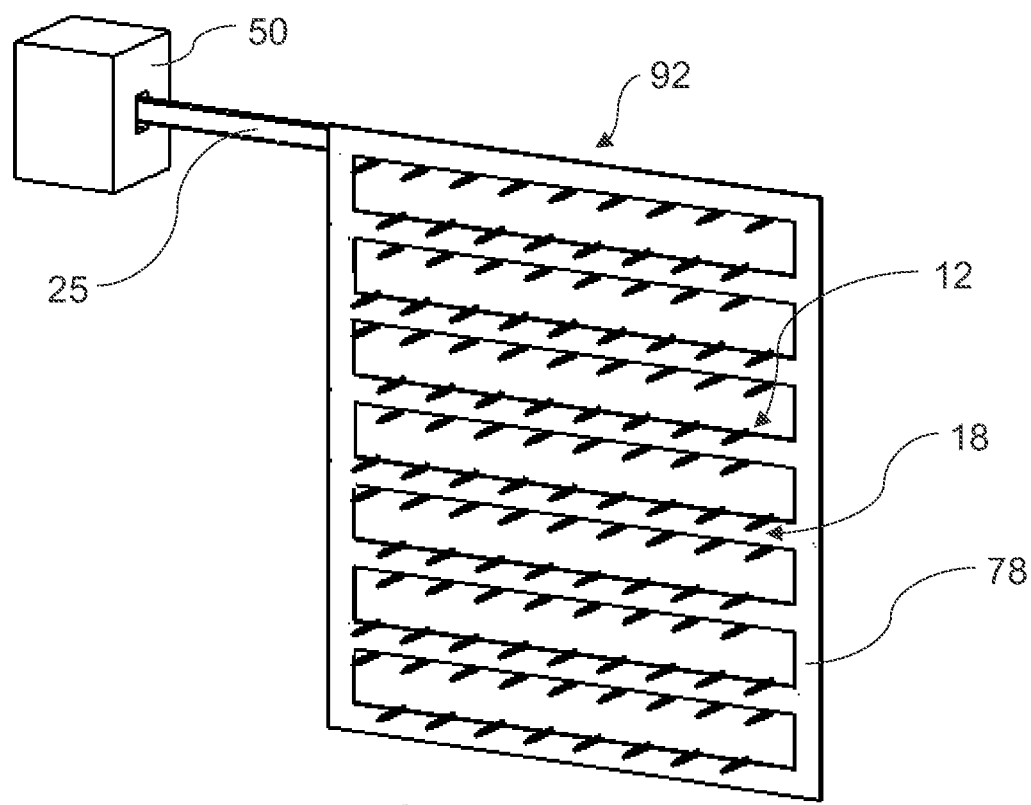
FIG. 47 depicts an embodiment of an element block array and a control system which is operatively coupled to the element block array.
Figure 49:
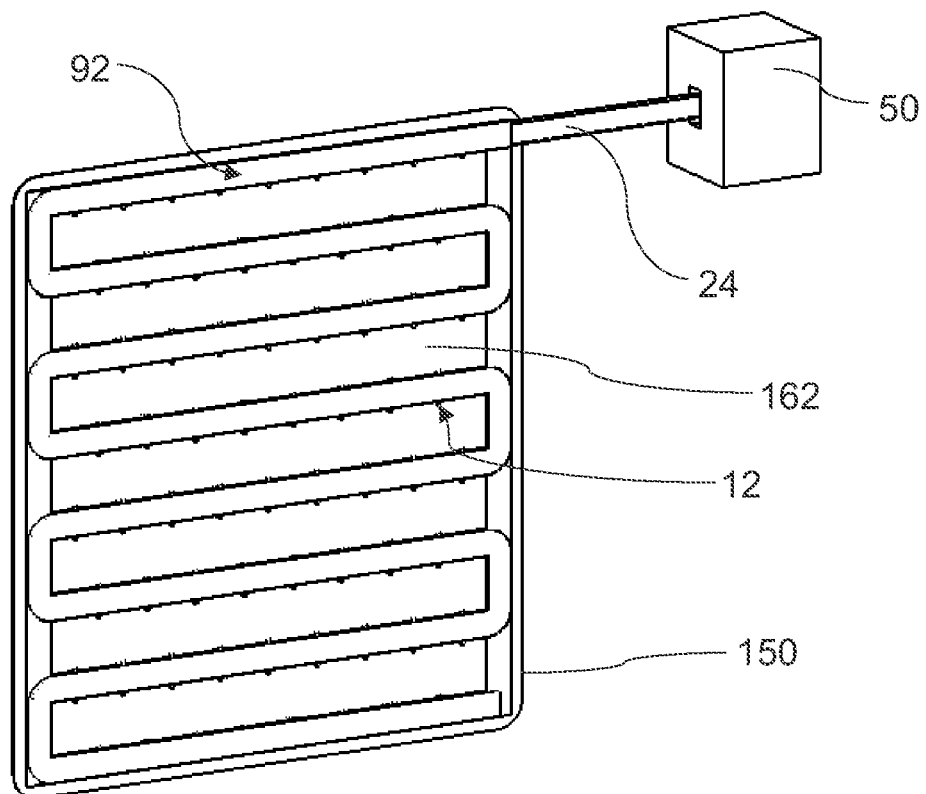
Figure 51:
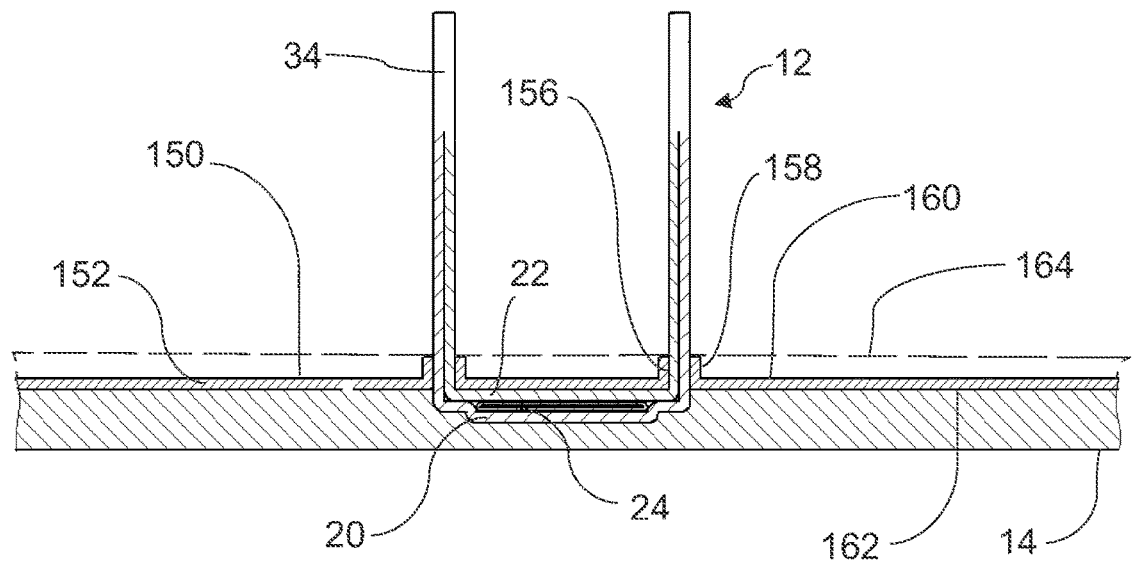
FIG. 51 is a sectional view of FIG. 48 depicting an element block assembly of the element block array of FIG. 50 with the engagement elements disposed in the deployment state.

The element guide sheet 150 may be formed from any suitable resilient rigid, semi-rigid, or flexible material. The element guide sheet 150 may be formed from any suitable polymer, metal, or composite material. The element guide sheet 150 may include an element guide body 152 and plurality of element guides 154, with each element guide 154 including an element slot 156 and an element boss 158. Each element boss 158 may extend from a top guide surface 160 of the element guide sheet 150, and each element slot 156 may extend from a bottom guide surface 162 through the element boss 158 as shown in FIG. 51. Each element guide 154 may be disposed on the element guide sheet 150 such that its location corresponds to the location of a respective engagement element 12 which is disposed on a suitably configured element block array 92. For example FIG. 47 shows an element block array 92 wherein element blocks assemblies 18 are connected by an element sheet frame 78 (a control system 50, and element transition mechanism 24 are also shown in FIG. 47). FIGS. 48 and 49 depict a suitably configured element guide sheet 150 which is operatively coupled to the element block array 92.

Each element guide 154 may have a respective engagement element 12 (which is operatively coupled to a respective element transition mechanism 24) inserted into its element slot 156 as shown in FIG. 51. Each element slot 156 mat have dimensions which substantially match the width and overall thickness of the respective engagement element 12. Each element slot 156 may be operatively coupled to the respective engagement element 12, in that the materials and dimensions of each element slot 156 may be configured to allow for the relative motion of the element activation section 26 with respect to the element deployment section 30 within the element body segment 100 of the respective engagement element 12.

After the element guide sheet 150 has been operatively coupled to the element block array 92 (thereby engaging the element guide sheet 150 with the element block array 92), an element support body 14 may be molded over each element transition mechanism 24 of the element block array 92 as shown in FIG. 50. For some embodiments of the adhesion device 148 (such as the embodiment shown in FIGS. 51 and 52), the element support body 14 may encompass each element transition mechanism 24 of the element block array 92 and may be adjacent to the bottom guide surface 162. For other adhesion device embodiments, the element support body 14 may encompass each element transition mechanism 24 of the element block array 92 and may also encompass the element guide sheet 150. That is to say that the element support body 14 may also encompass the top guide surface 160 and the element bosses 158 of the element guide sheet 150 as indicated by the dashed line 164 in FIGS. 51 and 52.

Figure 52:
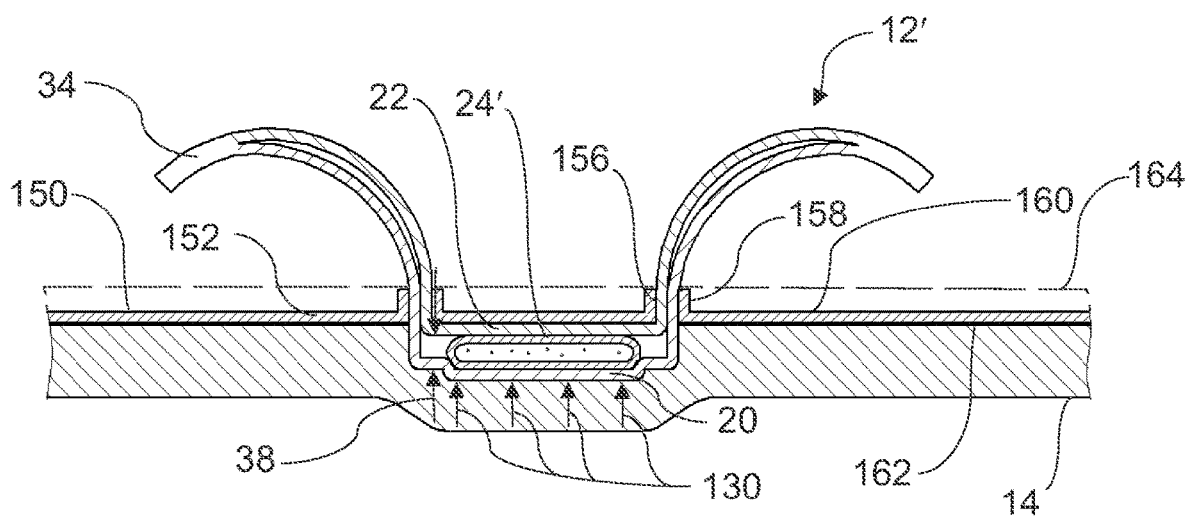
FIG. 52 is the sectional view of FIG. 51 depicting the element block assembly of the element block array of FIG. 50 with the engagement elements disposed in the engagement state.

The element support body 14 may be configured to provide restorative forces 130 to the element activation sheet 20 of each element transition mechanism when each element transition mechanism is disposed in the expanded configuration 24' (see FIG. 52). The restorative forces may 130 facilitate the transition of the respective element transition mechanism from the expanded configuration 24' to the neutral configuration 24.

Each element guide 154 may be configured while each respective element transition mechanism is disposed in the neutral configuration 24 to constrain each respective engagement element in the deployment state 12 which is suitable for insertion into (or the removal from) the target material 48. When disposed in the deployment state 12, each engagement element may be substantially perpendicular to the top guide surface 160. When the respective element transition mechanism is disposed in the expanded configuration 24', each element guide 154 may be configured to constrain each respective engagement element in an engagement state 12' wherein each respective engagement element 12' is eccentrically tensioned as the result of the resulting transition gap 38 into a reactive flexure which is configured to mechanically capture surrounding target material 48.

Figure 53:
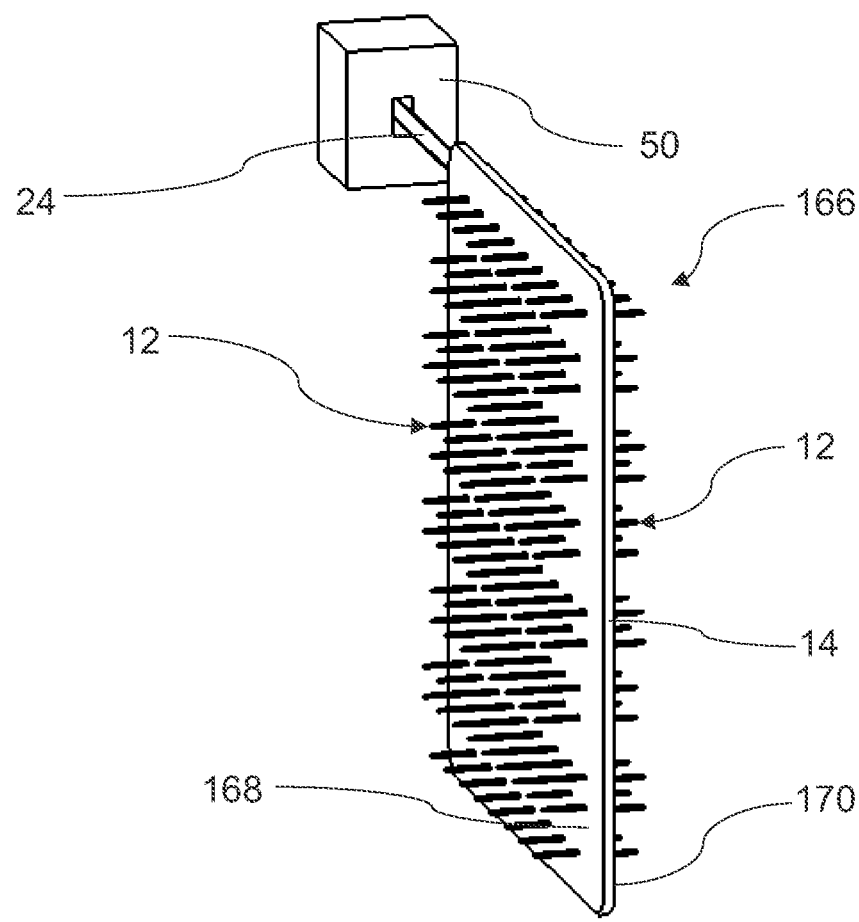
FIG. 53 is an isometric view of an adhesion device which incorporates multiple engagement elements which extend from a first engagement surface, and multiple engagement elements which extend from a second engagement surface.

Some embodiments of adhesion devices may incorporate engagement elements on more than one surface. This configuration may be useful for applications wherein two materials/surfaces are joined together. Thus medical applications may include wound closure, tissue grafting, tissue joining, tissue modification or the like. Industrial applications may include bonding two materials together. The adhesion deice 166 which is depicted in FIG. 53 has a first engagement surface 168 and a second engagement surface 170. A plurality of engagement elements 12 extend from the first engagement surface 168, and a plurality of engagement elements 12 extend from the second engagement surface 170.

Figure 54:
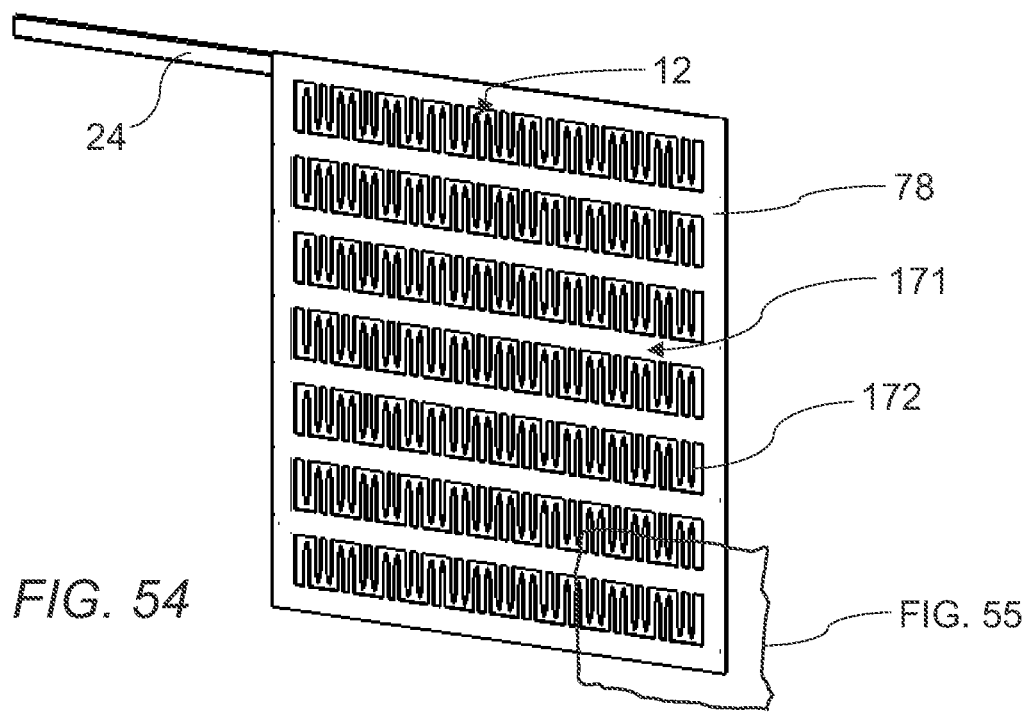
FIGS. 54 and 55 are an isometric views of an element block cut pattern which is used to fabricate the adhesion device embodiment of FIG. 53.
Figure 55:
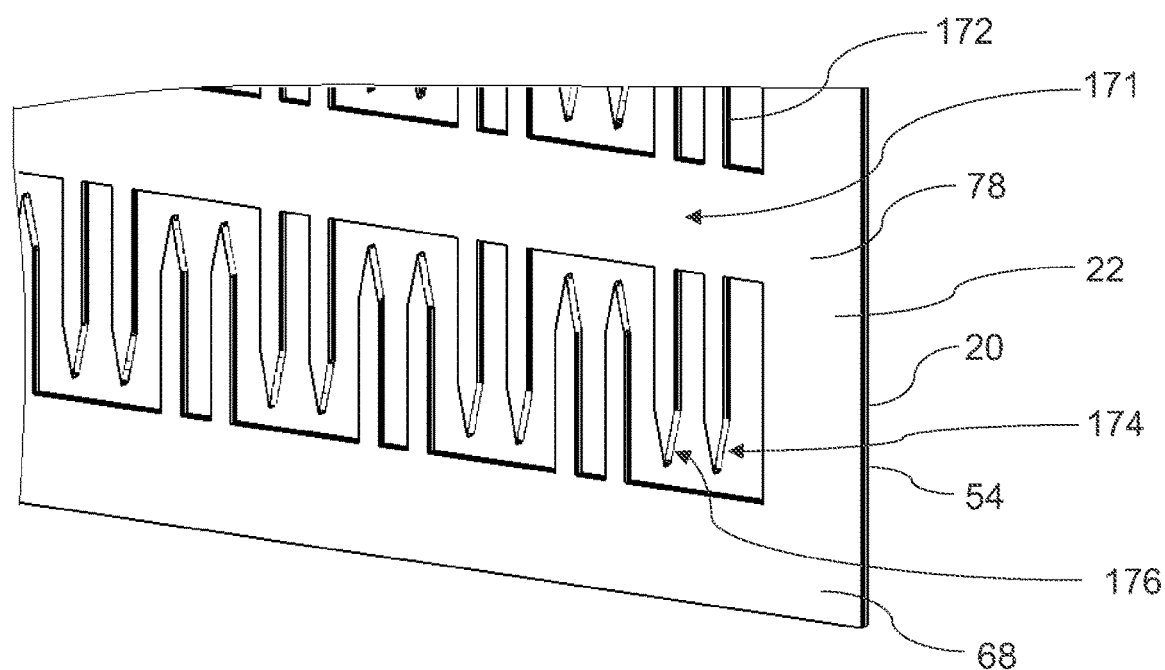

FIG. 54 depicts a pattern of element block assemblies 171 which are connected by an element sheet frame 78. The element block cut pattern 172 (which is depicted in FIG. 55) differs from the element block cut pattern 76 which was previously discussed and depicted in FIG. 17. In the element block cut pattern 172 shown in FIG. 55, two adjacent engagement elements a first engagement element 174 and a second engagement element 176 are disposed where a single engagement element 12 was disposed in the element block cut pattern depicted 76 in FIG. 17.

Figure 56:
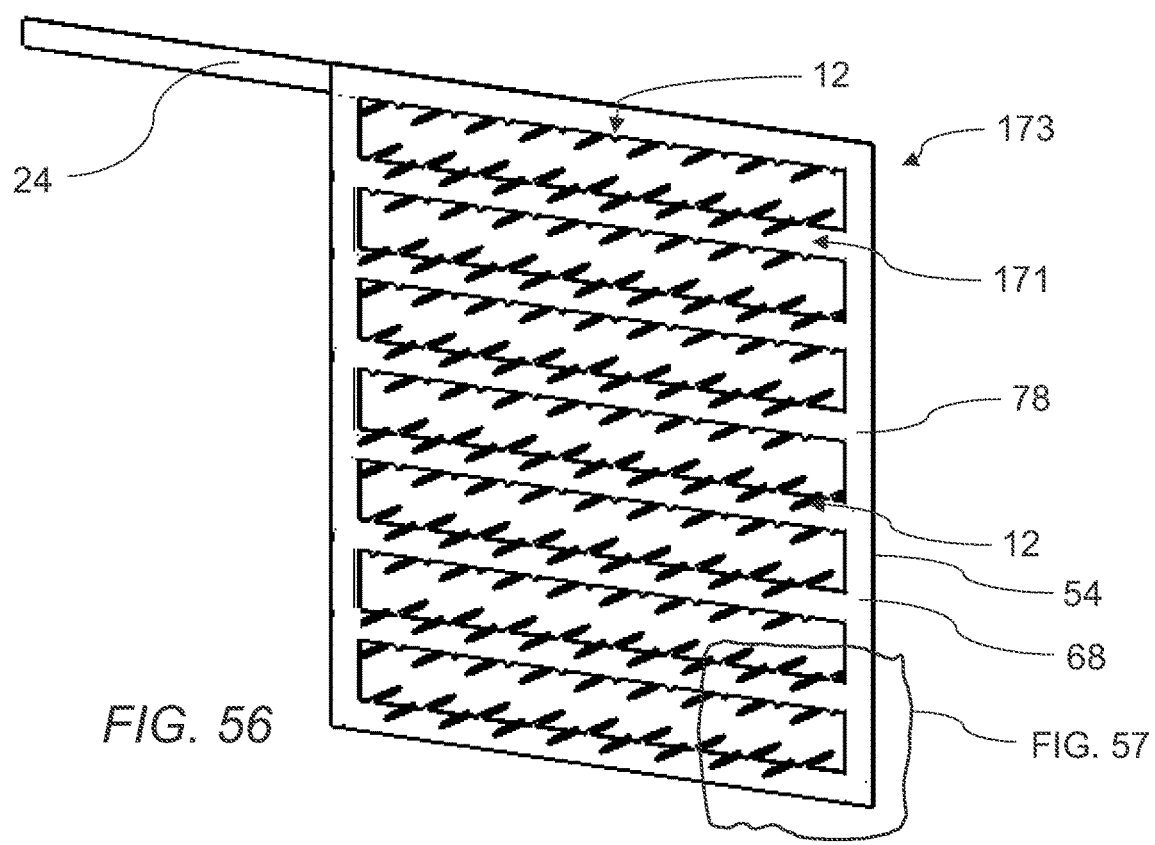
FIGS. 56 and 57 are an isometric views of an element block array formed from the element block cut pattern of FIGS. 54 and 55, with the engagement elements disposed in the deployment state.
Figure 57:
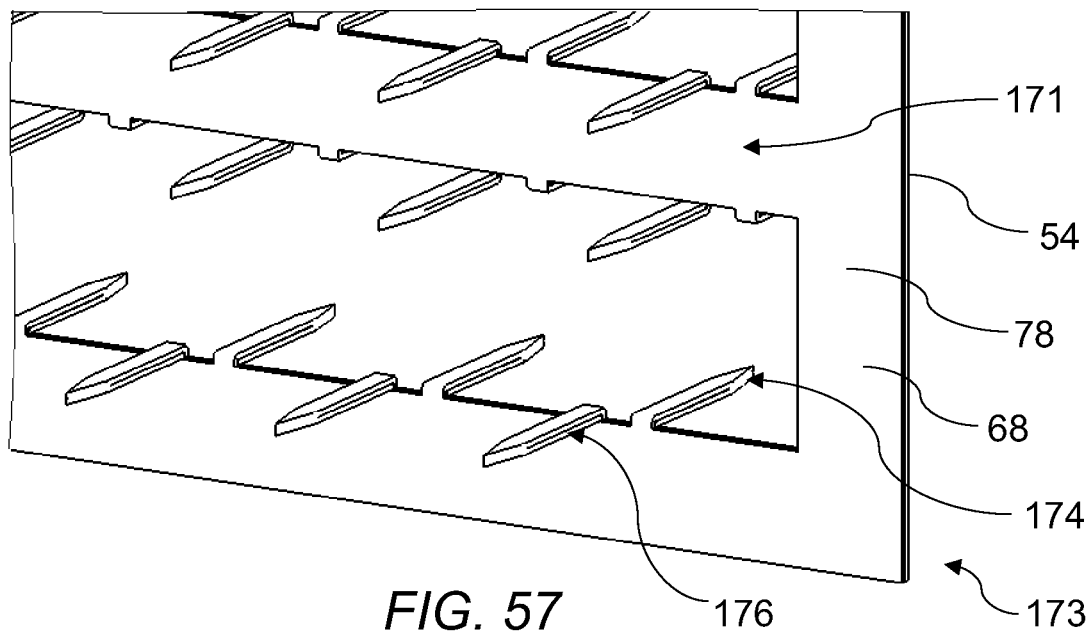

FIGS. 56 and 57 depict the pattern of element block assemblies 171 with some of the engagement elements 12 formed such that they are perpendicular to the deployment sheet upper surface 68, and some of the engagement elements 12 formed such that they are perpendicular to the activation sheet lower surface 54 within an element block array 173. As shown in FIG. 57, adjacent engagement elements 12 may be formed such that they each extend in a perpendicular fashion from the respective element block assembly 171, yet in opposite directions to each other. That is to say that the first engagement element 174 may be formed such that it is substantially perpendicular to the activation sheet upper surface 68 and the second engagement element 176 may be formed such that it is substantially perpendicular to the activation sheet lower surface 54. Thus the first engagement element 174 points in a direction which is substantially 180 degrees from the second engagement element 176. Other adjacent engagement elements 12 which are disposed on the element block array 173 may be similarly configured.

Figure 58:
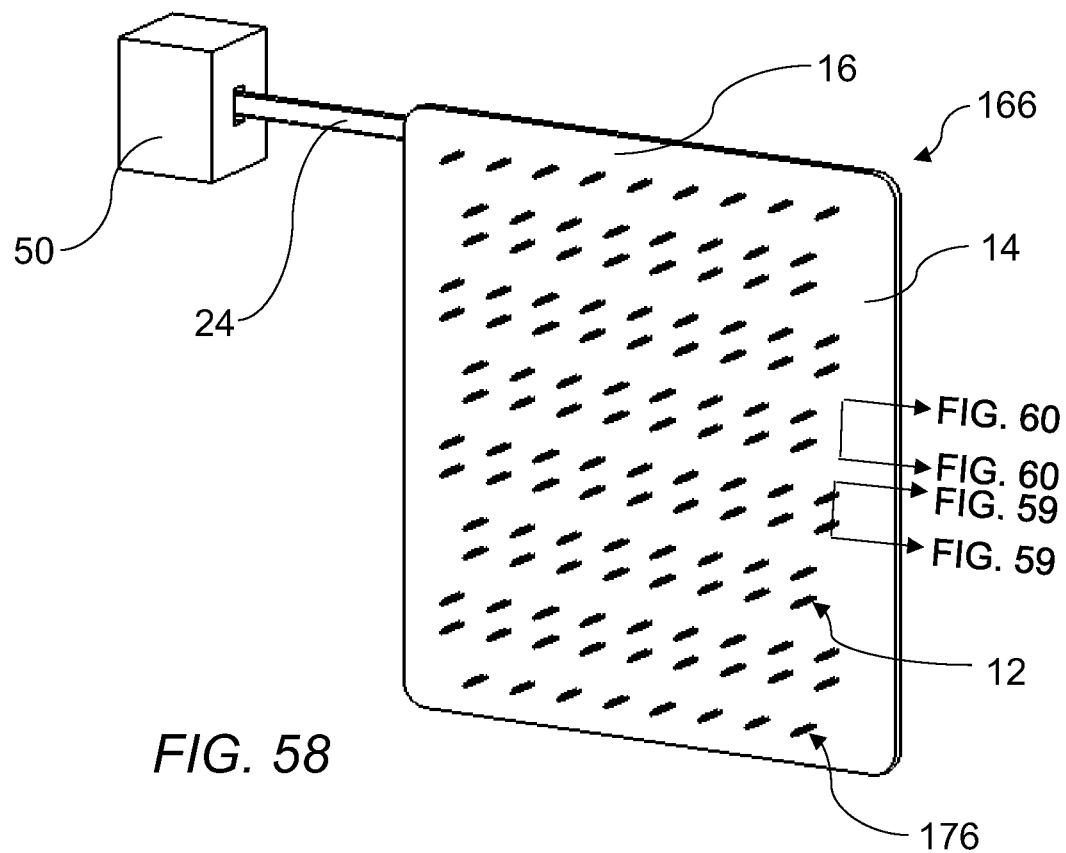
FIG. 58 depicts the element block array of FIG. 55 with the addition of an element support body.

FIG. 58 depicts an element support body 14 which is molded over the element block array 173 such that each element transition mechanism 24 is encompassed by the element support body 14. FIG. 58 also includes a control system 50 and an element transition mechanism 24 which is configured as a single balloon. The adhesion device 166 is deployed in a manner that is analogous to the method which has been previously discussed with regards to FIGS. 23-31, with the exception that a given element block assembly 171 will have respective engagement elements 12 which extend from the first engagement surface 168 and respective engagement elements 12 which extend from the second engagement surface 170.

Figure 59:
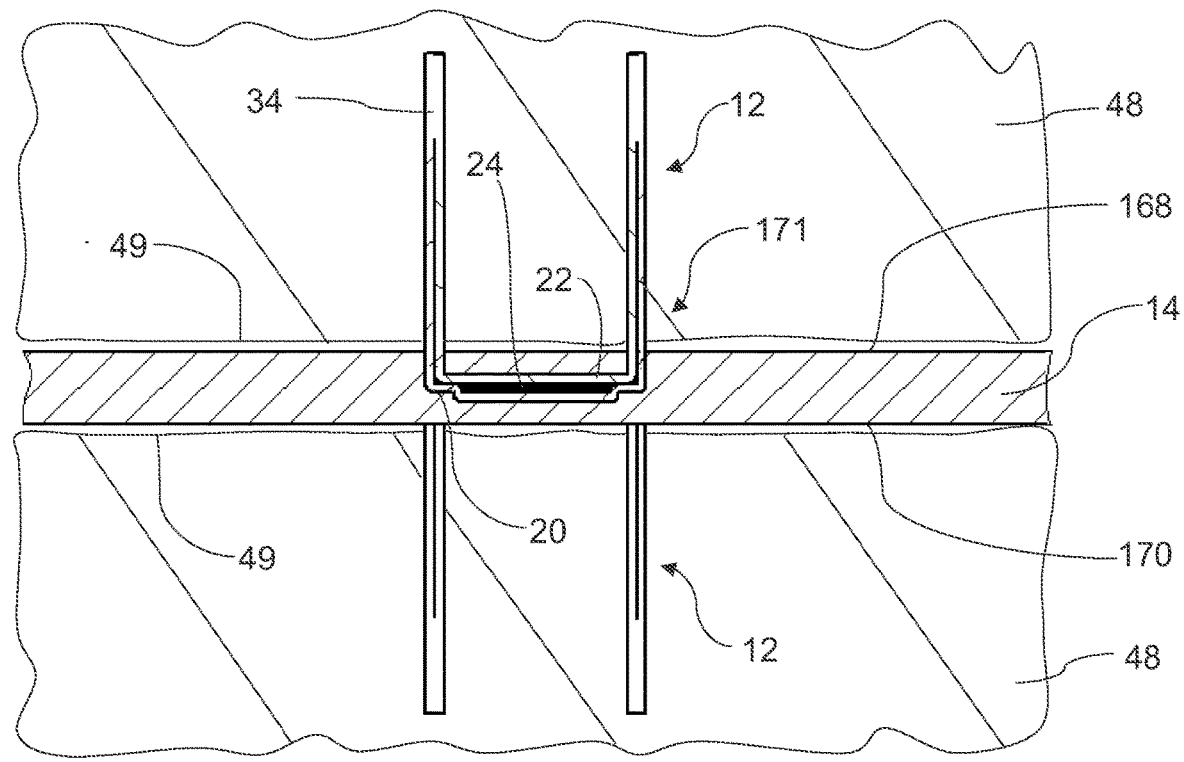
FIGS. 59 and 60 are sectional views of FIG. 58.
Figure 60:
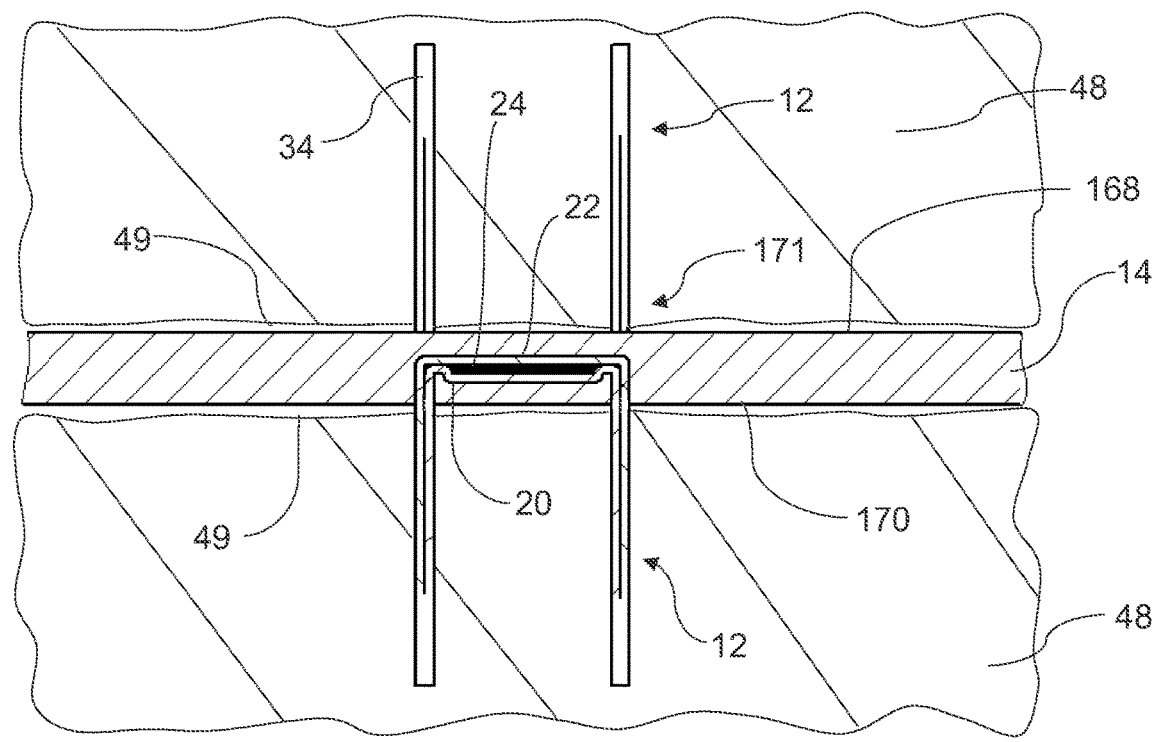
Figure 61:
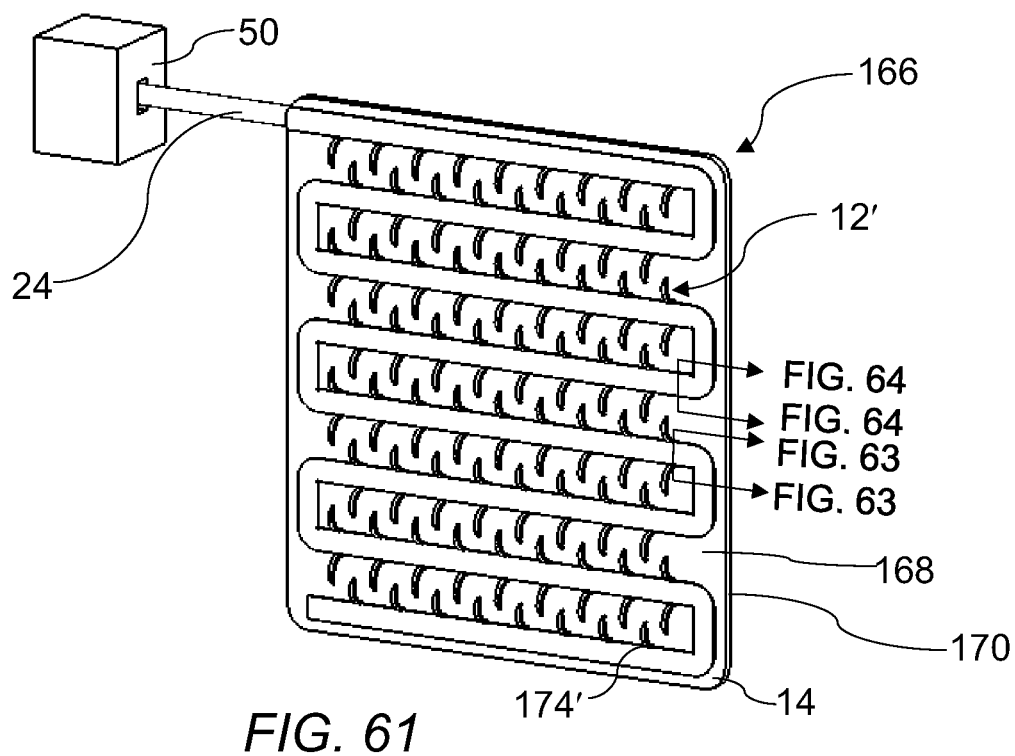
FIGS. 61 and 62 are isometric views of the adhesion device of FIG. 53 with the engagement elements disposed in the engagement state.
Figure 62:
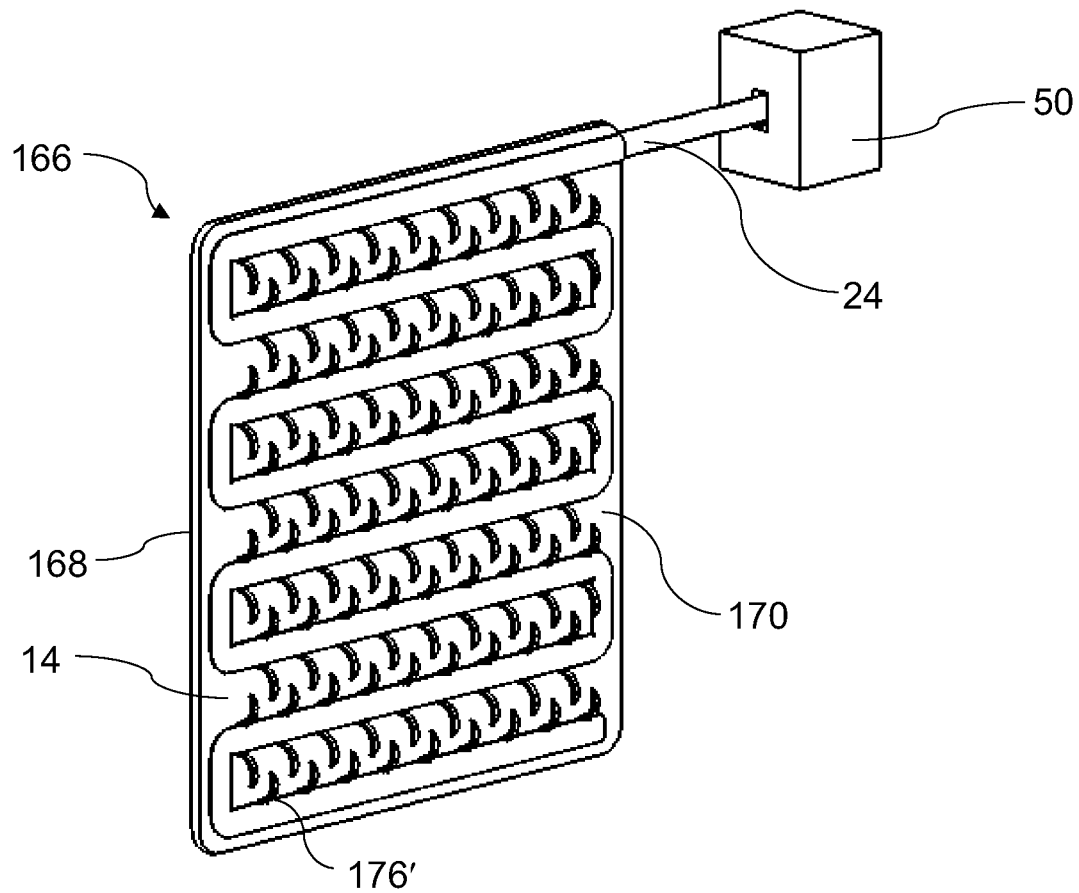

FIGS. 59-64 depict a deployment sequence for the adhesion device 166. FIG. 58 is a section view of an element block assembly 171 depicting engagement elements 12 in the deployment state which extend from the first engagement surface 168. The element block assembly 171 includes the element transition mechanism 24, an element activation sheet 20, and an element deployment sheet 22. FIG. 60 is a section view of the element block assembly 171 depicting engagement elements in the deployment state 12 which extend from the second engagement surface 176. FIGS. 61 and 61 depict the adhesion device 166 with the engagement elements transitioned to the engagement state 12' (including engagement elements 174' and 176').

Figure 63:
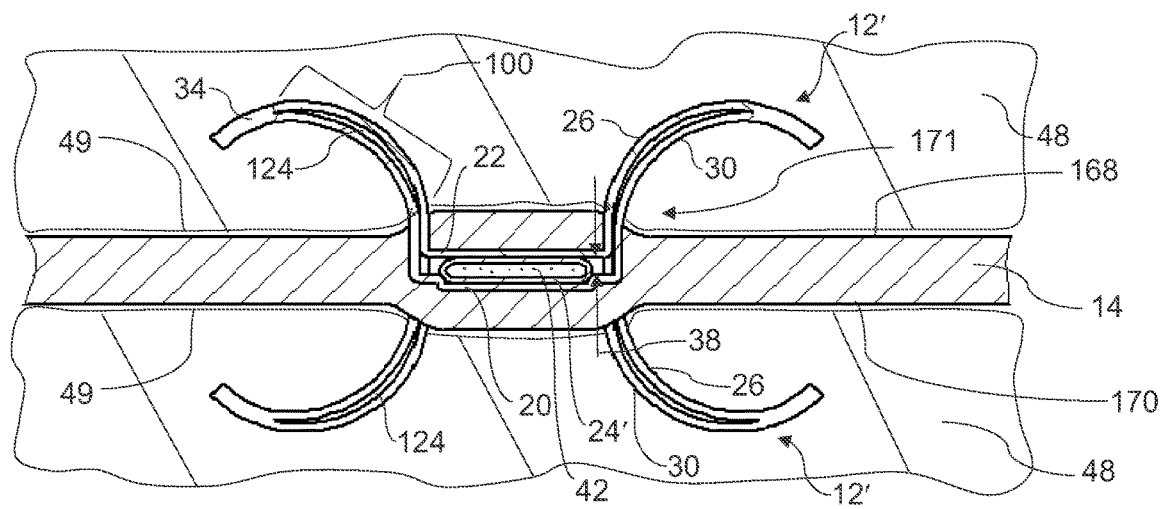
FIGS. 63 and 64 are sectional views of FIG. 61.
Figure 64:
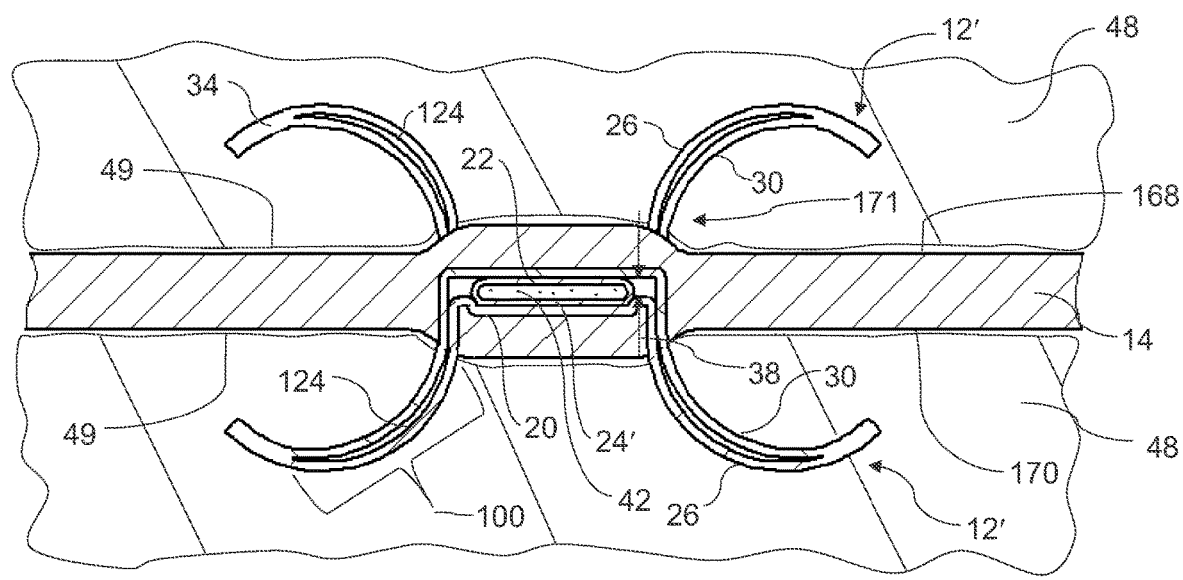

FIG. 63 is the same section view as FIG. 59 but with the engagement elements transitioned to the engagement state 12', while FIG. 64 is the same section view as FIG. 60 but with the engagement elements transitioned to the engagement state 12'. The engagement elements 12' which are shown in section view in FIG. 63 are transitioned as follows: a transition gap 38 caused by the transition of the element transition mechanism from the neutral configuration 24 to the expanded configuration 24' causes translational motion of each element activation section 26 with respect to each element deployment section 30 within each respective element body segment 100. This results in eccentric tensioning of each engagement element 12' by the respective element activation section 26 and a reactive flexure of each engagement element 12'.

The engagement elements 12' which are shown in section view in FIG. 64 are transitioned as follows: the transition gap 38 caused by the transition of the element transition mechanism from the neutral configuration 24 to the expanded configuration 24' causes translational motion of each element deployment section 26 with respect to each element activation section 30 within each respective element body segment 100. This results in a shortening of each element deployment section 30 with respect to each element activation section 26 within the element body segment 100. This results in eccentric tensioning of each engagement element 12' by the respective element activation section 26 and a reactive flexure of each engagement element 12'. Thus within one element block assembly 171 the element transition mechanism 24' has transitioned engagement elements which extend from the first engagement surface 174 to the engagement state 12', and engagement elements which extend from the second engagement surface 170 to the engagement state 12'. All of the engagement elements of the adhesion device 166 which have been transitioned to the engagement state 12' can be subsequently transitioned back to the deployment state 12 as has been previously described with regards to FIGS. 23-31.

The adhesion device 166 can thus be deployed into and removed from multiple surfaces 49 of a given target material 50 in a manner which is similar to that which has been previously discussed. That is to say that the first engagement surface 168 could be deployed into a first target surface, and the second engagement surface 170 could be deployed into a second target surface, then then engagement elements could be transitioned from the deployment state 12 to the engagement state 12'. Removal of the adhesion device 166 would involve transitioning the engagement elements from the engagement state 12' to the deployment state 12, and subsequently removing the adhesion device 166 from the first and second target surfaces.

The embodiments of activation devices which have been discussed thus far have utilized a balloon apparatus as the element transition mechanism 24. The balloon apparatus utilizes fluid pressure in order to reversibly transition from the neutral configuration 24 to the expanded configuration 24'. Some embodiments of the balloon apparatus which have been discussed may be configured to facilitate in the transition of respective engagement elements from the engagement state 12' to the deployment state 12. For example, a vacuum may be applied to the balloon apparatus in order to transition the balloon apparatus from the expanded configuration 24' to the neutral configuration 24. As the balloon apparatus is transitioned from the expanded configuration 24' to the neutral configuration 24, respective engagement elements may in turn be transitioned from the engagement state 12' to the deployment state 12. In some cases, the vacuum applied to the balloon apparatus may act in addition to the restorative forces 130 applied to the element activation sheet 26 and the element deployment sheet 30 by the element support body 14 which have been previously discussed.

FIGS. 65-85 illustrate alternate embodiments of element transition mechanisms which utilize various other means in order to facilitate the reversible transition of the respective element transition mechanism from the neutral configuration to the expanded configuration. The other means utilized to reversibly transition the respective element transition mechanism from the neutral configuration to the expanded configuration may include the shape memory transition of an insert, manipulation of multiple patterned inserts, and electrical capacitance. As with the balloon apparatus element transition mechanism 24 theses element transition mechanisms are configured to reversibly transition from a neutral configuration with respective engagement elements which are operatively coupled to the element transition mechanism disposed in the deployment state 12, to an expanded configuration with the respective engagement elements disposed in the engagement state 12'. Any configuration of element transition mechanism which is discussed herein may be used with any suitable configuration of adhesion device which is discussed herein.

Figure 65:
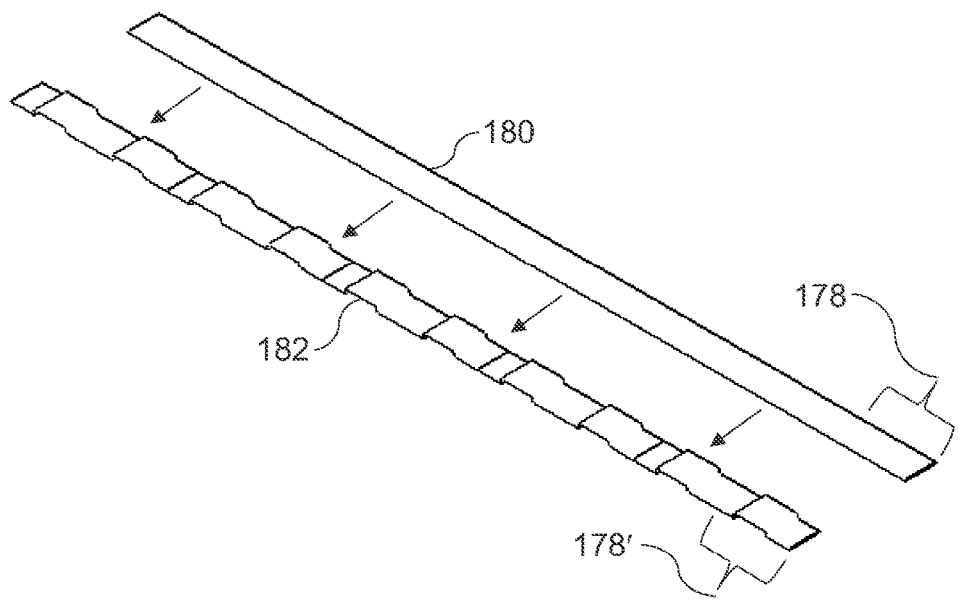
FIG. 65 is a pictorial view of linear pattern of shape memory inserts depicted transitioning from the neutral configuration to the expanded configuration.

FIGS. 65-71 depict an embodiment of an element transition mechanism 178 which is configured as a shape memory insert. The shape memory insert 178 may be fabricated from a shape memory metal or a shape memory polymer. The shape memory insert may be configured to reversibly transition between a neutral configuration 178 wherein the shape memory insert has a neutral insert profile 180, and an expanded configuration 178' wherein the shape memory insert has an expanded insert profile 182. A difference in height between the neutral insert profile 180 and the expanded insert profile 180 being the transition gap 38. This is illustrated in FIG. 65, which depicts a linear pattern of shape memory inserts 178 which are suitably connected together. In FIG. 65, the linear pattern of shape memory inserts are depicted transitioning from the neutral configuration 178 to the expanded configuration 178'.

The transition may occur as the result of the appropriate shape memory transition stimulus which is applied to the shape memory insert element transition mechanism 178. For example shape memory inserts which are fabricated from shape memory materials which are thermally transitioned may be transitioned from the neutral configuration 178 to the expanded configuration 178' with the application of heat to the shape memory insert. The same procedure would apply to shape memory inserts 178 which are fabricated from shape memory materials which are transitioned using a change in Ph of the surrounding environment, the application of electric current, the application of a magnetic field, the application of UV light, or any other suitable shape memory transition method. For the example discussed below, a shape memory metal which is thermally activated is used. However, any suitable shape memory material with any suitable associated shape memory transition method may be used to respectively fabricate and transition the shape memory inserts 178.

Figure 66:
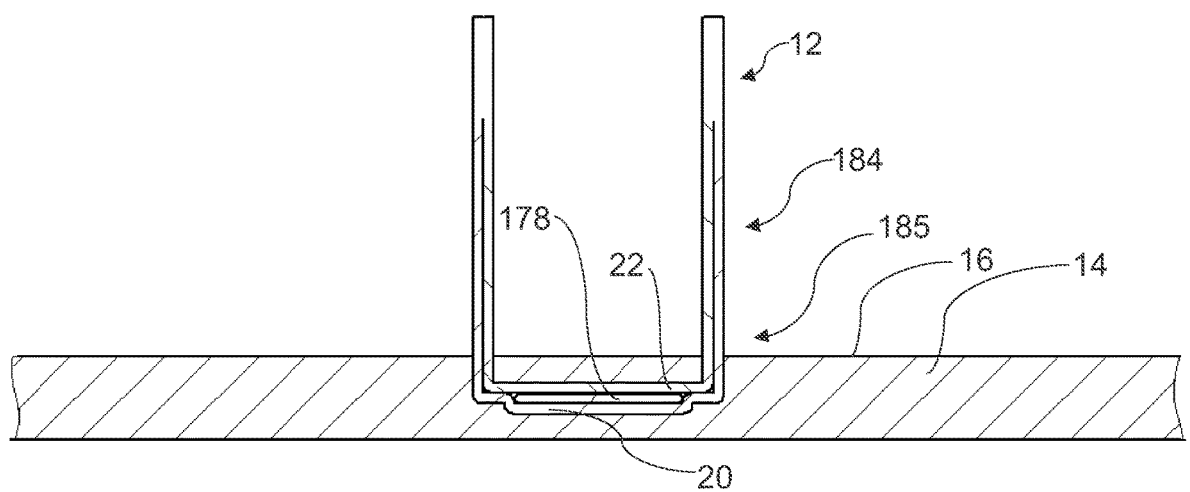
FIGS. 66-68 are sectional views of an element block assembly which utilizes the shape memory insert of FIG. 65 as the element transition mechanism, in each case the shape memory insert being disposed in the neutral configuration and the engagement elements being disposed in the deployment state.
Figure 67:
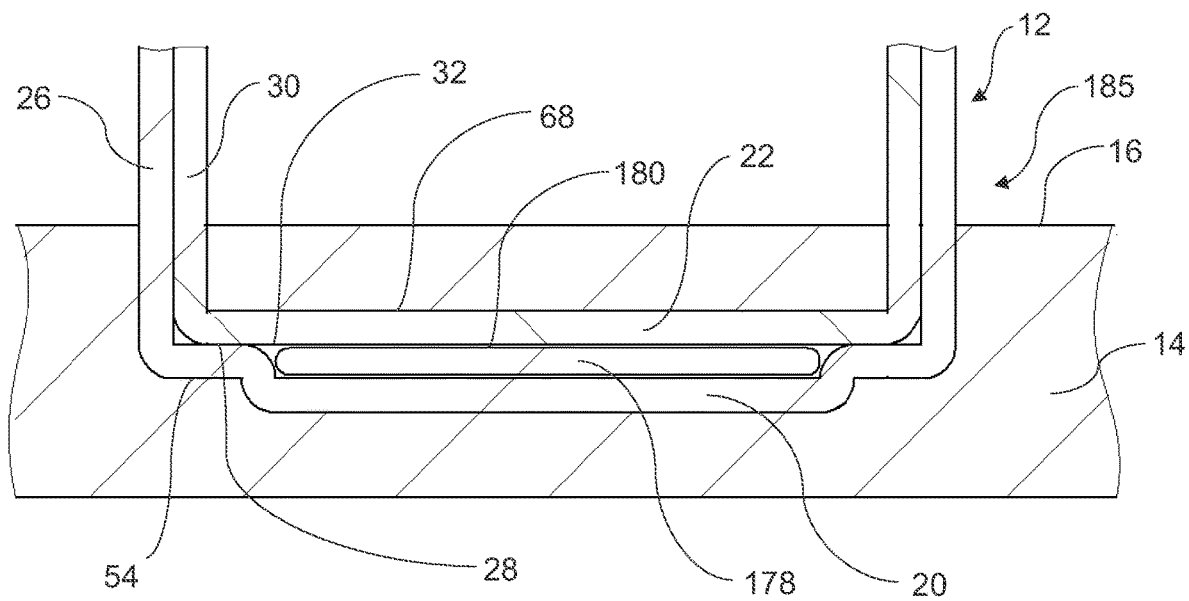
Figure 68:
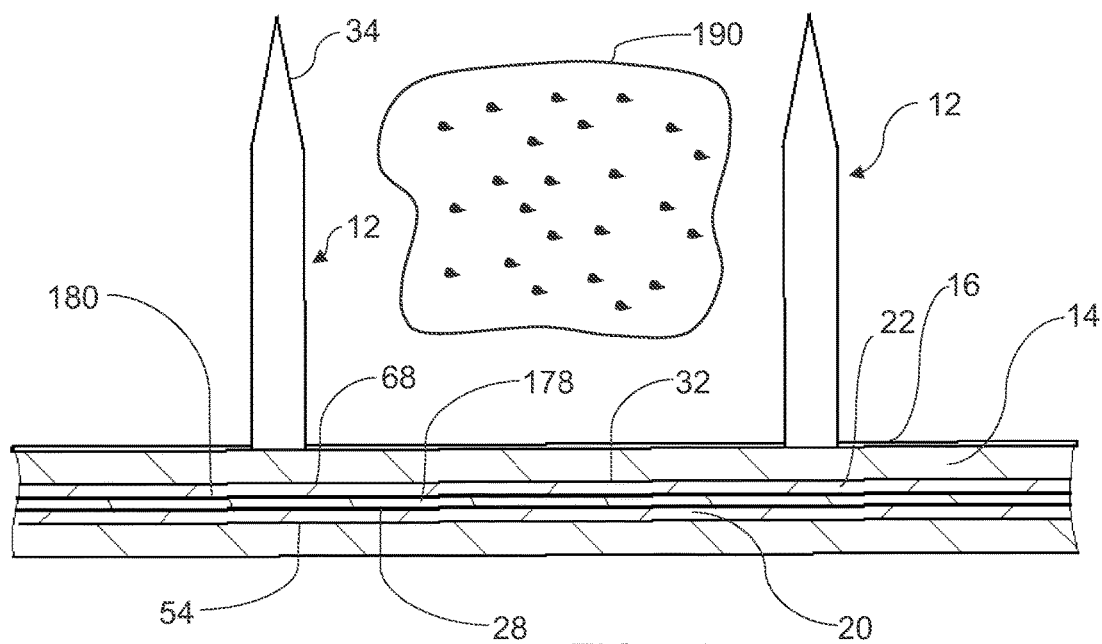

FIGS. 66-71 are section views of an adhesion device 184 embodiment which utilizes a shape memory insert 178 in order to reversibly transition the engagement elements from the deployment state 12 to the engagement state 12'. The adhesion device embodiment 184 could be any of the adhesion device configurations which are discussed herein. FIGS. 66-68 are section views of the adhesion device embodiment 184 showing an element block assembly 185, an element support body 14, an element activation sheet 20, an element deployment sheet 22, an element transition mechanism which is configured as a shape memory insert 178, and multiple engagement elements which are disposed in the deployment state 12 and which are operatively coupled to the shape memory insert 178.

The element transition mechanism is configured as a shape memory insert 178, which in this case of this example is fabricated from a shape memory metal (such as Nitinol) which is thermally transitioned (that is to say that the shape memory material is transitioned with the application of thermal energy). The shape memory insert 178 material may have a transition temperature Af, wherein if the temperature of the shape memory material is raised above Af, a shape memory transition of the material will occur. A shape memory polymer insert which was thermally activated would have a transition temperature T which would correspond to Af for the metallic material (thus allowing for shape memory polymer material to be substituted into this example using transition temperature T instead of Af). For the most part when the shape memory material is maintained at a temperature above Af the material is disposed in austenite state (wherein a "programmed" shape is assumed), and when the material is maintained at a temperature below Af it is disposed in the martensite state (wherein it is essentially malleable). The shape memory insert may be disposed in the neutral configuration 178 as depicted in FIGS. 66-68, wherein the shape memory insert has the neutral insert profile 180 (see FIG. 67), this may correspond to the shape memory material being below Af in the martensite state.

Figure 69:
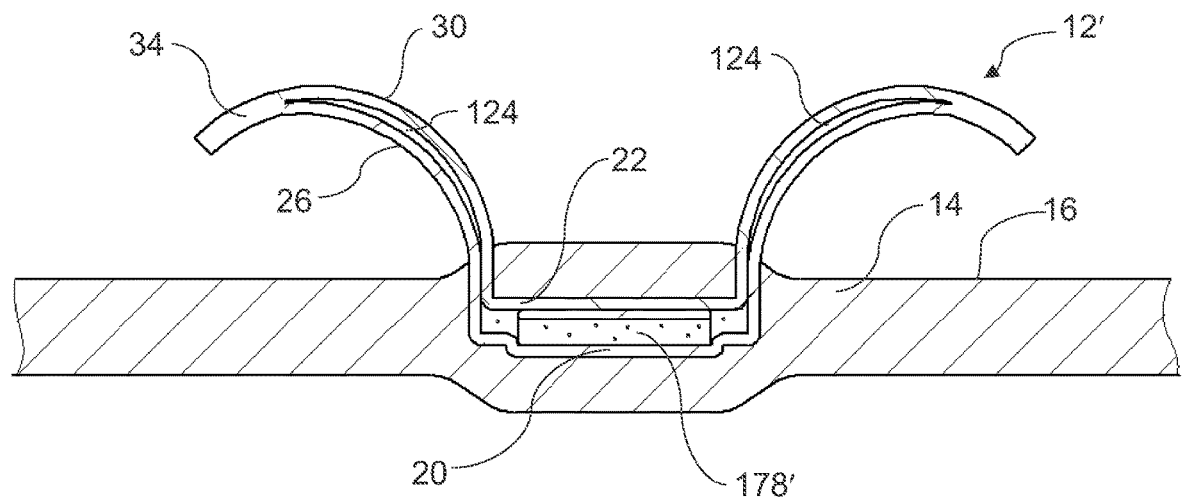
FIGS. 69-71 are sectional views of the element block assembly of FIG. 65, in each case the shape memory insert being disposed in the expanded configuration and the engagement elements being disposed in the engagement state.
Figure 70:
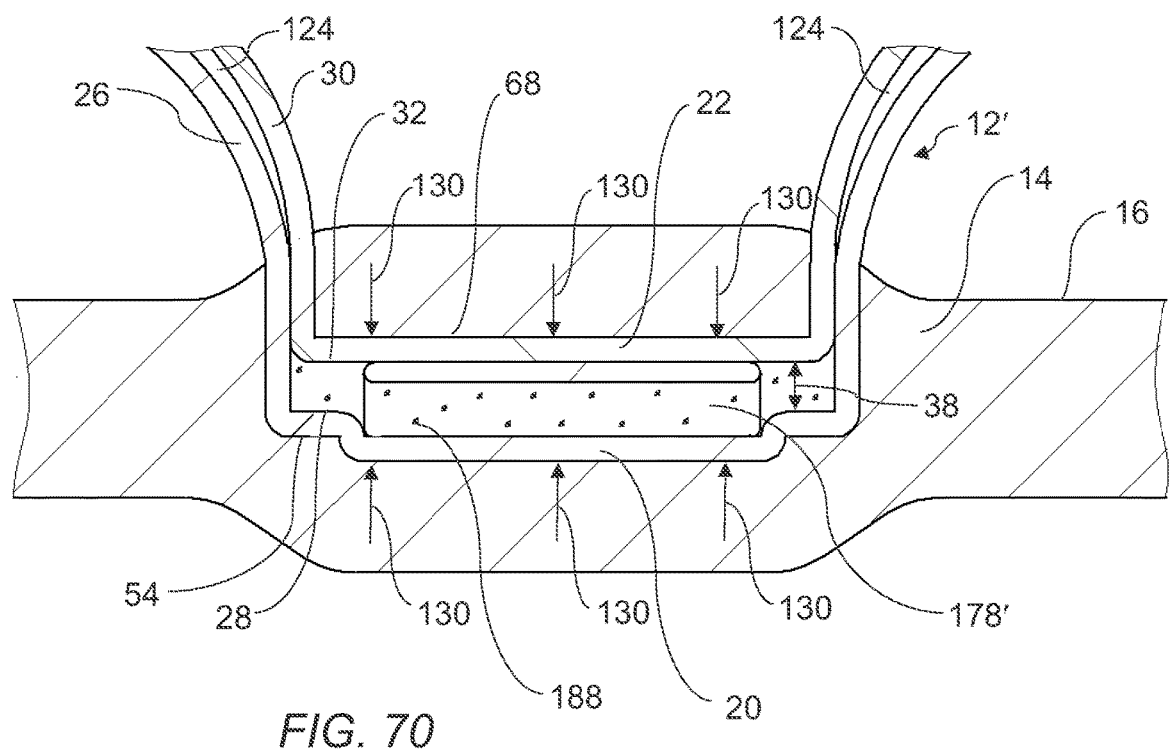
Figure 71:
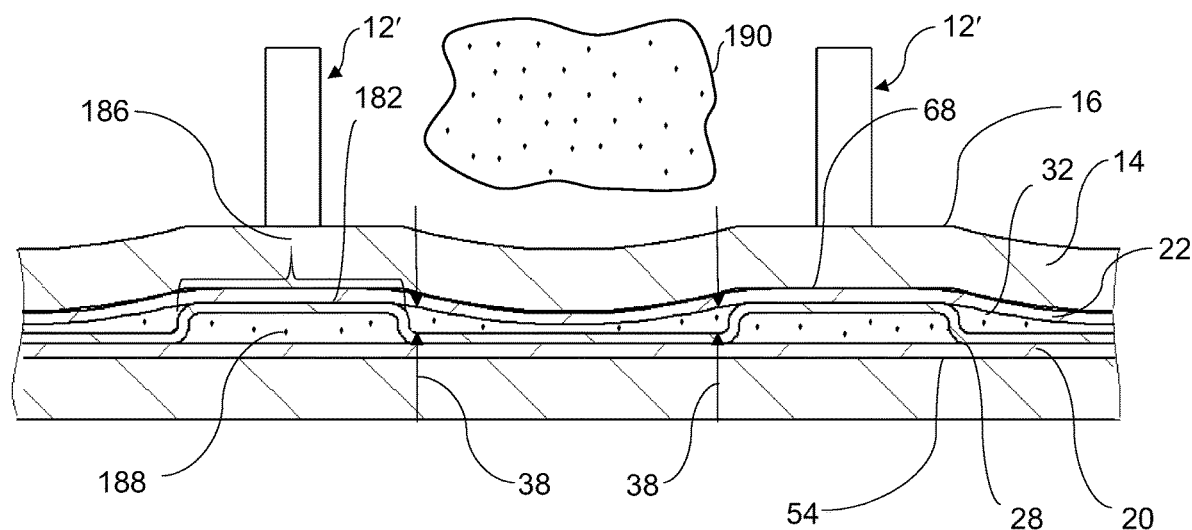

The application of thermal energy (heat) to the shape memory insert may transition the shape memory insert from the neutral configuration 178 to the expanded configuration 178' (thus raising the material above Af and transitioning the material to the austenite state), the expanded configuration 178' being depicted in FIGS. 69-71. Each shape memory insert 178 may include an expansion segment 186. The expansion segment 186 being the portion of the shape memory insert 178 which changes shape during the transition of the shape memory insert from the neutral configuration 178 to the expanded configuration 178'.

An example of an expansion segment 186 is depicted in FIG. 71. The expansion segment 186 is configured with an expanded insert profile 182 that is substantially rectangular in shape. For some embodiments of the shape memory insert 178, the expanded insert profile 182 may be shape set into the shape memory insert 178. This is to be contrasted with the neutral insert profile 180 which is depicted in FIG. 68 wherein the overall shape of the shape memory insert 178 is substantially flat. For some other embodiments of the shape memory inserts, the expansion segment 186 may be configured with any suitable expanded insert profile 182 such as a circular profile (not shown). In most cases, the expansion segment 186 of the shape memory insert 178' will be disposed within the adhesion device 184 such that the expansion segment 186 (and respective transition gaps 38) are substantially aligned with respective engagement elements 12' of the adhesion device 184 as shown in FIG. 71.

In some cases, a heated activation fluid 188 may be injected between the deployment sheet lower surface 32 and the activation sheet upper surface 28 in order to transition the shape memory inserts from the neutral configuration 178 to the expanded configuration 178'. In some cases, the temperature of the activation fluid 188 may be above the transition temperature Af of the shape memory insert 178 thereby transitioning the material to the austenite state. The activation fluid 188 may thus act to transition the shape memory insert from the neutral configuration 178 to the expanded configuration 178'. A removal fluid which is below the transition temperature Af could then be injected between the deployment sheet lower surface 32 and the activation sheet upper surface 28. This would transition the shape memory material to the martensite state, and the restorative forces 130 (as have been previously discussed) which are applied to the shape memory insert 178' by the element support body 14 can transition the shape memory insert 178' back to the neutral configuration 178 (thus transitioning respective engagement elements from the engagement state 12' to the deployment state 12).

In other cases, the adhesion device 184 may be inserted into a fluid environment 190 wherein the temperature of the fluid environment 190 is greater than Af. The fluid environment 190 is partially depicted in FIGS. 68 and 71, the fluid environment 190 would completely encompass the adhesion device 184 in most cases. In this case the shape memory insert 178 is insulated from the fluid environment 190 which surrounds the adhesion device 184 by the element support body 14 material. In this case, the shape memory insert may be transitioned to the expanded configuration 178' by thermal conduction through the element support body 14. That is to say that heat from the fluid environment 190 may conduct through the element support body 14 and into the shape memory insert 178 thereby transitioning the shape memory insert to the expanded configuration 178' after it has been heated above Af. In some cases an activation fluid 188 which is below the transition temperature Af may be injected between the deployment sheet lower surface 32 and the activation sheet upper surface 28, with the activation fluid 188 acting as a thermal conductor between the element support body 14 and the shape memory insert 178. In summary, the shape memory insert 178 being disposed within the element support body 14 temporarily thermally isolates the shape memory insert 178 from the surrounding environment (which in some cases may be a fluid environment 190). This may prevent premature transition of the engagement elements from the deployment state 12 to the engagement state 12'.

In order to remove the adhesion device 184 from the surface 49 of the target material 48, a removal fluid which is at a temperature which is below Af could be injected between the deployment sheet lower surface 32 and the activation sheet upper surface 28. This would transition the shape memory material of the shape memory insert 178' to the martensite state. The restorative forces 130 which are applied to the element activation sheet 20 and the element deployment sheet 22 could then transition the shape memory insert from the expanded insert profile 182 to the neutral insert profile 180. This would in turn transition respective engagement elements from the engagement state 12' to the deployment state 12 there by allowing for the removal of the adhesion device 184 from the target material 48.

Some adhesion device embodiments 192 may utilize element transition mechanisms which are configured as patterned insert assemblies 194. Each patterned insert assembly 194 may include multiple patterned inserts, with each patterned insert being configured to interlock with a suitably configured mating patterned insert. In some cases the patterned insert assembly 194 may include a first patterned insert 196 and a second patterned insert 198, with translational motion of the first patterned insert 196 with respect to the second patterned insert 198 resulting in interference between the first patterned insert 196 and the second patterned insert 198. The interference between the first patterned insert 196 and the second patterned insert 198 resulting in an overall increase in height of the interlocking patterned inserts. Translational motion of the first patterned insert 196 with respect to the second patterned insert 198 in the opposite direction can subsequently decrease the overall height of the interlocking patterned inserts.

Thus the height of the interlocking patterned inserts can be adjusted via translational motion of one patterned insert with respect to the other patterned insert. For some patterned insert assembly embodiments 194, an increase in height resulting from interference between the first patterned insert 196 and the second patterned insert 198 can be used in order to transition respective engagement elements from the deployment state 12 to the engagement state 12' for an adhesion device. A decrease in height between the first patterned insert 196 and the second patterned 198 insert may in turn result in the facilitation of the transition of respective engagement elements from the engagement state 12' to the deployment state 12.

Figure 72:
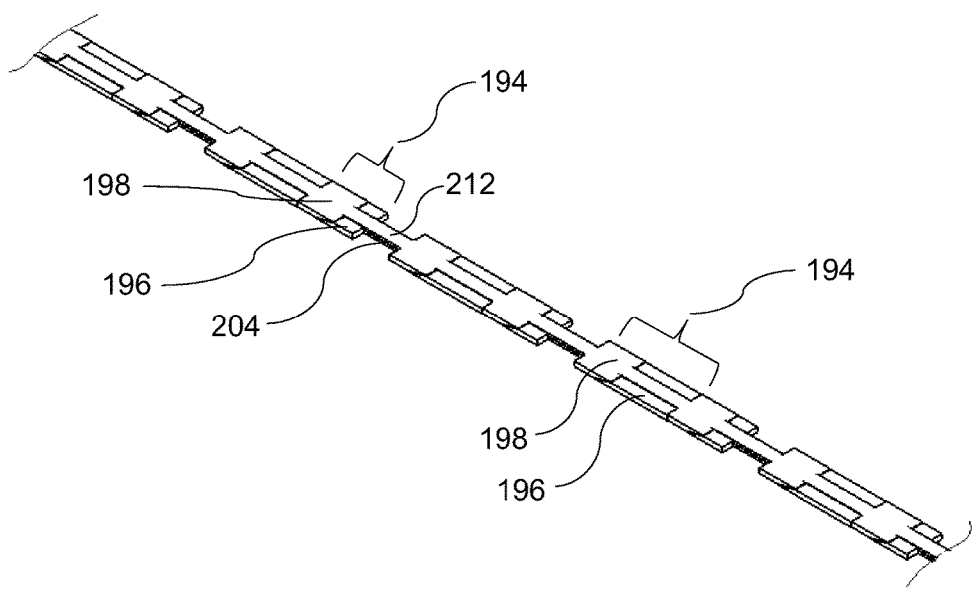
FIG. 72 is an isometric view of an embodiment of a patterned insert assembly which is disposed in a neutral configuration.

FIGS. 72-76 depict multiple embodiments of patterned insert assemblies 194 which are connected to each other in a linear fashion. FIGS. 77-80 are sectional views of an adhesion device 192 which is configured with multiple patterned insert assemblies 194 which act as the element transition mechanisms for the adhesion device 192. The adhesion device embodiment 192 could be any of the adhesion device configurations which are discussed herein. FIG. 72 depicts the multiple patterned insert assemblies which are disposed in the neutral configuration 194. Each patterned insert assembly 194 may include a first patterned insert 196 and a second patterned insert 198.

Figure 73:
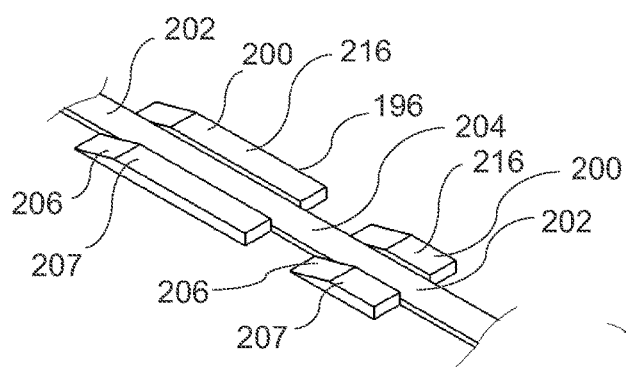
FIG. 73 is an isometric view of a first patterned insert.

As shown in FIG. 73 each first patterned insert 196 may include a first insert boss 200, a first insert slot 202, and a first insert rail 204 which may connect the first patterned insert 196 to adjacent first patterned inserts 196. Each first insert boss 200 and respective first insert slot 202 may have a variable length as depicted in FIG. 73. The first insert slot 202 may be substantially aligned with the first insert rail 204. That is to say that the first insert rail 204 may extend through the first insert boss 200 with the first insert slot 202 bifurcating the first insert boss 200 into two sections which are connected by the first insert rail 204. Each first insert boss 200 may also include a first boss ramp section 206 which is disposed a proximal portion 207 of each first insert boss 200.

Figure 74:
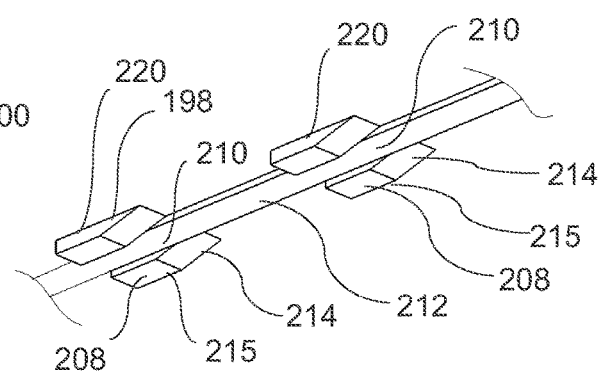
FIG. 74 is an isometric view of a second patterned insert.
Figure 75:
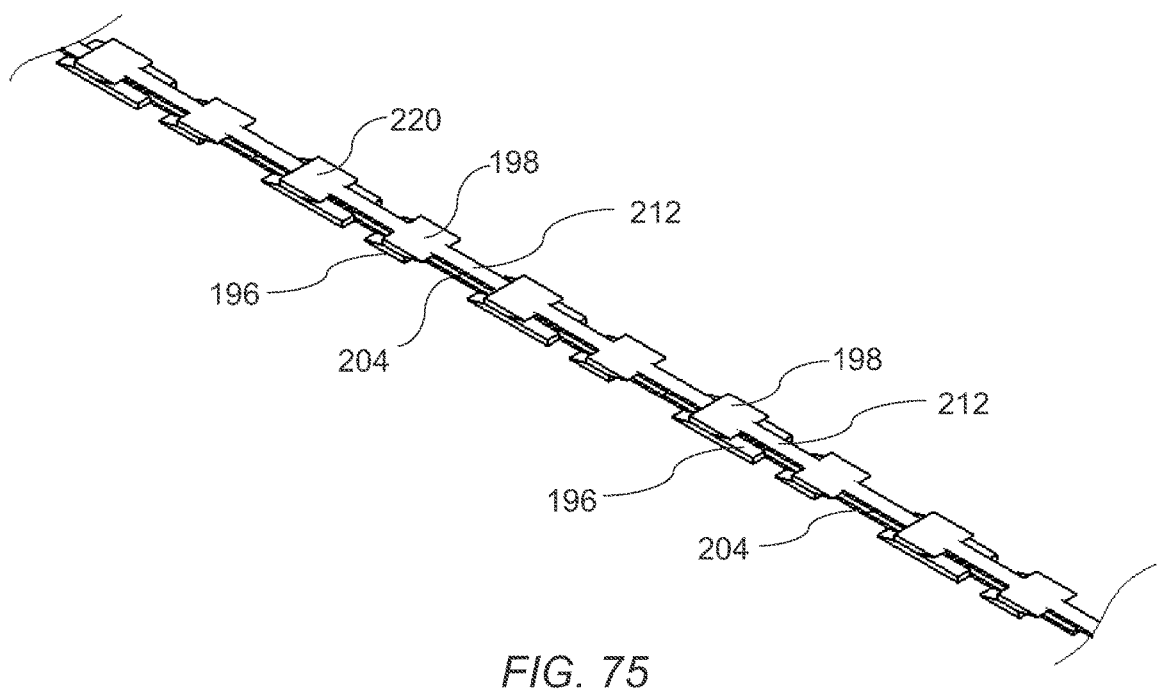
FIG. 75 depicts the patterned insert assembly of FIG. 72 when it is disposed in an expanded configuration.

As shown in FIG. 74, each second patterned insert 198 may include a second insert boss 208, a second insert slot 210, and a second insert rail 212 which may connect the second patterned insert 198 to adjacent second patterned inserts 198. Each second insert boss 208 and respective second insert slot 210 may have a variable length in some cases. The second insert slot 210 may be substantially aligned with the second insert rail 212. That is to say that the second insert rail 212 may extend through the second insert boss 208 with the second insert slot 210 bifurcating the second insert boss 208 into two sections which are connected by the second insert rail 212. Each second insert boss 208 may also include a second boss ramp section 214 which is disposed on a distal portion 215 of each second insert boss 208.

Figure 76A:
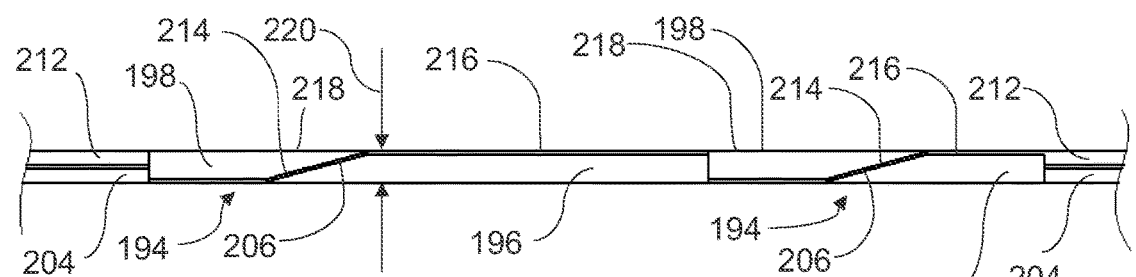
FIGS. 76A and 76B are elevation views of the patterned insert assembly depicting a neutral configuration and an expanded configuration respectively.

Each first insert slot 202 may be configured to couple to a respective section of the second insert rail 212, and in turn each second insert slot 210 may be configured to couple to a respective section of the first insert rail 204. This interlocking configuration allows for a top surface 216 of each first insert boss 200 to be substantially aligned with a top surface 218 of each second insert boss 208 as shown in FIG. 76A when the patterned insert assembly is disposed in a neutral configuration 194. When the patterned insert assembly is disposed the the neutral configuration 194, each first patterned insert 196 and each respective interlocking second patterned insert 198 may have a combined neutral insert profile 220 which is shown in FIG. 76A.

Figure 76B:
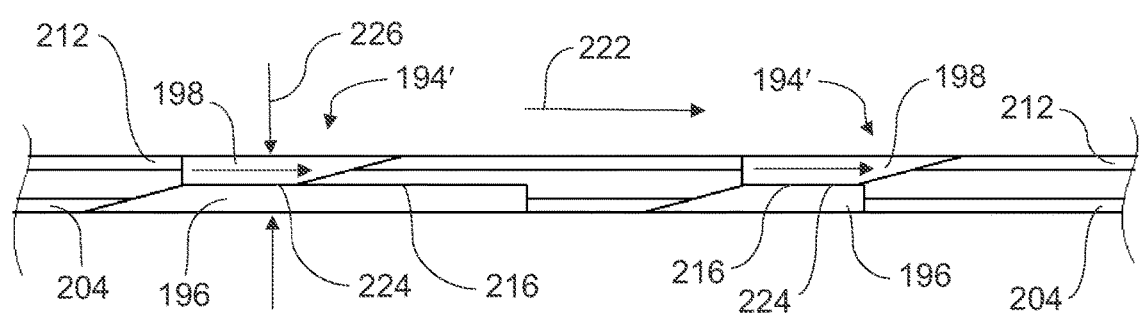

FIG. 76B depicts translational motion in a first linear direction (as indicated by axis 222 of each second patterned insert 198 with respect to each first patterned insert 196. The translational motion of each second patterned insert 198 in the first linear direction 222 results in interference between each first insert boss 200 and each second insert boss 208. During translational motion of each second patterned insert 198 in the first linear direction 222, each first boss ramp section 206 may contact a respective second boss ramp section 214 thereby facilitating the translational motion of each second patterned insert 198 with respect to a respective first patterned insert 196 (for some embodiments, the first patterned insert may 196 may be configured to move with respect to the second patterned insert 198 in the first linear direction 222). The motion of the second patterned insert 198 with respect to the first patterned insert 196 results in the transition of the patterned insert assembly to the expanded configuration 194'. While disposed in the expanded configuration 194' a bottom surface 224 of each second insert boss 208 may be disposed adjacent to the top surface 216 of each first insert boss 200. Thus in the expanded configuration 194' the patterned insert assembly may have an expanded insert profile 226 which is shown in FIG. 76B. The difference between the expanded insert profile 226 and the neutral insert profile 220 being the transition gap 38.

Figure 77:
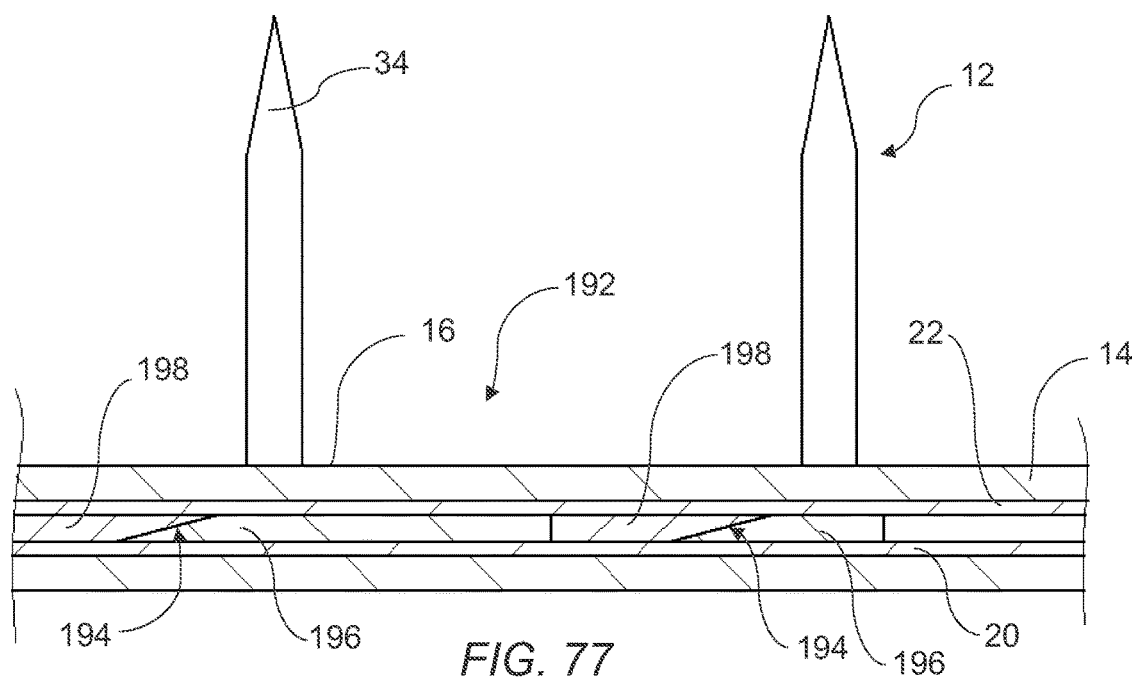
FIGS. 77-79 are sectional views of an element block assembly which utilizes the patterned insert assembly of FIG. 72 as the element transition mechanism, in each case the patterned insert assembly being disposed in the neutral configuration and the engagement elements being disposed in the deployment state.
Figure 78:
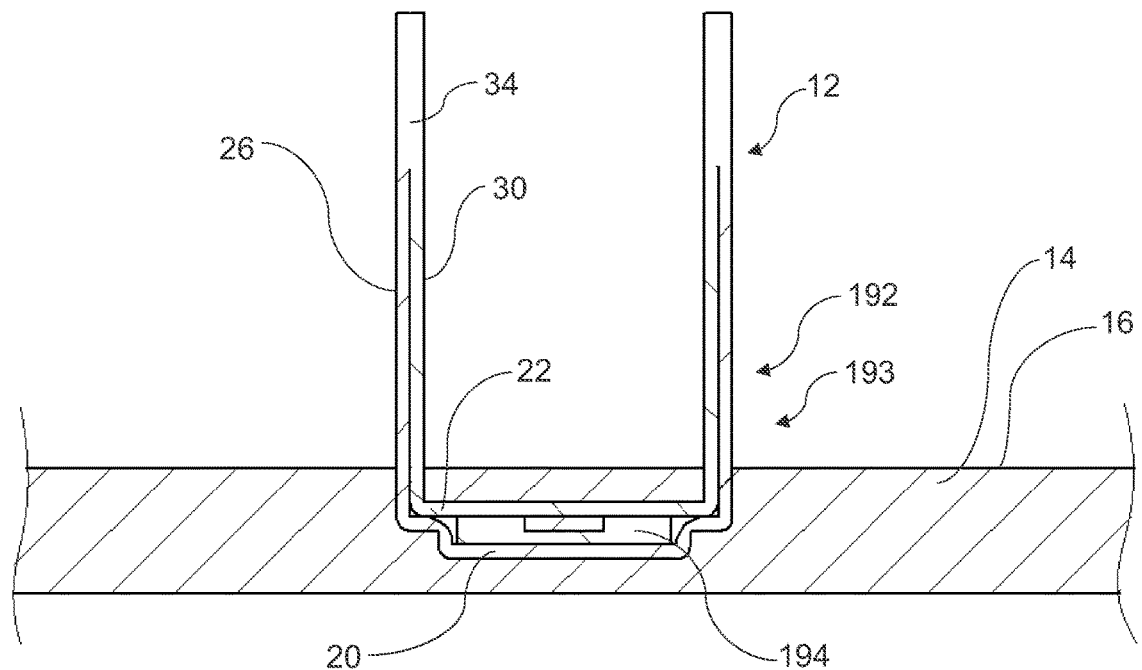
Figure 79:
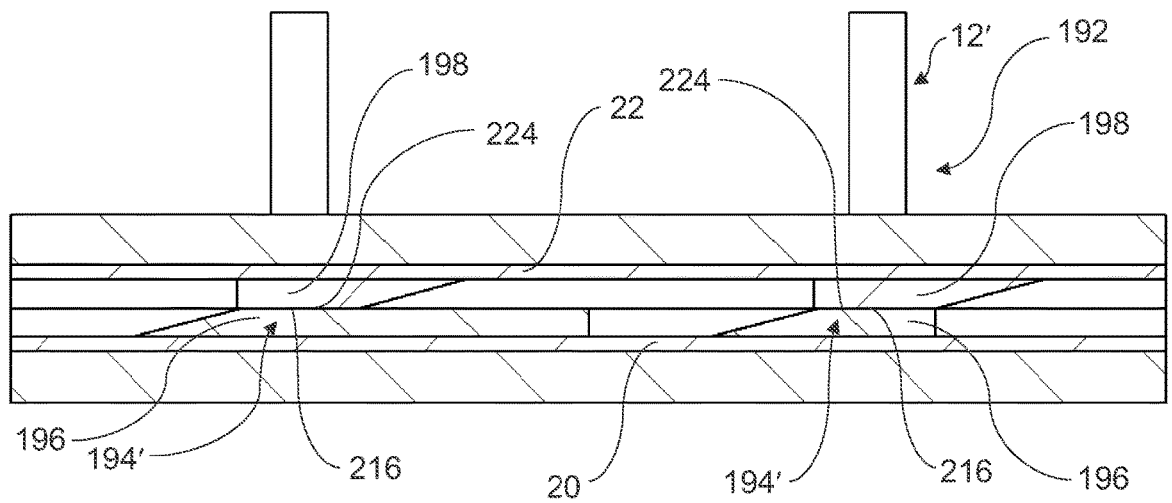
Figure 80:
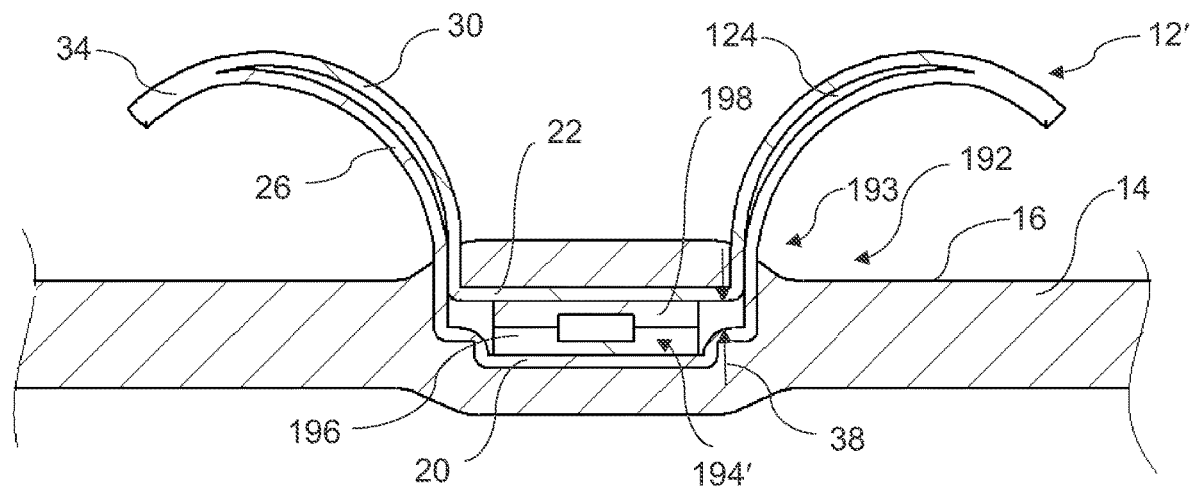

FIGS. 77-80 depict an embodiment of an adhesion device 192 wherein the element transition mechanism is configured as a patterned insert assembly 194. The adhesion device 192 may include an element support body 14 and multiple element block assemblies 193, with each element block assembly 193 including an element activation sheet 20, an element deployment sheet 22, multiple engagement elements 12, and a patterned insert assembly 194 which includes a first patterned insert and a second patterned insert. FIGS. 77 and 78 depict the patterned insert assembly in the neutral configuration 194 wherein the patterned insert assembly 194 has a neutral insert profile 220 and the respective engagement elements are disposed in the deployment state 12. FIGS. 79 and 80 depict the patterned insert assembly in the expanded configuration 194' wherein the patterned insert assembly 194' has an expanded insert profile 226 and the respective engagement elements are disposed in the engagement state 12'. The difference in height between the neutral insert profile 220 and the expanded insert profile 226 being the transition gap 38 which transitions the respective engagement elements to the engagement state 12' as has been discussed previously.

In order to remove the adhesion device 192 from the target material 48 after deployment, the patterned insert assembly may be transitioned from the expanded configuration 194' having the expanded insert profile 226 to the neutral configuration 194 having the neutral insert profile 220 by translational motion of the first patterned insert 196 with respect to the second patterned insert 198 in a second linear direction (which is opposite to the first linear direction 222). Restorative forces 130 which are applied to the element activation sheet 20 and the element deployment sheet 22 would then transition respective engagement elements from the engagement state 12' to the deployment state 12 thereby allowing for the removal of the adhesion device from the surface 49 of the target material 48.

For some embodiments of adhesion devices, the element transition mechanisms may be configured as a capacitor plates assemblies 228, each of which may include a first capacitor plate 230 and a second capacitor plate 232. Such an adhesion device embodiment 234 is depicted in FIGS. 81-85. Each capacitor plates assembly 228 would function as follows: repulsive charges are applied to a first capacitor plate 232 and a second capacitor plate 234 (se FIG. 84). The repulsive charges result in repulsive electrical forces between the first capacitor plate 232 and the second capacitor plate 234 which cause a separation between the first capacitor plate 232 and the second capacitor plate 234, the separation being the transition gap 38. The capacitor plates assembly thus transitions from a neutral configuration 228 wherein respective engagements are disposed in the deployment state 12 to an expanded configuration 228' wherein the respective engagement elements are disposed in the engagement state 12'.

Figure 81:
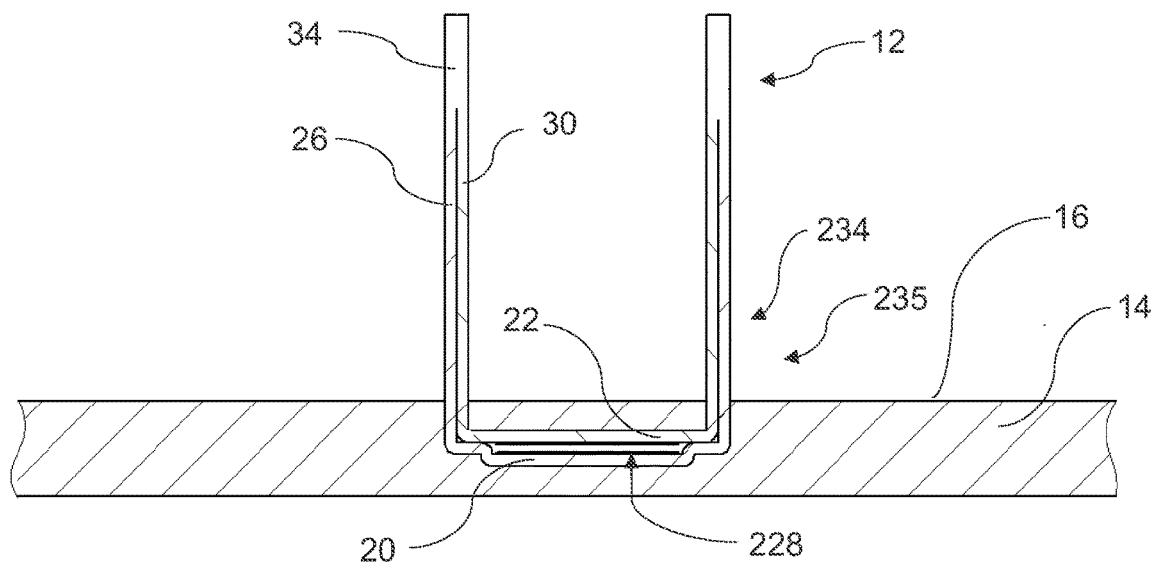
FIG. 81 is a sectional view of an element block assembly disposed within an element support body, the element block assembly utilizing a capacitor plates assembly as the element transition mechanism.

FIG. 81 is a sectional view of the adhesion device embodiment 234 which incorporates an element transition mechanism which is configured as a capacitor plates assembly 228. The adhesion device embodiment 234 could be any of the adhesion device configurations which are discussed herein. Each capacitor plate may be operatively coupled to a voltage supply 236 which may in turn be disposed within the control system 50. The adhesion device embodiment 234 also includes an element block assembly 235, an element support body 14, with each element block assembly 235 having an element activation sheet 20, an element deployment sheet 22, and multiple engagement elements 12.

For some embodiments, each capacitor plate may be configured as multiple conductive plates and an insulating plate all of which have substantially equivalent profiles. The insulating plate may be disposed between the two conductive plates, and the capacitor plate may be coated with an insulating material. Each conductive plate may be operatively coupled to the voltage supply 236. This capacitor plate configuration allows for the manipulation of the charge distribution between the two conductive plates. That is to say that a positive charge could be applied to one conductive plate and a negative charge could be applied to the other conductive plate. Each capacitor plate assembly 228 may be configured with any suitable dimensions which allow it to be coupled to a respective element block assembly 18.

Figure 82:
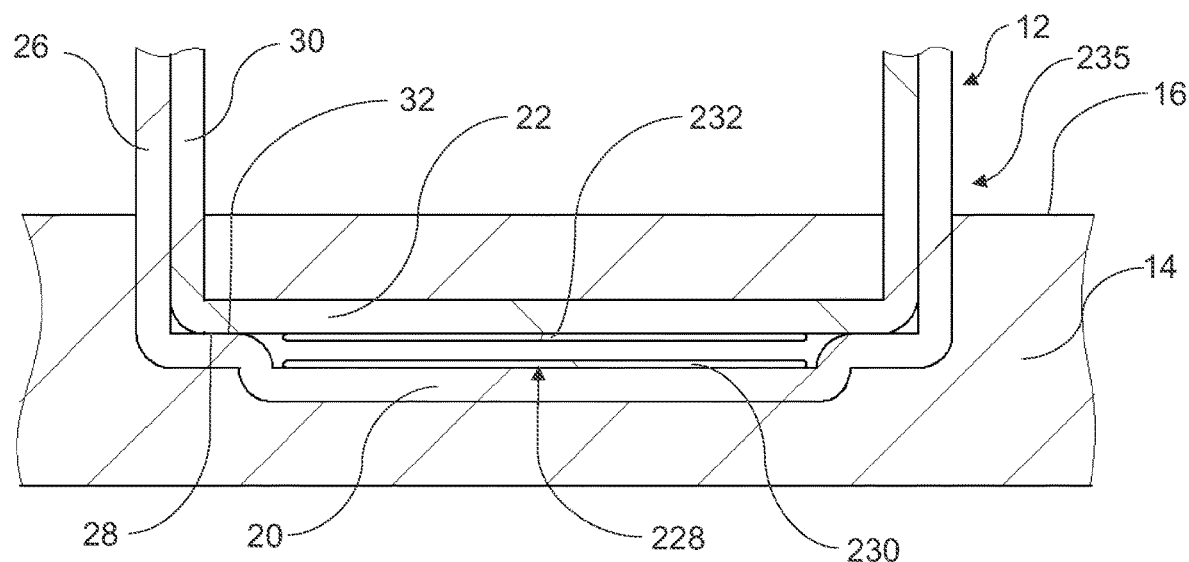
FIG. 82 is an enlarged view of FIG. 81, depicting the capacitor plates assembly which is disposed in a neutral configuration and multiple engagement elements which are disposed in a deployment state.
Figure 83:
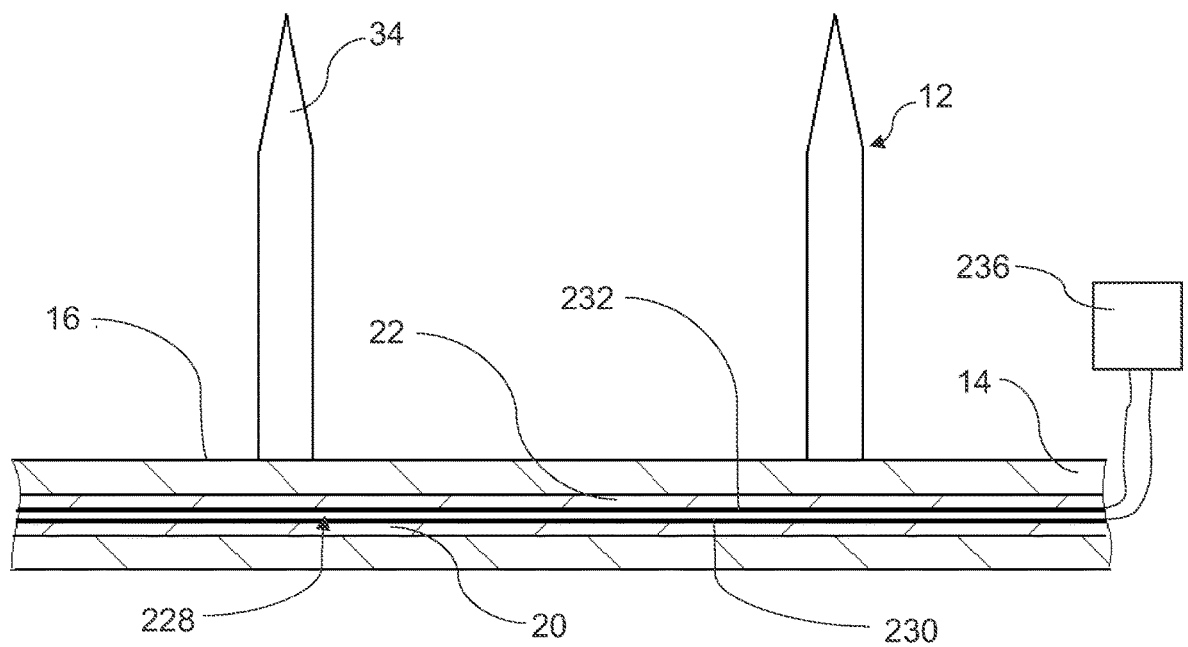
FIG. 83 is a sectional view of the element block assembly of FIG. 81 depicting the capacitor plates assembly which is disposed in a neutral configuration, multiple engagement elements which are disposed in a deployment state, and a voltage supply.
Figure 84:
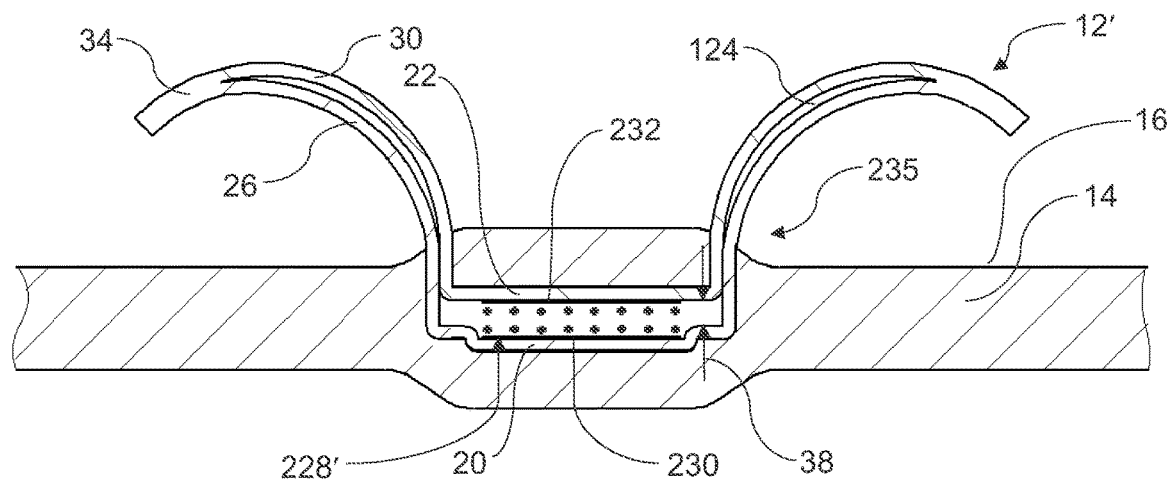
FIGS. 84-85 are sectional views of the element block assembly of FIG. 81 depicting the capacitor plates assembly in an expanded configuration, and multiple engagement elements in the engagement state.
Figure 85:
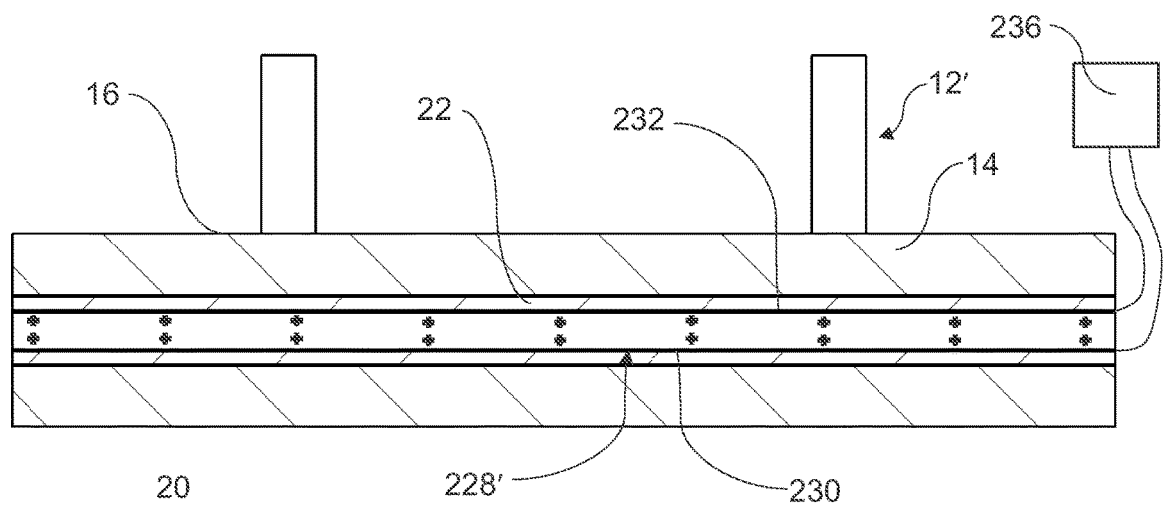

FIGS. 81-83 depict the first capacitor plate 230 and the second capacitor plate 232 in a neutral configuration 228 wherein there is a net minimal charge between the first capacitor plate 230 and the second capacitor plate 232. In this case, there is no charge applied from the voltage supply 236 to the first capacitor plate 230 and the second capacitor plate 232. FIGS. 84-85 depict the application of a net repulsive charge from the voltage supply 236 to the first capacitor plate 230 and the second capacitor plate 232. The first capacitor plate 230 and second capacitor plate 232 are shown as being positively charged, however each capacitor plate could be negatively charged. Electrical repulsive forces between the first capacitor plate 230 and the second capacitor plate 232 result in the creation of the transition gap 38 between the first capacitor plate 230 and the second capacitor plate 232. Thus the capacitance plates assembly is transitioned from the neutral configuration 228 to the expanded configuration 228' with the application of the repulsive charges.

Removal of the repulsive charges from the first capacitor plate 230 and the second capacitor plate 232 allows the restorative forces 130 of the element support body 14 to eliminate the transition gap 38 and return the respective engagement elements to the deployment state 12. Some embodiments the adhesion device 234 may be removed from target material 48 through the application of a net attractive charge which may be applied between the first capacitor plate 230 and the second capacitor plate 232. For example, the first capacitor plate 230 could be positively charged and the second capacitor plate 232 could be negatively charged (or vice versa). This would result in attractive electrical forces between the first capacitor plate 230 and the second capacitor plate 232. The attractive forces would facilitate the transition of the transition of the capacitor plates assembly from the expanded configuration 228' to the neutral configuration 228 and the transition of respective engagement elements from the engagement state 12' to the deployment state 12.

Thus the first capacitor plate 230 and the second capacitor plate 232 which form the capacitance plates assembly are configured to reversibly transition from a neutral configuration 228 wherein there is a net minimal charge between the first capacitance plate 230 and the second capacitor plate 232 and an expanded configuration 228' wherein there is a net repulsive charge between the first capacitor plate 230 and the second capacitor plate 232 with the net repulsive charge resulting in the creation of the transition gap 38 between the first capacitor plate 230 and the second capacitor plate 232.

Some embodiments of element transition mechanisms may be configured to allow for multiple expanded configurations. For example, the interior lumen 40 of a given balloon apparatus 24 may be filled with activation fluids 42 at different pressures, a first lumen pressure and a second lumen pressure with the second lumen pressure being greater than the first lumen pressure. The activation fluid 42 at the first lumen pressure would expand the balloon apparatus 24 to a first expanded balloon profile. This would result in a first transition gap between the activation sheet upper surface 28 and the deployment sheet lower surface 32, the first transition gap in turn resulting in a first reactive flexure of the respective engagement elements. The second lumen pressure would expand the balloon apparatus 24 to a second expanded balloon profile. This would result in a second transition gap between the activation sheet upper surface 28 and the deployment sheet lower surface 32, the second transition gap in turn resulting in a second reactive flexure of the respective engagement elements.

In this case, the second reactive flexure would be greater than the first reactive flexure. Hence, the magnitude of the reactive flexure of each engagement element can be "adjusted" by transitioning the respective element transition mechanism to different expanded configurations. In this manner the adhesion strength of a given adhesion device could be adjusted. A similar adjustment method could be used with an element transition mechanism which is configured as a capacitor plates assembly 228, or with any other suitably configured element transition mechanism.

Embodiments of adhesion devices which are discussed herein may be suitably configured with any combination of element transition mechanisms which have been discussed which may include balloon apparatuses 24, shape memory inserts 178, patterned insert assemblies 194, or capacitor plates assemblies 228. For example an adhesion device with a suitably configured control system 50 may incorporate engagement elements 12 which are operatively coupled to multiple element block assemblies 18 which are configured with patterned inserts assemblies 194, and may incorporate engagement elements 12 which are operatively coupled to multiple element block assemblies 18 which are configured with multiple balloon apparatuses 24.

Embodiments of adhesion devices which have been discussed so far have incorporated element block assemblies 18 wherein the position of a given element block assembly 18 with respect to other element block assemblies 18 remains substantially fixed within the element support body 14 (or within the element guide sheet 150) during deployment and removal of the adhesion device. In some cases, the element block assemblies 18 are positioned within an element sheet frame 78 which fixes the position of each element block assembly 18 with respect to adjacent element block assemblies 18. For some medical and industrial applications, it may be desirable to allow for the expansion and/or contraction of the element support body 14. For example, in the medical field flexible bandages and expandable balloons could be configured with multiple engagement elements 12 which could be used as an adhesive for the given device. Applications such as this must allow for the expansion and/or contraction of the device, and in turn must allow for the expansion and/or contraction of the engagement elements 12, element activation sheets 20, element deployment sheets 22, and element transition mechanisms (whatever configuration) which form a respective element block assembly 18.

Figure 88:
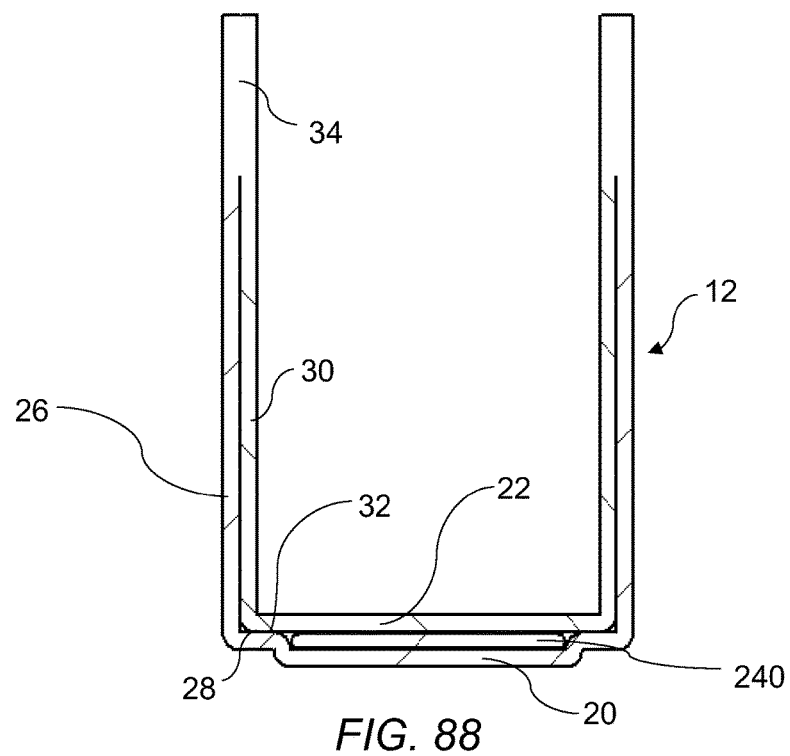
FIG. 88 is a sectional view of FIG. 86.
Figure 89:
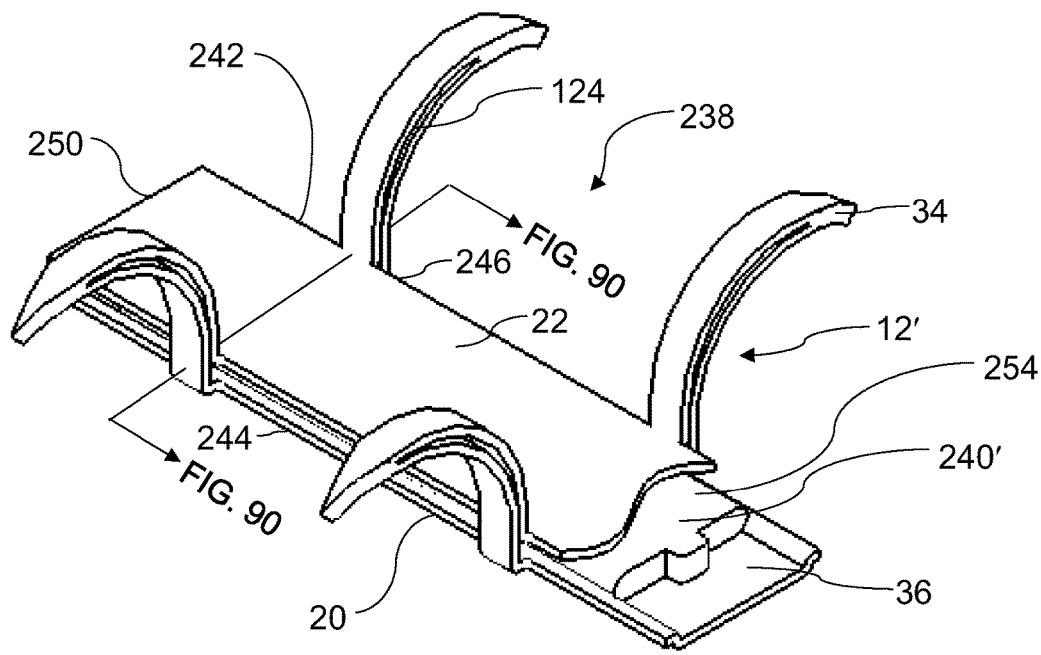
FIG. 89 is an isometric view of the element block assembly of FIG. 86 depicting the element transition mechanism disposed in an expanded configuration and multiple engagement elements disposed in an engagement state.
Figure 90:
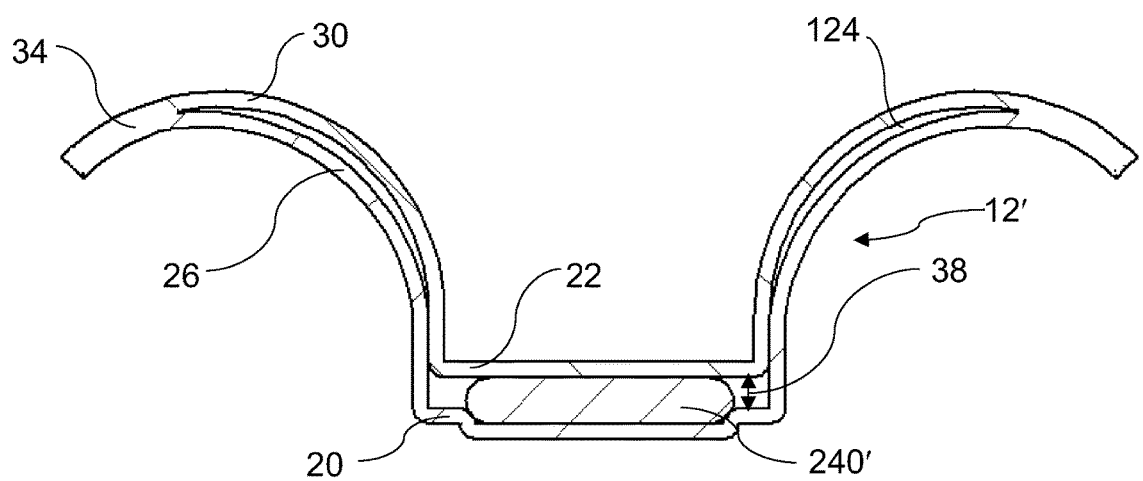
FIG. 90 is a sectional view of FIG. 89.

FIGS. 86-90 depict an embodiment of a "stand alone" element block assembly 238 which includes an element activation sheet 20, an element deployment sheet 22, a plurality of engagement elements 12, and an element transition mechanism 240 which is operatively coupled to the engagement elements 12. FIG. 88 is a section view of the element block assembly 238 showing the element transition mechanism 240 in the neutral configuration and the coupled engagement elements in the deployment state 12. FIGS. 89 and 90 depict the element transition mechanism in the expanded configuration 240' and the coupled engagement elements in the engagement state 12'. The materials, dimensions, functions, and configurations of each element block assembly 240 may be substantially similar to those of element block assemblies 18 which have been previously discussed herein.

Figures 86, 87:
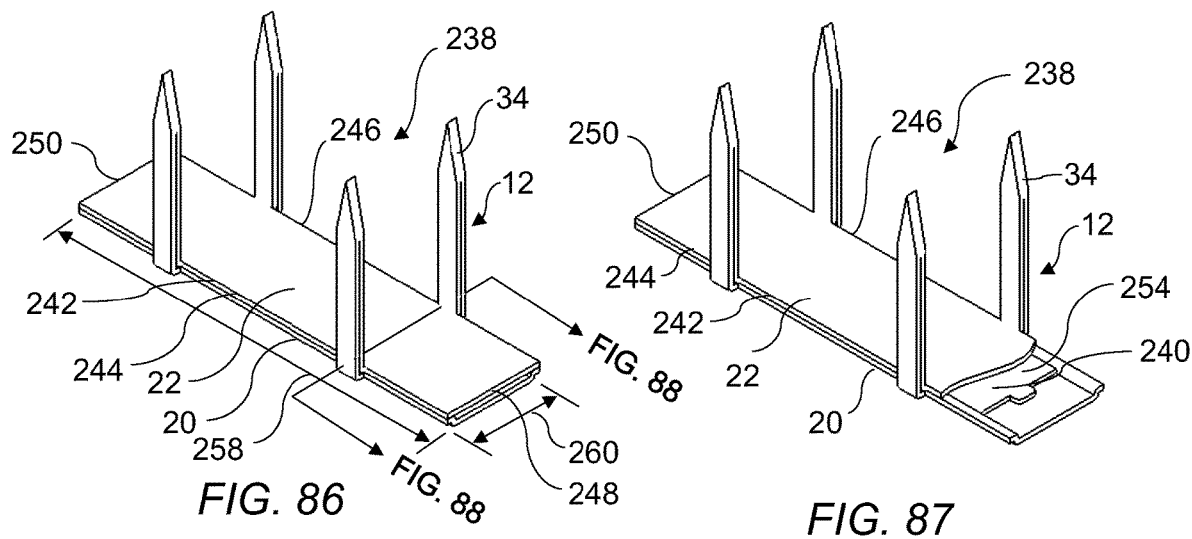
FIGS. 86 and 87 are isometric views of a stand alone element block assembly including an element transition mechanism disposed in a neutral configuration and multiple engagement elements disposed in a deployment state

The element block assembly 238 which is depicted in FIG. 86 is configured with a substantially rectangular element block profile 242, and incorporates four engagement elements 12. The engagement elements 12 may be distributed on a first block element side 244 and a second block element side 246, with each block element side configured to incorporate multiple engagement elements 12. The element block assembly 238 may also include a first block transition side 248 and a second block transition side 250, with each block transition side being configured to couple to adjacent element block assemblies 238. In this manner, each element block assembly 238 may be configured to assume a position within an element block array 252 (see FIG. 91), with adjacent element block assemblies 238 aligned such that the block transition sides (248, 250) of respective engagement elements 12 are substantially adjacent to each other within the element block array 252 and the block element sides (244, 246) are substantially adjacent to each other within the element block array 252. The adjacent block transition sides (248, 250) allow for the operative coupling of the respective adjacent element transition mechanisms 240.

The dimensions of the element transition mechanism 240 may be configured such that portions 254 of the element transition mechanism 240 extends beyond the engagement elements 12 as depicted in FIG. 87. This is to ensure that when the element transition mechanism is transitioned to an expanded configuration 240' (see FIGS. 89 and 90), it will fully engage with the respective engagement elements which are disposed in the engagement state 12'. Additionally, a transition mechanism profile 256 (see FIG. 95) may be configured to substantially align with the element block profile 242, thereby assuring that the element transition mechanism 240 is operatively coupled to the respective engagement elements 12.

Embodiments of element block assemblies 238 may be configured with any suitable element block profile 242. For example element block assemblies 238 may be configured with substantially rectangular element block profiles 242 as has been discussed, or element block assemblies 238 may be configured with a substantially square element block profile 242. Some embodiments of element block assemblies 238 may be configured with curved element block profiles 242 (see FIG. 127). Some embodiments of element block arrays 252 may be configured with any suitable combination of element block assemblies 238 having any suitable element block profiles 242. For example, an element block array 252 can be configured with element block assemblies 238 having rectangular element block profiles 242 which are coupled to element block assemblies having curved element block profiles 242.

Element block assemblies 238 may have any suitable element block length 258 or element block width 260 (see FIG. 86). Element block assemblies 238 may also incorporate any suitable number of engagement elements 12. The engagement elements 12 which are disposed upon a given element block assembly 238 may be configured such that opposing engagement elements 12 are substantially aligned as shown in FIG. 17. Or the engagement elements 12 which are disposed upon a given element block assembly 238 may be configured such that opposing engagement elements 12 are substantially skewed as shown in FIG. 143.

For the purposes of illustration, the element transition mechanism 240 of the element block assembly 238 is depicted in a generic sense. That is to say that it is generically represented as having a neutral configuration 240 and an expanded configuration 240' in order to graphically depict the element transition mechanism in those two states. The element transition mechanism 240 can be configured as the balloon apparatus 24, the shape memory insert 178, the patterned inserts 194, or the capacitance plates assembly 228 which have been previously discussed. Element block assemblies 238 which are disposed within an element block array 252 may be configured with any suitable combination of element transition mechanism embodiments.

For some embodiments of adhesion devices, multiple element block assemblies 238 may be disposed within an element support body 14 thereby allowing for the expansion and/or contraction of the element support body 14 and the respective element block assemblies 238. In some cases each element transition mechanism 240 of each element block assembly 238 may be operatively coupled to element transition mechanisms 240 of respective adjacent element block assemblies 238, with the coupled element transition mechanisms 240 operatively coupled to a control system 50 of the adhesion device in a serial manner. In other cases, each element transition mechanism 240 of each respective element block assembly 238 may be operatively coupled to the control system 50 in a direct manner.

For the purposes of manufacturing, each element block assembly 238 may be releasably secured to adjacent element block assemblies 238 within the element block array 252. That is to say that each element block assembly 238 may be temporarily secured to adjacent element block assemblies 238 such that manufacturing procedures may be simultaneously performed on each element block assembly 238. The manufacturing procedures may include constraining each engagement element 12 such that it is substantially perpendicular to a respective deployment sheet upper surface 68, and molding the element support body 14 about each element block assembly 238.

Figure 91:
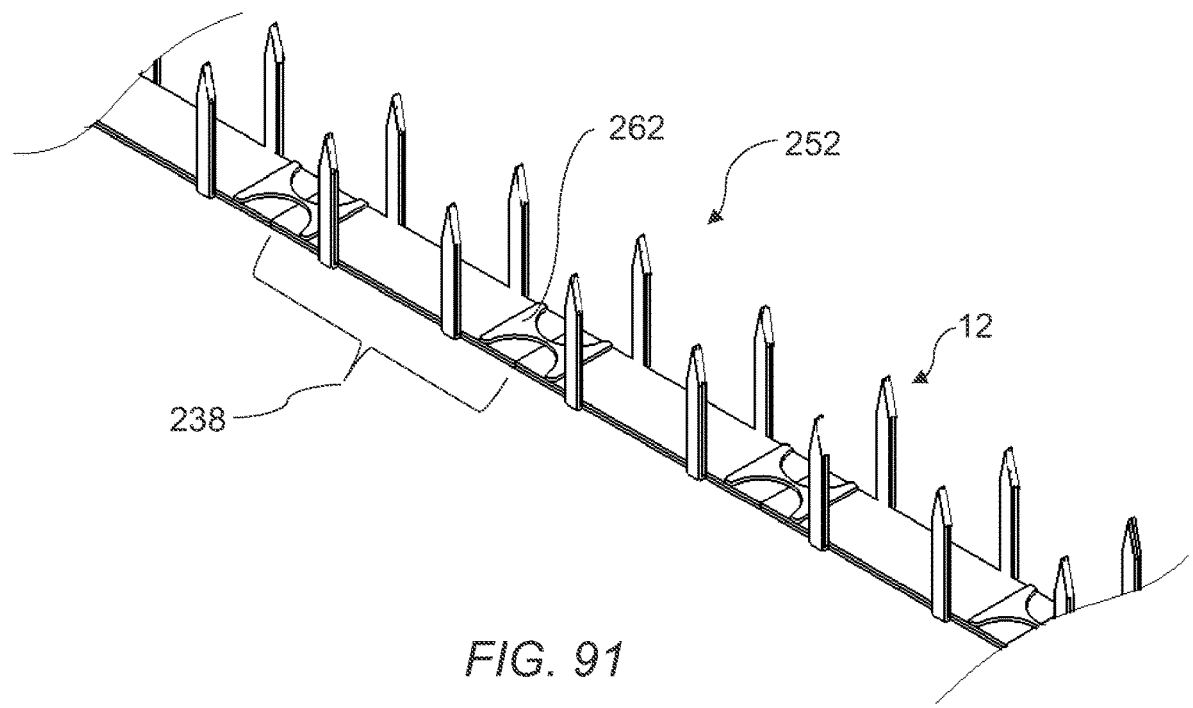
FIG. 91 is an isometric view of an element block array which includes multiple break-away tabs, the element block array being disposed within an element support body which is not shown, and the element block array including multiple element block assemblies incorporating multiple respective element transition mechanisms disposed in a neutral configuration and multiple respective engagement elements disposed in a deployment state.
Figure 92:
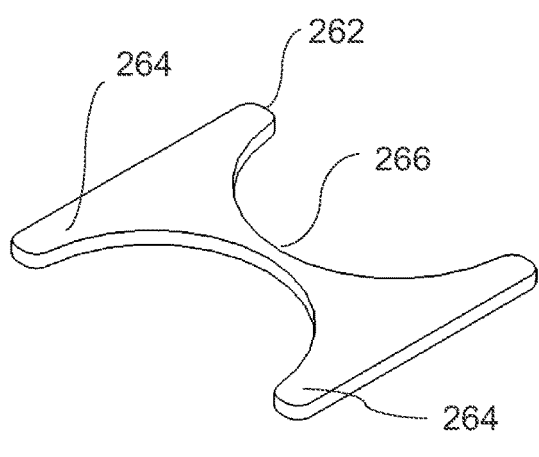
FIG. 92 is an isometric view of a break-away tab embodiment.
Figure 93:
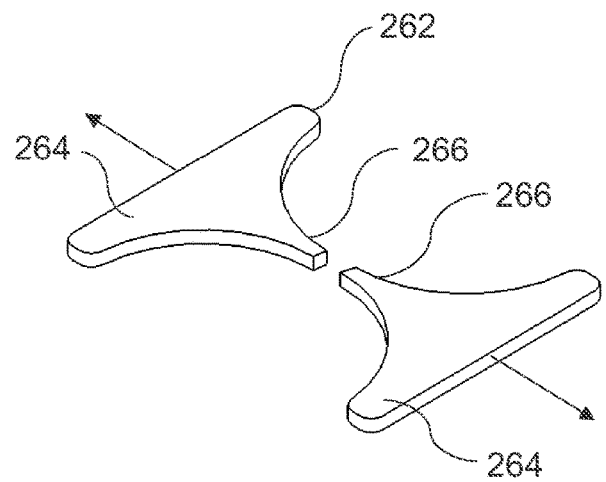
FIG. 93 depicts the break-away tab of FIG. 92 after the break-away tab has been broken.
Figure 94:
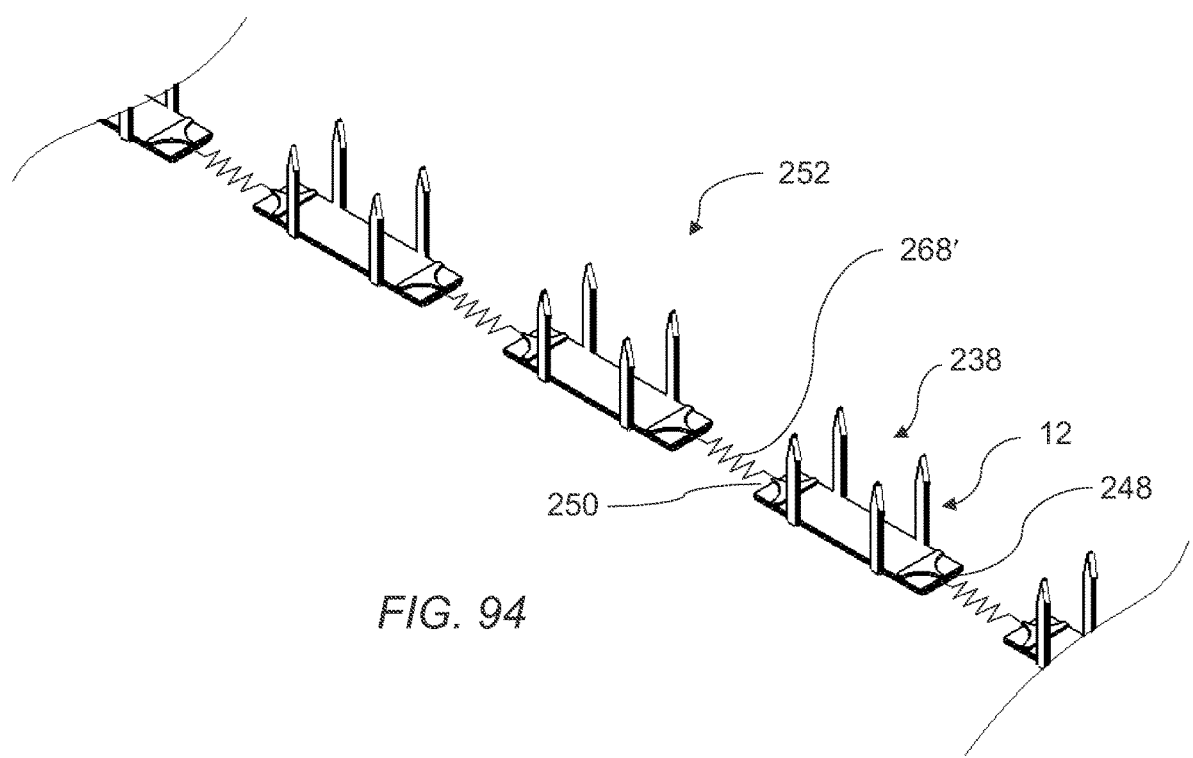
FIG. 94 depicts the element block array of FIG. 91 after the element block assemblies have been separated by the expansion of the element support body, each element block assembly being operatively connected to adjacent element block assemblies by an expandable transition coupler.

FIGS. 92 and 93 depict an embodiment of a break-away tab 262, and FIG. 91 depicts an element block array 252 that includes multiple element block assemblies 238 which are releasably secured to adjacent element block assemblies 238 using multiple break-away tabs 262. Each break-away tab 262 may include multiple expanded sections 264 which are configured to secure to suitable surfaces of respective element block assemblies 238. Each break-away tab 262 may also include a tapered section 266, with the tapered section 266 being configured to break when a sufficient force is applied to respective expanded sections 264 as shown in FIG. 93. FIG. 94 depicts the element block array 252 of FIG. 91 after the element block assemblies 238 have been separated through the expansion of an element support body 14 (not shown) which the element block assemblies 238 are partially disposed within. The separation of the element block assemblies 238 from the expansion of the element support body 14 results in the breaking of each break-away tab 262.

As shown in FIG. 91, each break-away tab 262 may be secured to respective element block assemblies 238 such that the tapered section 266 is substantially aligned with respective block transition sides (248, 250) of adjacent element block assemblies 238. The break-away 262 tab may be secured to the element block assemblies 238 by any suitable means such as an adhesive. Some embodiments of the break-away tab 262 may be fabricated from a flexible material such as a polymer. Other embodiments of the break-away tab 262 may be fabricated from metal or composite materials.

Figure 95:
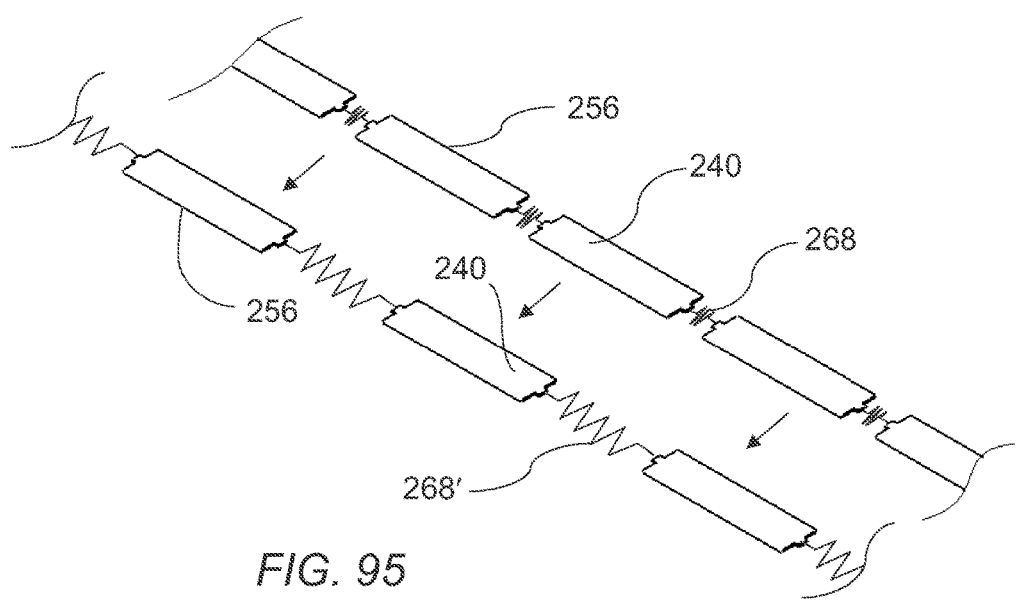
FIG. 95 depicts multiple element transition mechanisms which are disposed in the neutral configuration before and after the expansion of the element support body, each element transition mechanism being operatively connected to adjacent element transition mechanisms by an expandable transition coupler.

As has been discussed previously each element transition mechanism 240 for each element block assembly 238 may need to be operatively coupled to adjacent element transition mechanisms 240 (or directly to the control system 50 for some embodiments). FIG. 95 depicts each element transition mechanism 240 of the element block array 252 which are depicted in FIGS. 91 and 94 (all components of the element block assemblies 238 are hidden in FIG. 95 in order to clearly depict the positions of the element transition mechanisms 240). There are two configurations of element transition mechanism 240 positions depicted in FIG. 95. The upper configuration corresponds to the positions of the element transition mechanisms 240 in FIG. 91 before the expansion of the element support body 14. The lower configuration corresponds to the positions of the element transition mechanisms 240 in FIG. 94 after the expansion of the element support body 14.

In each case, a given element transition mechanism 240 is operatively secured to a respective adjacent element transition mechanism 240 by an expandable transition coupler 268. Each expandable transition coupler 268 may be configured to expand as the respective element block assemblies 238 to which it operatively coupled expand with the element support body 14. This is illustrated in FIG. 95 wherein each expandable transition coupler is depicted in a compressed state 268 and an expanded state 268'. Each expandable coupler may be configured to reversibly transition from the compressed state 268 to the expanded state 268' (and vice versa). The configuration of the expandable transition coupler 268 is dependent upon the configuration of the respective element transition mechanism 240.

Figure 96:
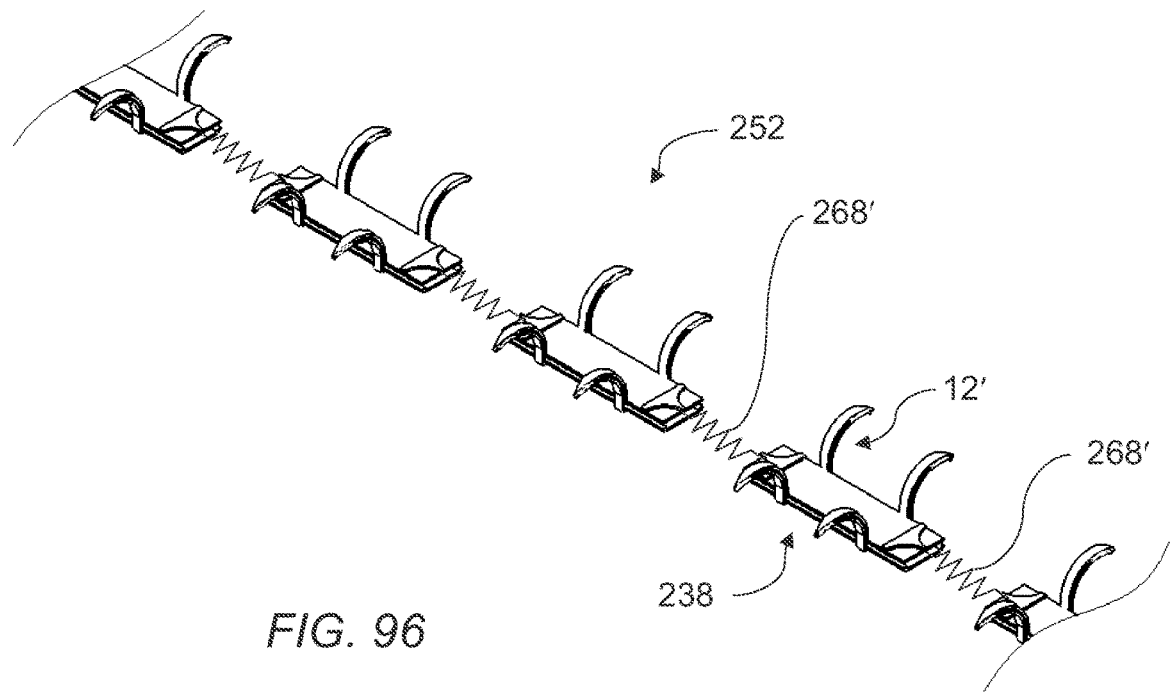
FIG. 96 depicts the element block assemblies of FIG. 94 with the respective element transition mechanisms disposed in an expanded configuration and the respective engagement elements disposed in the engagement state.
Figure 97:
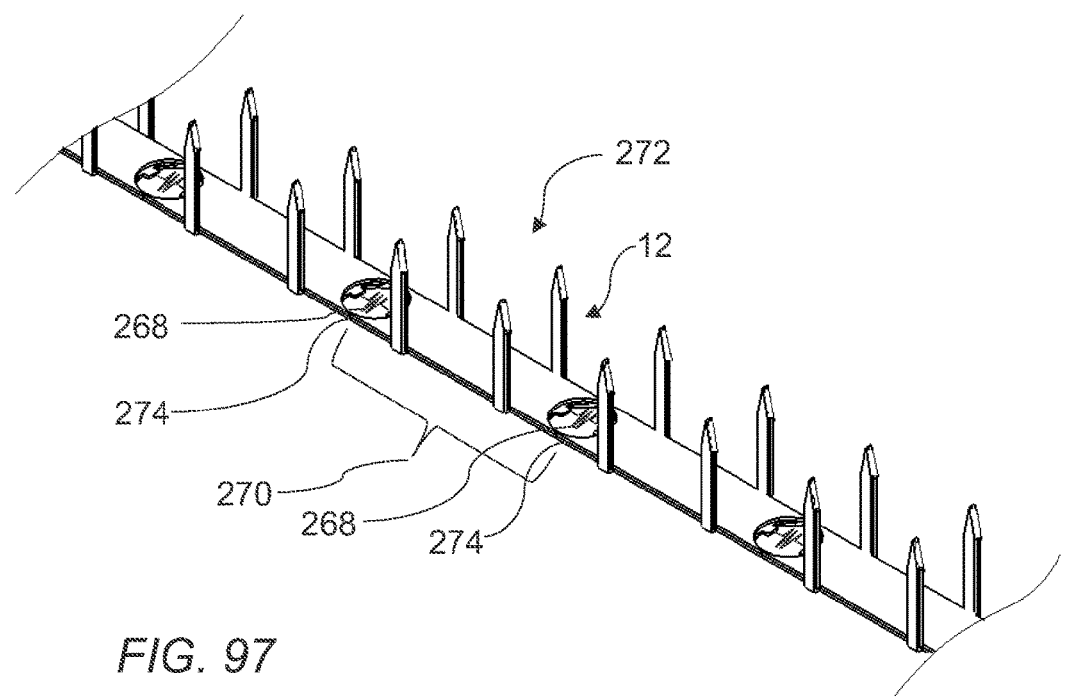
FIG. 97 is an isometric view of an element block array which includes multiple break-away sections, the element block array being disposed within an element support body which is not shown, and the element block array including multiple element block assemblies incorporating multiple respective element transition mechanisms disposed in a neutral configuration and multiple respective engagement elements disposed in a deployment state.

For example if the given element transition mechanism 240 is configured as a balloon apparatus 24, the respective expandable transition coupler 268 may be configured as a flexible tube having an interior lumen. If the given element transition mechanism 268 is configured as a shape memory insert 178, the respective expandable transition coupler 268 may be configured as a flexible tube having an interior lumen (such that high temperature or low temperature activation fluid 188 can be delivered to the shape memory insert 178). If the given element transition mechanism 240 is configured as a patterned insert assembly 192, the respective expandable transition coupler 268 may be configured as a flexible cable or wire which is attached to the first patterned insert 196. If the given element transition mechanism 240 is configured as a capacitor plate assembly 228, the respective expandable transition coupler 268 may be configured as a flexible conductive wires. The expandable transition couplers 268 thus allow each element block assembly 238 to move with respect to adjacent element block assemblies 238, with each element block assembly 238 remaining operatively coupled to adjacent element block assemblies 238 via the expandable transition couplers 268. This allows for the reversible transition of each element transition mechanism to the expanded configuration 240' and the reversible transition of respective engagement elements to the engagement state 12' as shown in FIG. 96.

Some embodiments of adhesion devices may incorporate multiple element transition mechanisms 240 wherein each element transition mechanism 240 is serially connected to the control system 50 by multiple expandable transition couplers 268. In this case adjacent element transition mechanisms 240 may be connected by an expandable transition coupler 268 (one which is ultimately operatively coupled to the control system 50), and a user of the adhesion device may selectively activate groups of element transition mechanisms 240. Other adhesion devices may have each element transition mechanism 240 directly coupled to the control system 50 by a respective expandable transition coupler 268. This configuration allows for a user of the adhesion system to selectively activate single element transition mechanisms 240.

FIGS. 98-101 depict another means by which multiple element block assemblies 270 can be releasably secured to adjacent element block assemblies 270 in order to form an element block array 272. In this case, a break-away section 274 can be formed into each respective element activation sheet 20 and each respective element deployment sheet 22 between adjacent element block assemblies 270. For some embodiments, each break-away section 274 can be cut into the respective element activation sheet 20 and element deployment sheet 22 during the cutting of the element block cut pattern 76 which has been previously discussed.

Figure 98:
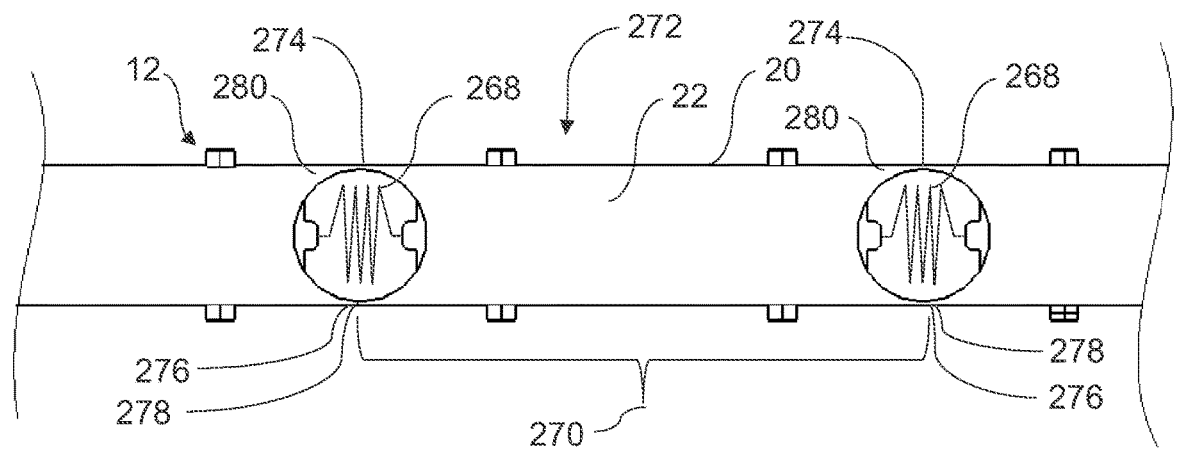
FIG. 98 is an elevation view of FIG. 97 depicting the element block assemblies and respective break-away sections.
Figure 99:
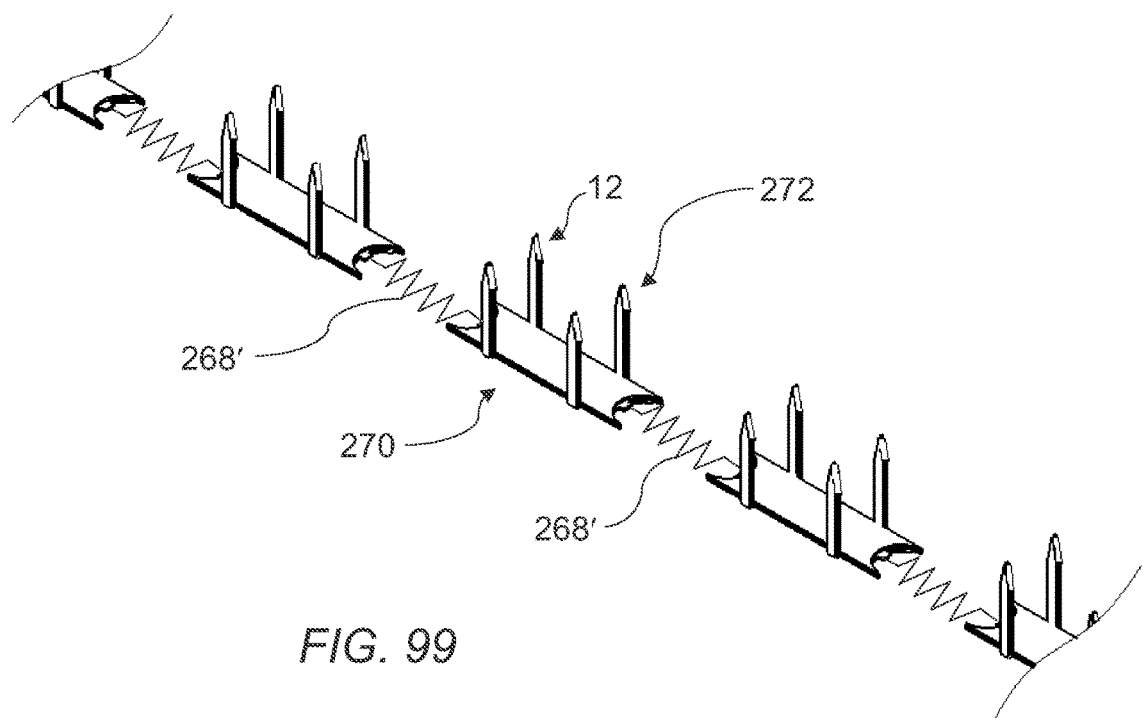
FIG. 99 depicts the element block array of FIG. 97 after the element block assemblies have been separated by the expansion of the element support body, each element block assembly being operatively connected to adjacent element block assemblies by an expandable transition coupler.
Figure 100:
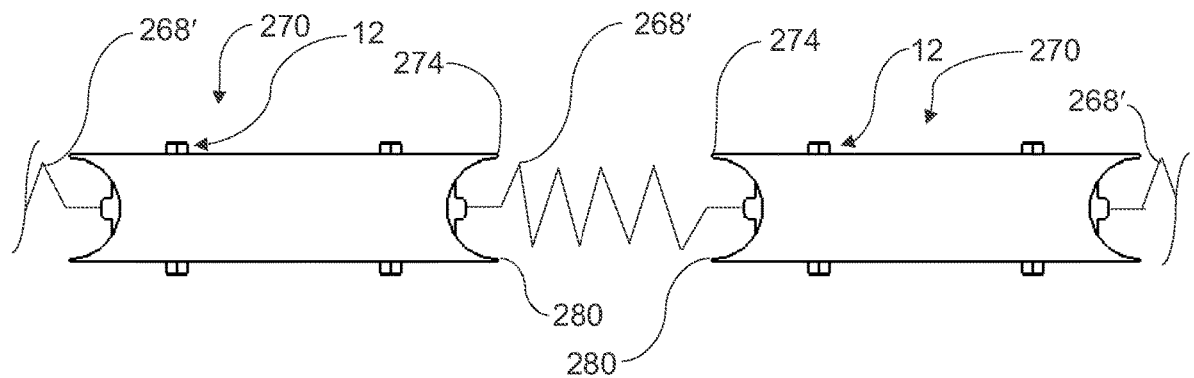
FIG. 100 is an elevation view of FIG. 99.

The break-away sections 274 which are disposed between adjacent element block assembles 270 are depicted in FIG. 98. Each break-away section 274 may include an activation break-away section 276 which is disposed within the element activation sheet 20 and a deployment break-away section 278 which is disposed within the element deployment sheet 22. Each break-away section 274 may include at least one tapered section 280 which is designed to break when respective element block assemblies 270 expand away from each other as depicted in FIGS. 99 and 100. The expansion of the element block assemblies 270 may be due to the expansion of an element support body (not shown) into which the element block assemblies 270 are partially disposed.

Figure 101:
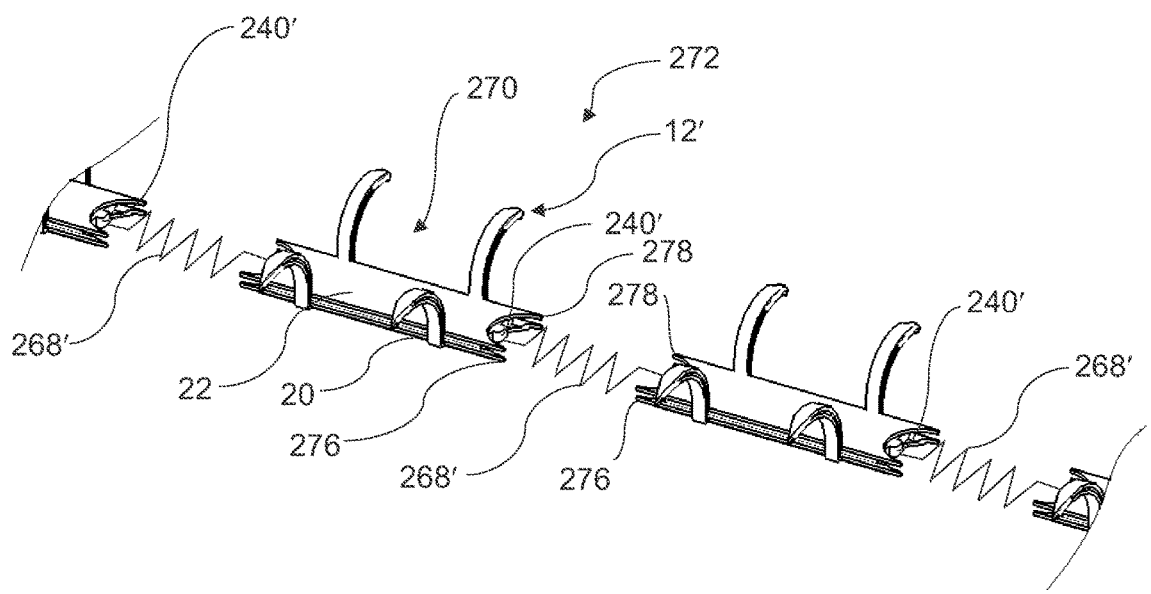
FIG. 101 depicts the element block assemblies of FIG. 99 with the respective element transition mechanisms disposed in an expanded configuration and the respective engagement elements disposed in the engagement state.

Again the expandable transition couplers 268 allow each element block assembly 270 to move with respect to adjacent element block assemblies 270, with the element block assembly 270 remaining operatively coupled to adjacent element block assemblies 270 via the expandable transition couplers 268. This allows for the reversible transition of each element transition mechanism to the expanded configuration 240' and the reversible transition of respective engagement elements to the engagement state 12' as shown in FIG. 101.

As has been discussed, adhesion devices which include element block assemblies which are releasably secured to adjacent element block assemblies to form element block arrays can be configured in a variety of different manners including but not limited to bandages, balloons, tubes, pads, or the like. Multiple device embodiments which utilize element block arrays will now be discussed, with the break-away section embodiment used in each case as the means by which each element block assembly is releasably secured to adjacent element block assemblies.

Figure 102:
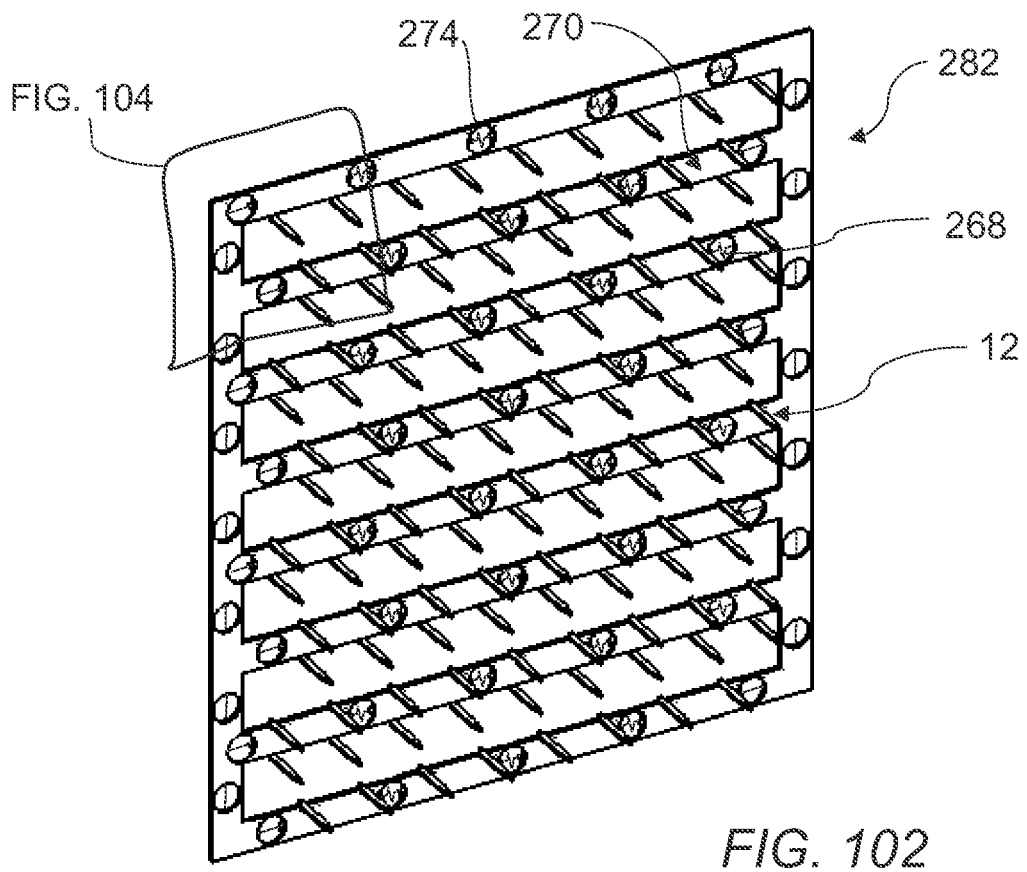
FIGS. 102 and 103 depict an embodiment of an element block array which incorporates multiple element block assemblies which are connected by respective break-away sections.
Figure 103:
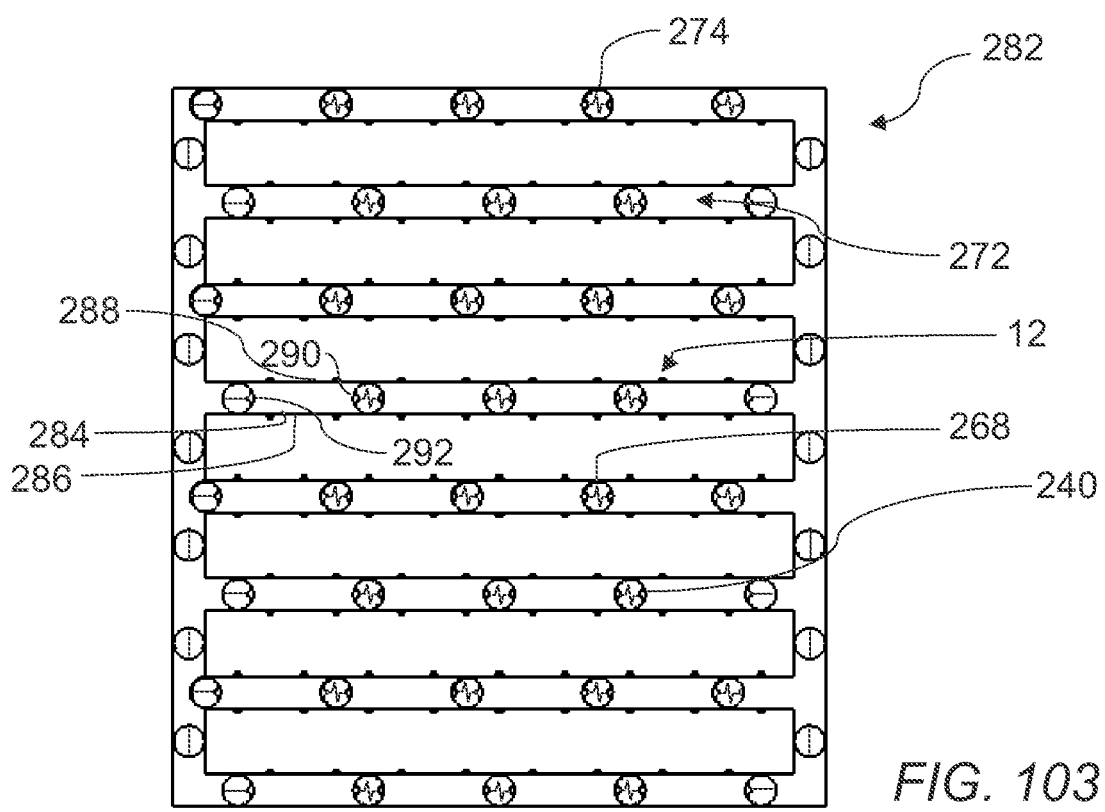
Figure 104:
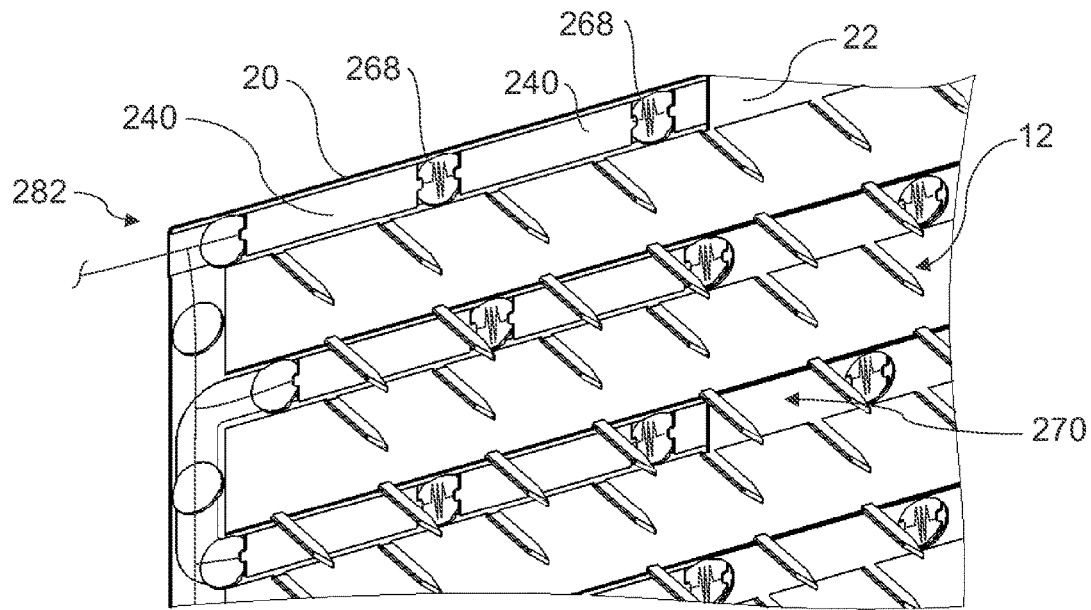
FIG. 104 is an enlarged view of FIG. 102.

FIGS. 102-104 depict an embodiment of an element block array 282 which includes multiple break-away sections 274. The element block array 282 which is depicted in FIGS. 102-104 may be manufactured in a manner which is similar to that which was discussed for the fused sheet assembly embodiment 72 which is depicted in FIG. 19 with the following exception. The break-away sections 274 may be cut into the fused sheet assembly 72 during the cutting of the element block pattern 76. FIGS. 102-104 thus depict an element block array 282 having multiple element block assemblies 270 which are releasably secured to adjacent element block assemblies 272. Each element block assembly 270 includes an element transition mechanism 240, and each element transition mechanism 240 may be operatively coupled to adjacent element transition mechanisms 240 by expandable transition couplers 268 as shown in FIG. 104 which is an enlarged view of FIG. 102 with a portion of the element deployment sheet 22 cut away. This allows for the expansion of the element block assemblies 270 as has previously been discussed with regard to FIGS. 97-101.

The element block assemblies 270 which are disposed within the element block array 282 may be configured with a substantially rectangular element block profile 284. That is to say that each activation sheet profile 286 and each corresponding deployment sheet profile 288 may be configured to be rectangular and may also be substantially aligned with one another. A first block transition side 290 and a second block transition side 292 of each element block assembly 270 may each be configured with a portions of respective break-away sections 274 which are shared with adjacent element block assemblies 270 (see FIG. 98). The coupling of multiple rectangular element block assemblies 270 results in the formation of a substantially rectangular element block array 282 profile as shown in FIG. 103.

Element block arrays 282 having a rectangular profile may be used to create a variety of different adhesion devices. As an example FIGS. 105-111 depict an adhesion device 294 which is configured as a bandage, the adhesion device 294 incorporating multiple embodiments of the element block array 282 of FIG. 102. The following discusses adhesion devices which are configured with element block arrays wherein the element block assemblies 270 are releasable secured to adjacent element block assemblies 270 by break-away sections 274. However, the adhesion device configurations could be configured with element block arrays 252 which are configured with element block assemblies 238 which are secured to adjacent element block assemblies 238 with break-away tabs 262.

Figure 105:
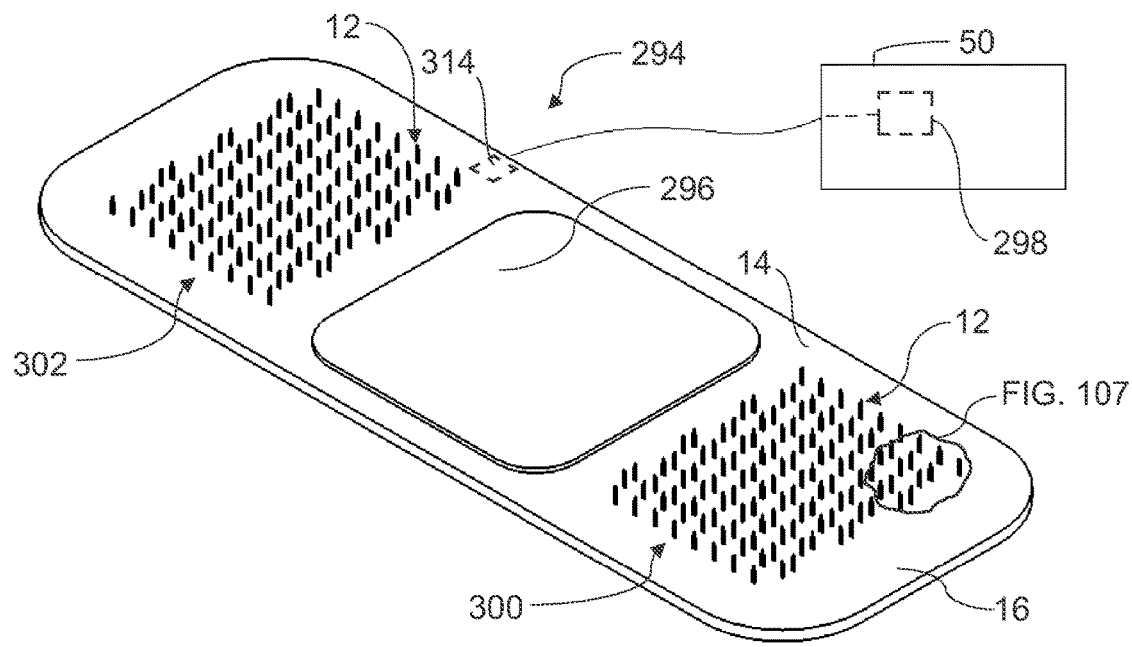
FIG. 105 depicts an adhesion device which is configured as a bandage, the adhesion device including a control system.

The adhesion device 294 which is depicted in FIG. 105 is configured as a bandage. The bandage 294 may be used for any suitable medical application such as wound care. The adhesion device embodiment 294 shown includes an element support body 14 with an engagement surface 16, a centrally disposed gauze section 296, a plurality of engagement elements 12 which are disposed on either side of the gauze section 296, and a control system 50 which is operatively coupled to the adhesion device 294. The control system 50 may incorporate at least one activation mechanism 298 which is operatively coupled to multiple element transition mechanisms 240 which are disposed within each element block array 282, the at least one activation mechanism 298 being configured to reversibly transition selective element transition mechanisms from the neutral configuration 240 to the expanded configuration 240'. The configuration of the activation mechanism 298 is dependent upon the configuration of the respective element transition mechanism 240. For example, if an element transition mechanism is configured as a balloon apparatus 24, the respective activation mechanism 298 could be configured as a fluid pump.

The gauze section 296 of the adhesion device 294 may be formed from any suitable gauze/dressing material which may in turn contain any suitable therapeutic agents. In this case the gauze section 296 is centrally located between a first engagement element section 300 and a second engagement element section 302, with multiple engagement elements 12 extending from the engagement surface 16 within each engagement element section. However, any configuration of gauze sections and engagement element sections could be fabricated for a given adhesion device which is configured as a bandage or the like. As an example, a circular gauze section could be surrounded by a continuous annular engagement element section (see FIG. 127).

Figure 106:
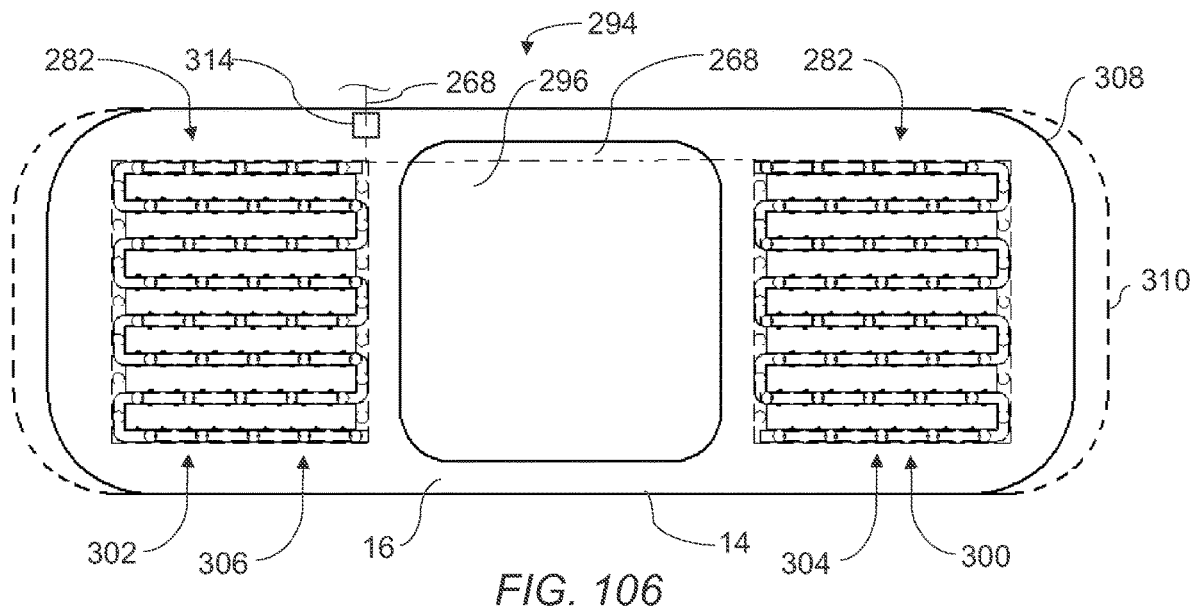
FIG. 106 is an elevation view of the adhesion device of FIG. 105, depicting a neutral profile and an expanded profile of the adhesion device.

FIG. 106 is an elevation view of the adhesion device 294 which incorporates multiple embodiments of the element block array 282 which is depicted in FIG. 102. In this case, a first element block array 304 may be operatively coupled to a second element block array 306 by a suitably configured expandable transition coupler 268. In turn the first element block array 304 may be operatively coupled to the control system 50 by a suitably configured expandable transition coupler 268. In this manner the first element block array 304 and the second element block array 306 are operatively coupled to the control system 50 in a serial manner.

The adhesion device 294 may be configured to stretch from a neutral profile 308 to an expanded profile 310 as depicted by the dashed line in FIG. 106. The expansion of the adhesion device 294 may take place during application, with the element support body 14 expanding from the neutral profile 308 to the expanded profile 310. As the element support body 14 expands, expansion forces 312 may be applied to element block assemblies 270 which are disposed within the first element block array 304 and the second element block array 306. The expansion forces 312 being applied to the element block assemblies 270 by the expanding element support body 14. The expansion forces 312 may result in the release of the break-away sections 274 which are disposed within the respective element block arrays 282 (as depicted in FIG. 108).

Figure 107:
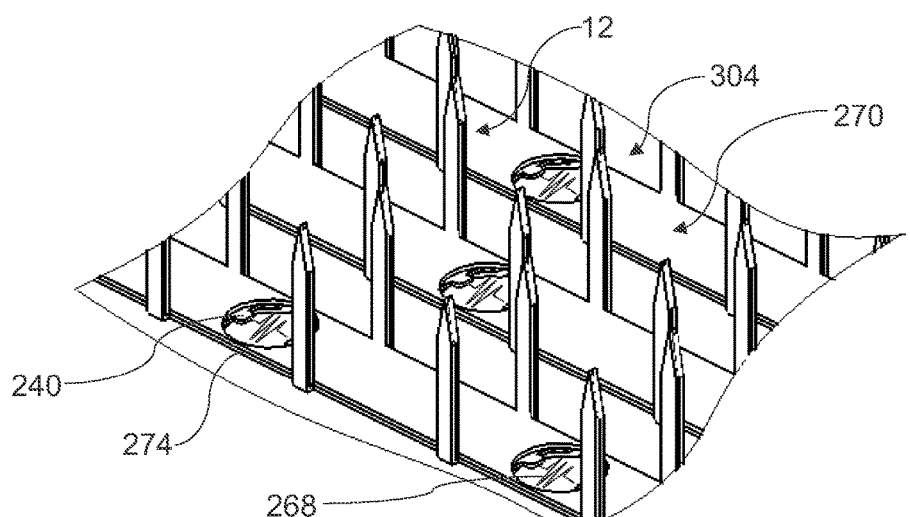
FIG. 107 is an isometric view of an element block array which is disposed within an element support body (not shown) of the adhesion device of FIG. 105.
Figure 108:
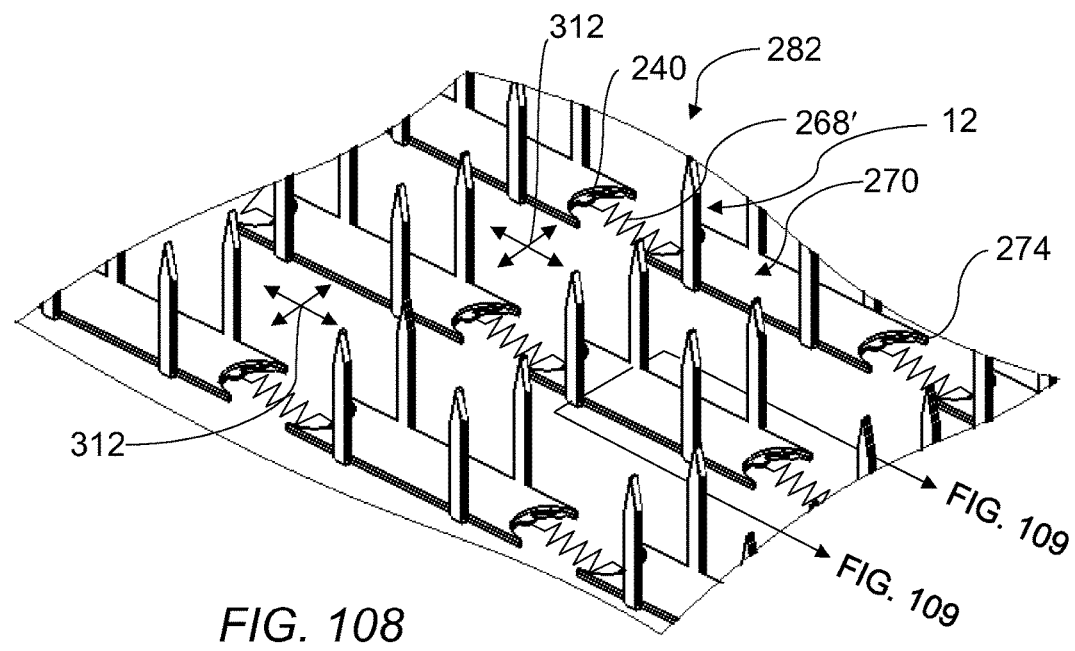
FIG. 108 depicts the separation of multiple element block assemblies of the element block array of FIG. 107 due to the expansion of the element support body (not shown), the multiple element block assemblies having respective element transition mechanisms which are disposed in a neutral configuration and multiple respective engagement elements which are disposed in the engagement state.
Figure 109:
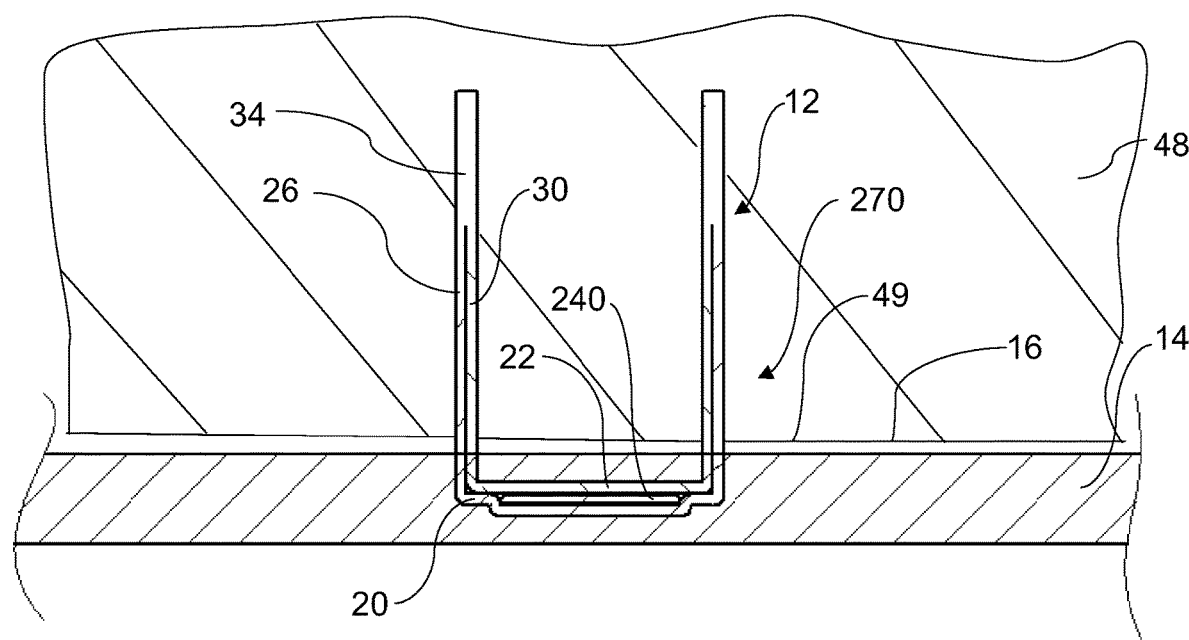
FIG. 109 is a sectional view of FIG. 108.
Figure 110:
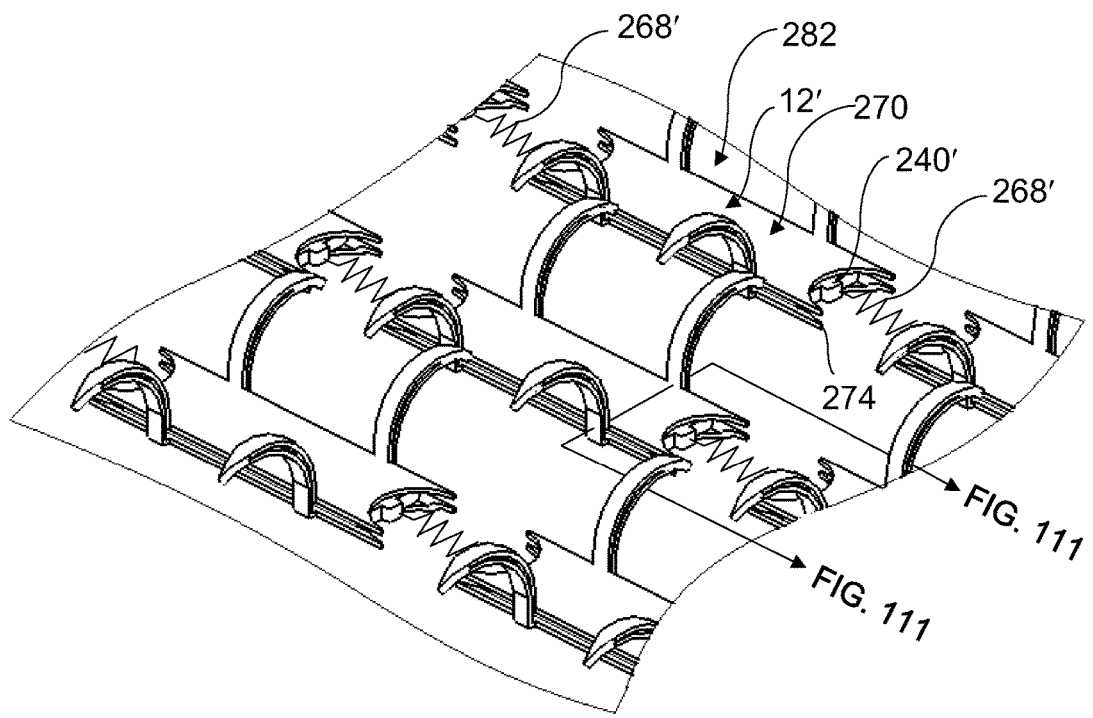
FIG. 110 depicts the element block assemblies of FIG. 108 with multiple respective element transition mechanisms disposed in an expanded configuration and multiple respective engagement elements disposed in an engagement state.

FIG. 107 is an isometric view of multiple element block assemblies 270 within the first element block array 304 of the adhesion device 294 (the element support body 14 and target material 48 are hidden in FIGS. 107, 108, and 110 in order to better illustrate each element block assembly 270). Each of the element block assemblies 270 which is depicted in FIG. 107 is connected to adjacent element block assemblies 270 by the break-away sections 274. FIG. 108 depicts the element block assemblies 270 of FIG. 107 after expansion forces 312 have released each element block assembly 270 from adjacent element block assemblies 270. As the element block assemblies 270 which are disposed within the element block arrays expand (with the expansion of the element support body 14), the respective expandable transition couplers transition from the compressed state 268 to the expanded state 268'. In this manner element transition mechanisms 240 remain operatively coupled to each other during the expansion of the element support body 14. FIG. 109 is a section view of FIG. 108 which depicts a section of a representative element block assembly 270 having the element transition mechanism disposed in the neutral configuration 240 and the respective engagement elements disposed in the deployment state 12.

Figure 111:
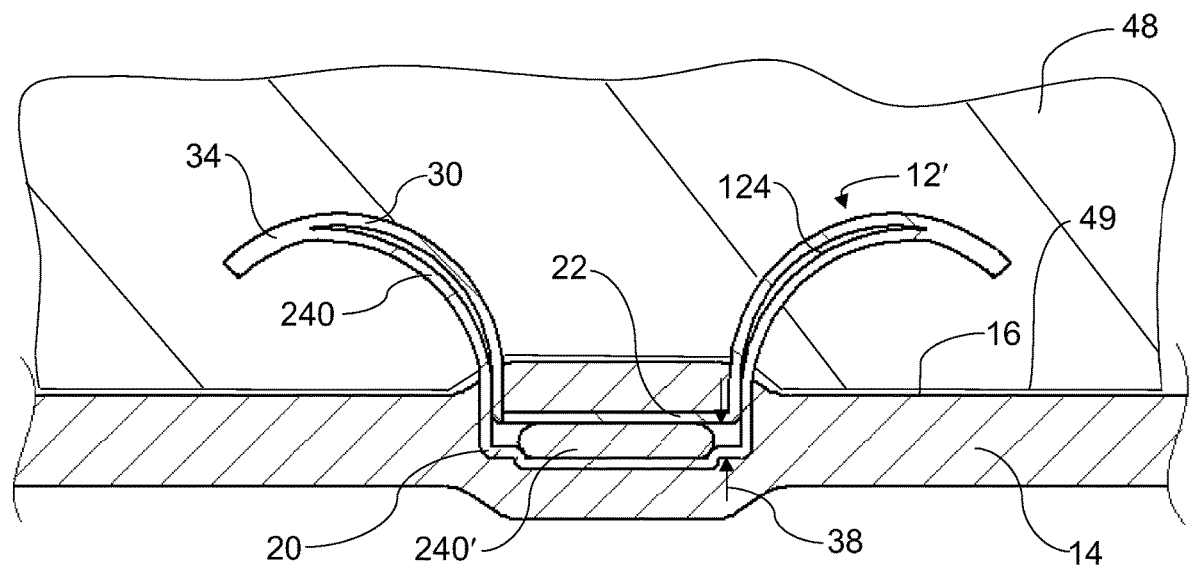
FIG. 111 is a sectional view of FIG. 110.

FIG. 110 depicts the element block assemblies 270 of FIG. 109 with the engagement elements transitioned to the engagement state 12'. FIG. 111 is a section view of a representative element block assembly 270 having the element transition mechanism disposed in the expanded configuration 240' and the respective engagement elements disposed in the engagement state 12'. Thus FIGS. 106-111 depict a deployment sequence for the adhesion device 294 of FIG. 105. The adhesion device 294 would be expanded from the neutral profile 308 to the expanded profile 310 during the application of the adhesion device 294 to the target material 48. The expansion of the adhesion device 294 results in the application of expansion forces 312 to the element block assemblies 270 disposed within the element block arrays 282. The expansion forces 312 result in the release of each element block assembly 270 from adjacent element block assemblies 270 (FIG. 108).

Each element transition mechanism of each element block assembly 270 can then be transitioned to the expanded configuration 240' thereby transitioning respective engagement elements to the engagement state 12' and securing the adhesion device 294 to the surface 49 of the target material 48 (FIGS. 108 and 109). The adhesion device 294 may then be removed by transitioning each element transition mechanism from the expanded configuration 240' to the neutral configuration 240 thereby transitioning respective engagement elements to the deployment state 12 (as shown in FIGS. 108 and 109). Some embodiments of the adhesion device 294 may be manufactured using methods and fixtures for similarly configured embodiments which have been disclosed in U.S. application Ser. No. 14/240,668.

Some embodiments of the adhesion device 294 may include an optional control system coupler 314 which is depicted in FIGS. 105 and 106. The control system coupler 314 may be configured to releasably secure the control system 50 to the adhesion device 294. The configuration of the control system coupler 314 may be dependent upon the configuration of the respective element transition mechanisms 240. For example element transition mechanisms 240 which are configured as balloon apparatuses 24 may be operatively connected to a control system coupler 314 which is configured as a quick connect fluid connector. Element transition mechanisms 240 which are configured as capacitor plates assemblies 228 may be operatively connected to a control system coupler 314 which is configured as a quick connect electrical connector.

In both cases the control system coupler 314 would be configured to allow for the decoupling of the adhesion device 294 from the control system 50, and the control system coupler 314 would be configured to allow for the coupling of the adhesion device 294 to the respective control system 50. In use, a user would deploy the adhesion device 294 into the target material 48 and transition the engagement elements to the engagement state 12'. The user could then decouple the control system 50 from the adhesion device 294 using the control system coupler 314. In some cases, the user could recouple the control system 50 to the adhesion device 294 using the control system coupler 314, thereby allowing for the removal of the adhesion device 294 from the target material 48. Any suitable adhesion device configuration which is discussed herein may be configured with a suitably configured control system coupler 314.

FIGS. 112-118 depict another adhesion device embodiment which may be manufactured utilizing at least one element block array 282 of FIGS. 102 and 103. In this case the adhesion device 316 is configured as a cylindrical tube having a cylindrical engagement surface 318, with a plurality of engagement elements 12 extending from the engagement surface 318. The adhesion device 316 also includes an interior surface 320 which is opposed to the engagement surface 318. The adhesion device 316 may also include a control system 50 which may incorporate at least one activation mechanism 298 which is operatively coupled to multiple element transition mechanisms 240 which are disposed within the at least one element block array 282, the at least one activation mechanism 298 being configured to reversibly transition selected element transition mechanisms from the neutral configuration 240 to the expanded configuration 240'. The adhesion device 316 may be used for a variety of different applications. For example, in the medical industry the adhesion device 316 may be used for anastomosis or the joining of two vessels together. The adhesion device 316 (or any other adhesion device embodiment discussed herein) could also be configured as an adhesive coating on an implant such as a stent or an artificial heart valve. The adhesive coating would allow for the attachment (and removal if required) of the given adhesion device to a target tissue.

Figure 112:
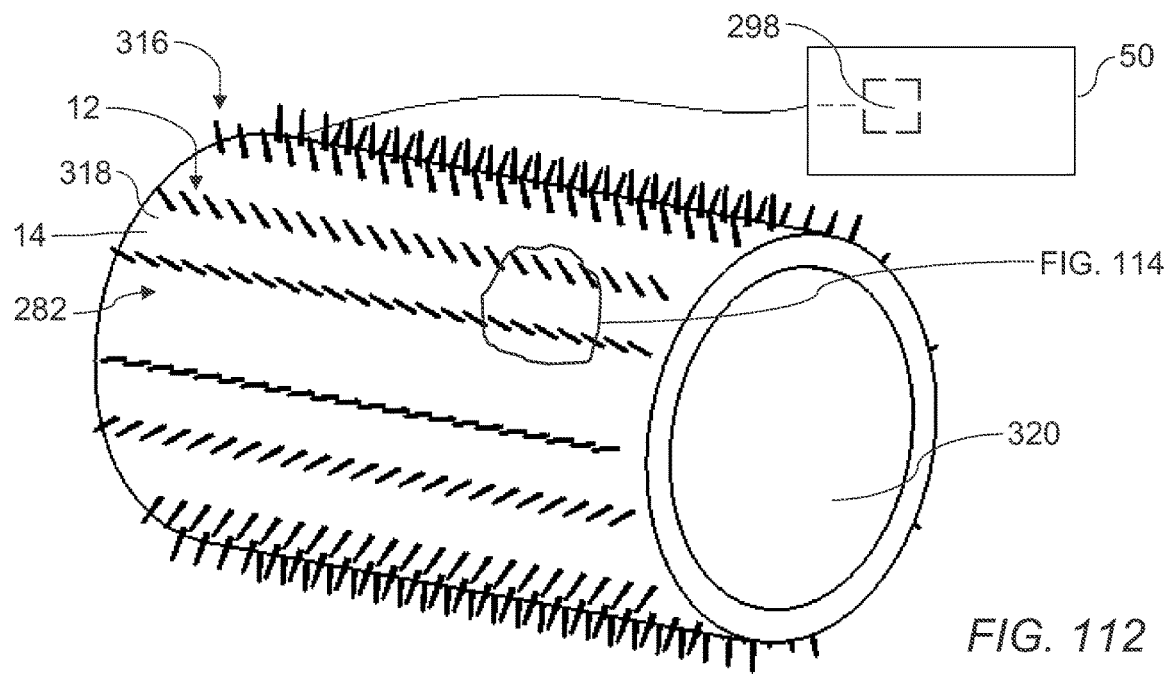
FIG. 112 depicts an adhesion device which is configured as a cylinder, the adhesion device including a control system.
Figure 113:
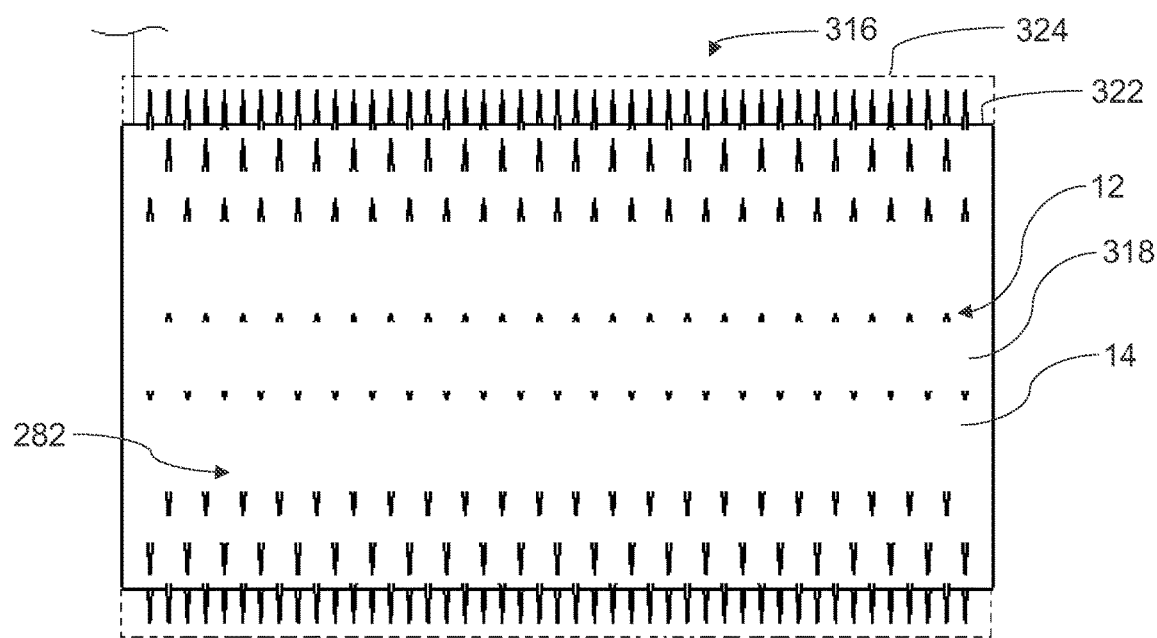
FIG. 113 is an elevation view of the adhesion device of FIG. 112, depicting a neutral profile and an expanded profile of the adhesion device.

FIG. 112 is an isometric view of the adhesion device 316 which may incorporate at least one embodiment of the element block array 282 (see FIG. 114) which is depicted in FIG. 102. The at least one element block array 282 may be operatively coupled to a control system 50 of the adhesion device 316. The adhesion device 316 may be configured to stretch from a neutral profile 322 to an expanded profile 324 as depicted by the dashed line in FIG. 113. The expansion of the adhesion device 316 may take place during application, with the element support body 14 expanding from the neutral profile 322 to the expanded profile 324. As the element support body 14 expands, expansion forces 312 may be applied to element block assemblies 270 which are disposed within the at least one element block array 282. The expansion forces 312 being applied to the element block assemblies 270 by the expanding element support body 14. The expansion forces 312 may result in the release of the break-away sections 274 which are disposed within the at least one element block array 272 (as shown in FIG. 115).

Figure 114:
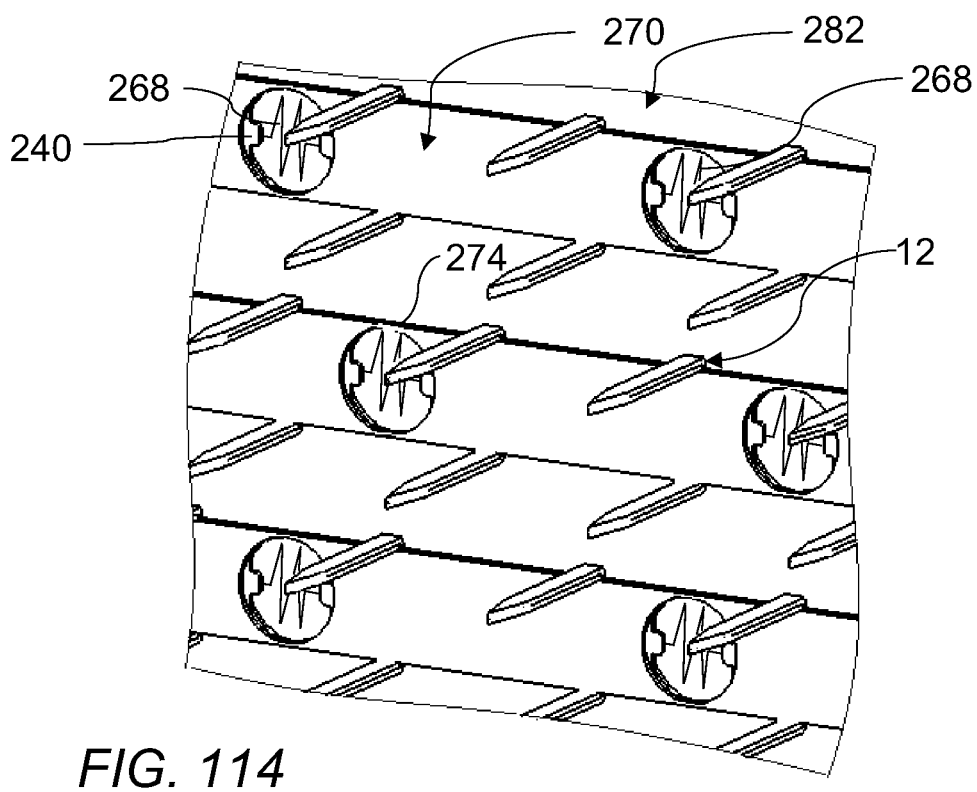
FIG. 114 is an isometric view of an element block array which is disposed within an element support body (not shown) of the adhesion device of FIG. 112.
Figure 115:
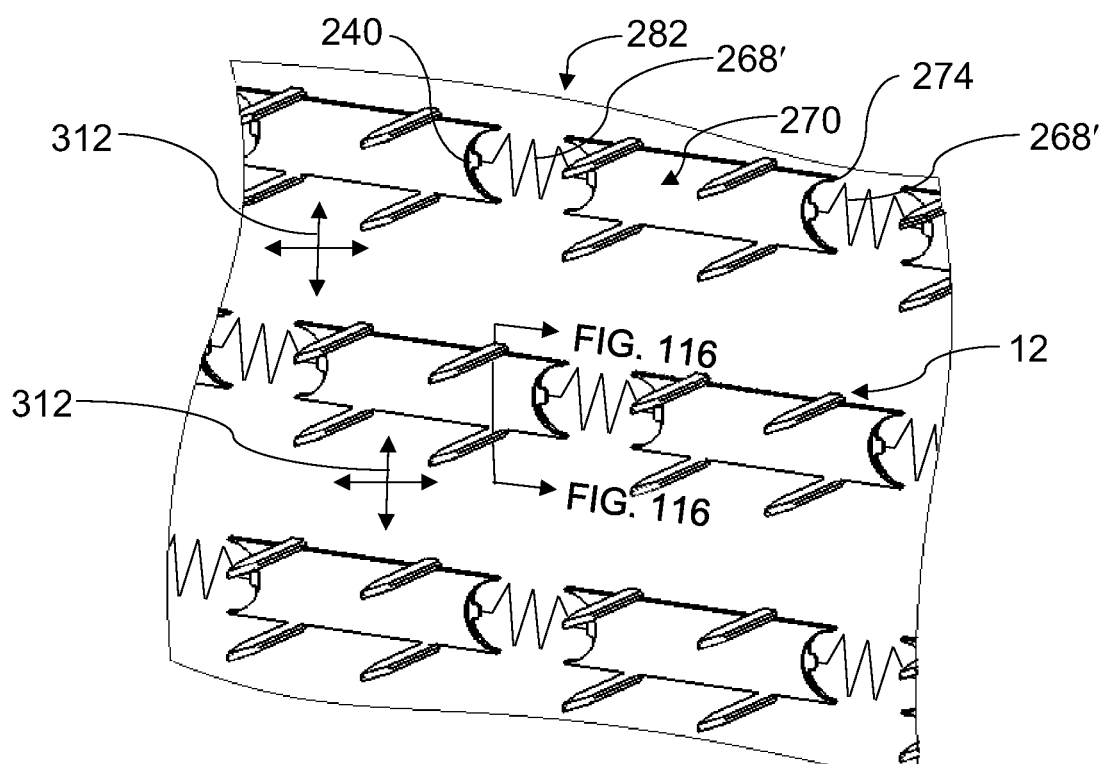
FIG. 115 depicts the separation of multiple element block assemblies of the element block array of FIG. 114 due to the expansion of the element support body (not shown), the multiple element block assemblies having respective element transition mechanisms which are disposed in a neutral configuration and multiple respective engagement elements which are disposed in the engagement state.
Figure 116:
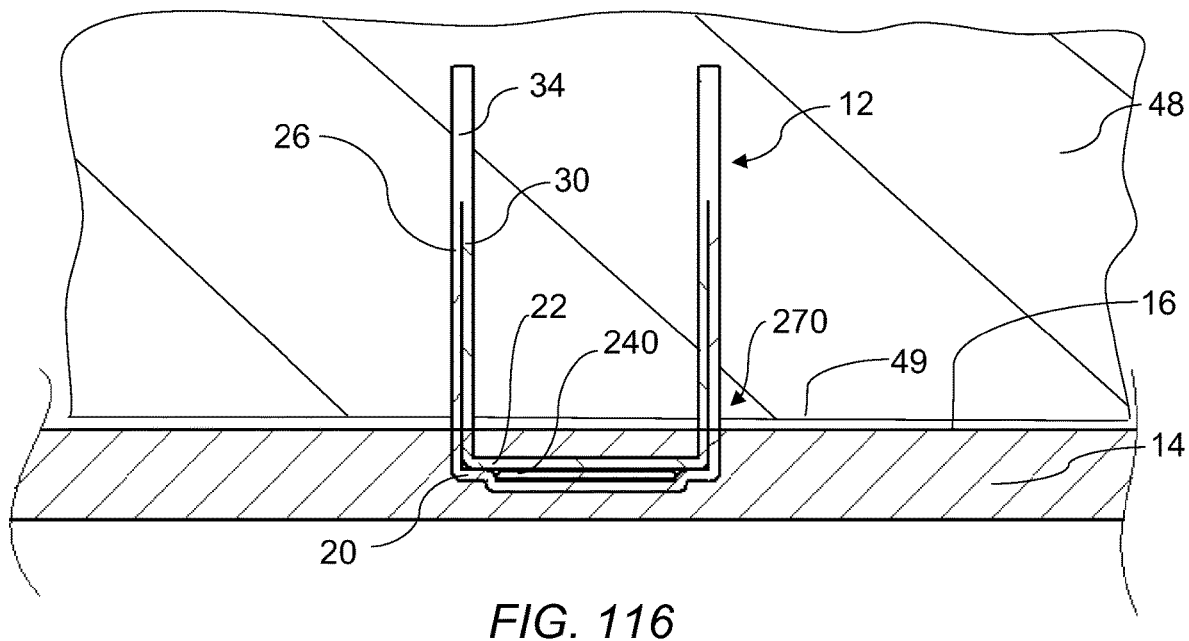
FIG. 116 is a sectional view of FIG. 115.
Figure 117:
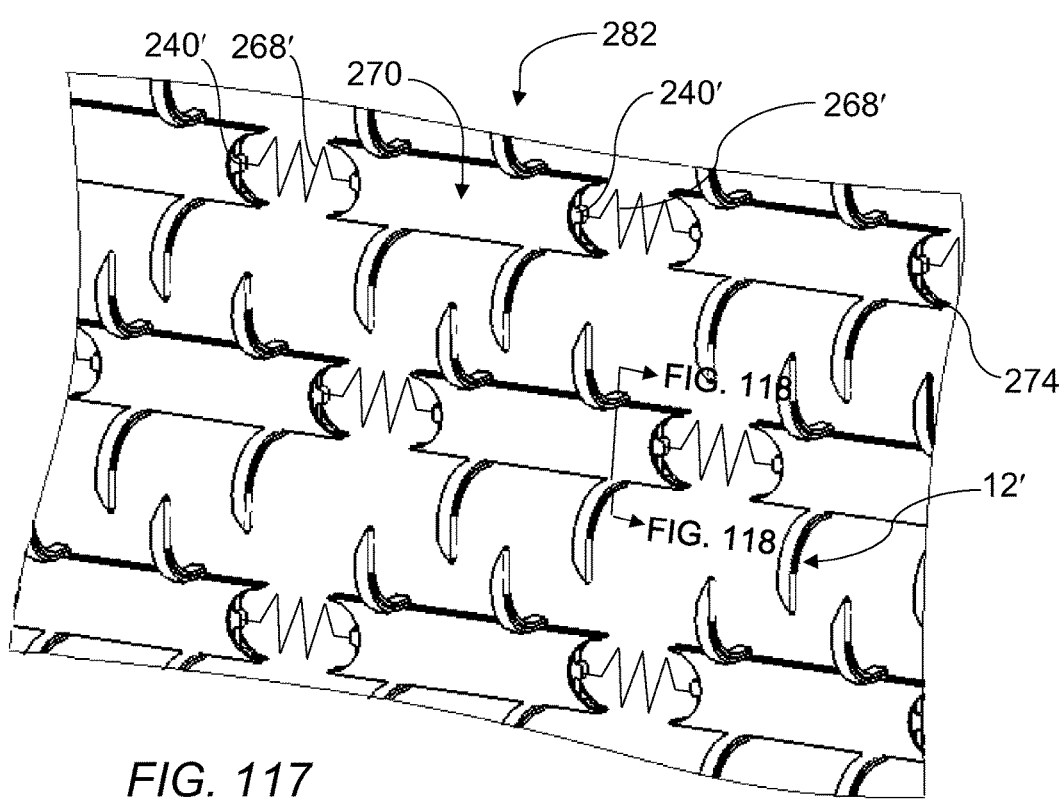
FIG. 117 depicts the element block assemblies of FIG. 114 with multiple respective element transition mechanisms disposed in an expanded configuration and multiple respective engagement elements disposed in an engagement state.

FIG. 114 is an isometric view of multiple element block assemblies 270 which are disposed within the at least one element block array 272 of the adhesion device 316 (the element support body 14 and target material 14 re hidden in FIGS. 114, 115, and 117 in order to better illustrate each element block assembly 270). Each of the element block assemblies 270 which is depicted in FIG. 114 is connected to adjacent element block assemblies 270 by the break-away sections 274. FIG. 115 depicts the element block assemblies 270 of FIG. 114 after expansion forces 312 have released each element block assembly 270 from adjacent element block assemblies 270. As the element block assemblies 270 which are disposed within the at least one element block array 272 expand (with the expansion of the element support body 14), the respective expandable transition couplers transition from the compressed state 268 to the expanded state 268'. In this manner element transition mechanisms 240 remain operatively coupled to each other during the expansion of the element support body 14. FIG. 116 is a section view of FIG. 115 which depicts a section of a representative element block assembly 270 having the element transition mechanism disposed in the neutral configuration 240 and the respective engagement elements disposed in the deployment state 12.

Figure 118:
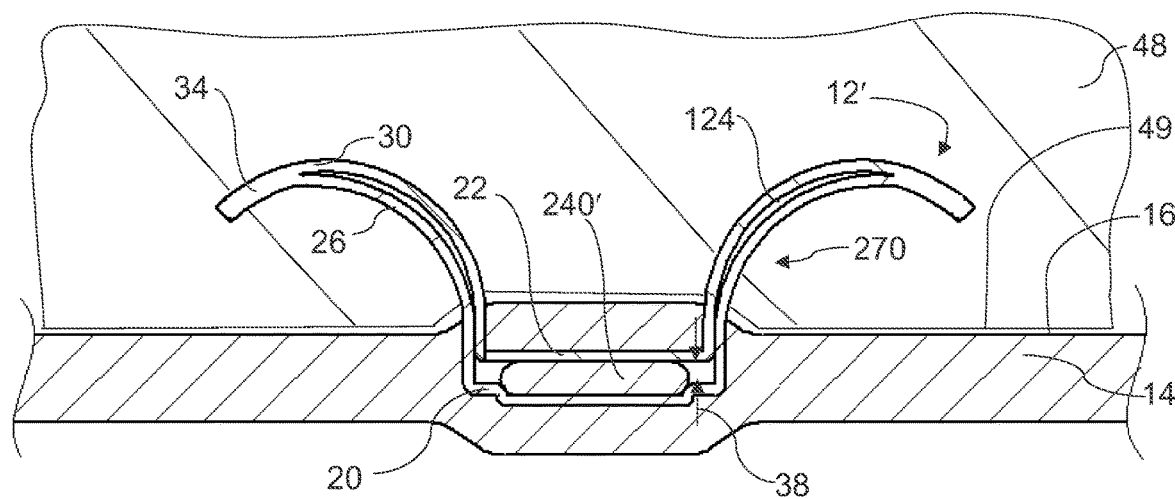
FIG. 118 is a sectional view of FIG. 117.

FIG. 117 depicts the element block assemblies 270 of FIG. 115 with the engagement elements transitioned to the deployment state 12'. FIG. 118 is a section view of a representative element block assembly 270 having the element transition mechanism disposed in the expanded configuration 240' and the respective engagement elements disposed in the engagement state 12'. Thus FIGS. 113-118 depict a deployment sequence for the adhesion device 316 of FIG. 112. The adhesion device 316 would be expanded from the neutral profile 322 to the expanded profile 324 during the application of the adhesion device 316 to the target material 48. The expansion of the adhesion device 316 results in the application of expansion forces 312 to the element block assemblies 270 disposed within the at least one element block array 272. The expansion forces 312 result in the release of each element block assembly 270 from adjacent element block assemblies 270 (see FIG. 115).

Each element transition mechanism of each element block assembly 270 can then be transitioned to the expanded configuration 240' thereby transitioning respective engagement elements to the engagement state 12' and securing the adhesion device to the surface of the target material 48 (FIGS. 117 and 118). The adhesion device 316 may then be removed by transitioning each element transition mechanism from the expanded configuration 240' to the neutral configuration 240 thereby transitioning respective engagement elements to the deployment state 12 (as shown in FIGS. 115 and 116). Some embodiments of the adhesion device 316 may be manufactured using methods and fixtures for similarly configured embodiments which have been disclosed in U.S. application Ser. No. 14/240,668.

FIGS. 119-125 depict another adhesion device embodiment which may be manufactured utilizing at least one element block array 282 of FIGS. 102 and 103. In this case the adhesion device 326 is configured as a cylindrical balloon having an engagement surface 328, with a plurality of engagement elements 12 extending from the engagement surface. The adhesion device 326 may include a balloon shaft 340 which is coupled to a control system 50. The control system 50 may incorporate at least one activation mechanism 298 which is operatively coupled to multiple element transition mechanisms 240 which are disposed within the at least one element block array 282, the at least one activation mechanism 298 being configured to reversibly transition selected element transition mechanisms from the neutral configuration 240 to the expanded configuration 240'. The control system 50 may also include an inflation mechanism 342 which is configured to inflate and deflate the cylindrical balloon from a neutral profile 344 to an expanded profile 346 (or any other suitable expanded profile). The adhesion device 326 may be used for a variety of different applications. In the medical industry the adhesion device 326 could be utilized for the closure of aneurisms or the like.

Figure 119:
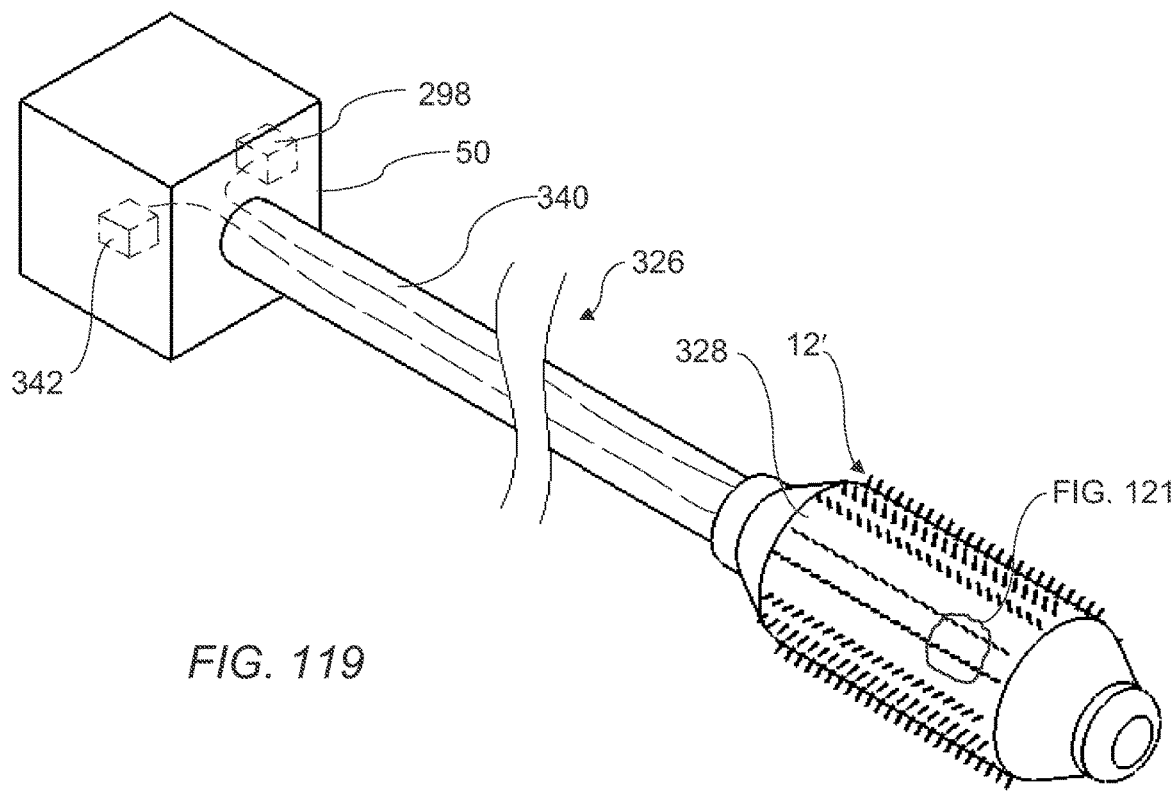
FIG. 119 depicts an adhesion device which is configured as a cylindrical balloon, the adhesion device including a control system.
Figure 120:
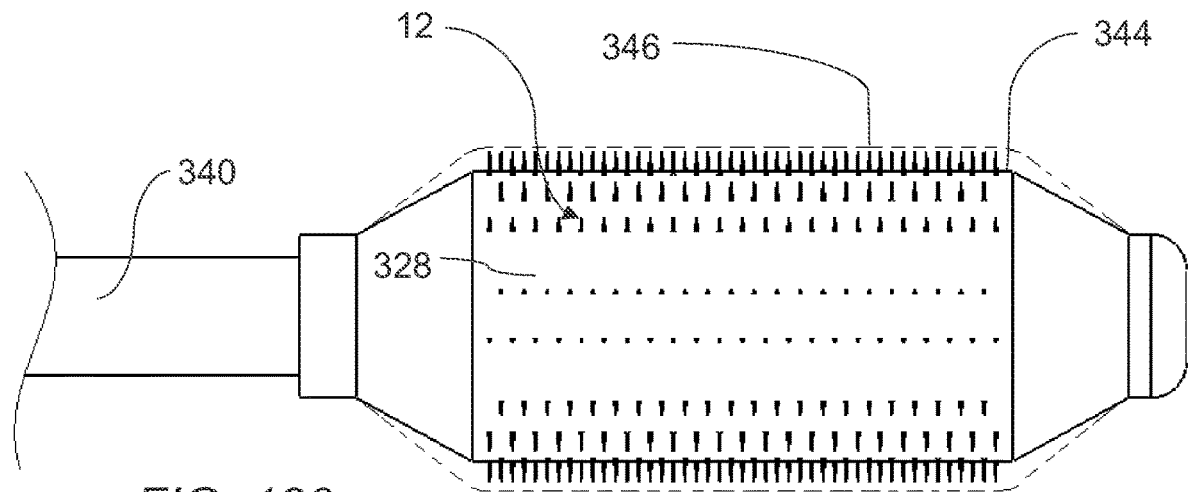
FIG. 120 is an elevation view of the adhesion device of FIG. 119, depicting a neutral profile and an expanded profile of the adhesion device.
Figure 121:
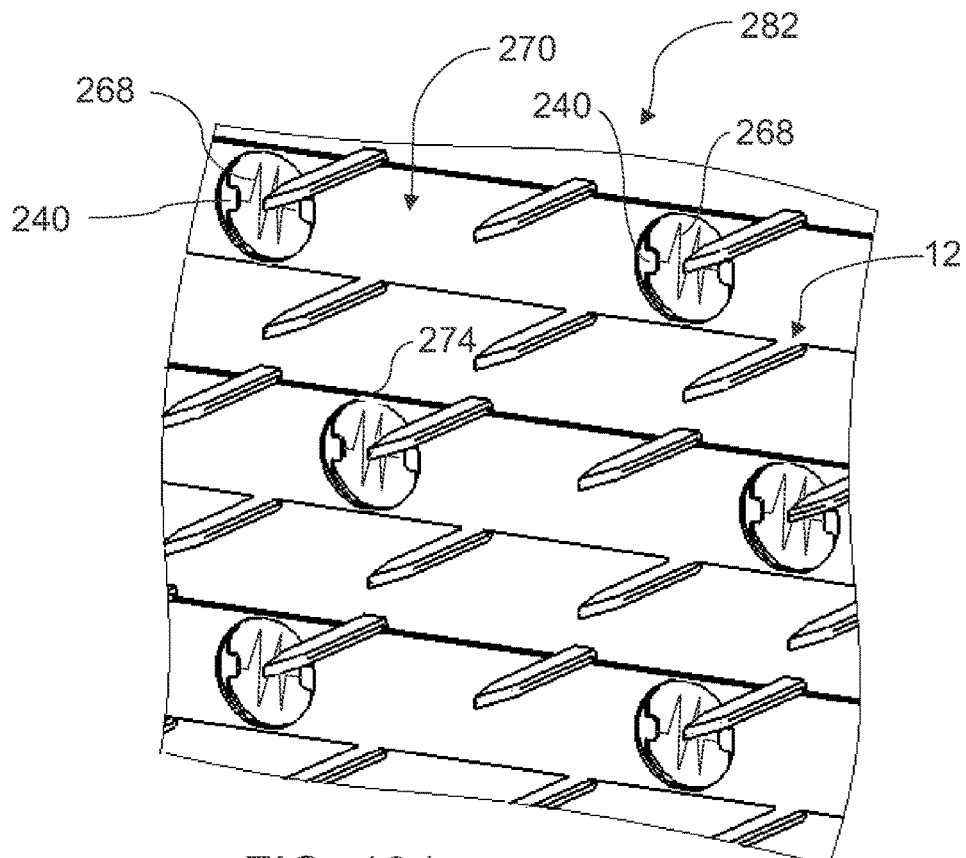
FIG. 121 is an isometric view of an element block array which is disposed within an element support body (not shown) of the adhesion device of FIG. 119.

FIG. 119 is an isometric view of the adhesion device 326 which may incorporate at least one embodiment of the at least one element block array 272 (see FIG. 114) which is depicted in FIG. 121. The at least one element block array 272 may be operatively coupled to the control system 50 of the adhesion device 326. The adhesion device 326 may be configured to inflate from the neutral profile 344 to the expanded profile 346 as depicted by the dashed line in FIG. 120 through the inflation of the cylindrical balloon. The expansion of the adhesion device 326 may take place during application, with the element support body 14 expanding from the neutral profile 344 to the expanded profile 346. As the element support body 14 expands, expansion forces 312 may be applied to element block assemblies 270 which are disposed within the at least one element block array 272. The expansion forces 312 being applied to the element block assemblies 270 by the expanding element support body 14 (which is expanding due to inflation of the cylindrical balloon). The expansion forces 312 may result in the release of the break-away sections 274 which are disposed within the at least one element block array (as shown in FIG. 122).

Figure 122:
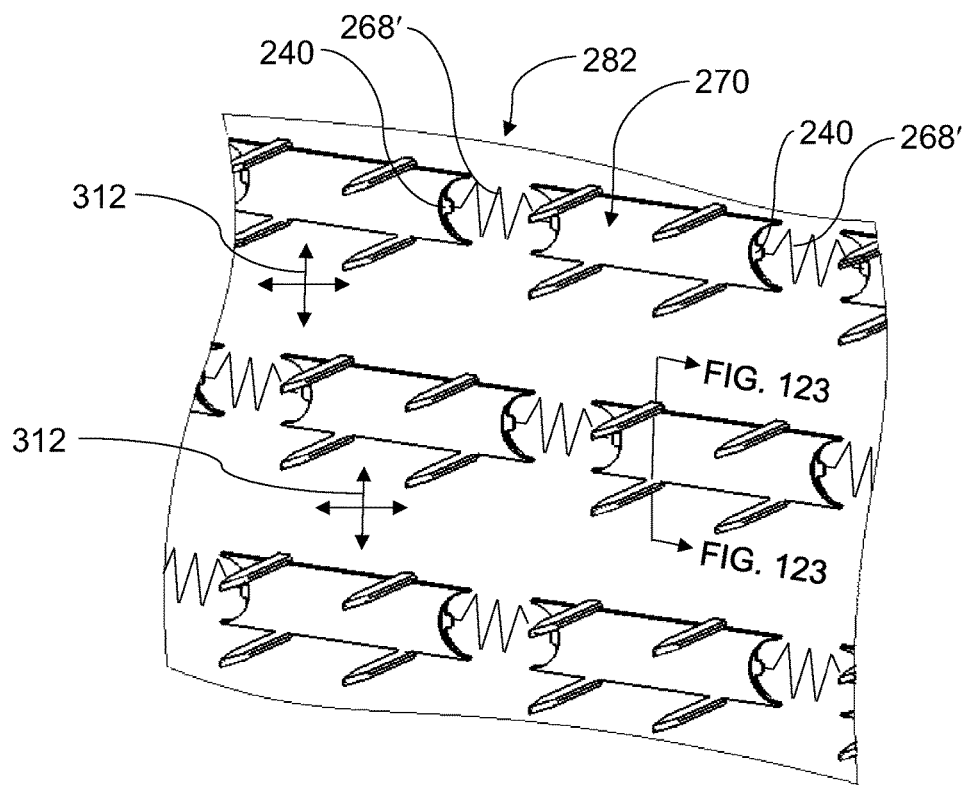
FIG. 122 depicts the separation of multiple element block assemblies of the element block array of FIG. 121 due to the expansion of the element support body (not shown), the multiple element block assemblies having respective element transition mechanisms which are disposed in a neutral configuration and multiple respective engagement elements which are disposed in the engagement state.
Figure 123:
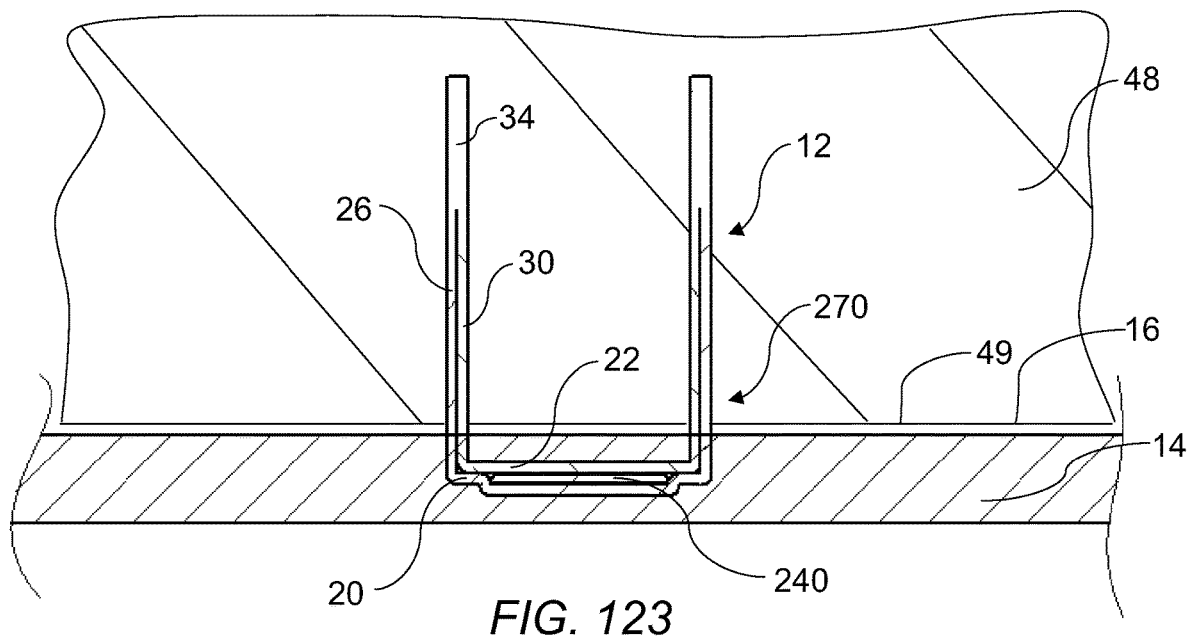
FIG. 123 is a sectional view of FIG. 122.
Figure 124:
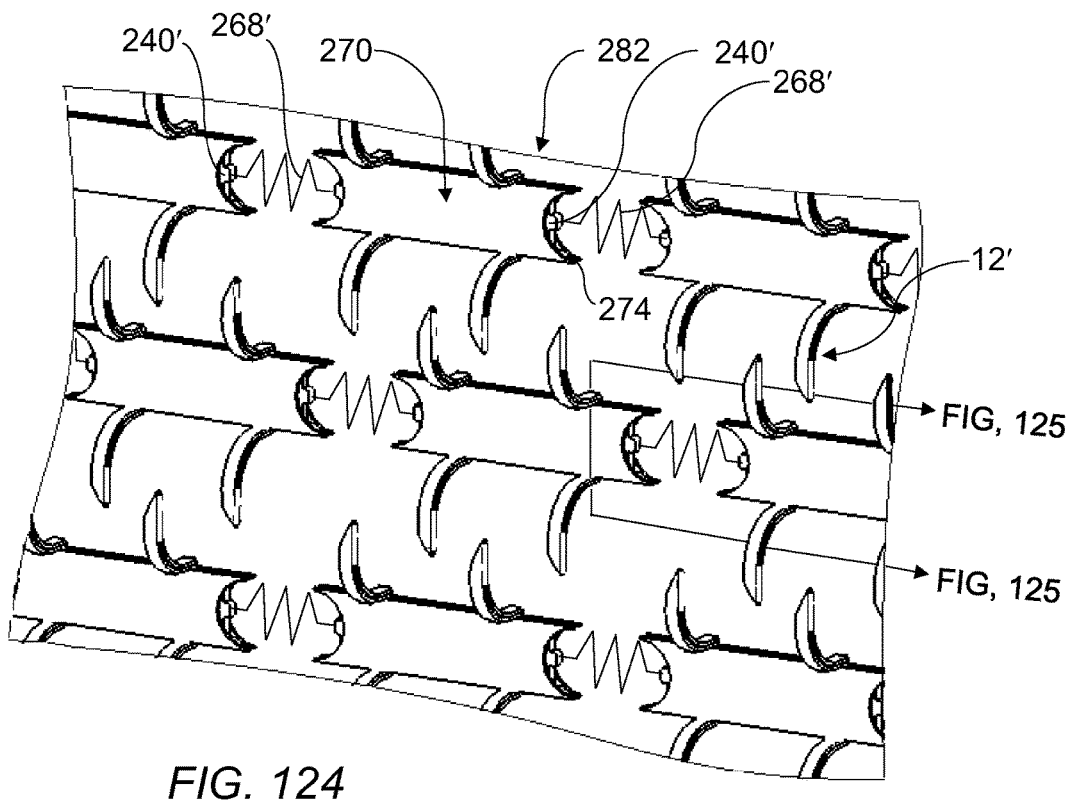
FIG. 124 depicts the element block assemblies of FIG. 122 with multiple respective element transition mechanisms disposed in an expanded configuration and multiple respective engagement elements disposed in an engagement state.

FIG. 244 is an isometric view of multiple element block assemblies 270 within the at least one element block array 272 of the adhesion device 326 (the element support body 14 and target material 48 are hidden in FIGS. 121, 122, and 124 in order to better illustrate each element block assembly 270). Each of the element block assemblies 270 which is depicted in FIG. 121 is connected to adjacent element block assemblies 270 by the break-away sections 274. FIG. 122 depicts the element block assemblies 270 of FIG. 121 after expansion forces 312 have released each element block assembly 270 from adjacent element block assemblies 270. As the element block assemblies 270 which are disposed within the at least one element block array 272 expand (with the expansion of the element support body 14), the respective expandable transition couplers transition from the compressed state 268 to the expanded state 268'. In this manner element transition mechanisms 240 remain operatively coupled to each other during the expansion of the element support body 14. FIG. 123 is a section view of FIG. 122 which depicts a section of a representative element block assembly 270 having the element transition mechanism disposed in the neutral configuration 240 and the respective engagement elements disposed in the deployment state 12.

Figure 125:
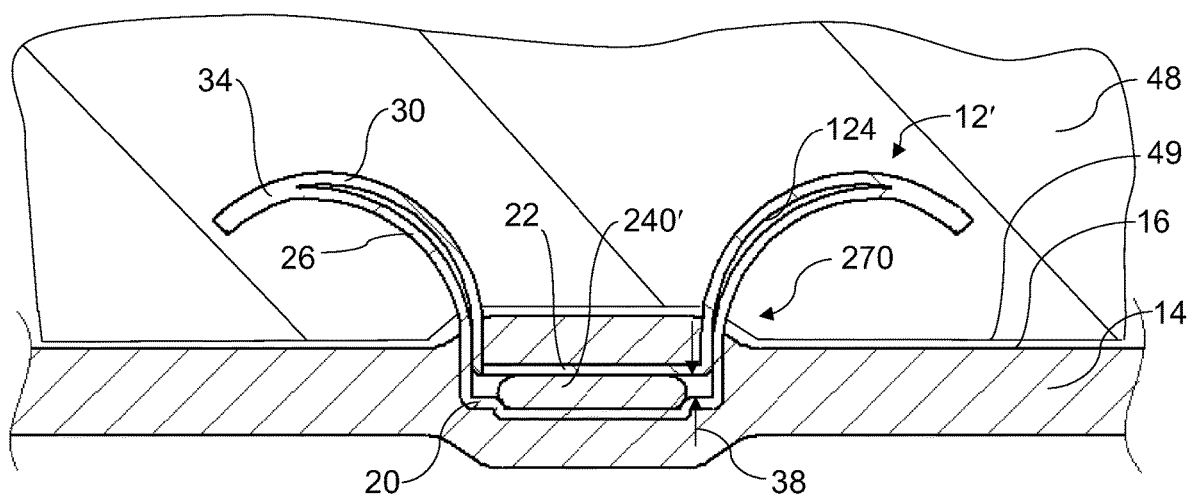
FIG. 125 is a sectional view of FIG. 124.

FIG. 124 depicts the element block assemblies 270 of FIG. 122 with the engagement elements transitioned to the deployment state 12'. FIG. 125 is a section view of a representative element block assembly having the element transition mechanism disposed in the expanded configuration 240' and the respective engagement elements disposed in the engagement state 12'. Thus FIGS. 120-125 depict a deployment sequence for the adhesion device 326 of FIG. 119. The adhesion device 326 would be expanded from the neutral profile 344 to the expanded profile 346 (by inflation of the cylindrical balloon) during the application of the adhesion device 326 to the target material 48. The expansion of the adhesion device 326 results in the application of expansion forces 312 to the element block assemblies 270 disposed within the at least one element block array 272. The expansion forces 312 result in the release of each element block assembly 270 from adjacent element block assemblies 270 (FIG. 122).

Each element transition mechanism of each element block assembly 270 can then be transitioned to the expanded configuration 240' thereby transitioning respective engagement elements to the engagement state 12' and securing the adhesion device 326 to the surface 49 of the target material 48 (FIGS. 124 and 125). The adhesion device 326 may then be removed by transitioning each element transition mechanism from the expanded configuration 240' to the neutral configuration 240 thereby transitioning respective engagement elements to the deployment state 12 (as shown in FIGS. 122 and 123). Some embodiments of the adhesion device 326 may be manufactured using methods and fixtures for similarly configured embodiments which have been disclosed in U.S. application Ser. No. 14/240,668.

Figure 126:
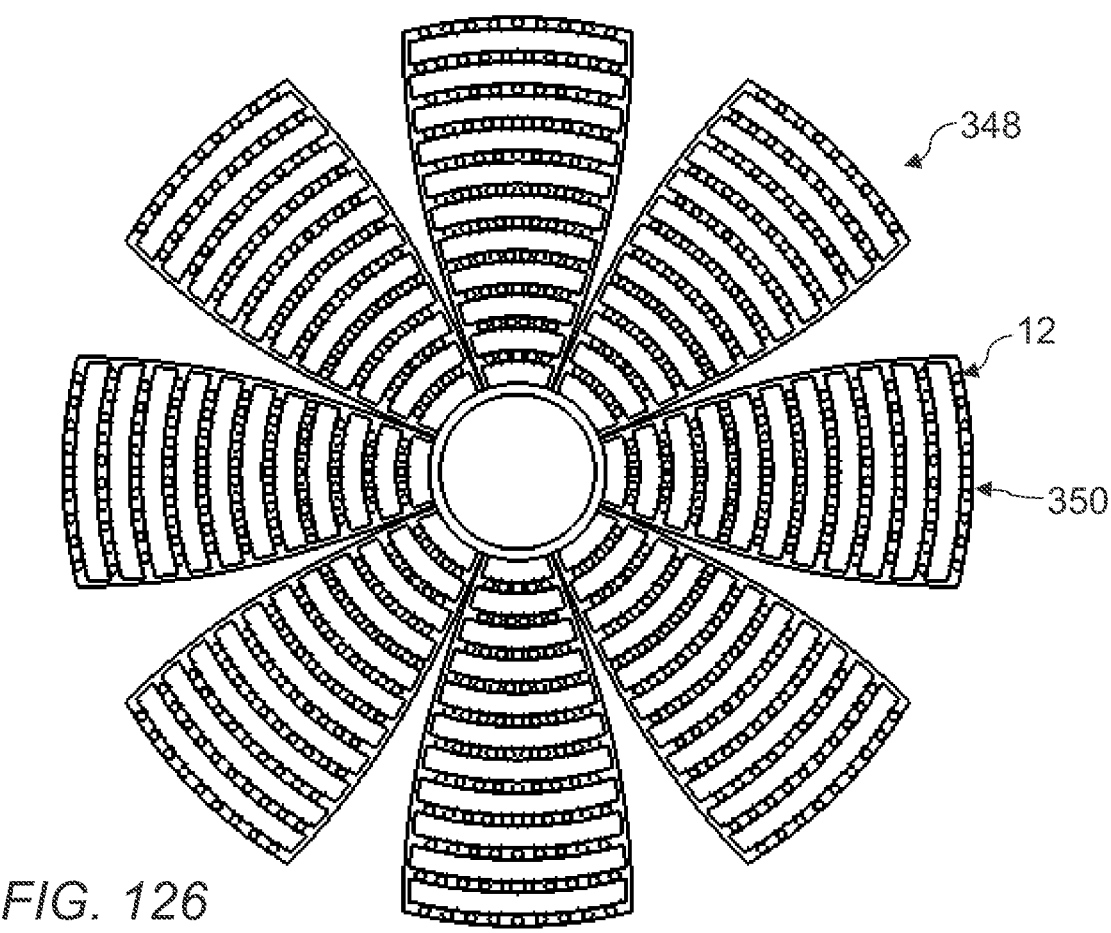
FIG. 126 is an elevation view of a spherical element block array.
Figure 127:
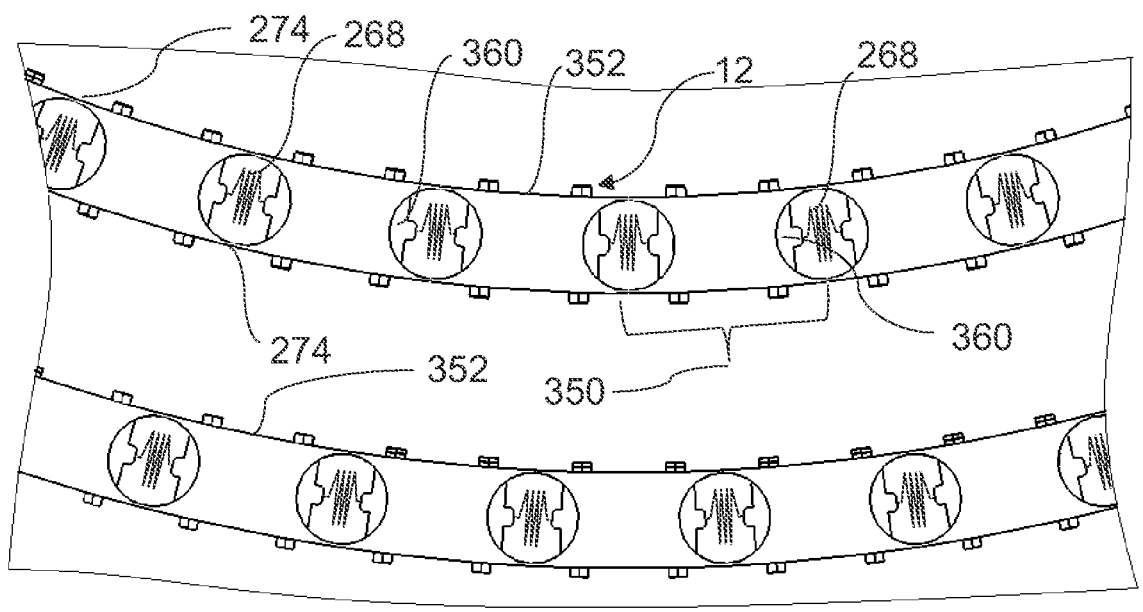
FIG. 127 is an enlarged view of FIG. 126.

FIGS. 126 and 127 depict an element block array 348 of element block assemblies 350 each of which are configured with a curved element block profile 352. Each element block assembly 350 may be coupled to adjacent element block assemblies 350 by break-away sections 274 as shown in FIG. 127. FIGS. 128-134 depict an adhesion device embodiment 354 which may be manufactured utilizing at least one element block array 348 of FIGS. 126 and 127. In this case the adhesion device 354 is configured as a spherical balloon having a spherical engagement surface 356, with a plurality of engagement elements 12 extending from the engagement surface 356. The adhesion device 354 may include a balloon shaft 358 which is coupled to a control system 50. The control system 50 may incorporate at least one activation mechanism 298 which is operatively coupled to multiple element transition mechanisms 360 which are disposed within the at least one element block array 348, the at least one activation mechanism 298 being configured to reversibly transition selected element transition mechanisms from a neutral configuration 360 to an expanded configuration 360'. The control system 50 may also include an inflation mechanism 362 which is configured to inflate and deflate the spherical balloon. The adhesion device 354 may be used for a variety of different applications. In the medical industry the adhesion device 354 could be utilized for the closure of aneurisms or the like.

Figure 128:
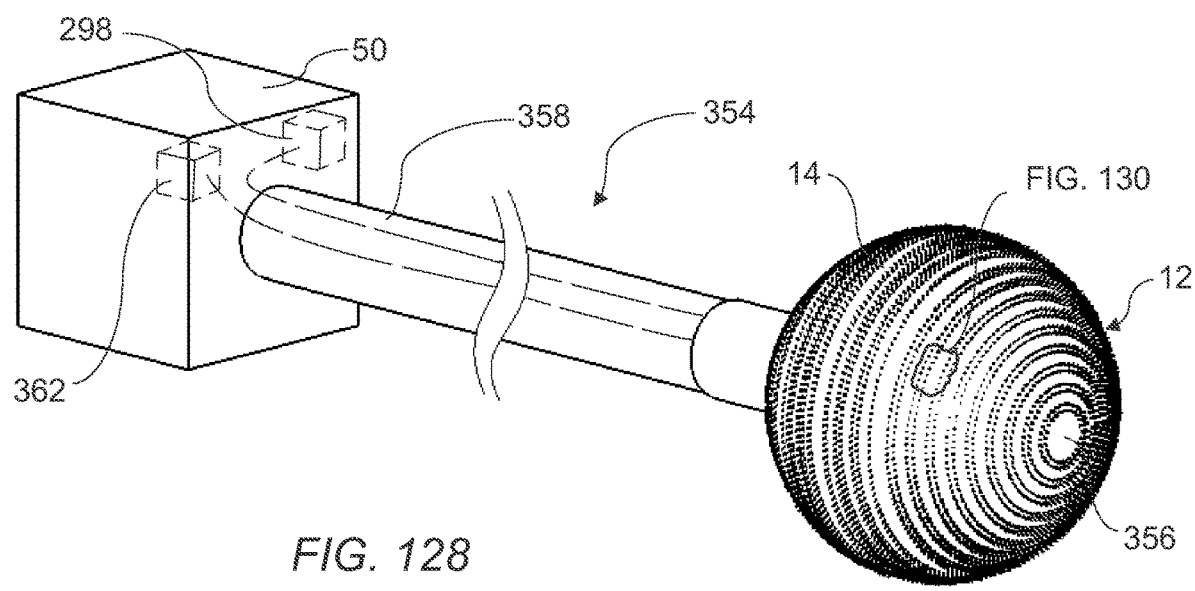
FIG. 128 depicts an adhesion device which is configured as a spherical balloon, the adhesion device including a control system.
Figure 129:
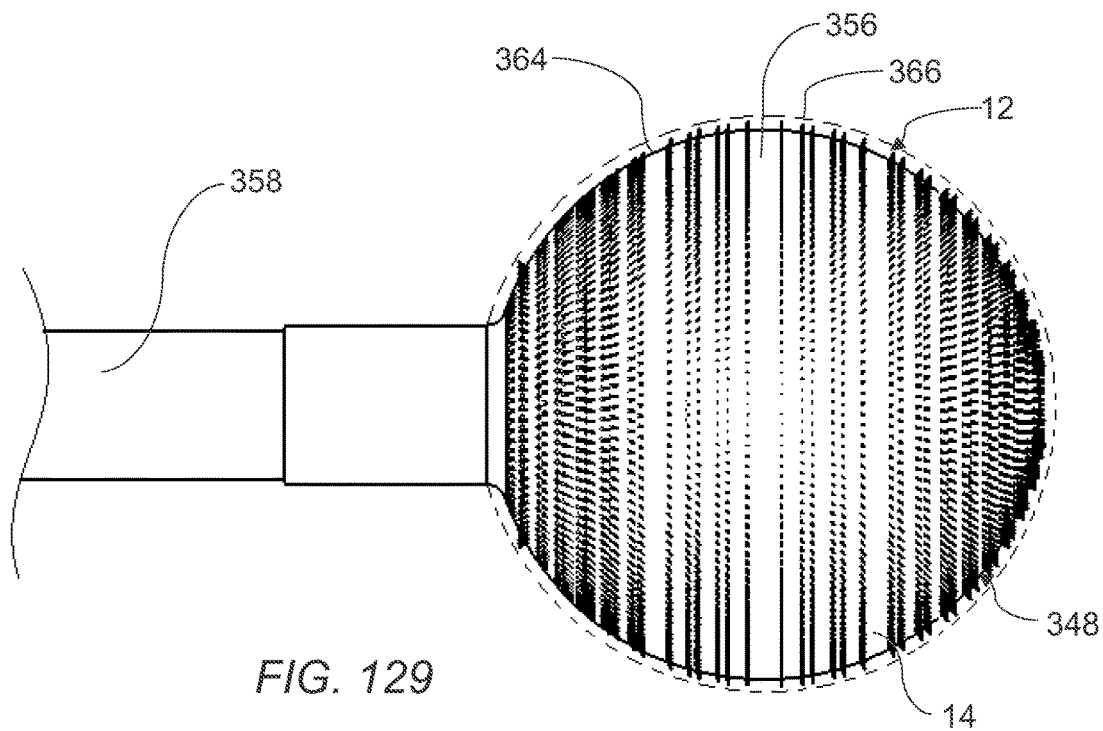
FIG. 129 is an elevation view of the adhesion device of FIG. 128, depicting a neutral profile and an expanded profile of the adhesion device.
Figure 130:
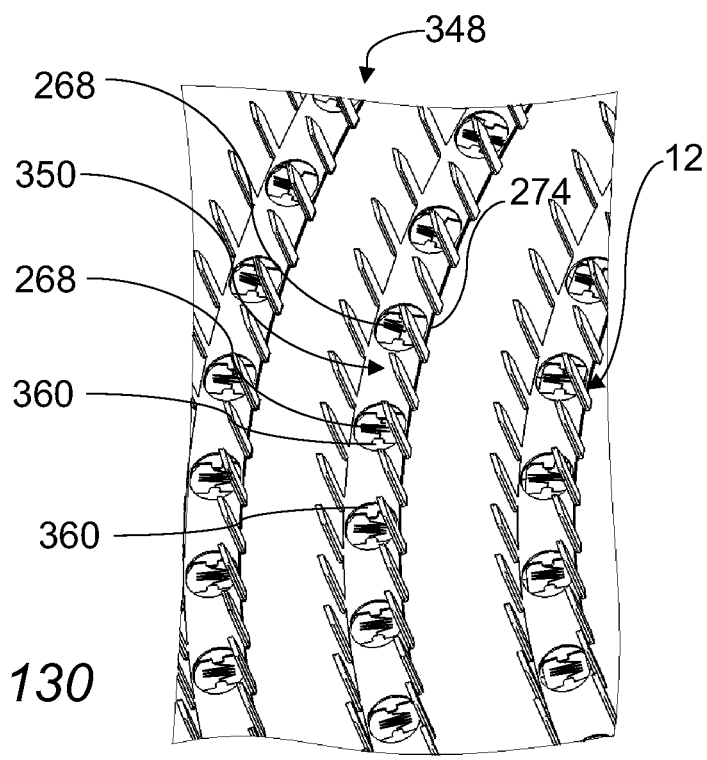
FIG. 130 is an isometric view of an element block array which is disposed within an element support body (not shown) of the adhesion device of FIG. 128.

FIG. 128 is an isometric view of the adhesion device 354 which may incorporate at least one embodiment of the element block array 348 (see FIG. 126) which is depicted in FIG. 130. The at least one element block array 348 may be operatively coupled to the control system 50 of the adhesion device 354. The adhesion device 354 may be configured to expand from a neutral profile 364 to an expanded profile 366 as depicted by the dashed line in FIG. 129 through the inflation of the spherical balloon. The expansion of the adhesion device 354 may take place during application, with the element support body 14 expanding from the neutral profile 364 to the expanded profile 366. As the element support body 14 expands (due to the inflation of the spherical balloon), expansion forces 312 may be applied to element block assemblies 350 which are disposed within the at least one element block array 348. The expansion forces 312 being applied to the element block assemblies 350 by the expanding element support body 14. The expansion forces 312 may result in the release of the break-away sections 274 which are disposed within the at least one element block array 348 (as shown in FIG. 131).

Figure 131:
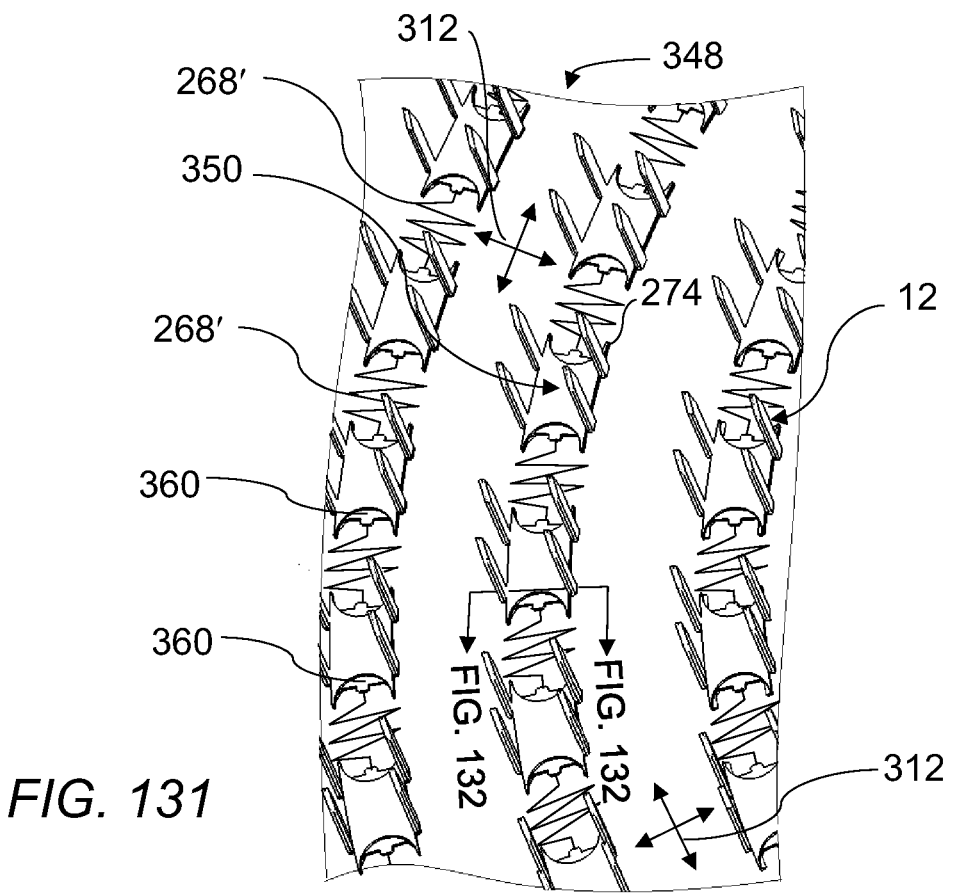
FIG. 131 depicts the separation of multiple element block assemblies of the element block array of FIG. 130 due to the expansion of the element support body (not shown), the multiple element block assemblies having respective element transition mechanisms which are disposed in a neutral configuration and multiple respective engagement elements which are disposed in the engagement state.
Figure 132:
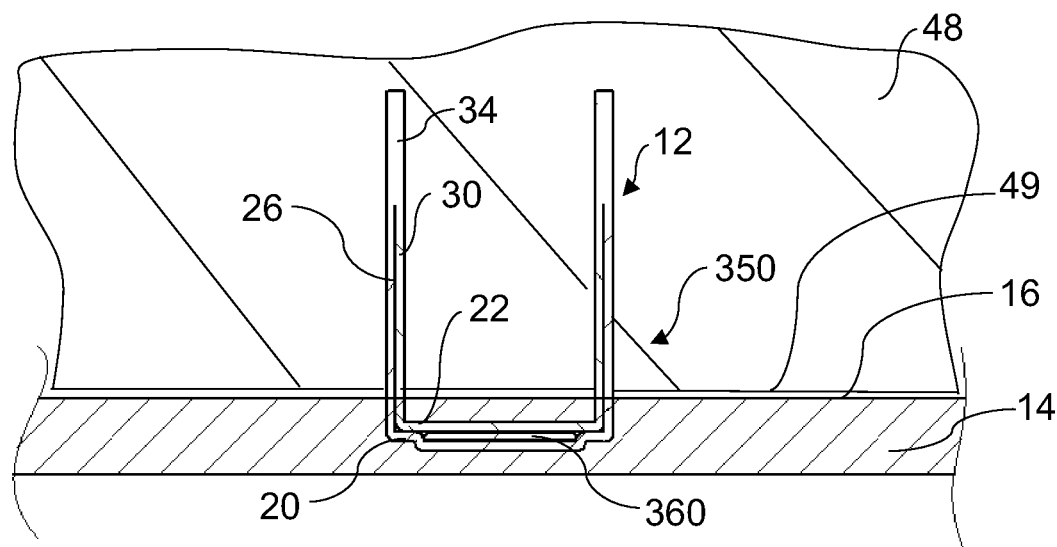
FIG. 132 is a sectional view of FIG. 131.
Figure 133:
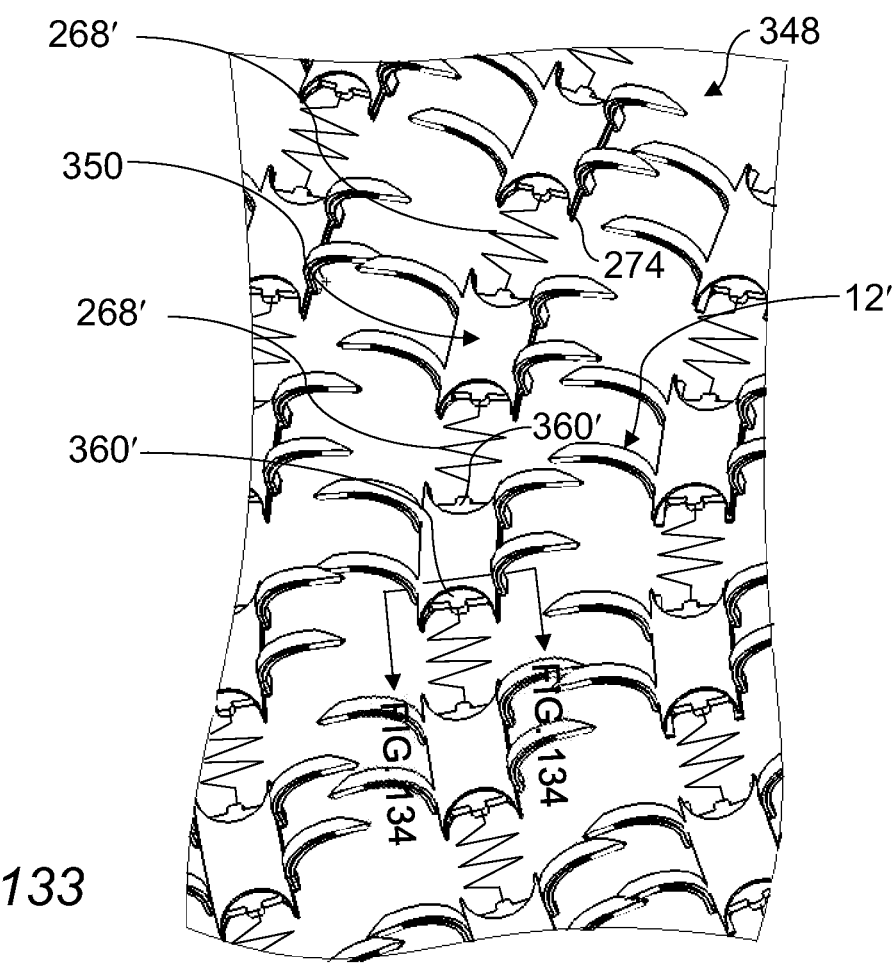
FIG. 133 depicts the element block assemblies of FIG. 131 with multiple respective element transition mechanisms disposed in an expanded configuration and multiple respective engagement elements disposed in an engagement state.

FIG. 130 is an isometric view of multiple element block assemblies 350 within the at least one element block array 348 of the adhesion device 354 (the element support body 14 and target material 48 are hidden in FIGS. 130, 131, and 133 in order to better illustrate each element block assembly 350). Each of the element block assemblies 350 which is depicted in FIG. 130 is connected to adjacent element block assemblies 350 by the break-away sections 274. FIG. 131 depicts the element block assemblies 350 of FIG. 130 after expansion forces 312 have released each element block assembly 350 from adjacent element block assemblies 350. As the element block assemblies 350 which are disposed within the at least one element block array 348 expand (with the expansion of the element support body 14), the respective expandable transition couplers transition from the compressed state 268 to the expanded state 268'. In this manner element transition mechanisms 360 remain operatively coupled to each other during the expansion of the element support body 14. FIG. 132 is a section view of FIG. 131 which depicts a section of a representative element block assembly 350 having the element transition mechanism disposed in the neutral configuration 360 and the respective engagement elements disposed in the deployment state 12.

Figure 134:
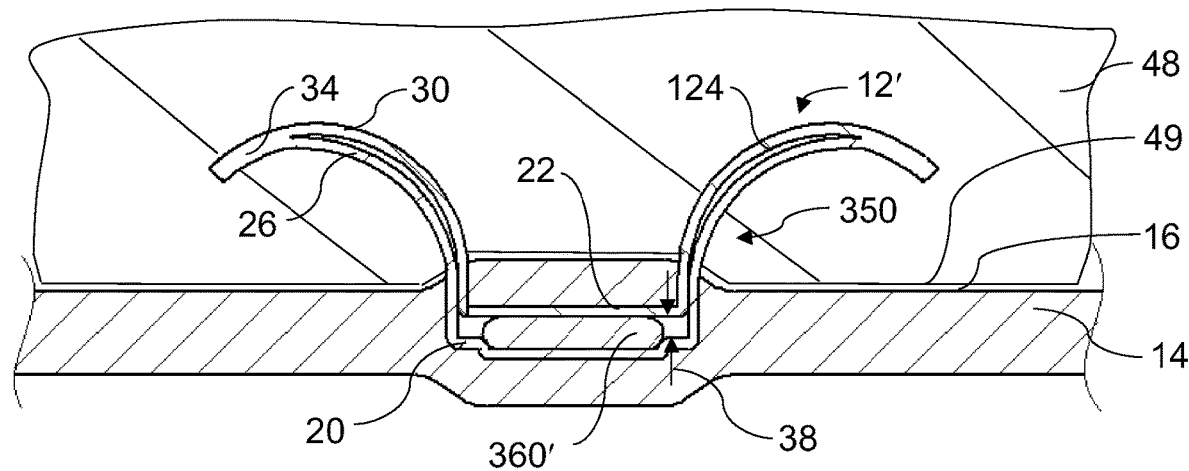
FIG. 134 is a sectional view of FIG. 133.

FIG. 133 depicts the element block assemblies 350 of FIG. 131 with the engagement elements transitioned to the deployment state 12'. FIG. 134 is a section view of a representative element block assembly 350 having the element transition mechanism disposed in the expanded configuration 360' and the respective engagement elements disposed in the engagement state 12'. Thus FIGS. 129-134 depict a deployment sequence for the adhesion device 354 of FIG. 128. The adhesion device 354 would be inflated from the neutral profile 364 to the expanded profile 366 during the application of the adhesion device 354 to the target material 348. The expansion of the adhesion device 354 results in the application of expansion forces 312 to the element block assemblies 350 disposed within the at least one element block array 348. The expansion forces 312 result in the release of each element block assembly 350 from adjacent element block assemblies 350 (FIG. 131).

Each element transition mechanism of each element block assembly 350 can then be transitioned to the expanded configuration 360' thereby transitioning respective engagement elements to the engagement state 12' and securing the adhesion device 354 to the surface 49 of the target material 48 (FIGS. 133 and 134). The adhesion device 354 may then be removed by transitioning each element transition mechanism from the expanded configuration 360' to the neutral configuration 360 thereby transitioning respective engagement elements to the deployment state 12 (as shown in FIGS. 131 and 132). Some embodiments of the adhesion device 354 may be manufactured using methods and fixtures for similarly configured embodiments which have been disclosed in U.S. application Ser. No. 14/240,668.

Some embodiments of adhesion devices which are discussed herein may be configured with element transition mechanisms wherein the relationship between the configurations of the element engagement mechanisms (neutral configuration, expanded configuration) and the configurations of the respective engagement elements (deployment state, engagement state) have been inverted. An example of such an element transition mechanism is depicted in FIGS. 135-141. This configuration of element activation mechanism and respective engagement elements may be used with any configuration of adhesion device which is discussed herein.

Figure 135:
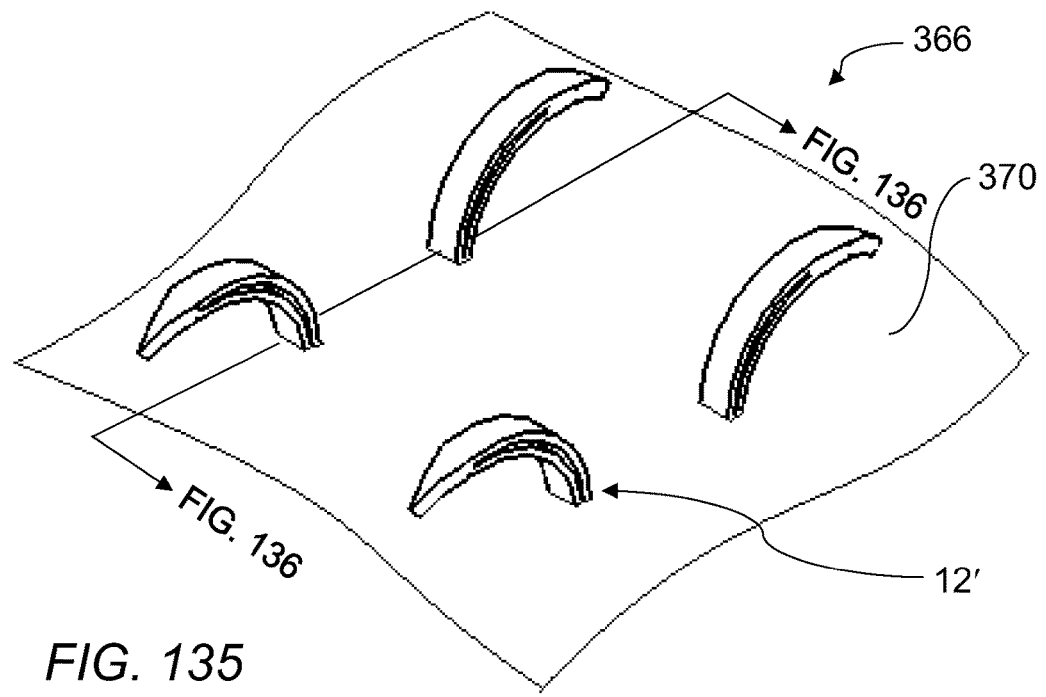
FIG. 135 depicts the surface of an adhesion device which incorporates element block assemblies wherein respective element transition mechanisms transition from a neutral configuration to a compressed configuration, engagement elements which extend from the surface being disposed in an engagement state.
Figure 136:
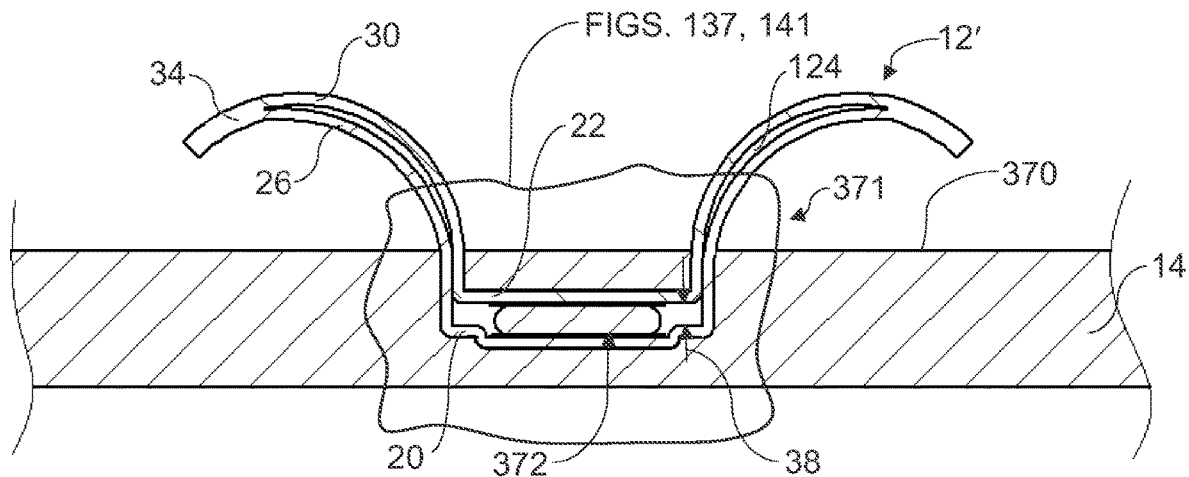
FIG. 136 is a sectional view of FIG. 135 depicting an element block assembly which includes an element transition mechanism which is disposed in a neutral configuration, and respective engagement elements which are disposed in an engagement state.

FIG. 136 depicts the engagement surface 370 of an adhesion device 368 which incorporates multiple engagement elements which are disposed in the engagement state 12'. FIG. 136 is a sectional view of FIG. 135 depicting a representative element block assembly 371, element transition mechanism 372, element activation sheet 20, element deployment sheet 22, and multiple engagement elements 12' which are operatively coupled to the element transition mechanism 372 as has been discussed previously. The element transition mechanism 372 differs from previous embodiments in that the element transition mechanism which is depicted in FIG. 136 is disposed in the neutral configuration 372 wherein there is a transition gap 38 disposed between an activation sheet upper surface 28 and a deployment sheet lower surface 32. That is to say that when the element transition mechanism is disposed in the neutral configuration 372 the element support body 14 is configured to constrain each engagement element in the engagement state 12' wherein each engagement element 12' is eccentrically tensioned as the result of the transition gap 38 into a reactive curvature which is configured to mechanically capture surrounding target material 48 (not shown).

In this case the element transition mechanism 372 may be configured as an elastic insert 374 which is disposed between a first conductive plate 376 which is suitably attached to the activation sheet upper surface 28 and a second conductive plate 378 which is suitably attached to the deployment sheet lower surface 32. When the element transition mechanism is disposed the in the neutral configuration 372, the elastic insert 374 provides expansion forces 380 between the activation sheet upper surface 28 and the deployment sheet lower surface 32. The expansion forces 380 act to maintain the transition gap 38 and thus maintain the tension on the respective engagement elements such that they remain disposed in the engagement state 12'.

Figure 137:
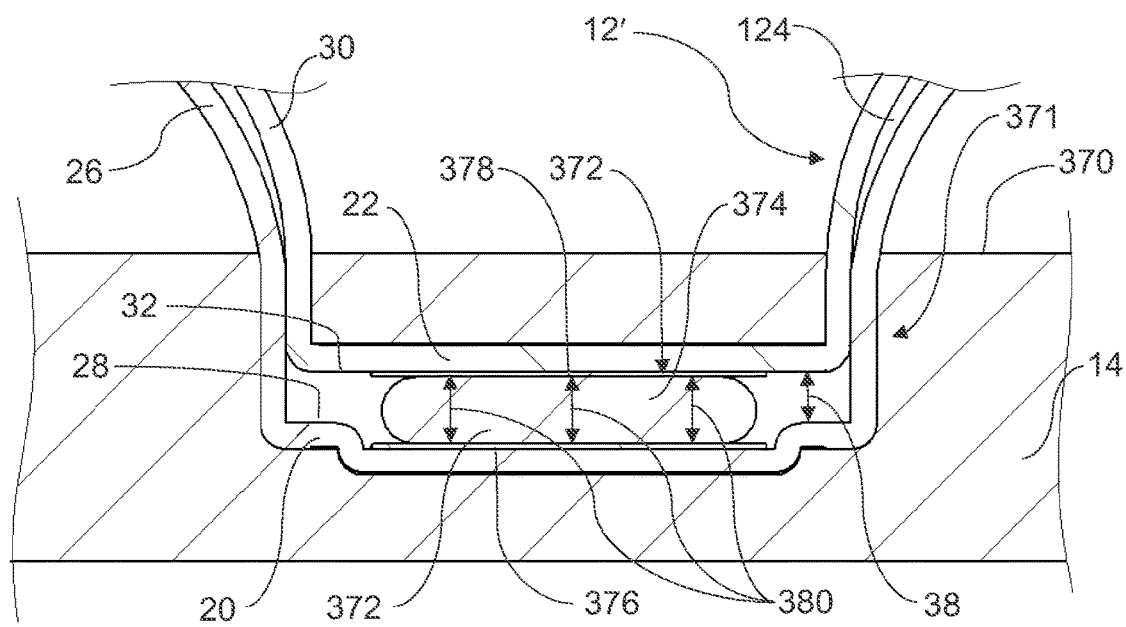
FIG. 137 is an enlarged view of FIG. 136.
Figure 138:
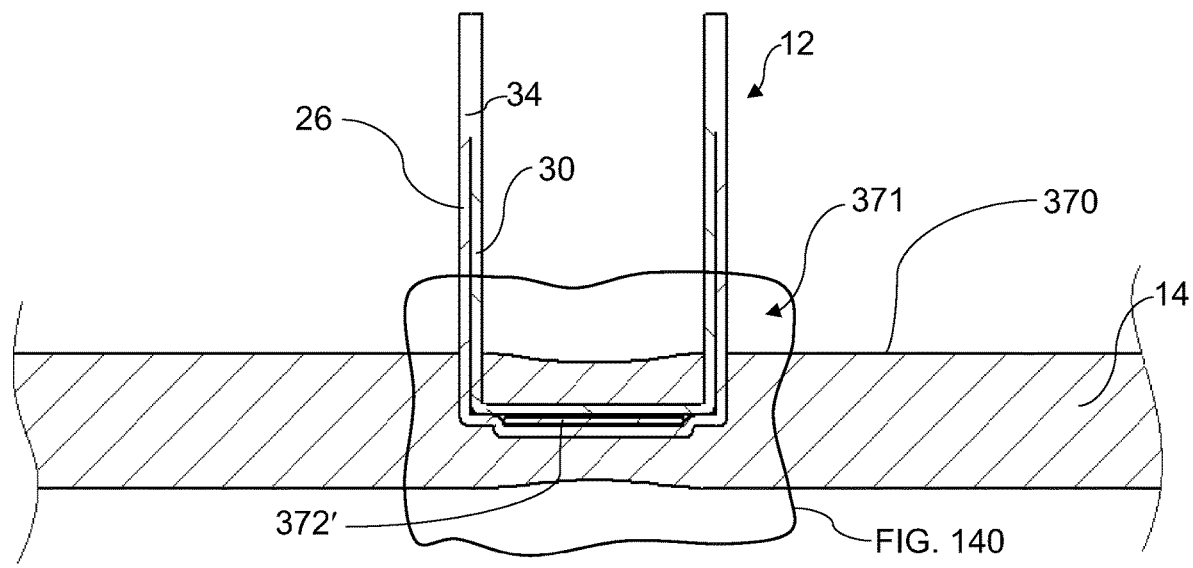
FIG. 138 is a sectional view of FIG. 139 depicting the element transition mechanism disposed in a compressed configuration and respective engagement elements disposed in a deployment state.
Figure 139:
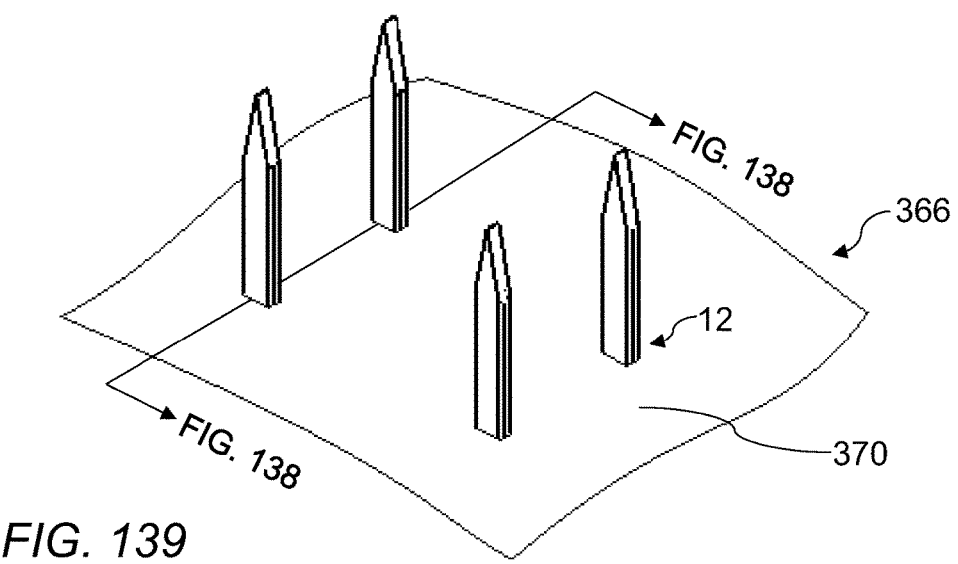
FIG. 139 depicts the adhesion device of FIG. 135 with the engagement elements disposed in a deployment state.
Figure 140:
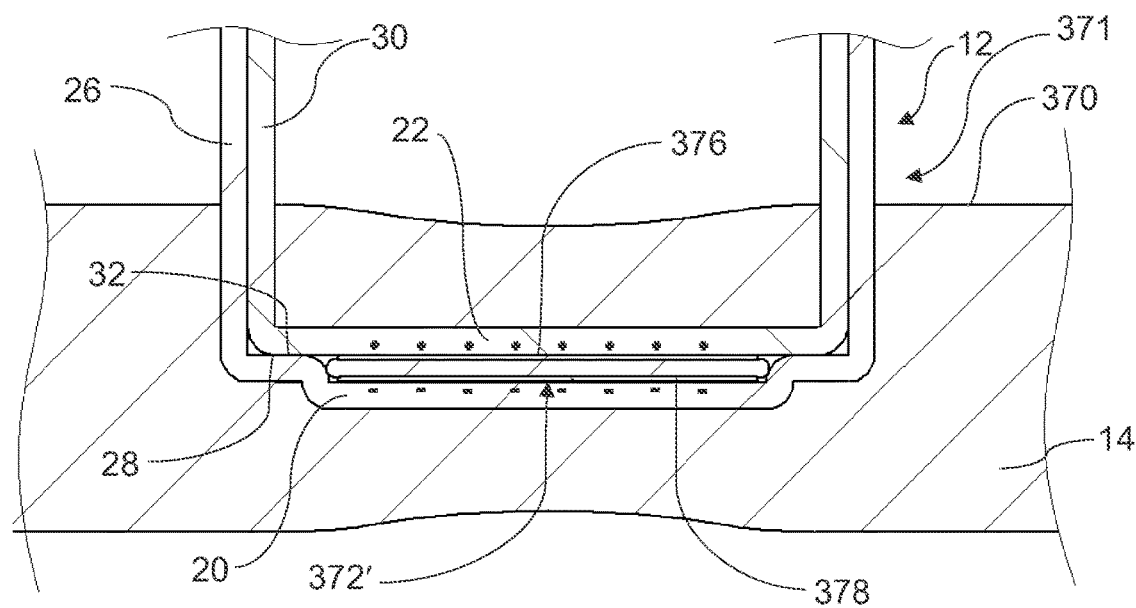
FIG. 140 is an enlarged view of FIG. 140.

A net attractive charge may be distributed to the first conductive plate 376 and the second conductive plate 378 as depicted in FIG. 137. This leads to electrical attraction forces between the first conductive plate 376 and the second conductive plate 378, and compression of the elastic insert 374 to a compressed configuration 372' (wherein the transition gap 38 is substantially reduced) as depicted in FIGS. 138 and 140. When the element transition mechanism is disposed in the compressed configuration 372', the element support body 14 is configured to maintain the respective engagement elements in the deployment state 12 which is suitable for insertion into (or removal from) the target material 48 with each engagement element 12 being substantially perpendicular to the engagement surface 370.

Figure 141:
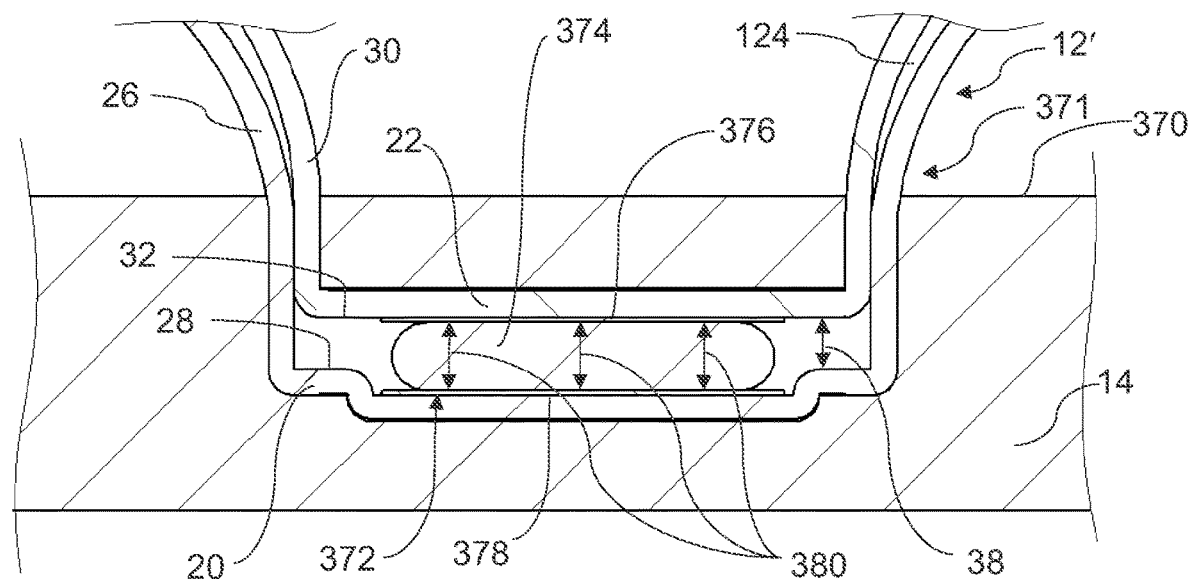
FIG. 141 depicts the element block assembly of FIG. 140 wherein the element transition mechanism has been returned to the neutral configuration and respective engagement elements have been returned to the engagement state.

When the net attractive charge is removed from the first conductive plate 376 and the second conductive plate 378, the elasticity of the elastic insert 374 returns it to the neutral configuration 372 with the expansion forces 380 applied to the activation sheet upper surface 28 and the deployment sheet lower surface 32 by the elastic insert 374 facilitating the return of the respective engagement elements to the engagement state 12' as depicted in FIG. 141. The element transition mechanism embodiment 372 could be configured with any suitable activation mechanism which has been discussed herein. For example, the element transition mechanism 372 could be configured as a balloon apparatus 24, with a vacuum applied to the balloon apparatus 24 in order to transition the balloon apparatus from a neutral configuration to a compressed configuration.

Some embodiments of the element transition mechanism 372 may be configured to allow for multiple compression configurations. For example different net attractive charges could be applied to the first conductive plate 376 and the second conductive plate 378, a first net attractive charge and a second net attractive charge with the second net attractive charge being greater than the first net attractive charge. The first net attractive charge would compress the elastic insert 374 to a first compressed profile. This would result in a first transition gap between the activation sheet upper surface 28 and the deployment sheet lower surface 32, the first transition gap resulting in a first reactive flexure of the respective engagement elements. The second net attractive charge could then compress the elastic insert to a second compressed profile. This would result in a second transition gap between the activation sheet upper surface 28 and the deployment sheet lower surface 32, the second transition gap resulting in a second reactive flexure of the respective engagement elements. In this case, the first reactive flexure would be greater than the second reactive flexure. Hence the magnitude of the reactive flexure of each engagement element 12' can be adjusted by transitioning the respective element transition mechanism 372 to different compressed configurations. In this manner the adhesion strength of a given adhesion device could be adjusted. A similar adjustment method could be used with an element transition mechanism which is configured as a balloon apparatus 24, or with any other suitable element transition mechanism configuration.

For some embodiments of adhesion devices, it may be desirable to incorporate physical stops which are configured to limit the travel between the element activation sheet 20 and the element deployment sheet 22 during the creation of the transition gap 38 and the transition of the respective engagement elements from the deployment state 12 to the engagement state 12'. The physical stops may prevent the "over-deployment" of the engagement elements 12 wherein the engagement elements 12 may be transitioned to a reactive curvature which may result in the plastic deformation of the engagement element 12 materials.

Figure 144:
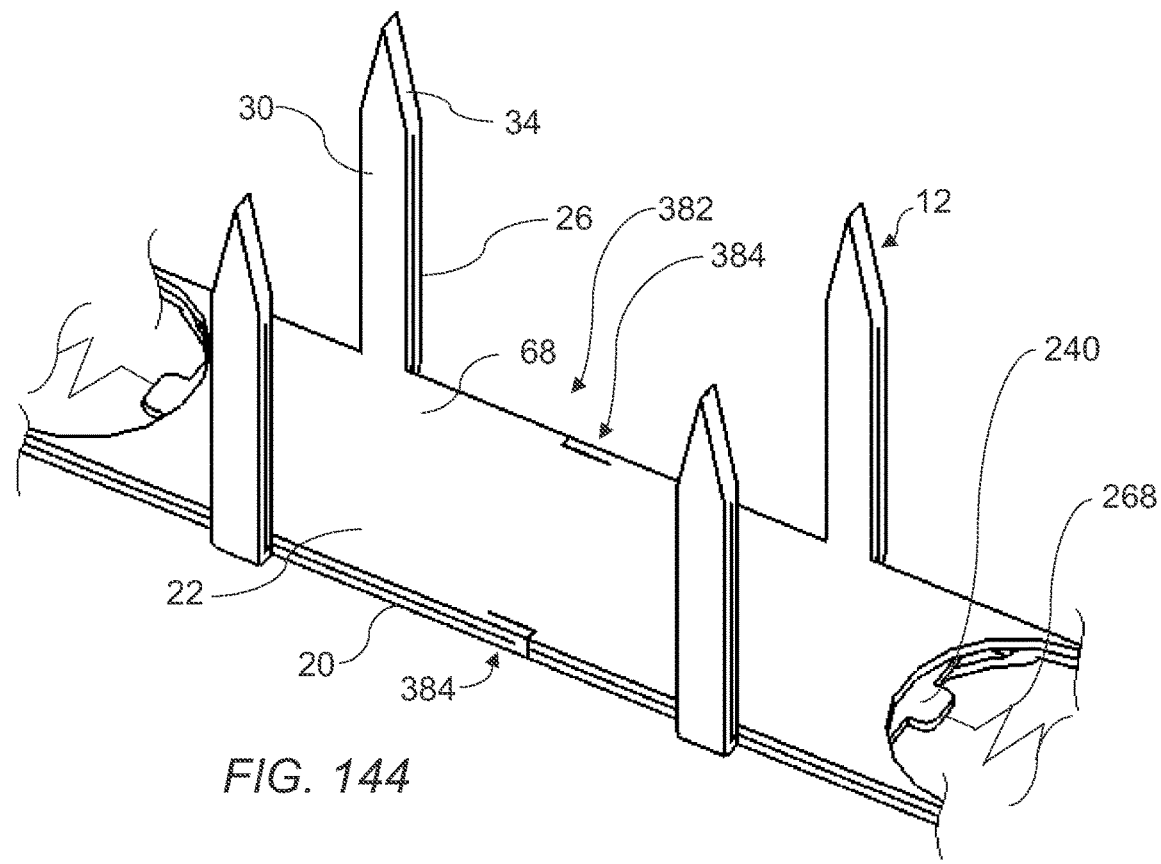
FIGS. 144-147 depict an embodiment of an element block assembly which incorporates multiple sheet stops.
Figure 145:
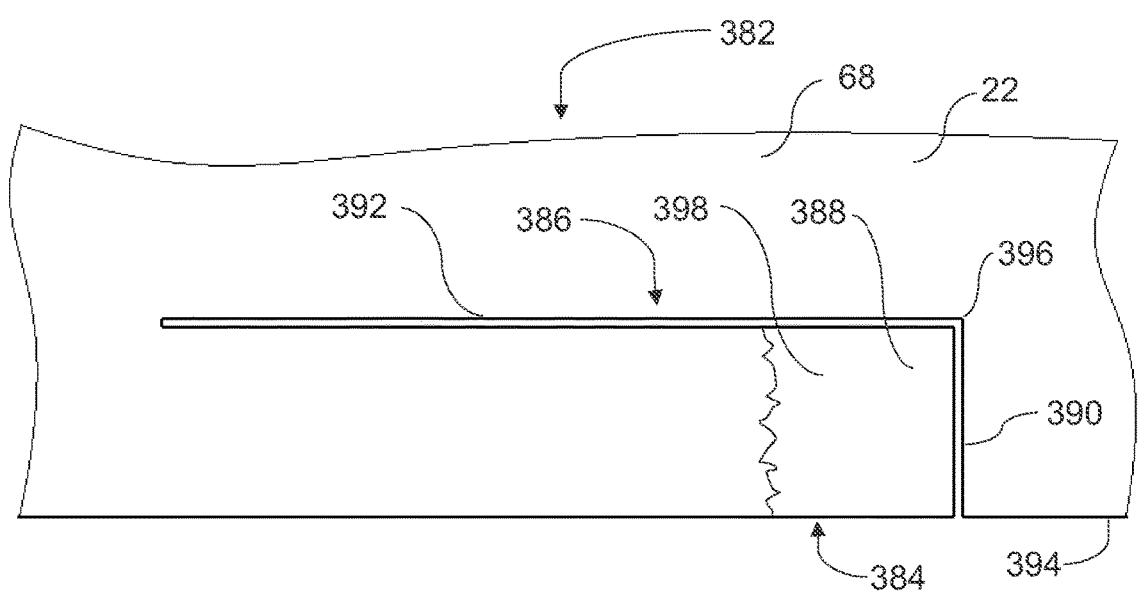

FIG. 144 depicts an embodiment of an element block assembly 382 which incorporates multiple sheet stops 384, the element block assembly 382 being disposed with an element transition mechanism in the neutral configuration 240 and the respective engagement elements disposed in the deployment state 12. Each sheet stop 384 may be created using a suitably configured cut section 386, and a suitably configured fused section 388. FIG. 145 is an enlarged elevation view of the element block assembly 382 depicting a sheet stop 384. The cut section 386 may include a first cut line 390 (which cuts transversely through the element activation sheet 20 material and the element deployment sheet 22 material) which extends into the element block assembly 382 such that it is substantially perpendicular to a block element side 394 of the element block assembly 382. The cut section 386 may also include a second cut line 392 (which cuts transversely through the element activation sheet 20 material and the element deployment sheet 22 material) which extends from a termination 396 of the first curt line 390 in a direction which is substantially parallel to the block element side 394.

Figure 146:
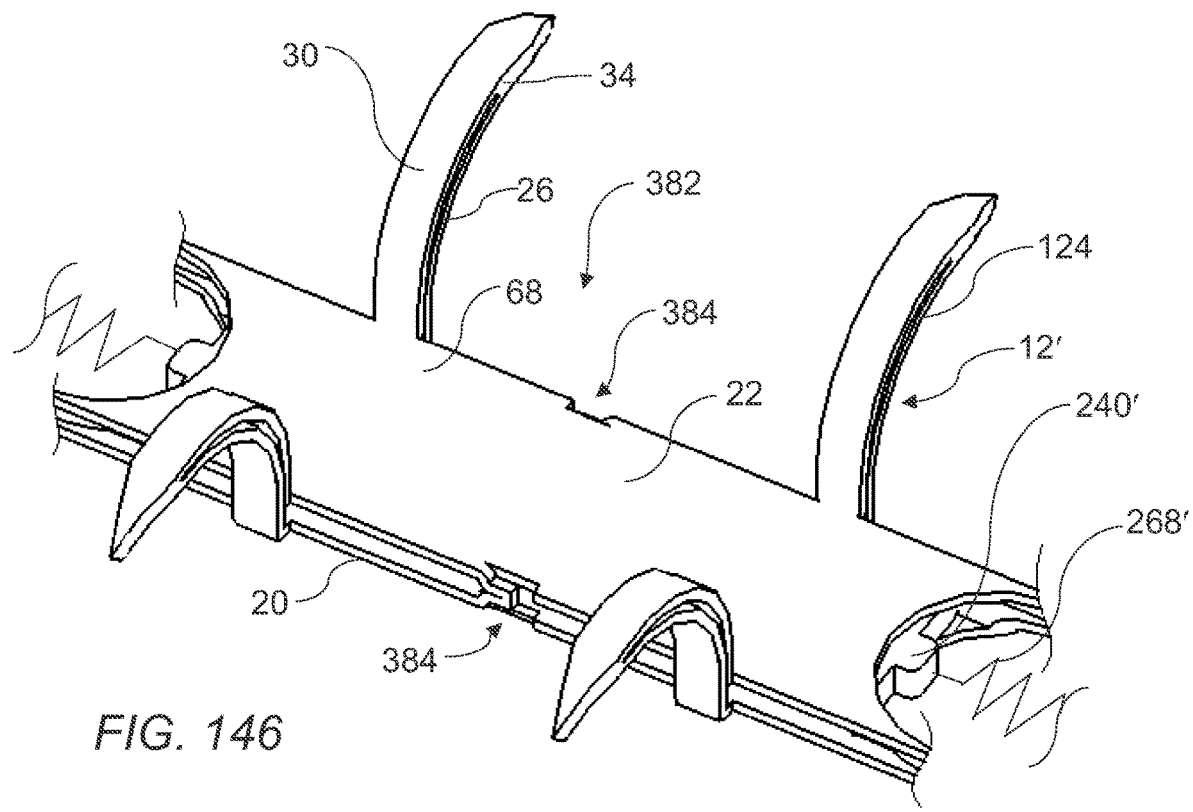
Figure 147:
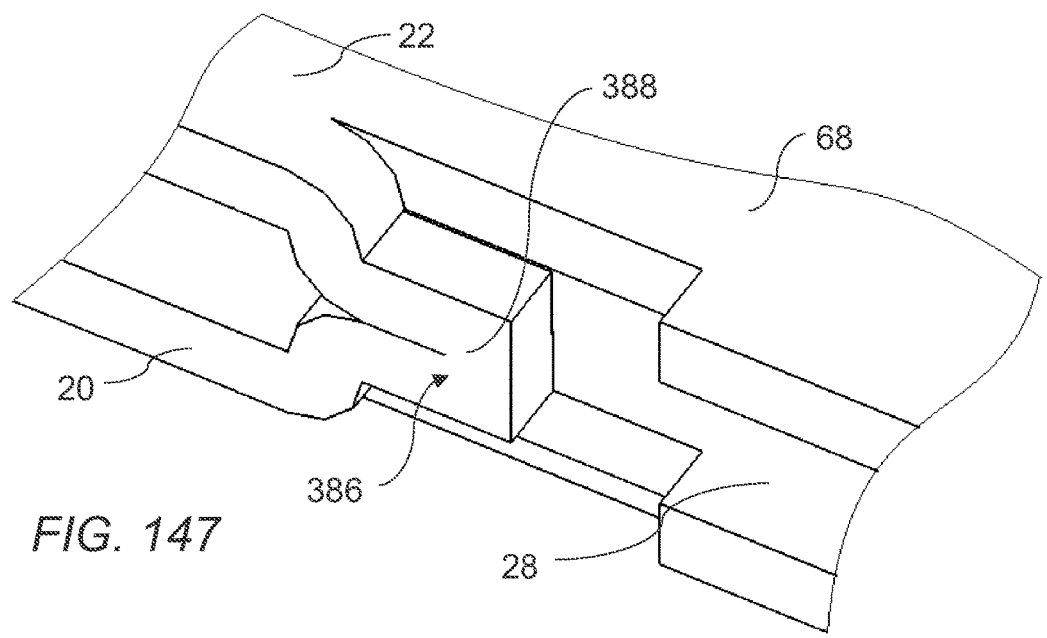

The element activation sheet 20 material may be fused to the element deployment sheet 22 material within a fused section 388 of the sheet stop 384 which is disposed at a distal portion 398 of the sheet stop 384. The element activation sheet 20 material may be fused to the element deployment sheet 22 material by any of the methods which have been previously described for fused sections 74. FIG. 146 depicts the element block assembly 382 with the element transition mechanism disposed in the expanded configuration 240' and the respective engagement elements disposed in the engagement state 12'. As depicted in FIGS. 146 and 147, the sheet stops 384 have deformed with the sheet stops 384 physically connecting the element activation sheet 20 and the element deployment sheet 22 and preventing any further motion of the element activation sheet 20 with respect to the element deployment sheet 22. The sheet stops 384 can thus be used to physically limit the travel between the element activation sheet 20 and the element deployment sheet 22. The sheet stops 384 can be configured to allow for any suitable maximum travel distance between the element activation sheet 20 and the element deployment sheet 22.

Typically element block assemblies may be initially formed such that respective engagement elements 12 are flat (that is they are substantially parallel to the deployment sheet upper surface 68). Engagement elements 12 must then be formed such that they are substantially perpendicular to the deployment sheet upper surface 68 as has been previously discussed. For engagement elements 12 which are formed from highly elastic materials, it may be desirable to add features which facilitate the forming of the engagement elements 12 such that they are substantially perpendicular to the deployment sheet upper surface 68.

Figure 148:
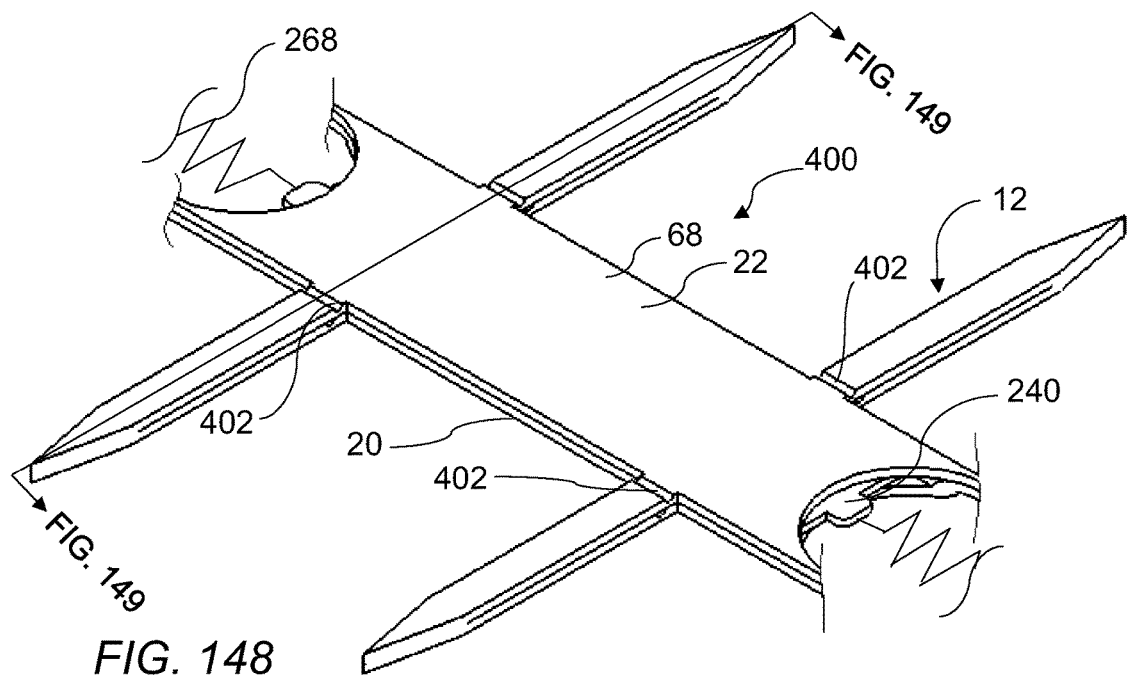
FIGS. 148-153 depict an embodiment of an element block array embodiment which incorporates multiple skived sections.

FIG. 148 depicts an element block assembly 400 which incorporates multiple skived sections 402. The skived sections 402 may be suitably located on the exterior activation surface 104, the interior activation surface 106, the exterior deployment surface 108, or the interior deployment surface 110 of a given engagement element 12. The skived sections 402 may have a depth 404 of up to ½ the thickness 56 of the respective element activation section 20 or the thickness 70 of the respective element deployment section 22 (see FIG. 150). Each skived section 402 contains less material than surrounding sections thereby facilitating a bend of the material at the skived section 402. FIGS. 148-153 depict the element block assembly 400 which incorporates multiple skived sections 402.

Figure 149:
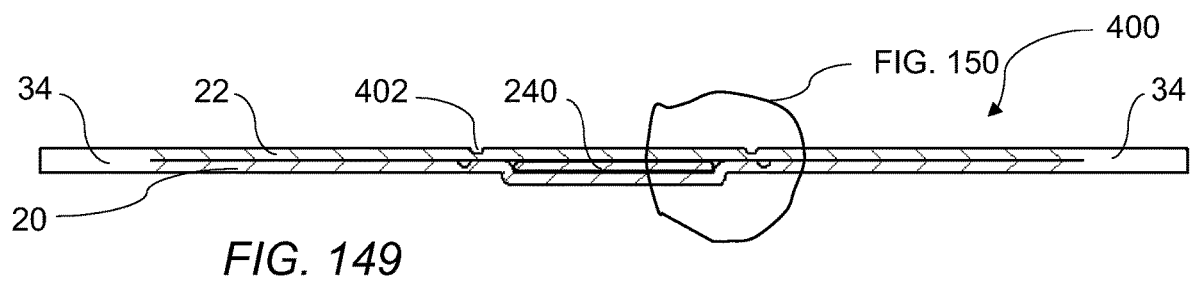
Figure 150:
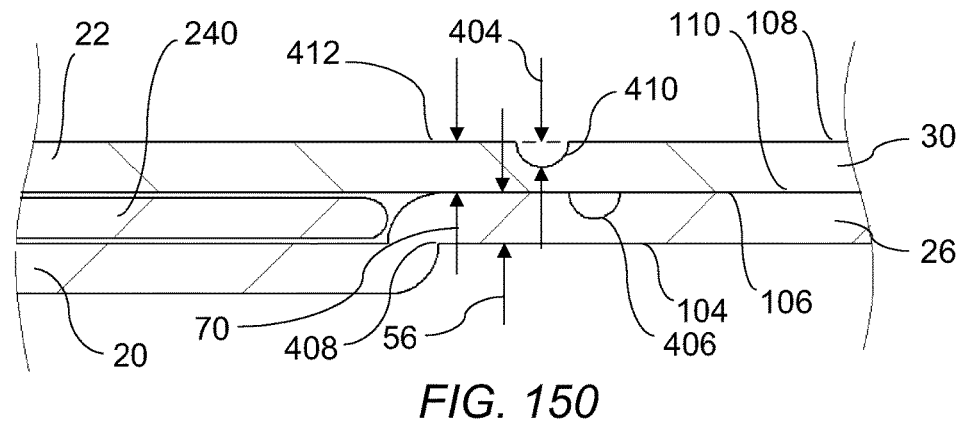
Figure 151:
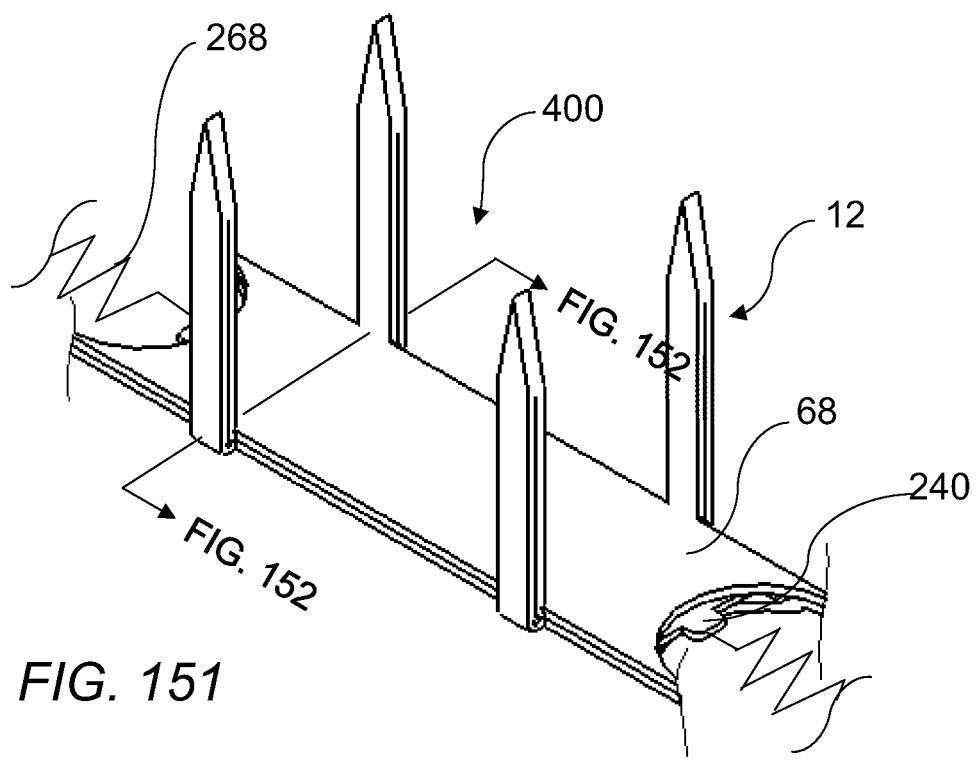
Figure 152:
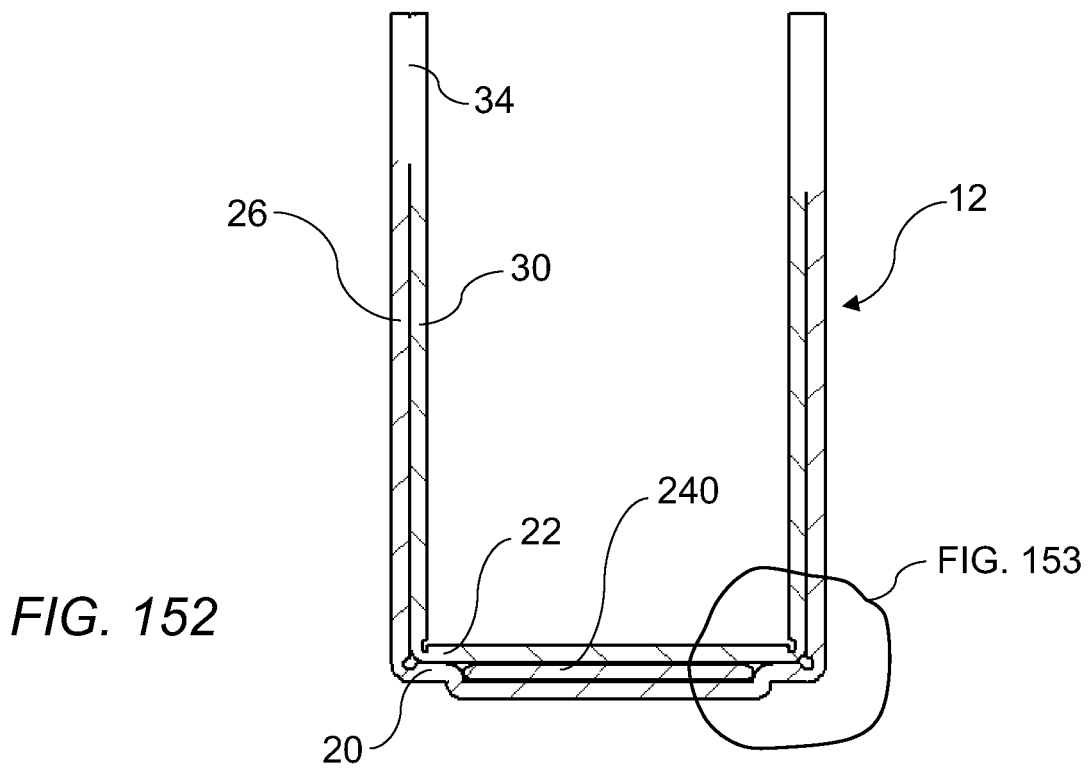
Figure 153:
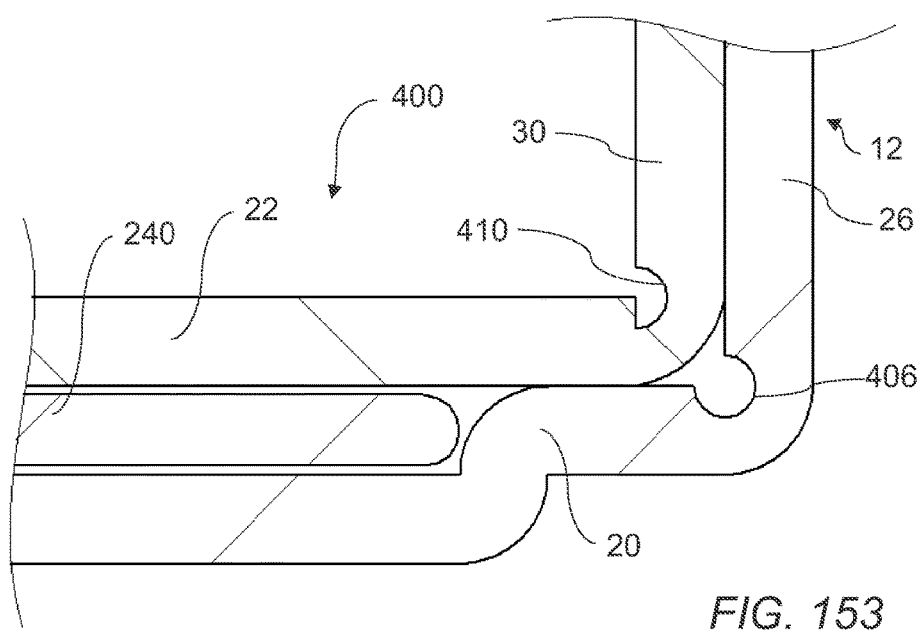

FIGS. 149 and 150 depict the element block assembly 400 with the engagement elements 12 in a flat configuration. Skived sections 402 are disposed within the exterior deployment surface 108 and the interior activation surface 106 of each engagement element 12. More specifically a first skived section 406 is incorporated in the interior activation surface 106 of each element activation section 26 near a junction 408 of the element activation section 26 with the element activation sheet 20, and a second skived section 410 is incorporated in the exterior deployment surface 108 of the element deployment section 30 near a junction 412 of the element deployment section 30 with the element deployment sheet 22. For some embodiments, the first skived section 406 may be staggered from the second skived section 410 as depicted in FIG. 150. FIGS. 151-153 depict the element block assembly 400 with each engagement element 12 formed such that it is substantially perpendicular to the deployment sheet upper surface 68. As seen in FIG. 153, the reduction of material in the skived sections 402 facilitates the formation of the engagement elements 12 to the substantially perpendicular position, in that the reduced material within the skived sections 402 facilitates bending of the engagement elements 12 at the skived sections 402.

Figures 154, 155:
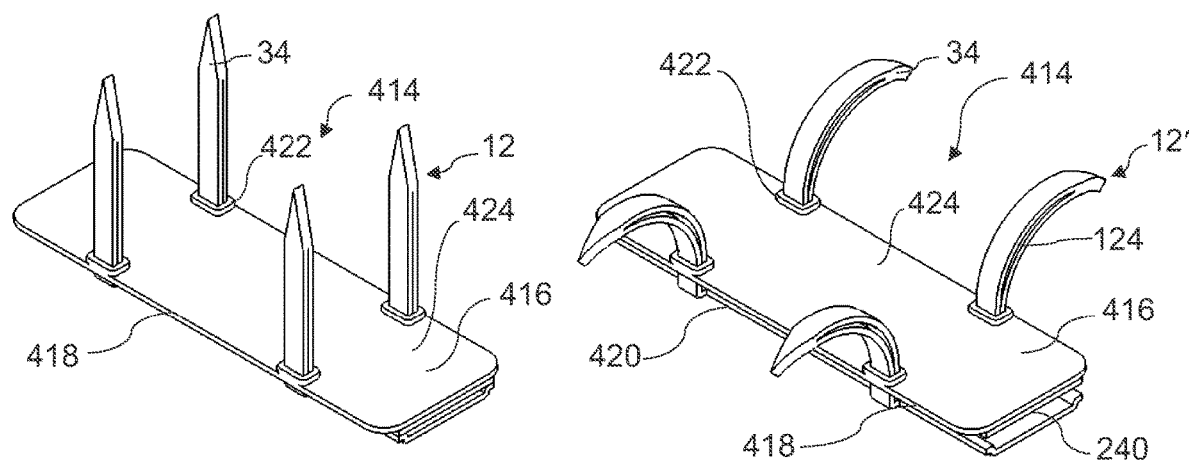
FIGS. 154 and 155 depict an embodiment of a stand alone element block assembly which incorporates an element guide sheet.

Some embodiments of the "stand alone" element block assembly 238 which has been discussed with regard to FIGS. 86-90 may be configured with a suitably configured embodiment of an element guide sheet 150 (see FIG. 46). The guide sheet may include features, functions, materials and dimensions which have been discussed for other element guide sheet embodiments 150 discussed herein. FIGS. 154 and 155 depict an element block assembly 414 which is operatively coupled to a respective element guide sheet 416. The element guide sheet 416 is configured such that a guide sheet profile 418 substantially aligns with an element block profile 420 of the element block assembly 414 which is substantially rectangular in this case. Element block assemblies which are configured with curved element block profile (see FIG. 127) could be operatively coupled to a suitably configured curved element guide sheet which has a substantially similar curved guide sheet profile. Thus a given guide sheet profile may be configured to substantially align with a respective element block profile of a respective element block assembly, for any length, width, shape, or number of engagement elements which the respective element block assembly is configured with. Multiple element block assemblies 400 may be disposed within an element support body 14 (having an engagement surface 16) of any suitably configured adhesion device which has been discussed herein.

The element guide sheet 416 may include a plurality of element guides 422, with each element guide 422 being operatively coupled to a respective engagement element 12 which in turn is operatively coupled to a respective element transition mechanism 240 of the element block assembly 414. Each element guide 422 may be configured while each respective element transition mechanism is disposed in the neutral configuration 240 to constrain each respective engagement element in a deployment state 12 which is suitable for insertion into (or the removal from) a target material wherein each engagement element is substantially perpendicular to the guide sheet upper surface 424 (as shown in FIG. 154).

Additionally, each element guide 422 may be configured while each respective element transition mechanism is disposed in the expanded configuration 240' to constrain each respective engagement element in an engagement state 12' wherein each respective engagement element 12' is eccentrically tensioned as the result of the transition gap 38 into a reactive flexure which is configured to mechanically capture surrounding target material 48 (as shown in FIG. 155). The element guide sheet 416 may be formed from any suitable resilient rigid material or any suitable resilient elastic material. Each element block assembly 414 which includes an element guide sheet 416 may be molded to the respective element support body 14 such that each guide sheet upper surface 424 is exposed. Alternatively, each element block assembly 414 which includes an element guide sheet 416 may be molded to the respective element support body 14 such that the element support body 14 encompasses each element guide sheet 416 (see FIGS. 51 and 52).

As has been discussed, a user may interact with the control system 50 of an adhesion device in order to reversibly transition the engagement elements of the adhesion device from the deployment state 12 to the engagement state 12'. This allows for a user of the adhesion device to choose when the transition of the engagement elements occur. Some embodiments of control systems 50 may include at least one activation mechanism 298 which may be operatively coupled to a plurality of respective element transition mechanisms 240 which are disposed within the adhesion device. The at least one activation mechanism 298 may be configured to reversibly transition respective element transition mechanisms from the neutral configuration 240 to the expanded (or contracted for some element transition mechanism embodiments) configuration 240'.

The configuration of a given activation mechanism 298 is dependent upon the configuration of the respective element transition mechanisms 240. Element transition mechanisms 240 which are configured as balloon apparatuses 24 could be operatively coupled (by suitably configured tubing for example) to an activation mechanism 298 which is configured as a fluid pump. Element transition mechanisms 240 which are configured as shape memory inserts 178 could be operatively coupled (by suitably configured tubing for example) to an activation mechanism 298 which is configured as a fluid pump. Element transition mechanisms 240 which are configured as patterned insert assemblies 192 could be operatively coupled (by suitably configured cable for example) to an activation mechanism 298 which is configured as a linear actuator. Element transition mechanisms 240 which are configured as capacitance plate assemblies 228 could be operatively coupled (by suitably configured conductive wires for example) to an activation mechanism 298 configured as a voltage supply. For adhesion devices having multiple configurations of element transition mechanisms 240 (any combination of balloon apparatuses, shape memory inserts, patterned insert assemblies, and/or capacitance plates assemblies), the respective control system 50 may be configured with the suitable combination of activation mechanisms 298 (fluid pumps, linear actuators, and/or voltage supplies).

Some embodiments of control systems 50 (see FIG. 156) may also include a processor 426 and processor instructions which are accessible by the processor 426, a battery 430 (which may be operatively connected to all of the controller components which require power), and a controller 432 which is operatively coupled to the processor 426 and the at least one activation mechanism 298. In some cases, such a control system 50 may be configured with at least one force feedback system 434 which is operatively coupled to a respective activation mechanism 298. Each force feedback system 434 may be configured to provide an alert to a user of the adhesion device when the adhesion device has been successfully deployed into the target material 48. That is to say that each force feedback system 434 may be configured to indicate to a user of the adhesion device whether or not the engagement elements 12 have penetrated into and engaged with the target material 48.

Each force feedback system 434 may use data from the respective element transition mechanisms 240 in order to determine whether the respective engagement elements 12 have successfully deployed into the target material. For example, a force feedback system 434 which is operatively coupled to an element transition mechanism 240 which is configured as a balloon apparatus 24 may rely on fluid pressure within the balloon apparatus 24 as an indication of successful (or unsuccessful) engagement element deployment 12 into and engagement with the target material 48.

A force feedback system 434 which is operatively coupled to an element transition mechanism 240 which is configured as a patterned insert assembly 192 may rely on wire tension from the patterned insert assembly 192 as an indication of successful (or unsuccessful) engagement element 12 deployment into the target material 48. A force feedback system which is operatively coupled to an element transition mechanism which is configured as a capacitance plates assembly may rely on voltage supplied to the patterned insert assembly as an indication of successful (or unsuccessful) engagement element deployment into and engagement with the target material 48.

The following will discuss a force feedback system 434 utilizing the balloon apparatus 24 as a specific example. In this case, the force feedback system 434 may record fluid pressure which is delivered to a given element transition mechanism 240 (which is configured as a balloon apparatus 24 during the transition of the element transition mechanism 240 from the neutral configuration 240 to the expanded configuration 240' (and transition of the respective engagement elements from the deployment state 12 to the engagement state 12'). In this manner, a fluid pressure vs. time fluid pressure profile could be generated for the transition of the given element transition mechanism 240.

The element transition mechanism 240 may display a first fluid pressure profile while transforming its respective engagement elements from the deployment state 12 to the engagement state 12' while the engagement elements are deployed into the target material 48. The element transition mechanism 240 may display a second fluid pressure profile while transforming its respective engagement elements from the deployment state 12 to the engagement state 12' while the engagement elements are not deployed into the target material 48. The engagement elements which are deployed into the target material 48 will encounter resistance from the target material 48 while transforming from the deployment state 12 to the engagement state 12'. The engagement elements which are not deployed into target material 48 will encounter no resistance during transition from the deployment state 12 to the engagement state 12'. Thus there will be a difference between the first fluid pressure profile and the second fluid pressure profile, a difference which the control system 50 may use (via the processor comparing to a library of data) to indicate successful (or unsuccessful) deployment of the engagement elements within the target material 48. The method which has been discussed above could be similarly applied to force feedback systems 434 which are operatively coupled to patterned insert assemblies 192 (higher/lower cable tension), or capacitance plates assemblies 228 (higher/lower voltages applied).

As has been discussed previously multiple element transition mechanisms 240 can be serially connected to the control system 50 (and respective activation mechanisms 298), or multiple element transition mechanisms 240 can be individually connected to the control system 50 (and the respective activation mechanisms 298). Adhesion device embodiments which are discussed herein can incorporate any appropriate combination of element transition mechanisms 240 which are serially connected to the control system 50 and element transition mechanisms 240 which are directly connected to the control system 50. As has been discussed, adhesion devices which are thus configured may allow for the selective activation of element transition mechanisms 240 by a user of the adhesion device. The following element transition mechanism 240 connection configuration examples may be similarly applied to any adhesion device configuration such as the bandage configuration 294, the tube configuration 316, the cylindrical balloon configuration, the spherical balloon configuration or the like.

FIG. 156 depicts an embodiment of an element block array 92 and associated control system 50. The element block assemblies 18 which are disposed within the element block array 92 are connected by an element sheet frame 78. FIG. 157 is a schematic of the element block array 92 of FIG. 156, the schematic depicting the control system 50 and multiple element transition mechanisms 240 which are operatively coupled to the control system 50. The element transition mechanisms 240 may be configured as any of the element transition mechanism discussed herein, with connectors 436 attached to each element transition mechanism 240 suitably configured facilitate the activation of the element transition mechanism 240. For example, the element transition mechanisms 240 may be configured as a balloon apparatuses 24 and the connectors 436 may be configured as tubing which incorporates an interior fluid lumen. In some cases, the connectors 436 which are disposed between adjacent element transition mechanisms 240 and/or the control system 50 may be configured as expandable transition couplers 268 which have been discussed previously.

FIG. 157 depicts multiple element transition mechanisms 240 which are directly individually connected to the control system 50 (more specifically to a respective activation mechanism 298 of the control system 50). Each element transition mechanism 240 may be in operative communication with a suitably configured connector 436, each connector 436 from each element transition mechanism may be bundled into a connector cable 438 which in turn connects to the control system 50. FIGS. 158-160 depict an adhesion device 440 which is fabricated using the element block array 92 of FIG. 156. The purpose of FIGS. 158-160 is to illustrate the ability of a user of the adhesion device 440 to selectively activate the element transition mechanisms 240 of the adhesion device 440.

In this case, each element transition mechanism 240 has been labeled using a letter (A-H) in order to differentiate it from the adjacent element transition mechanisms 240. Thus FIGS. 158-160 depict the transition of element transition mechanisms E, F, G, and H from the neutral configuration 240 to the expanded configuration 240' (and the transformation of respective engagement elements from the deployment state 12 to the engagement state 12'). Element transition mechanisms A, B, C, and D remain in the neutral configuration 240 and their respective engagement elements remain in the deployment state 12 as depicted in FIGS. 158-160. Thus FIGS. 158-160 depict an adhesion device embodiment 440 wherein selected element transition mechanisms (A-D) have been transitioned (by a user) to the expanded configuration 240', while the element transition mechanisms (E-H) which have not been selected remain in the neutral configuration 240.

FIG. 161 depicts yet another embodiment of an element block array 442. In this case, multiple element block assemblies 270 are serially connected to the control system 50 (more specifically to a respective activation mechanism 298 of the control system 50). FIG. 162 is a schematic representation of the element block array 442 depicting element transition mechanisms 240 which have been labeled with a letter in order to further illustrate the connection configuration. In this case, element transition mechanisms A, B, C, and D may be serially connected to each other via connectors 436, and element transition mechanism A may be directly connected to the control system via a connector 436. Again, the connectors 436 may be configured as expandable transition couplers 268 in some cases. Thus, if a user utilizes the control system 50 to transition element transition mechanism A, Element transition mechanisms B, C, and D will be likewise transitioned. Similarly, element transition mechanisms E, F, G, and H may be serially connected to each other by connectors 436, and element transition mechanism E may be directly connected to the control system 50 by a connector 436. Thus, if a user utilizes the control system 50 to transition element transition E, element transition mechanisms F, G, and H will be likewise transitioned. For the adhesion device embodiments discussed herein, any suitable combination of element transition mechanisms 240 which are serially coupled or directly coupled to the control system 50 is possible.

As has been discussed, the control system 50 may be operatively coupled to a respective adhesion device. For some embodiments, the control system 50 may be operatively coupled to the respective adhesion device by a control system coupler 314 as has been previously discussed. For some adhesion device embodiments, the control system 50 may be integrated into the given adhesion device. For other embodiments, some features of the control system 50 may be integrated into the given adhesion device, while other features may remain external to the adhesion device. In this case the external control system 50 features may be operatively coupled to the internal control system 50 features via RF (Radio-Frequency) communications.

FIGS. 163 and 164 depict an adhesion device 444 which is remotely controlled by a user. The adhesion device 444 may incorporate an external control system 446 and an internal control system 448. The internal control system 448 may include at least one activation mechanism 298 (which is operatively coupled to respective element transition mechanisms 240 of the adhesion device 444), a processor 426, processor instructions which are accessible by the processor 426, a battery 430, a controller 432 which is operatively coupled to the processor 426 and the at least one activation mechanism 298, a force feedback system 434 (which may be operatively coupled to the at least one activation mechanism 298), and an internal RF chip 450 which is operatively coupled to the processor 426 (all of which may be configured as shown in FIG. 161). The external control system 446 may include a suitably configured user interface 452, and an external RF chip 454 which may operatively couple to the internal RF chip 450 via RF signals. A user of the adhesion device 444 could thus utilize the user interface 452 of the external control system 446 in order to reversibly transition the engagement elements of the adhesion device 444 from the deployment state 12 to the engagement state 12' as has been previously discussed.

FIGS. 165 and 166 depict an embodiment of an adhesion device 456 which incorporates an integrated control system 458. In this case, the integrated control system 458 is disposed within the element support body 14 of the adhesion device which is configured as a bandage (similar to embodiment 294). The integrated control system 458 may include a user interface 460, at least one activation mechanism 298, a processor 426, processor instructions which are accessible by the processor 426, a battery 430, a controller 432 which is operatively coupled to the processor 426 and the at least one activation mechanism 298, and a force feedback system 434 which may be operatively coupled to the at least one activation mechanism 298 (all of which may be configured as shown in FIG. 161). A user of the adhesion device 456 may utilize the user interface 460 in order to reversibly transition the engagement elements from the deployment state 12 to the engagement state 12' as has been discussed previously.

FIGS. 167 and 168 depict another embodiment of an adhesion device 462 which utilizes an integrated control system 458. In this case, the integrated control system 458 is disposed within the element support body 14 of the adhesion device 462 which is configured as a cylindrical tube (similar to embodiment 316). The integrated control system 458 may include a user interface 460, at least one activation mechanism 298, a processor 426, processor instructions which are accessible by the processor 426, a battery 430, a controller 432 which is operatively coupled to the processor 426 and the at least one activation mechanism 298, and a force feedback system 434 which may be operatively coupled to the at least one activation mechanism 298 (all of which may be configured as shown in FIG. 161). A user of the adhesion device 462 may utilize the user interface 460 in order to reversibly transition the engagement elements from the deployment state 12 to the engagement state 12' as has been discussed previously.

The features which are disposed within the control system 50 may be alternatively be disposed within an adhesion device deployment apparatus 464. The adhesion device deployment apparatus 464 may be used in order to deploy an adhesion device 466 onto the surface 49 of any suitable target material 48. In some cases, the adhesion device deployment apparatus 464 may be utilized in order to deliver an adhesion device 466 to target materials 48 which are difficult to access. For example, in the medical industry an appropriately configured adhesion device deployment apparatus 464 may be utilized in order to apply an adhesion device 466 to target tissue during robotic or endoscopic "key hole" surgery wherein access to the target tissue may be severely limited. Similarly in industry a suitably configured adhesion device deployment apparatus 464 could be utilized in order to deliver an adhesion device 466 to target material with limited access.

FIGS. 169-174 depict an embodiment of an adhesion device deployment apparatus 464. The adhesion device deployment apparatus 464 may include a deployment apparatus body 468 which is formed from a rigid resilient material. The adhesion device deployment apparatus 464 may also incorporate an articulation arm 470, with the articulation arm 470 being configured to access difficult to reach target material 48 regions. The articulation arm 470 may be configured as an elongated rectangular boss which is secured to and extends from the deployment apparatus body 468. The articulation arm 470 is depicted with a rectangular sectional profile 472 (see FIG. 169B), however the articulation arm 470 may be configured with any suitable sectional profile 472 such as a circular sectional profile 472 or the like. The length and reduced sectional profile 472 of the articulation arm 470 facilitate its ability to access difficult to reach target material 48 regions. The distal portion 476 of the articulation arm 470 may also include a camera 477 to allow for a user of the adhesion device deployment apparatus 462 to visualize limited access trget areas.

An adhesion device interface 474 may be disposed on a distal portion 476 of the articulation arm 470, with the adhesion device interface 474 being configured to releasably secure an adhesion device 466 to the adhesion device interface 474. The adhesion device 466 may be releasably secured to the adhesion device interface 474 by an interface release mechanism 478. The interface release mechanism 478 may releasably secure the adhesion device 466 to the adhesion device interface 474 by any suitable means. For example, the interface release mechanism 478 may be configured as multiple vacuum holes which are disposed on a surface 480 of the adhesion device interface 474. The application of a vacuum to the vacuum holes would secure the adhesion device 466 to the adhesion device interface 474, and the removal of the vacuum from the vacuum holes would release the adhesion device 466 form the adhesion device interface 474.

The adhesion device 466 which is releasably secured to the adhesion device interface 474 may include a plurality of element block assemblies 18 which are partially disposed within an element support body 14 as has been described previously. Each element block assembly 18 may include an element activation sheet 20, an element deployment sheet 22, an element transition mechanism 240, and a plurality of engagement elements 12 which are operatively coupled to the element transition mechanism 240. Each element transition mechanism 240 of the adhesion device may be operatively coupled to respective activation mechanisms 298 which are disposed within the adhesion device deployment apparatus 464 by the adhesion device interface 474. When the adhesion device 466 is secured to the adhesion device interface 474, an adhesion device coupling surface 482 of the adhesion device may be substantially adjacent to the surface 480 of the adhesion device interface 474.

The adhesion device interface 474 may be configured to couple to any configuration of adhesion device which is discussed herein. For the embodiment which is depicted in FIG. 169, the adhesion device interface 474 is depicted as a flat rectangular surface which is configured to couple to bandage embodiments 294 or pad embodiments 10 (including the adhesion device embodiment 166 which is depicted in FIG. 53). However, the adhesion device interface could be configured as a cylindrical boss which could be configured to couple to the adhesion device embodiment 316 which was discussed with regard to FIG. 112. The adhesion device interface may be suitably configured to couple to any adhesion device embodiment which is discussed herein.

Figure 173:
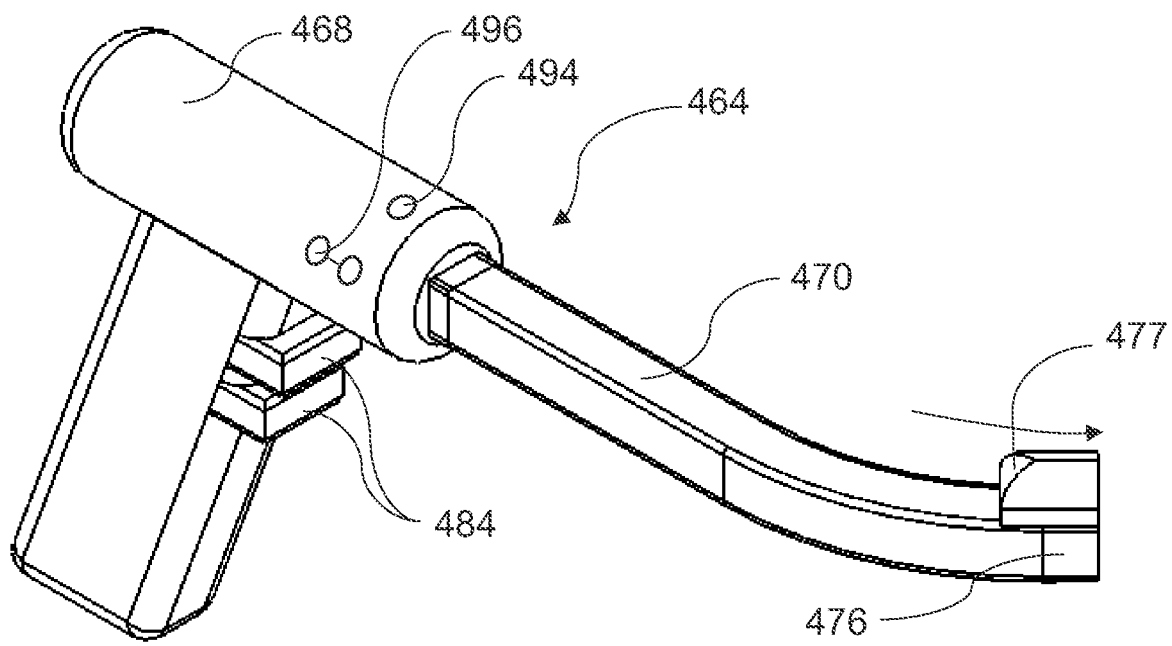

For some embodiments, the articulation arm 470 may articulate as depicted in FIGS. 173 and 174. The articulation of the articulation arm 470 allows for a user of the adhesion device deployment apparatus 464 to "steer" the distal portion 476 of the articulation arm 470 in order to properly position the adhesion device 466. The adhesion device deployment apparatus 464 may include an articulation arm user interface 484 and an articulation arm control system 486 which is operatively coupled to the articulation arm user interface 484. In turn the articulation arm control system 486 may be operatively coupled to the articulation arm 470 such that user activation of the articulation arm control system 486 via the articulation arm user interface 484 allows for the flexure of the articulation arm 470 about multiple axis. For some embodiments, the articulation arm control system 486 may be configured as multiple linear actuators which are operatively coupled to the articulation arm 470 by multiple respective actuation wires 488 (see FIG. 169B. The actuation wires 488 may be suitably terminated at the actuation arm distal portion 476, and the application of tension to a given actuation wire 488 from a respective linear actuator may result in the flexure of the articulation arm 470 as depicted in FIGS. 173 and 174.

The adhesion device deployment apparatus 464 may also include an adhesion device control system 490 which is operatively coupled to the adhesion device interface 474. The adhesion device control system 490 may include at least one activation mechanism 298 and a control release mechanism 492 which is operatively coupled to the interface release mechanism 478. The control release mechanism 492 being configured to release the adhesion device 466 from the adhesion device interface 474 with an appropriate user command. For some embodiments, the adhesion device control system 490 may further include a processor 426, processor instructions which are accessible by the processor 426, a battery 430, and a controller 432 which is operatively coupled to the processor 426. The adhesion device control system 490 may also include a force feedback mechanism 434 (which has previously been discussed) which is operatively coupled to the at least one activation mechanism 298 (all of the adhesion device control system 490 components may be configured as shown in FIG. 161). The force feedback mechanism 434 may include a force feedback indicator 494 which indicates the successful transition of the plurality of engagement elements from the deployment state 12 to the engagement state 12' within the target material 48.

The adhesion device deployment apparatus may also include an adhesion device user interface 496 which is operatively coupled to the adhesion device control system 490. The adhesion device user interface 496 may be configured to allow a user of the adhesion device deployment apparatus 464 to reversibly transform a plurality of engagement elements of the adhesion device 466 from the deployment state 12 to the engagement state 12', and to subsequently release the adhesion device 466 from the adhesion device interface 474.

Figure 170:
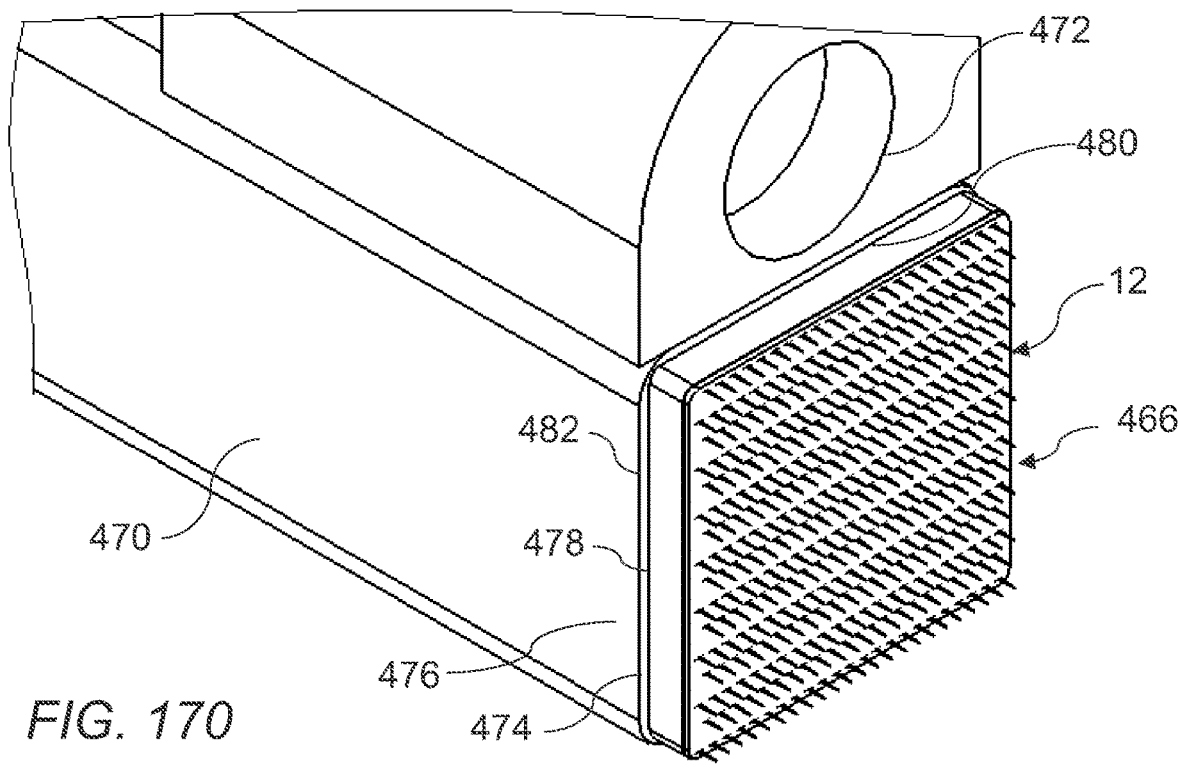
Figure 171:
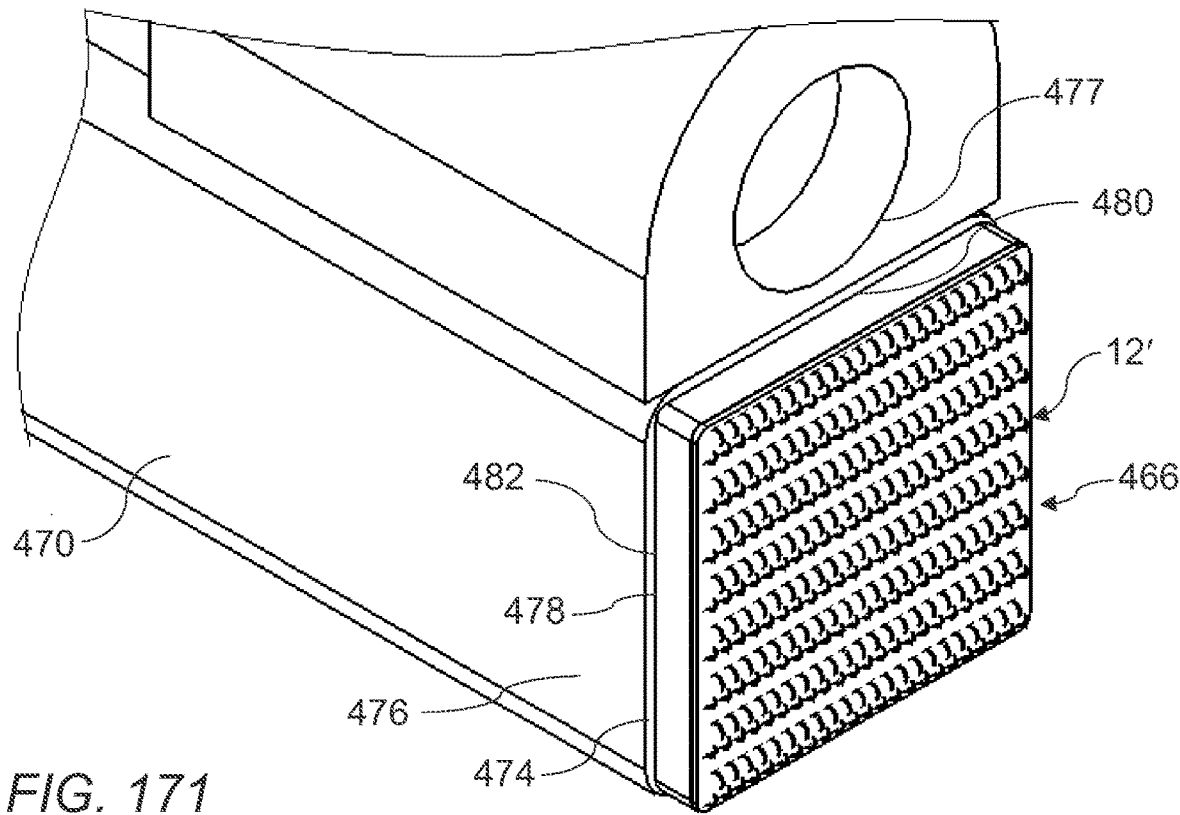
Figure 172:
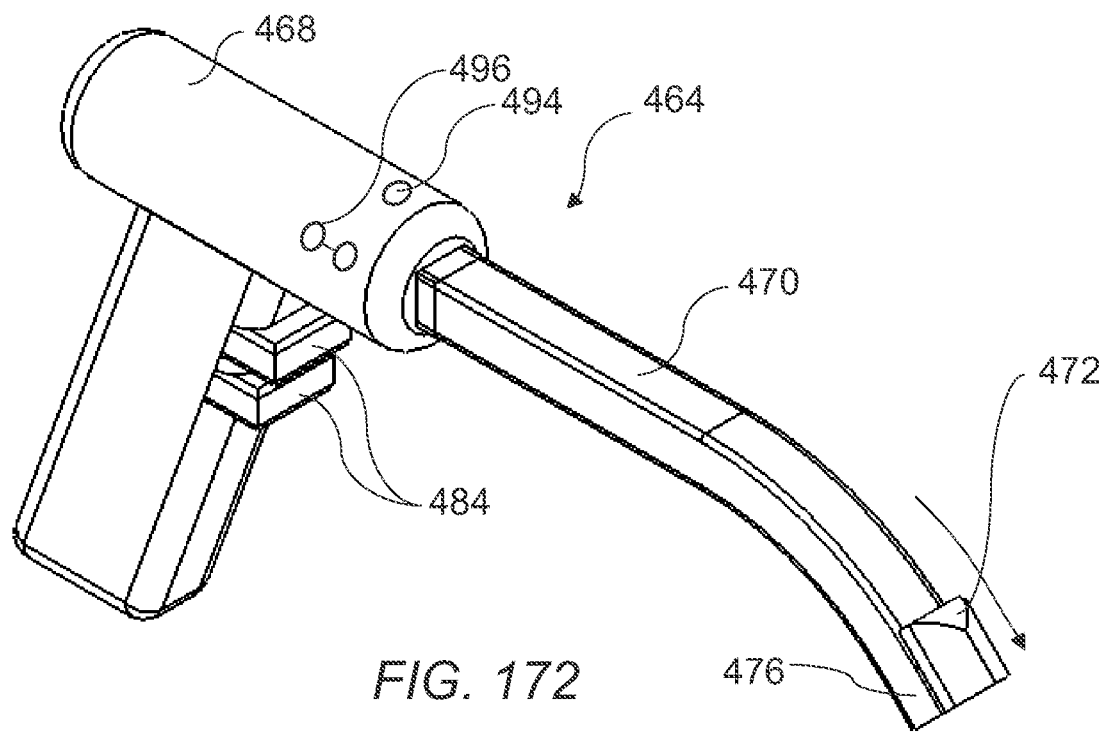

Thus a user of the adhesion device deployment apparatus 464 could deploy an adhesion device 466 to a difficult to access target area as follows. The user could apply appropriate flexure (FIGS. 173 and 174) to the articulation arm 470 using the articulation arm interface 484 in order to direct the distal portion 476 of the articulation arm 470 such that it is adjacent to the desired target material 48. The engagement elements 12 of the adhesion device 466 could then be inserted into the target material 48 while they are disposed in the deployment state 12 (FIG. 170). The user could then use the adhesion device user interface 496 to transition the engagement elements from the deployment state 12 to the engagement state 12' (FIG. 171) thereby securing the adhesion device 466 to the target material 48. The user could then use the adhesion device user interface 496 to release the adhesion device 466 from the adhesion device interface 474, and the adhesion device deployment apparatus 464 could be removed from the target site.

Certain embodiments of the technology are set forth in the claims that follow.

What is claimed is:

1. An adhesion device comprising:
   A. a plurality of element block assemblies with each element block assembly releasably secured to at least one adjacent element block assembly, each element block assembly comprising:
      (i) a plurality of engagement elements with each engagement element having an elongated element activation section which extends monolithically from an element activation sheet and an elongated element deployment section which extends monolithically from an element deployment sheet, each element activation section being fused to a respective element deployment section within a respective element tip segment;
      (ii) an element transition mechanism disposed between an element activation sheet upper surface and an element deployment sheet lower surface with the element transition mechanism being operatively coupled to each engagement element, the element transition mechanism being configured to reversibly transition between a neutral configuration wherein the activation sheet upper surface is substantially adjacent to the deployment sheet lower surface an expanded configuration wherein the activation sheet upper surface and the deployment sheet lower surface are separated by a transition gap; and
   B. an element support body having an engagement surface and engaging the plurality of element block assemblies constraining each engagement element in a deployment state which is suitable for insertion into (or removal from) a target material with the associated transition mechanism disposed in the neutral configuration, and the element support body constraining each engagement element in an engagement state which is configured to mechanically capture surrounding target material with the associated transition mechanism disposed in the expanded configuration; and
   C. a user operated control system which is operatively coupled to each element transition mechanism, the control system being configured to reversibly transition selected element transition mechanisms from the neutral configuration to the expanded configuration.

2. The adhesion device of claim 1 wherein at least one element block assembly is releasably secured to an adjacent element block assembly by a break-away tab.

3. The adhesion device of claim 2 wherein the break-away tab material is a polymer.

4. The adhesion device of claim 1 wherein at least one element block assembly is releasably secured to an adjacent element block assembly by a break-away section, each break-away section comprising an activation break-away section disposed in the element activation sheet and a deployment break-away section disposed in the element deployment sheet.

5. The adhesion device of claim 1 wherein the adhesion device is configured as a pad.

6. The adhesion device of claim 1 wherein the adhesion device is configured as a bandage.

7. The adhesion device of claim 1 wherein each element block assembly further comprises an element guide sheet.

8. The adhesion device of claim 7 wherein each element guide sheet includes a plurality of element guides with each element guide being operatively coupled to a respective engagement element, each element guide engaging the element block assembly and constraining each engagement element in a deployment state which is suitable for insertion into (or removal from) a target material with the associated transition mechanism disposed in the neutral configuration, and each element guide constraining each engagement element in an engagement state which is configured to mechanically capture surrounding target material with the associated transition mechanism disposed in the expanded configuration.

9. The adhesion device of claim 8 wherein each element guide sheet is formed from a rigid resilient material.

10. The adhesion device of claim 8 wherein each element guide is formed from a resilient elastic material.

11. The adhesion device of claim 8 wherein the element support body encompasses each element guide sheet.

12. The adhesion device of claim 1 wherein multiple element transition mechanisms are serially connected to the control system by expandable transition couplers.

13. The adhesion device of claim 12 wherein adjacent element transition mechanisms are connected by expandable transition couplers.

* * * * *